United States Patent
Naidu et al.

(10) Patent No.: US 9,193,720 B2
(45) Date of Patent: Nov. 24, 2015

(54) PYRIDIN-3-YL ACETIC ACID DERIVATIVES AS INHIBITORS OF HUMAN IMMUNODEFICIENCY VIRUS REPLICATION

(71) Applicant: BRISTOL-MYERS SQUIBB COMPANY, Princeton, NJ (US)

(72) Inventors: B. Narasimhulu Naidu, Durham, CT (US); Manoj Patel, Berlin, CT (US); Jeffrey Lee Romine, Meriden, CT (US); Denis R. St. Laurent, Newington, CT (US); Tao Wang, Farmington, CT (US); Zhongxing Zhang, Madison, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/619,438

(22) Filed: Feb. 11, 2015

(65) Prior Publication Data

US 2015/0232463 A1   Aug. 20, 2015

Related U.S. Application Data

(60) Provisional application No. 61/942,207, filed on Feb. 20, 2014.

(51) Int. Cl.
*C07D 213/24* (2006.01)
*A61K 31/00* (2006.01)
*C07D 417/14* (2006.01)
*C07D 401/04* (2006.01)
*C07D 401/14* (2006.01)
*C07D 409/14* (2006.01)
*C07D 413/14* (2006.01)

(52) U.S. Cl.
CPC ............ *C07D 417/14* (2013.01); *C07D 401/04* (2013.01); *C07D 401/14* (2013.01); *C07D 409/14* (2013.01); *C07D 413/14* (2013.01)

(58) Field of Classification Search
None
See application file for complete search history.

(56) References Cited

FOREIGN PATENT DOCUMENTS

| WO | WO 2010/130034 | 11/2010 |
| WO | WO 2011/076765 | 6/2011 |
| WO | WO 2012/140243 | 10/2012 |

*Primary Examiner* — Heidi Reese
(74) *Attorney, Agent, or Firm* — James Epperson

(57) ABSTRACT

The disclosure generally relates to compounds of formula I, II, III and IV, including compositions and methods for treating human immunodeficiency virus (HIV) infection. The disclosure provides novel inhibitors of HIV, pharmaceutical compositions containing such compounds, and methods for using these compounds in the treatment of HIV infection.

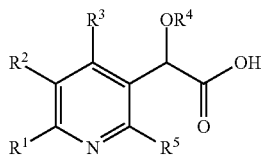

I

13 Claims, No Drawings

PYRIDIN-3-YL ACETIC ACID DERIVATIVES AS INHIBITORS OF HUMAN IMMUNODEFICIENCY VIRUS REPLICATION

CROSS-REFERENCE TO RELATED APPLICATIONS

This application claims priority to Provisional Patent Application U.S. Ser. No. 61/942,207 filed Feb. 20, 2014, hereby incorporated by reference in its entirety.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that an estimated 35.3 million people worldwide are infected with the virus (UNAIDS: Report on the Global HIV/AIDS Epidemic, 2013). In addition to the large number of individuals already infected, the virus continues to spread. Estimates from 2013 point to close to 3.4 million new infections in that year alone. In the same year there were approximately 1.6 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: however, the effect is only temporary as the virus readily develops resistance to all known agents used as monotherapy. However, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130034, WO2010130842, WO2011015641, WO2011076765, WO2012033735, WO2013123148, WO2013134113, WO2014164467, and WO2014159959.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formulas I, II, III, and IV, including pharmaceutically acceptable salts, their pharmaceutical compositions, methods for making these compounds and their use in inhibiting HIV integrase and treating those infected with HIV or AIDS.

One aspect of the invention is a compound of Formula I

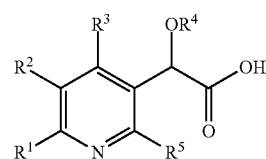

where:
$R^1$ is alkyl;
$R^2$ is phenyl, pyridinyl, pyridazinyl, pyrimidinyl, or pyridazinyl, and is substituted with 1 substituent selected from hydroxy, alkoxy, $(Ar^1)O$, and $(Ar^1)$alkoxy, $(Ar^1)$(alkoxy)alkoxy, and is also substituted with 0-3 substituents selected from halo, alkyl, haloalkyl, alkoxy, and haloalkoxy;
$R^3$ is azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, alkyl, haloalkyl, cycloalkyl, halocycloalkyl, alkenyl, alkoxy, haloalkoxy, $CON(R^6)(R^7)$, phenyl, benzyl, or (alkyl)oxadiazolyl;
$R^4$ is alkyl or haloalkyl;
$R^5$ is alkyl;
$R^6$ is hydrogen or alkyl;
$R^7$ is hydrogen or alkyl; and
$Ar^1$ is phenyl, naphthyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, pyridinyl, pyridazinyl, pyrimidinyl, or pyridazinyl, and is substituted with 0-3 substituents selected from halo, alkyl, haloalkyl, alkoxy, haloalkoxy, phenyl, and benzyloxy;
or a pharmaceutically acceptable salt thereof.

Another aspect of the invention is a compound of formula I where:
$R^1$ is alkyl;
$R^2$ is phenyl or pyridinyl and is substituted with 1 substituent selected from alkoxy, $(Ar^1)O$, and $(Ar^1)$alkoxy, and is also substituted with 0-3 substituents selected from halo, alkyl, haloalkyl, alkoxy, and haloalkoxy;
$R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, alkoxy, and haloalkoxy;

$R^4$ is alkyl or haloalkyl;
$R^5$ is alkyl; and
$Ar^1$ is phenyl substituted with 0-3 substituents selected from halo, alkyl, haloalkyl, alkoxy, and haloalkoxy;
or a pharmaceutically acceptable salt thereof.

Another aspect of the invention is a compound of Formula I where $R^1$ is alkyl; $R^2$ is phenyl or pyridinyl and is substituted with 1 substituent selected from alkoxy, $(Ar^1)O$, or $(Ar^1)$alkoxy, and is also substituted with 0-3 substituents selected from halo, alkyl, haloalkyl, alkoxy, and haloalkoxy; $R^3$ is piperidinyl substituted with 0-3 alkyl substituents; $R^4$ is alkyl; $R^5$ is alkyl; and $Ar^1$ is phenyl substituted with 0-3 substituents selected from halo, alkyl, haloalkyl, alkoxy, and haloalkoxy; or a pharmaceutically acceptable salt thereof.

Another aspect of the invention is a compound of Formula I where $R^2$ is phenyl substituted with 1 substituent selected from hydroxy, alkoxy, $(Ar^1)O$, and $(Ar^1)$alkoxy, $(Ar^1)$(alkoxy)alkyl, and is also substituted with 0-3 substituents selected from halo, alkyl, haloalkyl, alkoxy, and haloalkoxy;

Another aspect of the invention is a compound of Formula I where $R^2$ is phenyl substituted with 1 substituent selected from alkoxy, $(Ar^1)O$, or $(Ar^1)$alkoxy, and is also substituted with 0-3 substituents selected from halo, alkyl, haloalkyl, alkoxy, and haloalkoxy.

Another aspect of the invention is a compound of Formula I where $R^2$ is pyridinyl, pyridazinyl, pyrimidinyl, or pyridazinyl, and is substituted with 1 substituent selected from hydroxy, alkoxy, $(Ar^1)O$, and $(Ar^1)$alkoxy, $(Ar^1)$(alkoxy)alkoxy, and is also substituted with 0-3 substituents selected from halo, alkyl, haloalkyl, alkoxy, and haloalkoxy.

Another aspect of the invention is a compound of Formula I where $R^3$ is piperidinyl, substituted with 0-3 substituents selected from cyano, halo, alkyl, haloalkyl, cycloalkyl, halocycloalkyl, alkenyl, alkoxy, haloalkoxy, $CON(R^6)(R^7)$, phenyl, benzyl, or (alkyl)oxadiazolyl.

Another aspect of the invention is a compound of Formula I where $R^3$ is piperidinyl, gem-disubstituted in the 4-position with 2 substituents selected from cyano, halo, alkyl, haloalkyl, cycloalkyl, halocycloalkyl, alkenyl, alkoxy, haloalkoxy, $CON(R^6)(R^7)$, phenyl, benzyl, or (alkyl)oxadiazolyl.

Another aspect of the invention is a compound of Formula II

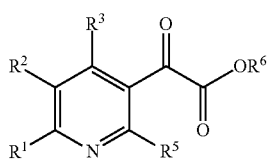

where $R^1$ is hydrogen or alkyl; $R^2$ is halo; $R^3$ is halo; $R^5$ is hydrogen or alkyl; and $R^6$ is alkyl.

Another aspect of the invention is a compound of Formula III

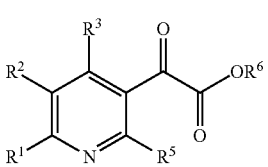

where $R^1$ is hydrogen or alkyl; $R^2$ is halo; $R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, alkoxy, cyano, and haloalkoxy; $R^5$ is hydrogen or alkyl; and $R^6$ is alkyl.

Another aspect of the invention is a compound of Formula IV

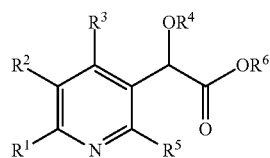

where $R^1$ is hydrogen or alkyl; $R^2$ is halo; $R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, alkoxy, cyano, and haloalkoxy; $R^4$ is hydrogen or alkyl; $R^5$ is hydrogen or alkyl; and $R^6$ is alkyl.

For a compound of Formula I, the scope of any instance of a variable substituent, including $R^1$, $R^2$, $R^3$, $R^4$, $R^5$, $R^6$ and $Ar^1$ can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Cycloalkenyl" means a monocyclic ring system composed of 4 to 7 carbons. "Halo" means fluoro, chloro, bromo, or iodo. "Haloalkyl" and "haloalkoxy" include all halogenated isomers from monohalo to perhalo. "Aryl" includes carbocyclic and heterocyclic aromatic substituents. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication:

A recombinant NL-RLuc proviral clone was constructed in which a section of the nef gene from NL4-3 was replaced with the *Renilla* Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC18 at the PvuII site. The NL-RLuc virus was prepared by transfection of 293T cells with the plasmid pNLR-Luc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). Results are shown in Table 1.

TABLE 1

| Example | $EC_{50}\ \mu M$ |
|---|---|
| 1 | 0.037 |
| 2 | 0.012 |
| 3 | 0.02 |
| 4 | 0.012 |
| 5 | 0.011 |
| 6 | 0.02 |
| 7 | 0.009 |
| 8 | 0.011 |
| 9 | 0.009 |
| 10 | 0.027 |
| 11 | 0.004 |
| 12 | 0.005 |
| 13 | 0.012 |
| 14 | 0.028 |
| 15 | 0.004 |
| 16 | 0.172 |
| 17 | 0.004 |
| 18 | 0.002 |
| 19 | 0.012 |
| 20 | 0.003 |
| 21 | 0.014 |
| 22 | 0.007 |
| 23 | 0.005 |
| 24 | 0.003 |
| 25 | 0.003 |
| 26 | 0.017 |
| 27 | 0.012 |
| 28 | 0.019 |
| 29 | 0.015 |
| 30 | 0.006 |
| 31 | 0.047 |
| 32 | 0.011 |
| 33 | 0.001 |
| 34 | 0.011 |
| 35 | 0.013 |
| 36 | 0.002 |
| 37 | 0.001 |
| 38 | 0.006 |
| 39 | 0.002 |
| 40 | 0.001 |
| 41 | 0.001 |
| 42 | 0.004 |
| 43 | 0.014 |
| 44 | 0.012 |
| 45 | 0.029 |
| 46 | 0.014 |
| 47 | 0.018 |
| 48 | 0.001 |
| 49 | 0.034 |
| 50 | 0.003 |
| 51 | 0.006 |
| 52 | 0.005 |
| 53 | 0.002 |
| 54 | 0.008 |
| 55 | 0.093 |
| 56 | 0.002 |
| 57 | 0.217 |
| 58 | 0.009 |
| 59 | 0.021 |
| 60 | 0.262 |
| 61 | 0.044 |
| 62 | 0.166 |
| 63 | 0.119 |
| 64 | 0.026 |
| 65 | 0.044 |
| 66 | 0.141 |
| 67 | 0.007 |
| 68 | 0.042 |
| 69 | 1.994 |
| 70 | 3.051 |
| 71 | 3.193 |
| 72 | 0.744 |
| 73 | 1.03 |
| 74 | 0.379 |
| 75 | 0.004 |
| 76 | 0.017 |
| 77 | 0.002 |
| 78 | 0.004 |
| 79 | 0.291 |
| 80 | 1.771 |
| 81 | 0.004 |
| 82 | 5.432 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regimen, however, will be determined by a physician using sound medical judgment.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse tranpscriptase inhibitors, HIV non-nucleoside reverse tranpscriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regimen, however, will be determined by a physician using sound medical judgment.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "$Et_2O$" for diethyl ether; "DMAP" for 4-dimethylaminopyridine; "DCE" for 1,2-dichloroethane; "DCM" for dichloromethane, "ACN" for acetonitrile; "DME" for 1,2-dimethoxyethane; "HOBt" for 1-hydroxybenzotriazole hydrate; and "DIEA" for diisopropylethylamine.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "A" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "prep-" for preparative, "RP HPLC" for reverse phase HPLC, "TLC" or "tlc" for thin layer chromatography, "NMR" for nuclear magnetic resonance spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I, Compounds I-1 and 1-6 are commercially available or synthesized by reactions well known in the art. Treatment of compound I-1 with bromine provided the dibromo intermediates I-2 which was converted to the chloropyridine I-3 by reacting with $POCl_3$. Intermediate I-3 conveniently transformed to ketoester I-5 using conditions well-known to those skilled in the art, including reacting I-3 with Grignard reagent in the presence of catalytic copper(I) bromide dimethylsulfide complex followed by alkyl 2-chloro-2-oxoacetate. Coupling of amines I-5 with intermediate I-6 in the presence of an organic base such as Hunig's base provided intermediate I-7. Chiral Lewis acid such as I-8 mediated reduction of ketoester I-7 with catecholborane furnished chiral alcohol I-9. Tertiary butylation of alcohol I-9 by well-known conditions, including but not limited to tertiary-butyl acetate and perchloric acid, gave intermediate I-10. Intermediates I-10 are conveniently transformed to intermediates I-11 using conditions well-known in the art, including but not limited to the Suzuki coupling between intermediates I-10 and $R^6B(OR)_2$. The boronate or boronic acid coupling reagents, well-known in the art, are commercially available or are prepared by reactions well-known to those skilled in the art. Hydrolysis of intermediate I-11 by using conditions well-known to those skilled in the art furnished carboxylic acid I-12.

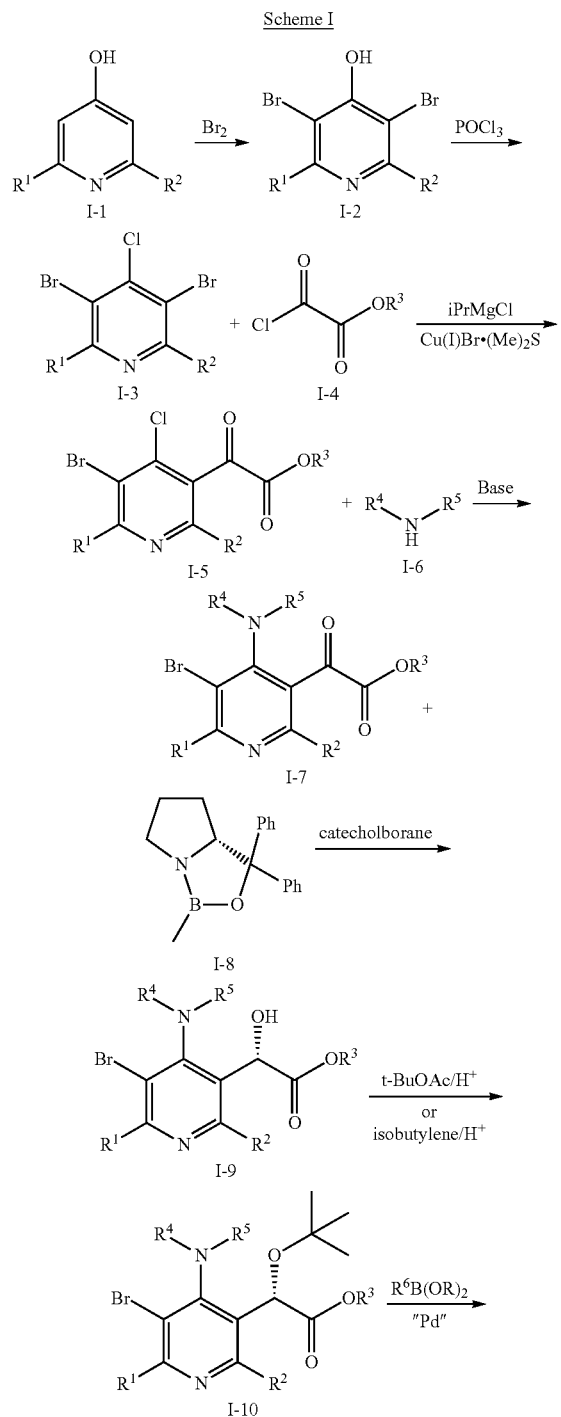

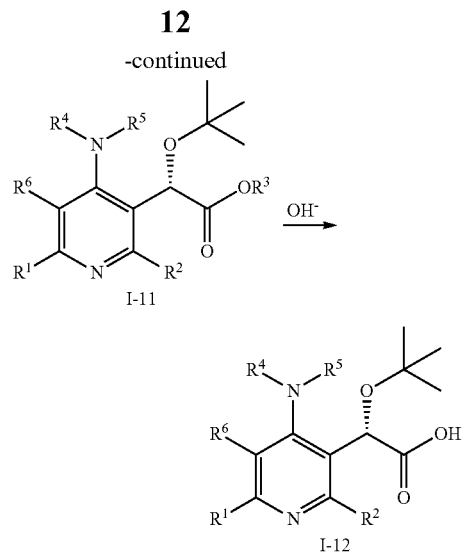

Intermediates I-10 are conveniently transformed to intermediates II-2 using conditions well-known in the art, including but not limited to the Suzuki coupling between intermediates I-10 and II-1. Cleavage of protecting group in II-2 provided phenol II-3. Alkylation of the phenol II-3 was achieved by using conditions well known to those skilled in the art, including but not limited to Mitshunobu reaction to provide the intermediate II-4. Hydrolysis of intermediate II-4 by using conditions well-known in the literature furnished carboxylic acid II-5.

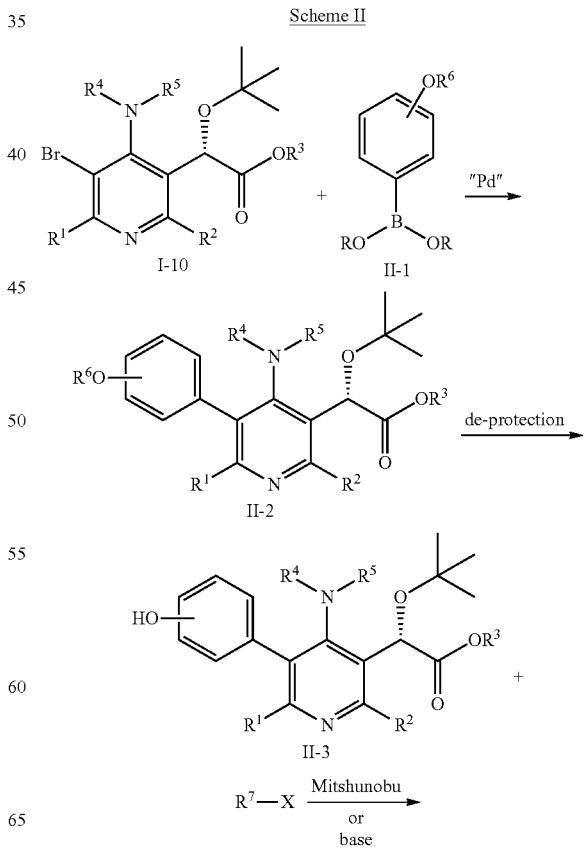

-continued

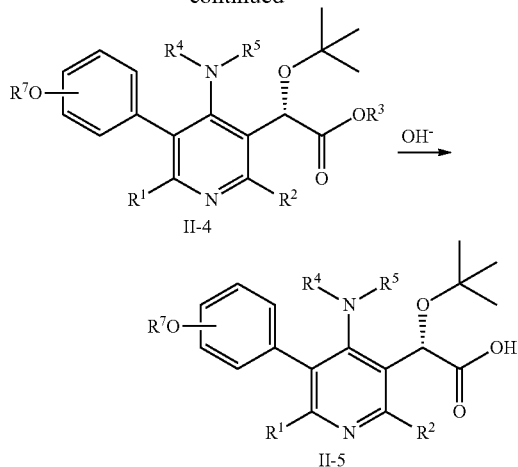

The compounds described herein were purified by the methods well known to those skilled in art by normal phase column chromatography on silica gel column using appropriate solvent system described. Preparative HPLC purifications mentioned in this experimentation section were carried out gradient elution either on Sunfire Prep C18 ODB column (5 µm; 19 or 30×100 mm) or Waters Xbridge column (5 µM; 19 or 30×100 mm) using the following mobile phases: Mobile phase A: 9:1 H$_2$O/acetonitrile with 10 mM NH$_4$OAc and mobile phase B:A: 9:1 acetonitrile/H$_2$O with: 10 mM NH$_4$OAc; or mobile phase A: 9:1 H$_2$O/acetonitrile with 0.1% TFA and mobile phase B:A: 9:1 acetonitrile/H$_2$O with: 0.1% TFA; or mobile phase A: water with 20 mM NH$_4$OAc and mobile phase B: 95:5 MeOH/H$_2$O with 20 mM NH$_4$OAc.

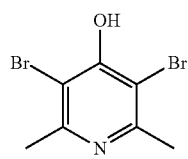

A 3-neck R.B-flask equipped with mechanical stirrer, addition funnel and condenser is charged with 2,6-dimethylpyridin-4-ol (100 g, 812 mmol), CH$_2$Cl$_2$ (1000 mL) and MeOH (120 mL). To the resulting light brown or tan solution was added tert-BuNH2 (176 ml, 1665 mmol), cooled in water bath maintained between 5-10° C. (ice-water) and added drop wise Br2 (84 ml, 1624 mmol) over 70 min. After the addition was complete cold bath was removed and stirred for 1.5 h at rt. Then, the light orange slurry was filtered and the filter cake was washed with ether (250 mL) and dried to afford 3,5-dibromo-2,6-dimethylpyridin-4-ol, hydrobromide (280.75 g, 776 mmol, 96% yield) as white solid which was used in the next step without further purification. $^1$H NMR (500 MHz, DMSO-d$_6$) δ 12.08 (br. s., 1H), 2.41 (s, 6H). LCMS (M+H)=281.9.

Alternative Procedure:
Bromine (72.8 mL, 1.4 mol) was added via addition funnel over 60 min to a mechanically stirred cold (ice-water bath) solution of 2,6-dimethylpyridin-4-ol (87 g, 706 mmol) and 4-methylmorpholine (156 mL, 1.4 mol) in dichloromethane (1 L) and methanol (100 mL) and then stirred for 2 h at rt. Additional bromine (~15 mL) was added based on monitoring by LCMS. The product was filtered, washed with ether, and dried under vacuum to give 3,5-dibromo-2,6-dimethylpyridin-4-ol 176.8 g (88%).

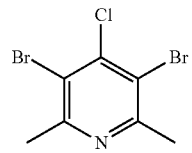

A 500-mL RB-flask was charged with solid 3,5-dibromo-2,6-dimethylpyridin-4-ol, hydrobromide (94 g, 260 mmol) and POCl3 (150 ml, 1609 mmol) was added. To this white slurry was added N,N-dimethylaniline (39.5 ml, 312 mmol) and the reaction mixture was heated to 130° C. (oil bath temp). After stirring for 2 h, the reaction mixture was cooled, concentrated and the brown residue taken up in toluene (100 mL) and concentrated to remove any unreacted POCl$_3$. Then, the residue was treated with ice (250 g) for 30 min and carefully neutralized with powder Na$_2$CO$_3$, extracted with CH$_2$Cl$_2$ (3×250 mL). The combined organic layers dried (MgSO$_4$/C), filtered, concentrated to give slurry which was dissolved in ether (500 mL), filtered through a plug of silica gel. The silica gel pad was washed with 1:1 Ether/Hex (1.5-lit). The filtrate was concentrated to give white slurry which was triturated with hexanes (200 mL) and left in the freezer (−10° C., 2 h). The liquid was decanted and solids were rinsed with cold hexanes (4×50 mL) and dried overnight under high vacuum (required to remove dimethylaniline) to afford 3,5-dibromo-4-chloro-2,6-dimethylpyridine (49.2 g, 164 mmol, 63.3% yield) as pale greenish-yellow solid. The decanted solvent was concentrated and purified by flash chromatography using 1-lit each hexanes, 0.5, 1, 2 and 5% EtOAc/Hex to afford additional 3,5-dibromo-4-chloro-2,6-dimethylpyridine (18.763 g, 62.7 mmol, 24.13% yield) as greenish-yellow solid. $^1$H NMR (500 MHz, CDCl$_3$) δ 2.59 (s, 6H). LCMS (M+H)=300.0.

Alternative Procedure:
Triethylamine (28.8 mL, 206 mmol) was added to a nitrogen purged solution of 3,5-dibromo-2,6-dimethylpyridin-4-ol (58 g, 206 mmol) and phosphorous oxychloride (57.7 mL, 619 mmol) in chloroform (450 mL) and stirred for 1 h at rt, then 3 h at 80° C. The reaction was removed from heating and immediately concentrated under house vaccum; then under high vacuum. The appearance was a cream colored solid, which was azeotroped with toluene (2×100 mL); treated with ice (200 g) for 10 min and carefully neutralized with NaHCO$_3$ (powder), and 1N NaOH solution, and extracted with DCM (2×400 mL). The combined organic layers were dried (MgSO$_4$), concentrated, and a beige solid was obtained that was washed with hexanes and dried under high vacuum to give 3,5-dibromo-4-chloro-2,6-dimethyl-pyridine 52.74 g (85.1%). Concentration of the hexanes gave 3.5 g of less pure product.

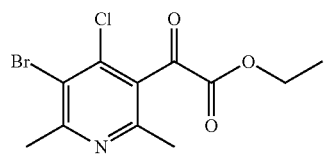 [SMILES: CCOC(=O)C(=O)c1c(C)nc(C)c(Br)c1Cl]

To a stirred mixture of 3,5-dibromo-4-chloro-2,6-dimethylpyridine (14.94 g, 49.9 mmol) and Cu(I)Br Me2S (0.513 g, 2.495 mmol) in THF (50 mL) was added drop wise 2M iPrMgCl/THF (26.2 ml, 52.4 mmol) at −30° C. over 5 min. Then, the resulting slurry was warmed to −10° C. over 30 min and stirred for 30 min. The homogeneous brown reaction mixture was rapidly transferred via cannula to a solution of ethyl 2-chloro-2-oxoacetate (6.14 ml, 54.9 mmol, degassed for 5 min by bubbling N2 through the solution) in THF (50 mL) maintained at −30° C. The resulting reaction mixture was stirred (1.5 h) while warming to 0° C. Then, taken up in to Et$_2$O (200 mL), washed with 1:1 sat Na$_2$CO$_3$/1M NH$_4$Cl (3×50 mL), dried (MgSO$_4$), filtered and concentrated to give brown viscous oil. Flash chromatography using 2.5, 5 and 7.5% EtOAc/Hex afforded ethyl 2-(5-bromo-4-chloro-2,6-dimethylpyridin-3-yl)-2-oxoacetate (14.37 g, 44.8 mmol, 90% yield) as white solid. $^1$H NMR (400 MHz, CDCl$_3$) δ 4.42 (q, J=7.0 Hz, 2H), 2.76 (s, 3H), 2.46 (s, 3H), 1.41 (t, J=7.2 Hz, 3H). LCMS (M+H)=322.1.

desired (S)-ethyl 2-(5-bromo-4-(4,4-dimethylpiperidin-1-yl)-2,6-dimethylpyridin-3-yl)-2-hydroxyacetate (2.2596 g, 5.66 mmol, 100% yield) contaminated with about 10% of (S)-ethyl 2-(5-bromo-4-chloro-2,6-dimethylpyridin-3-yl)-2-hydroxyacetate. Used in the next step without further purification. $^1$H NMR (500 MHz, CDCl$_3$) δ 5.71 (d, J=7.3 Hz, 1H), 5.54 (d, J=7.4 Hz, 1H), 4.29 (dq, J=10.8, 7.1 Hz, 1H), 4.16 (dq, J=10.8, 7.1 Hz, 1H), 3.94-3.83 (m, 2H), 2.71 (d, J=11.9 Hz, 1H), 2.67 (s, 3H), 2.59 (s, 3H), 2.54 (d, J=12.0 Hz, 1H), 1.71 (td, J=12.7, 4.7 Hz, 1H), 1.62 (td, J=13.0, 4.7 Hz, 1H), 1.42 (dd, J=13.1, 2.2 Hz, 1H), 1.37 (dd, J=12.9, 2.4 Hz, 1H), 1.25 (t, J=7.1 Hz, 3H), 1.09 (s, 3H), 1.04 (s, 3H). LCMS (M+H)=401.3.

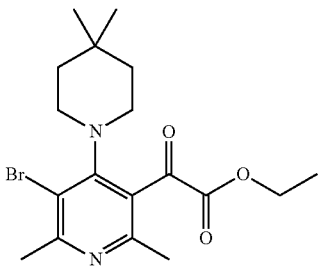 [SMILES: CCOC(=O)C(=O)c1c(C)nc(C)c(Br)c1N1CCC(C)(C)CC1]

To a solution of 4,4-dimethylpiperidine (1.245 g, 11.00 mmol) and DIEA (3.49 ml, 20.00 mmol) in anhydrous CH$_3$CN (40 mL) was added ethyl 2-(5-bromo-4-chloro-2,6-dimethylpyridin-3-yl)-2-oxoacetate (3.21 g, 10 mmol) at rt. The resulting mixture was placed in a pre-heated oil bath (80° C.). After 22 h, the reaction mixture was concentrated and the residue was purified by flash chromatography using 1-lit each 2.5, 5, 7.5 and 10% EtOAc/Hex to afford ethyl 2-(5-bromo-4-(4,4-dimethylpiperidin-1-yl)-2,6-dimethylpyridin-3-yl)-2-oxoacetate (2.846 g, 7.16 mmol, 71.6% yield) as yellow solid. $^1$H NMR (500 MHz, CDCl$_3$) δ 4.37 (q, J=7.1 Hz, 2H), 3.67-2.75 (br.s., 4H), 2.71 (s, 3H), 2.44 (s, 3H), 1.42 (t, J=7.1 Hz, 3H), 1.38 (t, J=5.6 Hz, 4H), 1.00 (s, 6H). LCMS (M+H)=399.4.

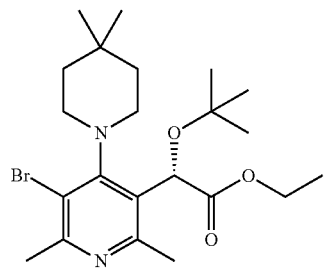

A stirred ice-cold yellow mixture of (S)-ethyl 2-(5-bromo-4-(4,4-dimethylpiperidin-1-yl)-2,6-dimethylpyridin-3-yl)-2-hydroxyacetate (2.45 g, 6.14 mmol) and 70% HClO$_4$ (1.054 ml, 12.27 mmol) in CH$_2$Cl$_2$ (100 mL) was saturated with isobutylene gas by bubbling through the reaction mixture (10 min). After 2 h, cold bath was removed and the turbid reaction mixture stirred for 22 h at rt. LCMS at this point showed 4:1 product to sm. So, saturated with isobutylene (5 min) at rt and stirred for additional 24 h. Then, neutralized with sat. Na$_2$CO$_3$ (30 mL), organic layer separated and aqueous layer extracted with CH$_2$Cl$_2$ (25 mL). The combined organic layers dried (MgSO$_4$), filtered, concentrated and purified by flash chromatography using 5, 10, 15, 20 and 40% EtOAc/hex to afford (S)-ethyl 2-(5-bromo-4-(4,4-dimethylpiperidin-1-yl)-2,6-dimethylpyridin-3-yl)-2-(tert-butoxy)acetate (2.3074 g, 5.07 mmol, 83% yield) as yellow oil: $^1$H NMR (500 MHz, CDCl$_3$) δ 6.19 (br. s., 1H), 4.17-4.24 (m, 1H), 4.08-4.14 (m, 1H), 4.04 (dt, J=2.5, 12.1 Hz, 1H), 3.51 (dt, J=2.5, 12.1 Hz, 1H), 2.85-2.91 (m, 1H), 2.64 (s, 3H), 2.57-2.62 (m, 1H), 2.55 (s, 3H), 1.55-1.66 (m, 2H), 1.41-1.46 (m, 1H), 1.32-1.37 (m, 1H), 1.21 (s, 9H), 1.20 (t, J=7.2 Hz, 2H), 1.08 (s, 3H), 1.03 (s, 3H). LCMS (M+H)=457.4. And (S)-ethyl 2-(5-bromo-4-(4,4-dimethylpiperidin-1-yl)-2,6-dimethylpyridin-3-yl)-2-hydroxyacetate (0.3 g, 0.751 mmol, 12.24% yield) as pale yellow paste: LCMS (M+H)=401.3.

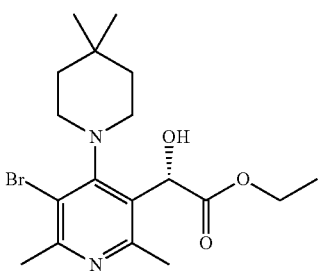 [SMILES: CCOC(=O)[C@@H](O)c1c(C)nc(C)c(Br)c1N1CCC(C)(C)CC1]

To stirred yellow solution of ethyl 2-(5-bromo-4-(4,4-dimethylpiperidin-1-yl)-2,6-dimethylpyridin-3-yl)-2-oxoacetate (2.25 g, 5.66 mmol) and (R)-1-methyl-3,3-diphenylhexahydropyrrolo[1,2-c][1,3,2]oxazaborole (0.314 g, 1.133 mmol) in toluene (30 mL) at −35° C. was added drop wise 50% catecholborane (1.819 ml, 8.49 mmol) over 10 min. The reaction mixture was slowly warmed to −15° C. over 1 h and then left for 2 h at −15° C. Then, diluted with EtOAc (100 mL), washed with sat Na$_2$CO$_3$ (4×25 mL) by vigorously stirring and separating aqueous layers. The organic layer dried (MgSO$_4$), filtered, concentrated and purified by flash chromatography using 10, 20 and 25% EtOAc/Hex to afford

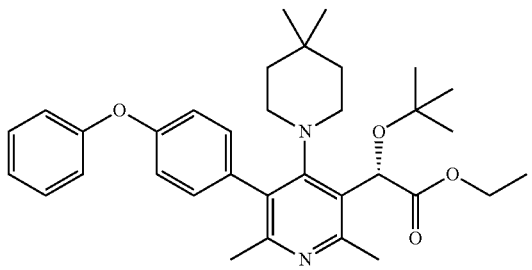 [SMILES: CCOC(=O)[C@@H](OC(C)(C)C)c1c(C)nc(C)c(-c2ccc(Oc3ccccc3)cc2)c1N1CCC(C)(C)CC1]

A mixture of (S)-ethyl 2-(5-bromo-4-(4,4-dimethylpiperidin-1-yl)-2,6-dimethylpyridin-3-yl)-2-(tert-butoxy)acetate (0.0462 g, 0.101 mmol), (4-phenoxyphenyl)boronic acid (0.033 g, 0.152 mmol) and 2M Na$_2$CO$_3$ (0.127 ml, 0.254 mmol) degassed for 10 min. Then, Pd(Ph$_3$P)$_4$ (0.012 g, 10.14 µmol) added, degassed for 5 min and placed in a pre-heated oil bath 110° C. After 2 h, cooled and purified by pre-HPLC to afford (S)-ethyl 2-(tert-butoxy)-2-(4-(4,4-dimethylpiperidin-1-yl)-2,6-dimethyl-5-(4-phenoxyphenyl)pyridin-3-yl)acetate (0.0162 g, 0.030 mmol, 29.3% yield) as white solid. $^1$H NMR (500 MHz, CDCl$_3$ δ7.34-7.39 (m, 2H), 7.24-7.28 (m, 1H), 7.09-7.17 (m, 4H), 7.04-7.08 (m, 2H), 6.09 (s, 1H), 4.14-4.30 (m, 2H), 3.20 (d, J=12.3 Hz, 1H), 2.88 (t, J=11.7 Hz, 1H), 2.62 (s, 3H), 2.33 (d, J=11.5 Hz, 1H), 2.25 (s, 3H), 2.12 (t, J=11.4 Hz, 1H), 1.57 (dt, J=4.3, 12.5 Hz, 1H), 1.37-1.44 (m, 1H), 1.26 (t, J=7.1 Hz, 4H), 1.19-124 (m, 1H), 1.22 (s, 9H), 1.12 (d, J=12.1 Hz, 1H), 0.93 (s, 3H), 0.72 (s, 3H). LCMS (M+H)=545.4.

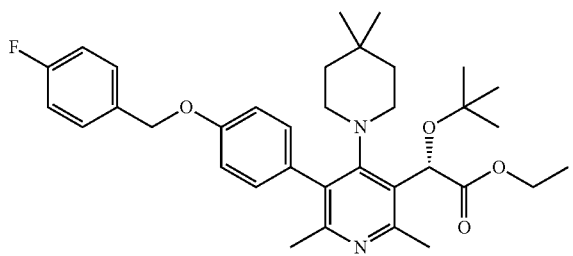 [SMILES: CCOC(=O)[C@@H](OC(C)(C)C)c1c(C)nc(C)c(-c2ccc(OCc3ccc(F)cc3)cc2)c1N1CCC(C)(C)CC1]

A mixture of (S)-ethyl 2-(5-bromo-4-(4,4-dimethylpiperidin-1-yl)-2,6-dimethylpyridin-3-yl)-2-(tert-butoxy)acetate (0.049 g, 0.108 mmol), (4-((4-fluorobenzyl)oxy)phenyl)boronic acid (0.040 g, 0.161 mmol) and 2M Na$_2$CO$_3$ (0.134 ml, 0.269 mmol) in DMF (2 mL) was degassed for 10 min. Then, Pd(Ph$_3$P)$_4$ (0.012 g, 10.76 µmol) was added, degassed for 5 min and placed in a pre-heated oil bath at 100° C. After 1.5 h at 110° C., cooled and purified by prep-HPLC to afford (S)-ethyl 2-(tert-butoxy)-2-(4-(4,4-dimethylpiperidin-1-yl)-5-(4-((4-fluorobenzyl)oxy)phenyl)-2,6-dimethylpyridin-3-yl)acetate (0.0372 g, 0.065 mmol, 59.9% yield) as tan color solid. LCMS (M+H)=577.6.

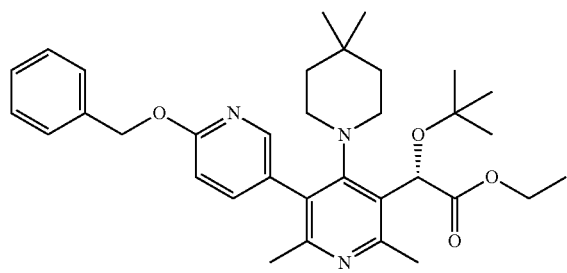 [SMILES: CCOC(=O)[C@@H](OC(C)(C)C)c1c(C)nc(C)c(-c2ccc(OCc3ccccc3)nc2)c1N1CCC(C)(C)CC1]

A mixture of (S)-ethyl 2-(5-bromo-4-(4,4-dimethylpiperidin-1-yl)-2,6-dimethylpyridin-3-yl)-2-(tert-butoxy)acetate (0.0553 g, 0.121 mmol), (6-(benzyloxy)pyridin-3-yl)boronic acid (0.042 g, 0.182 mmol) and 2M Na$_2$CO$_3$ (0.152 ml, 0.304 mmol) in DMF (2 mL) was degassed for 10 min. Then, Pd(Ph$_3$P)$_4$ (0.014 g, 0.012 mmol) added, degassed for 5 min and placed in a pre-heated oil bath at 110° C. After 2 h, cooled and purified by prep-HPLC to afford (S)-ethyl 2-(6'-(benzyloxy)-4-(4,4-dimethylpiperidin-1-yl)-2,6-dimethyl-[3,3'-bipyridin]-5-yl)-2-(tert-butoxy)acetate (0.016 g, 0.029 mmol, 23.54% yield) as white solid. $^1$H NMR (500 MHz, CDCl$_3$) δ 8.08-8.10 (m, 0.5H), 8.00 (d, J=1.9 Hz, 0.5H), 7.51-7.54 (m, 2.5H), 7.39-7.44 (m, 2.5H), 7.34-7.38 (m, 1H), 6.92-6.96 (m, 1H), 6.05 (s, 1H), 5.41-5.55 (m, 2H), 4.23-4.30 (m, 1H), 4.15-4.22 (m, 1H), 3.26 (d, J=12.3 Hz, 0.5H), 3.19 (d, J=11.5 Hz, 0.5H), 2.87-2.96 (m, 0.5H), 2.75-2.83 (m, 0.5H), 2.63 (s, 1.5H), 2.62 (s, 1.5H), 2.38 (d, J=11.2 Hz, 0.5H), 2.26-2.31 (m, 0.5H), 2.25 (s, 1.5H), 2.23 (s, 1.5H), 2.05-2.18 (m, 1H), 1.50-1.57 (m, 1H), 1.35-1.44 (m, 1H), 1.27 (dt, J=2.2, 7.1 Hz, 3H), 1.22 (s, 4.5H), 1.21 (s, 4.5H), 1.06-1.16 (m, 2H), 0.92 (s, 3H), 0.67 (br. s., 3H). LCMS (M+H)=560.4.

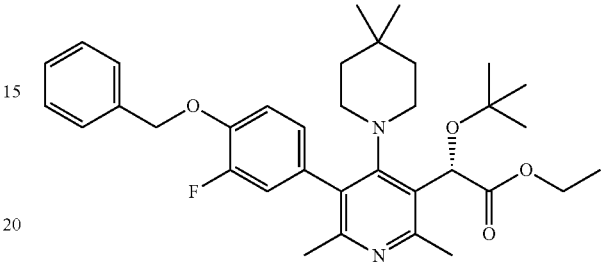

A mixture of (S)-ethyl 2-(5-bromo-4-(4,4-dimethylpiperidin-1-yl)-2,6-dimethylpyridin-3-yl)-2-(tert-butoxy)acetate (0.0266 g, 0.058 mmol), (4-(benzyloxy)-3-fluorophenyl)boronic acid (0.022 g, 0.088 mmol) and 2M Na$_2$CO$_3$ (0.073 ml, 0.146 mmol) in DMF (2 mL) was degassed for 10 min. Then, Pd(Ph$_3$P)$_4$ (6.75 mg, 5.84 µmol) was added, degassed for 5 min and placed in a pre-heated oil bath at 110° C. After 2 h, cooled and purified by pre-HPLC to afford(S)-ethyl 2-(5-(4-(benzyloxy)-3-fluorophenyl)-4-(4,4-dimethylpiperidin-1-yl)-2,6-dimethylpyridin-3-yl)-2-(tert-butoxy)acetate (0.0216 g, 0.037 mmol, 64.1% yield) as white solid. $^1$H NMR (500 MHz, CDCl$_3$) δ 7.48-7.51 (m, 2H), 7.40-7.45 (m, 2H), 7.34-7.39 (m, 1H), 7.02-7.10 (m, 1.5H), 6.92-6.98 (m, 1H), 6.82-6.86 (m, 0.5H), 6.05 (s, 1H), 5.20-5.27 (m, 2H), 4.23-4.30 (m, 1H), 4.18 (qd, J=7.1, 10.8 Hz, 1H), 3.19 (d, J=11.4 Hz, 1H), 2.78-2.92 (m, 1H), 2.61 (s, 1.3H), 2.60 (s, 1.7H), 2.26-2.32 (m, 1H), 2.22 (s, 1.7H), 2.21 (s, 1.3H), 1.99-2.11 (m, 1H), 1.51-1.58 (m, 1H), 1.33-1.42 (m, 1H), 1.26 (t, J=7.1 Hz, 3H), 1.20 (s, 9H), 1.04-1.18 (m, 2H), 0.91 (br. s., 1H), 0.70 (s, 1.3H), 0.62 (s, 1.7H). LCMS (M+H)=577.4.

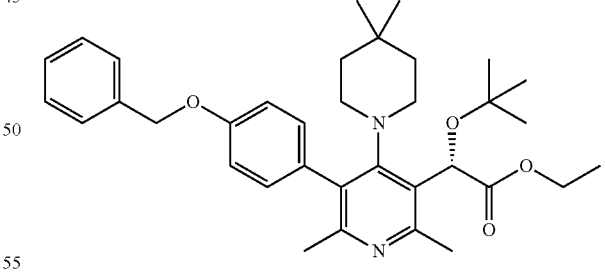

A mixture of (S)-ethyl 2-(5-bromo-4-(4,4-dimethylpiperidin-1-yl)-2,6-dimethylpyridin-3-yl)-2-(tert-butoxy)acetate (0.514 g, 1.129 mmol), (4-(benzyloxy)phenyl)boronic acid (0.515 g, 2.257 mmol) and 2M Na$_2$CO$_3$ (1.693 ml, 3.39 mmol) in DMF (10 mL) was degassed for 10 min. Then, Pd(Ph$_3$P)$_4$ (0.065 g, 0.056 mmol) was added, degassed for 5 min and placed in a pre-heated oil bath at 110° C. After 2 h, cooled, diluted with ether (50 mL), washed with water (4×10 mL), brine (10 mL), dried (MgSO$_4$), filtered, concentrated and purified by flash chromatography using 10, 20 and 30% EtOAc/Hex to afford (S)-ethyl 2-(5-(4-(benzyloxy)phenyl)-

4-(4,4-dimethylpiperidin-1-yl)-2,6-dimethylpyridin-3-yl)-2-(tert-butoxy)acetate (0.4345 g, 0.778 mmol, 68.9% yield) as white solid. ¹H NMR (500 MHz, CDCl₃) δ 7.48-7.51 (m, 2H), 7.40-7.45 (m, 2H), 7.34-7.38 (m, 1H), 7.16-7.20 (m, 1H), 7.04-7.10 (m, 3H), 6.09 (s, 1H), 5.13-5.20 (m, 2H), 4.26 (qd, J=7.1, 10.7 Hz, 1H), 4.17 (qd, J=7.1, 10.7 Hz, 1H), 3.18 (d, J=11.8 Hz, 1H), 2.87 (t, J=11.8 Hz, 1H), 2.27 (d, J=11.8 Hz, 1H), 2.21 (s, 3H), 2.05 (t, J=11.7 Hz, 1H), 1.56 (dt, J=4.6, 12.9 Hz, 2H), 1.32-1.41 (m, 1H), 1.26 (t, J=7.1 Hz, 3H), 1.21 (s, 9H), 1.18 (br. s., 1H), 1.05-1.11 (m, 1H), 0.91 (s, 3H), 0.64 (s, 3H). LCMS (M+H) 559.5.

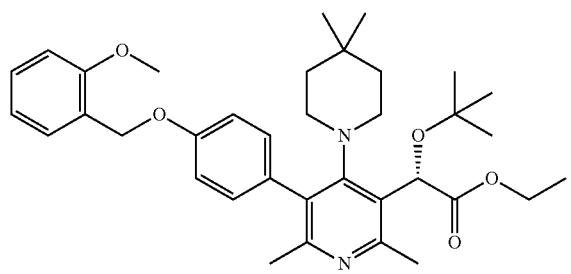 [SMILES: CCOC(=O)[C@@H](OC(C)(C)C)c1c(C)nc(C)c(-c2ccc(OCc3ccccc3OC)cc2)c1N1CCC(C)(C)CC1]

A mixture of (S)-ethyl 2-(5-bromo-4-(4,4-dimethylpiperidin-1-yl)-2,6-dimethylpyridin-3-yl)-2-(tert-butoxy)acetate (0.0433 g, 0.095 mmol), (4-((2-methoxybenzyl)oxy)phenyl)boronic acid (0.037 g, 0.143 mmol) and 2M Na₂CO₃ (0.119 ml, 0.238 mmol) in DMF (2 mL) was degassed for 10 min. Then, Pd(Ph₃P)₄ (10.99 mg, 9.51 μmol) was added, degassed for 5 min and placed in a oil bath pre-heated to 110° C. After 2 h, cooled and purified by pre-HPLC to afford (S)-ethyl 2-(tert-butoxy)-2-(4-(4,4-dimethylpiperidin-1-yl)-5-(4-((2-methoxybenzyl)oxy)phenyl)-2,6-dimethylpyridin-3-yl)acetate (0.038 g, 0.065 mmol, 67.9% yield) as white solid. ¹H NMR (500 MHz, CDCl₃) δ 7.51 (dd, J=1.6, 7.4 Hz, 1H), 7.34 (dt, J=1.7, 7.8 Hz, 1H), 7.15-7.18 (m, 1H), 7.04-7.10 (m, 3H), 7.01 (dt, J=0.9, 7.5 Hz, 1H), 6.96 (d, J=8.2 Hz, 1H), 6.03 (br. s., 1H), 5.17-5.25 (m, 2H), 4.23-4.31 (m, 1H), 4.19 (qd, J=7.1, 10.7 Hz, 1H), 3.91 (s, 3H), 3.05-3.28 (m, 1H), 2.87 (br. s., 1H), 2.66 (br. s., 3H), 2.28 (br. s., 3H), 1.95-2.15 (m, 1H), 1.27 (t, J=7.1 Hz, 3H), 1.20 (s, 9H), 0.9 (br.s., 3H), 0.68 (br. s., 3H). 5H of piperidine were not resolved. LCMS (M+H)=589.4.

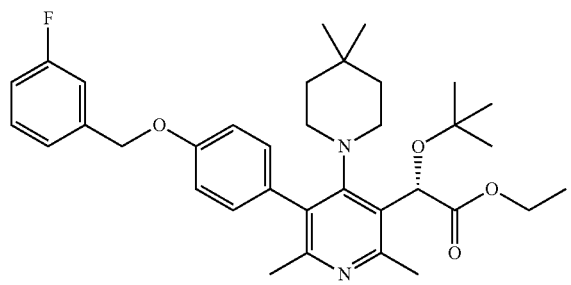 [SMILES: CCOC(=O)[C@@H](OC(C)(C)C)c1c(C)nc(C)c(-c2ccc(OCc3cccc(F)c3)cc2)c1N1CCC(C)(C)CC1]

A mixture of (S)-ethyl 2-(5-bromo-4-(4,4-dimethylpiperidin-1-yl)-2,6-dimethylpyridin-3-yl)-2-(tert-butoxy)acetate (0.0443 g, 0.097 mmol), (4-((3-fluorobenzyl)oxy)phenyl)boronic acid (0.036 g, 0.146 mmol) and 2M Na₂CO₃ (0.122 ml, 0.243 mmol) in DMF 92 mL) was degassed for 10 min. Then, Pd(Ph₃P)₄ (0.011 g, 9.73 μmol) was added, degassed for 5 min and placed in a oil bath pre-heated to 110 C. After 2 h, cooled and purified by pre-HPLC to afford (S)-ethyl 2-(tert-butoxy)-2-(4-(4,4-dimethylpiperidin-1-yl)-5-(4-((3-fluorobenzyl)oxy)phenyl)-2,6-dimethylpyridin-3-yl)acetate (0.0361 g, 0.063 mmol, 64.3% yield) as white solid. ¹H NMR (500 MHz, CDCl₃) δ 7.39 (dt, J=5.8, 7.9 Hz, 1H), 7.24-7.27 (m, 1H), 7.22 (dd, J=2.1, 9.5 Hz, 1H), 7.17-7.20 (m, 1H), 7.02-7.10 (m, 4H), 6.03 (br. s., 1H), 5.12-5.20 (m, 2H), 4.23-4.31 (m, 1H), 4.19 (qd, J=7.1, 10.7 Hz, 1H), 3.06-3.28 (m, 1H), 2.85 (br. s., 1H), 2.65 (br. s., 3H), 2.26 (br. s., 3H), 1.96-2.11 (m, 1H), 1.27 (t, J=7.1 Hz, 4H), 1.20 (s, 9H), 0.90 (br.s., 3H), 0.66 (br. s., 3H). 5H of piperidine were not resolved. LCMS (M+H)=577.4.

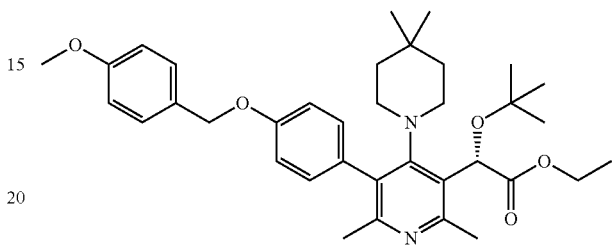

A mixture of (S)-ethyl 2-(5-bromo-4-(4,4-dimethylpiperidin-1-yl)-2,6-dimethylpyridin-3-yl)-2-(tert-butoxy)acetate (0.0454 g, 0.100 mmol), (4-((4-methoxybenzyl)oxy)phenyl)boronic acid (0.039 g, 0.150 mmol) and 2M Na₂CO₃ (0.125 ml, 0.249 mmol) in DMF 92 mL) was degassed for 10 min. Then, Pd(Ph₃P)₄ (0.012 g, 9.97 μmol) was added, degassed for 5 min and placed in a oil bath pre-heated to 110 C. After 2 h, cooled and purified by pre-HPLC to afford (S)-ethyl 2-(tert-butoxy)-2-(4-(4,4-dimethylpiperidin-1-yl)-5-(4-((4-methoxybenzyl)oxy)phenyl)-2,6-dimethylpyridin-3-yl)acetate (0.0376 g, 0.064 mmol, 64.1% yield) as white solid. ¹H NMR (500 MHz, CDCl₃) δ 7.40-7.44 (m, 2H), 7.15-7.18 (m, 1H), 7.04-7.09 (m, 3H), 6.94-6.98 (m, 2H), 6.05 (br. s., 1H), 5.05-5.11 (m, 2H), 4.27 (qd, J=7.1, 10.8 Hz, 1H), 4.18 (qd, J=7.1, 10.7 Hz, 1H), 3.86 (s, 3H), 3.19 (br. s., 1H), 2.87 (br. s., 1H), 2.63 (br. s., 3H), 2.24 (br. s., 4H), 2.05 (br.s., 1H), 1.26 (t, J=7.1 Hz, 3H), 1.20 (s, 9H), 0.90 (m, 3H), 0.66 (br. s., 3H). 4H of piperidine were not resolved. LCMS (M+H)=589.4.

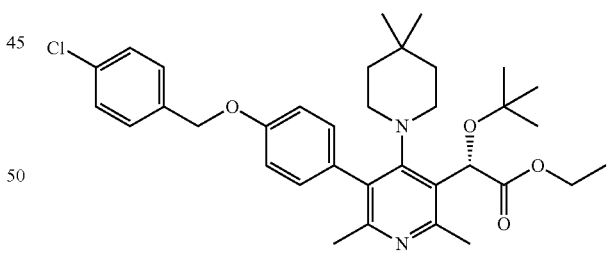

A mixture of (S)-ethyl 2-(5-bromo-4-(4,4-dimethylpiperidin-1-yl)-2,6-dimethylpyridin-3-yl)-2-(tert-butoxy)acetate (0.0473 g, 0.104 mmol), (4-((4-chlorobenzyl)oxy)phenyl)boronic acid (0.041 g, 0.156 mmol) and 2M Na₂CO₃ (0.130 ml, 0.260 mmol) in DMF 92 mL) was degassed for 10 min. Then, Pd(Ph₃P)₄ (0.012 g, 10.39 μmol) was added, degassed for 5 min and placed in a oil bath pre-heated to 110 C. After 2 h, cooled and purified by pre-HPLC to afford (S)-ethyl 2-(tert-butoxy)-2-(5-(4-((4-chlorobenzyl)oxy)phenyl)-4-(4,4-dimethylpiperidin-1-yl)-2,6-dimethylpyridin-3-yl)acetate (0.0368 g, 0.062 mmol, 59.7% yield) as white solid. ¹H NMR (500 MHz, CDCl₃) δ 7.38-7.44 (m, 4H), 7.16-7.19 (m, 1H), 7.02-7.09 (m, 3H), 6.01 (br. s., 1H), 5.09-5.16 (m, 2H), 4.24-

4.31 (m, 1H), 4.19 (qd, J=7.1, 10.8 Hz, 1H), 3.04-3.27 (m, 1H), 2.83 (br. s., 1H), 2.67 (br. s., 3H), 2.28 (br. s., 4H), 1.94-2.13 (m, 1H), 1.27 (t, J=7.1 Hz, 3H), 1.20 (s, 9H), 0.88 (m, 3H), 0.68 (br. s., 3H). 4H of piperidine were not resolved. LCMS (M+H)=593.3.

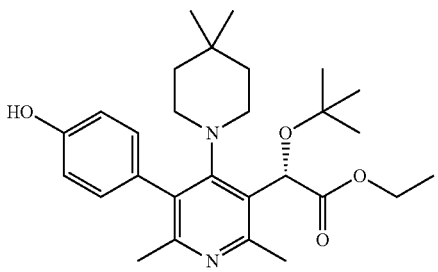 [SMILES: CCOC(=O)[C@@H](OC(C)(C)C)c1c(C)nc(C)c(-c2ccc(O)cc2)c1N1CCC(C)(C)CC1]

A mixture of (S)-ethyl 2-(5-(4-(benzyloxy)phenyl)-4-(4,4-dimethylpiperidin-1-yl)-2,6-dimethylpyridin-3-yl)-2-(tert-butoxy)acetate (0.434 g, 0.777 mmol) and 10% Pd/C (0.083 g, 0.078 mmol) in EtOAc (25 mL) was evacuated and released to H₂ three times and left under balloon H₂ atmosphere for h. Then, filtered through a plug of celite and concentrated to afford (S)-ethyl 2-(tert-butoxy)-2-(4-(4,4-dimethylpiperidin-1-yl)-5-(4-hydroxyphenyl)-2,6-dimethylpyridin-3-yl)acetate (0.36 g, 0.768 mmol, 99% yield) as white solid which was used in subsequent reactions without purification. $^{1}$H NMR (500 MHz, CDCl₃) δ 7.11 (dd, J=2.0, 8.6 Hz, 1H), 6.99-7.03 (m, 1H), 6.94 (tdd, J=2.2, 4.4, 6.4 Hz, 2H), 6.09 (s, 1H), 4.23-4.30 (m, 1H), 4.19 (qd, J=7.1, 10.8 Hz, 1H), 3.18 (d, J=11.4 Hz, 1H), 2.88 (t, J=12.1 Hz, 1H), 2.62 (s, 3H), 2.28 (d, J=10.9 Hz, 1H), 2.22 (s, 3H), 2.10 (t, J=11.7 Hz, 1H), 1.51-1.60 (m, 1H), 1.33-1.42 (m, 1H), 1.27 (t, J=7.1 Hz, 3H), 1.21 (s, 9H), 1.18-1.20 (m, 1H), 1.09 (d, J=9.9 Hz, 1H), 0.91 (br. s., 3H), 0.66 (br. s., 3H). LCMS (M+H)=469.3.

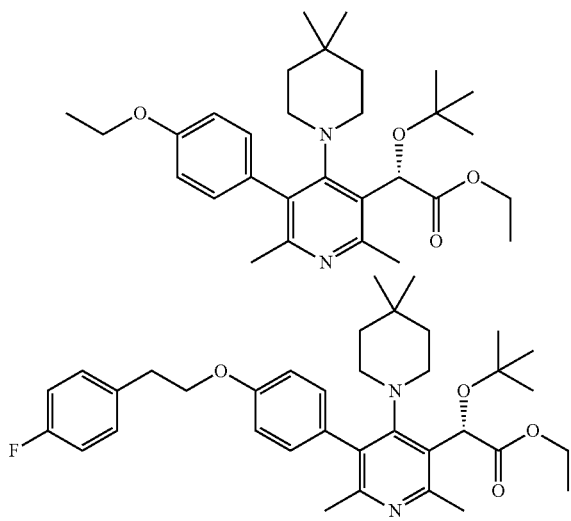

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (0.0397 g, 0.085 mmol), 2-(4-fluorophenyl)ethanol (0.059 g, 0.424 mmol) and Ph₃P (0.067 g, 0.254 mmol) in THF (5 mL) was added DEAD (0.040 ml, 0.254 mmol) at rt. After 18 h, the reaction mixture was concentrated and the residue was purified by prep-HPLC to afford two products.

Product 1: (S)-ethyl 2-(tert-butoxy)-2-(4-(4,4-dimethylpiperidin-1-yl)-5-(4-ethoxyphenyl)-2,6-dimethylpyridin-3-yl) acetate (0.013 g, 0.026 mmol, 30.9% yield), pale yellow solid. $^{1}$H NMR (400 MHz, CDCl₃) δ 7.11-7.17 (m, 1H), 7.04-7.08 (m, 1H), 6.96 (d, J=8.5 Hz, 2H), 6.07 (s, 1H), 4.06-4.30 (m, 4H), 3.18 (d, J=11.8 Hz, 1H), 2.87 (t, J=12.1 Hz, 1H), 2.59 (s, 3H), 2.26 (d, J=11.5 Hz, 1H), 2.20 (s, 3H), 2.05 (t, J=11.7 Hz, 1H), 1.77 (br. s., 1H), 1.54 (dt, J=4.0, 12.7 Hz, 1H), 1.47 (t, J=7.0 Hz, 3H), 1.31-1.41 (m, 1H), 1.25 (t, J=7.2 Hz, 3H), 1.19 (s, 9H), 1.07 (d, J=12.8 Hz, 1H), 0.89 (s, 3H), 0.65 (s, 3H). LCMS (M+H)=497.4.

Product 2: (S)-ethyl 2-(tert-butoxy)-2-(4-(4,4-dimethylpiperidin-1-yl)-5-(4-(4-fluorophenethoxy)phenyl)-2,6-dimethylpyridin-3-yl)acetate (0.0092 g, 0.016 mmol, 18.38% yield), off-white solid. $^{1}$H NMR (400 MHz, CDCl₃) δ 7.25-7.31 (m, 2H), 7.12-7.17 (m, 1H), 7.00-7.09 (m, 3H), 6.93-6.98 (m, 2H), 6.06 (s, 1H), 4.11-4.30 (m, 4H), 3.18 (d, J=10.0 Hz, 1H), 3.12 (t, J=6.9 Hz, 2H), 2.86 (t, J=11.3 Hz, 1H), 2.59 (s, 3H), 2.22-2.30 (m, 1H), 2.19 (s, 3H), 2.04 (t, J=11.0 Hz, 1H), 1.71 (br. s., 1H), 1.53 (t, J=10.5 Hz, 1H), 1.31-1.41 (m, 1H), 1.25 (t, J=7.2 Hz, 3H), 1.19 (s, 9H), 1.02-1.10 (m, 1H), 0.89 (br. s., 3H), 0.65 (br. s., 3H). LCMS (M+H)=591.4.

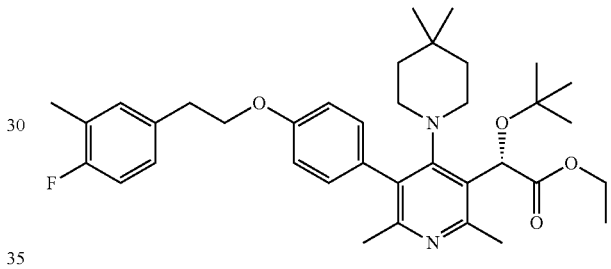

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (0.04 g, 0.085 mmol), 2-(4-fluoro-3-methylphenyl)ethanol (0.066 g, 0.427 mmol) and Ph₃P (0.067 g, 0.256 mmol) in THF (5 mL) was added DEAD (0.041 ml, 0.256 mmol) at 0° C. After 1 h, the cold bath was removed and stirred for 7 h at rt. Then, the reaction mixture was concentrated and the residue purified by prep-HPLC to afford (S)-ethyl 2-(tert-butoxy)-2-(4-(4,4-dimethylpiperidin-1-yl)-5-(4-(4-fluoro-3-methylphenethoxy)phenyl)-2,6-dimethylpyridin-3-yl)acetate (0.0374 g, 0.062 mmol, 72.4% yield) as glassy paste. $^{1}$H NMR (500 MHz, CDCl₃) δ 7.12-7.17 (m, 2H), 7.06-7.12 (m, 2H), 6.95-7.00 (m, 3H), 6.08 (s, 1H), 4.14-4.30 (m, 4H), 3.19 (d, J=11.2 Hz, 1H), 3.09 (t, J=7.0 Hz, 2H), 2.87 (t, J=12.0 Hz, 1H), 2.61 (s, 3H), 2.30 (d, J=1.9 Hz, 3H), 2.25-2.29 (m, 1H), 2.20 (s, 3H), 2.06 (t, J=11.7 Hz, 1H), 1.52-1.58 (m, 1H), 1.33-1.42 (m, 1H), 1.26 (t, J=7.1 Hz, 3H), 1.21 (s, 9H), 1.16-1.20 (m, 1H), 1.05-1.10 (m, 1H), 0.90 (s, 3H), 0.66 (s, 3H). LCMS (M+H)=605.3.

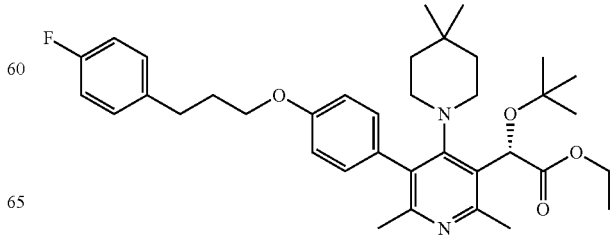

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (0.04 g, 0.085 mmol), 3-(4-fluorophenyl)propan-1-ol (0.066 g, 0.427 mmol) and Ph₃P (0.067 g, 0.256 mmol) in THF (5 mL) was added DEAD (0.041 ml, 0.256 mmol) at 0° C. After 1 h, cold bath was removed and stirred overnight (13 h) at rt. LCMS at this point showed presence of about 50% unreacted phenol. So, added additional 3-(4-fluorophenyl)propan-1-ol (0.066 g, 0.427 mmol), Ph3P (0.067 g, 0.256 mmol) and DEAD (0.041 ml, 0.256 mmol) at r. After stirring for 5 h, reaction mixture was concentrated and purified by prep-HPLC to afford (S)-ethyl 2-(tert-butoxy)-2-(4-(4,4-dimethylpiperidin-1-yl)-5-(4-(3-(4-fluorophenyl)propoxy)phenyl)-2,6-dimethylpyridin-3-yl)acetate (0.0351 g, 0.058 mmol, 68.0% yield) as glassy solid. ¹H NMR (500 MHz, CDCl₃) δ 7.14-7.23 (m, 3H), 7.06-7.09 (m, 1H), 6.95-7.03 (m, 4H), 6.09 (s, 1H), 4.27 (qd, J=7.1, 10.8 Hz, 1H), 4.18 (qd, J=7.1, 10.7 Hz, 1H), 3.99-4.07 (m, 2H), 3.19 (d, J=12.0 Hz, 1H), 2.88 (t, J=12.3 Hz, 1H), 2.82-2.91 (t, J=7.6 Hz, 2H), 2.61 (s, 3H), 2.28 (d, J=12.0 Hz, 1H), 2.21 (s, 3H), 2.11-2.18 (m, 2H), 2.06 (t, J=11.5 Hz, 1H), 1.56 (dt, J=3.9, 12.6 Hz, 1H), 1.38 (dt, J=3.6, 12.7 Hz, 1H), 1.26 (t, J=7.1 Hz, 3H), 1.21 (s, 9H), 1.18-1.21 (m, 1H), 1.08 (d, J=12.1 Hz, 1H), 0.91 (s, 3H), 0.66 (s, 3H). LCMS (M+H)=605.3.

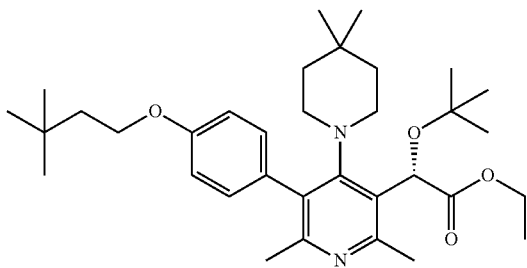 [SMILES: CCOC(=O)[C@@H](OC(C)(C)C)c1c(C)nc(C)c(-c2ccc(OCCC(C)(C)C)cc2)c1N1CCC(C)(C)CC1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (0.042 g, 0.090 mmol), 3,3-dimethylbutan-1-ol (0.046 g, 0.448 mmol) and Ph₃P (0.071 g, 0.269 mmol) in THF (5 mL) was added DEAD (0.043 ml, 0.269 mmol) at 0° C. After 1 h, cold bath was removed and stirred overnight (15 h) at rt. Then, reaction mixture was concentrated and purified by prep-HPLC to afford (S)-ethyl 2-(tert-butoxy)-2-(5-(4-(3,3-dimethylbutoxyl)phenyl)-4-(4,4-dimethylpiperidin-1-yl)-2,6-dimethylpyridin-3-yl)acetate (0.0205 g, 0.037 mmol, 41.4% yield) as white solid. ¹H NMR (500 MHz, CDCl₃) δ 7.14-7.17 (m, 1H), 7.05-7.09 (m, 1H), 6.95-6.99 (m, 2H), 6.09 (s, 1H), 4.27 (qd, J=7.1, 10.8 Hz, 1H), 4.17 (qd, J=7.1, 10.7 Hz, 1H), 4.08-4.13 (m, 2H), 3.19 (d, J=11.8 Hz, 1H), 2.88 (t, J=12.1 Hz, 1H), 2.61 (s, 3H), 2.28 (d, J=11.8 Hz, 1H), 2.21 (s, 3H), 2.07 (t, J=11.8 Hz, 1H), 1.79 (t, J=7.3 Hz, 2H), 1.56 (td, J=3.7, 12.4 Hz, 1H), 1.34-1.42 (td, J=3.5, 12.5 Hz, 1H), 1.26 (t, J=7.1 Hz, 3H), 1.21 (s, 9H), 1.17-1.20 (m, 1H), 1.08 (d, J=12.9 Hz, 1H), 1.04 (s, 9H), 0.90 (s, 3H), 0.66 (s, 3H). LCMS (M+H)=553.4.

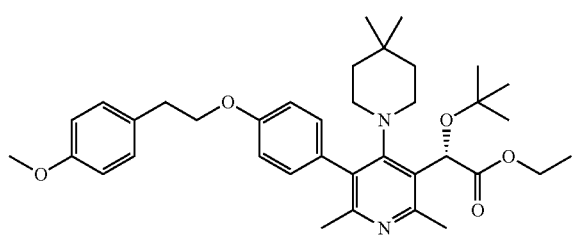 [SMILES: CCOC(=O)[C@@H](OC(C)(C)C)c1c(C)nc(C)c(-c2ccc(OCCc3ccc(OC)cc3)cc2)c1N1CCC(C)(C)CC1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (0.04 g, 0.085 mmol), 2-(4-methoxyphenyl)ethanol (0.065 g, 0.427 mmol) and Ph₃P (0.067 g, 0.256 mmol) in THF (5 mL) was added DEAD (0.041 ml, 0.256 mmol) at 0° C. After 1 h, the cold bath was removed and stirred for 16 h at rt. Then, the reaction mixture was concentrated and the residue purified by prep-HPLC to afford (S)-ethyl 2-(tert-butoxy)-2-(4-(4,4-dimethylpiperidin-1-yl)-5-(4-(4-methoxyphenethoxy)phenyl)-2,6-dimethylpyridin-3-yl)acetate (0.0362 g, 0.060 mmol, 70.4% yield) as white solid. ¹H NMR (500 MHz, CDCl₃) δ 7.27-7.23 (m, 2H), 7.17-7.13 (m, 1H), 7.09-7.04 (m, 1H), 7.00-6.95 (m, 2H), 6.92-6.88 (m, 2H), 6.08 (s, 1H), 4.29-4.12 (m, 4H), 3.83 (s, 3H), 3.18 (br. s., 1H), 3.11 (t, J=7.1 Hz, 2H), 2.88 (br. s., 1H), 2.61 (s, 3H), 2.28 (br.s., 1H), 2.20 (s, 3H), 2.12-2.00 (m, 1H), 1.71-1.81 (m, 1H), 1.60-1.49 (m, 1H), 1.41-1.32 (m, 1H), 1.26 (t, J=7.1 Hz, 3H), 1.21 (s, 9H), 1.08-1.12 (m, 1H), 0.90 (br.s., 2H), 0.67 (br. s., 2H). LCMS (M+H)=603.5.

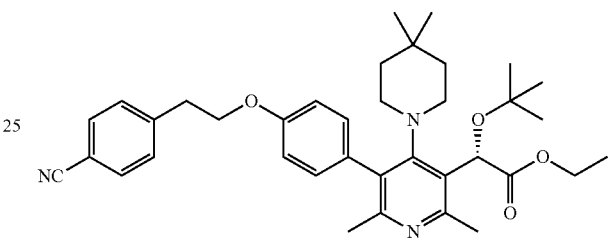

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (0.04 g, 0.085 mmol), 4-(2-hydroxyethyl)benzonitrile (0.063 g, 0.427 mmol) and Ph₃P (0.067 g, 0.256 mmol) in THF (5 mL) was added DEAD (0.041 ml, 0.256 mmol) at 0° C. After 1 h, the cold bath was removed and stirred for 16 h at rt. Then, the reaction mixture was concentrated and the residue purified by prep-HPLC to afford (S)-ethyl 2-(tert-butoxy)-2-(5-(4-(4-cyanophenethoxy)phenyl)-4-(4,4-dimethylpiperidin-1-yl)-2,6-dimethylpyridin-3-yl)acetate (0.0327 g, 0.055 mmol, 64.1% yield) as white solid. ¹H NMR (500 MHz, CDCl₃) δ 7.65 (d, J=8.2 Hz, 2H), 7.46 (d, J=8.2 Hz, 2H), 7.17 (dd, J=8.5, 2.0 Hz, 1H), 7.08 (dd, J=8.5, 2.0 Hz, 1H), 6.96 (qd, J=4.2, 2.4 Hz, 2H), 6.07 (s, 1H), 4.31-4.24 (m, 3H), 4.18 (dq, J=10.8, 7.1 Hz, 1H), 3.22 (t, J=6.5 Hz, 2H), 3.18 (br. s., 1H), 2.86 (t, J=12.2 Hz, 1H), 2.61 (s, 3H), 2.28 (d, J=11.3 Hz, 1H), 2.19 (s, 3H), 2.05 (t, J=11.6 Hz, 1H), 1.54 (br. s., 1H), 1.42-1.33 (m, 1H), 1.26 (t, J=7.1 Hz, 3H), 1.21 (s, 9H), 1.20-1.16 (m, 1H), 1.07 (d, J=10.7 Hz, 1H), 0.91 (s, 3H), 0.65 (s, 3H). LCMS (M+H)=598.4.

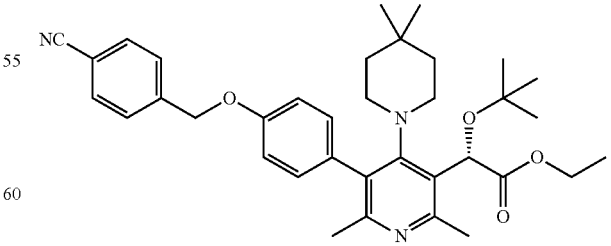

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (0.04 g, 0.085 mmol), 4-(hydroxymethyl)benzonitrile (0.057 g, 0.427 mmol) and Ph₃P (0.067 g, 0.256 mmol) in THF (5 mL) was added DEAD (0.041 ml, 0.256 mmol) at 0° C. After 1 h, the cold bath was removed and stirred for 16 h at rt. Then, the reaction mixture was concentrated and the residue purified by prep-HPLC to afford (S)-ethyl 2-(tert-butoxy)-2-(5-(4-((4-cyanobenzyl)oxy)phenyl)-4-(4,4-dimethylpiperidin-1-yl)-2,6-dimethylpyridin-3-yl) acetate (0.0324 g, 0.056 mmol, 65.0% yield) as white solid. $^1$H NMR (500 MHz, CDCl$_3$) δ 7.74-7.70 (m, 2H), 7.61 (d, J=8.5 Hz, 2H), 7.22-7.18 (m, 1H), 7.12-7.09 (m, 1H), 7.06-7.01 (m, 2H), 6.07 (s, 1H), 5.26-5.19 (m, 2H), 4.27 (dq, J=10.7, 7.1 Hz, 1H), 4.18 (dq, J=10.7, 7.1 Hz, 1H), 3.19 (d, J=12.1 Hz, 1H), 2.84 (t, J=12.1 Hz, 1H), 2.61 (s, 3H), 2.28 (d, J=11.3 Hz, 1H), 2.20 (s, 3H), 2.03 (t, J=11.6 Hz, 1H), 1.57-1.53 (m, 1H), 1.42-1.34 (m, 1H), 1.26 (t, J=7.1 Hz, 3H), 1.21 (s, 9H), 1.18 (br. s., 1H), 1.07 (d, J=13.4 Hz, 1H), 0.91 (s, 3H), 0.63 (s, 3H). LCMS (M+H)=584.4.

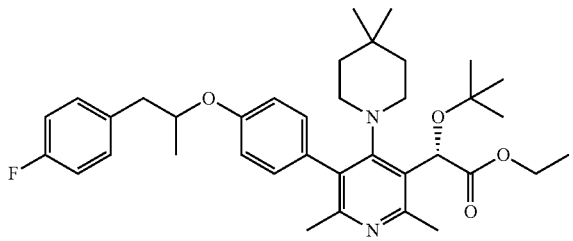 [SMILES: CCOC(=O)[C@@H](OC(C)(C)C)c1c(C)nc(C)c(-c2ccc(OC(C)Cc3ccc(F)cc3)cc2)c1N1CCC(C)(C)CC1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (0.09 g, 0.192 mmol), 1-(4-fluorophenyl)propan-2-ol (0.08 g, 0.519 mmol) and Ph$_3$P (0.151 g, 0.576 mmol) in THF (5 mL) was added DEAD (0.091 ml, 0.576 mmol) at 0° C. After 2 h, cold bath was removed and stirred for 15 h at rt. Then, purified by prep-HPLC to afford (2S)-ethyl 2-(tert-butoxy)-2-(4-(4,4-dimethylpiperidin-1-yl)-5-(4-((1-(4-fluorophenyl)propan-2-yl)oxy)phenyl)-2,6-dimethylpyridin-3-yl)acetate (0.0778 g, 0.129 mmol, 67.0% yield) as white solid. $^1$H NMR (500 MHz, CDCl$_3$) δ 7.27-7.21 (m, 2H), 7.15 (dd, J=8.6, 2.3 Hz, 1H), 7.07 (dt, J=8.2, 2.1 Hz, 1H), 7.03-6.93 (m, 4H), 6.08 (s, 1H), 4.63 (qd, J=6.1, 3.8 Hz, 1H), 4.26 (dq, J=10.8, 7.1 Hz, 1H), 4.17 (dq, J=10.9, 7.1 Hz, 1H), 3.18 (d, J=11.0 Hz, 1H), 3.08 (dd, J=13.9, 6.0 Hz, 1H), 2.93-2.83 (m, 2H), 2.61 (s, 3H), 2.27 (d, J=8.8 Hz, 1H), 2.22 (s, 3H), 2.04 (t, J=11.7 Hz, 1H), 1.67-1.60 (m, 1H), 1.59-1.51 (m, 1H), 1.36 (d, J=6.1 Hz, 3H), 1.34 (d, J=6.1 Hz, 3H), 1.26 (t, J=7.2 Hz, 3H), 1.21 (s, 9H), 1.19-1.15 (m, 1H), 1.09-1.03 (m, 1H), 0.90 (br. s., 3H), 0.62 (br. s., 3H). LCMS (M+H)=605.4.

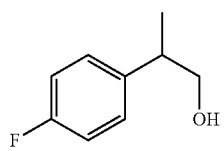

To a solution of 2-(4-fluorophenyl)propanoic acid (1 g, 5.95 mmol) in THF (20 mL) at 0° C. was added 1M BH$_3$.THF (11.89 mL, 11.89 mmol) in THF and the resulting mixture was stirred at room temp for 3 h. Then, 1N HCl (3 mL) was added and the mixture was extracted with ethyl acetate 100 mL), washed with brine (50 mL), dried (Na$_2$SO$_4$), filtered and concentrated. The residue was then purified by Biotage (5-50% EtOAc/hexane) to afford 2-(4-fluorophenyl)propan-1-ol (300 mg, 1.946 mmol, 32.7% yield) as colorless oil. $^1$H NMR (500 MHz, CDCl$_3$) δ 7.23 (dd, J=8.5, 5.5 Hz, 2H), 7.04 (t, J=8.7 Hz, 2H), 3.79-3.63 (m, 2H), 2.97 (sxt, J=6.9 Hz, 1H), 1.34 (t, J=5.5 Hz, 1H), 1.29 (d, J=7.1 Hz, 3H).

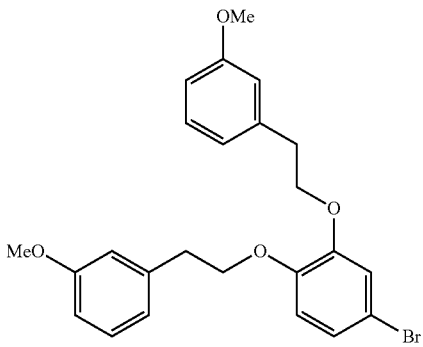 [SMILES: COc1cccc(CCOc2ccc(Br)cc2OCCc2cccc(OC)c2)c1]

To a stirred solution of 4-bromobenzene-1,2-diol (300 mg, 1.587 mmol), 2-(3-methoxyphenyl)ethanol (966 mg, 6.35 mmol) and Ph$_3$P (2082 mg, 7.94 mmol) in THF (15 mL) was added DEAD (1.256 mL, 7.94 mmol) at rt. After 18 h, water (10 mL) was added and the mixture was extracted with ether (50 mL), dried (Na$_2$SO$_4$), filtered and concentrated. The residue was then purified by Biotage (5-25% EtOAc/hexane) to afford 3,3'-(((4-bromo-1,2-phenylene)bis(oxy))bis(ethane-2,1-diyl))bis(methoxybenzene) (140 mg, 0.306 mmol, 19.29% yield) as light yellow oil. $^1$H NMR (500 MHz, CDCl$_3$) δ 7.27-7.18 (m, 2H), 7.05-6.97 (m, 2H), 6.94-6.86 (m, 4H), 6.81 (d, J=8.2 Hz, 2H), 6.75 (d, J=8.2 Hz, 1H), 4.25-4.05 (m, 4H), 3.82 (d, J=1.3 Hz, 6H), 3.12 (q, J=7.4 Hz, 4H).

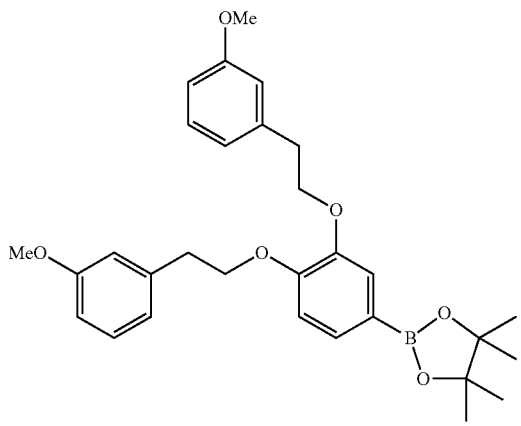 [SMILES: COc1cccc(CCOc2ccc(B3OC(C)(C)C(C)(C)O3)cc2OCCc2cccc(OC)c2)c1]

A mixture of 3,3'-(((4-bromo-1,2-phenylene)bis(oxy))bis(ethane-2,1-diyl))bis(methoxybenzene) (140 mg, 0.306 mmol), bis(pinacolateo)diboron (117 mg, 0.459 mmol) and KOAc (90 mg, 0.918 mmol) in 1,4-dioxane (5 mL) was sparged with N2 for 15 min. Then, 1,1-bis(diphenylphosphino)ferrocene]dichloropalladium(II).CH$_2$Cl$_2$ complex (12.50 mg, 0.015 mmol) was added, sparged for additional 5 min and heated at 95° C. for 16 h. Then, cooled, diluted with Ethyl acetate (50 mL), washed with water (2×25 mL), brine (25 mL), dried (Na$_2$SO$_4$), filtered and concentrated to give brow paste which was purified by flash chromatography (5-45% EtOAc/hexane) to afford 2-(3,4-bis(3-methoxyphenethoxy)phenyl)-4,4,5,5-tetramethyl-1,3,2-dioxaborolane as off-white solid. $^1$H NMR (500 MHz, CDCl$_3$) δ 7.42-7.37 (m, 1H), 7.32 (s, 1H), 7.27-7.21 (m, 2H), 6.95-6.87 (m, 5H), 6.80 (d, J=8.2 Hz, 2H), 4.29-4.19 (m, 4H), 3.82 (s, 3H), 3.83 (s, 3H), 3.15 (t, J=7.3 Hz, 4H), 1.34 (s, 12H).

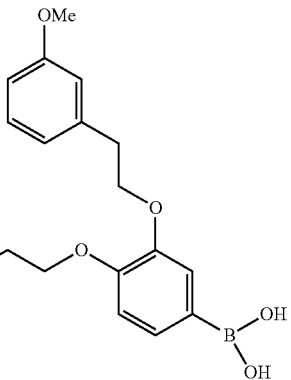

To a solution of 2-(3,4-bis(3-methoxyphenethoxy)phenyl)-4,4,5,5-tetramethyl-1,3,2-dioxaborolane (40 mg, 0.079 mmol) in Acetone (5 mL)/Water (2.500 mL) was added sodium periodate (50.9 mg, 0.238 mmol) and ammonium acetate (18.34 mg, 0.238 mmol) and the resulting mixture was stirred at room temp for 16 h. Then, 1N HCl (1 mL) was added and the mixture was stirred for 1 h. The mixture was diluted with EtOAc (10 mL) and washed with brine (5 mL), dried (Na$_2$SO$_4$), filtered and concentrated to afford (3,4-bis(3-methoxyphenethoxy)phenyl)boronic acid (29 mg, 0.069 mmol, 87% yield) as white solid. $^1$H NMR (400 MHz, CDCl$_3$)) δ 7.82 (dd, J=8.0, 1.3 Hz, 1H), 7.69 (d, J=1.3 Hz, 1H), 7.28-7.22 (m, 2H), 7.02 (s, 1H), 6.96-6.90 (m, 4H), 6.85-6.77 (m, 2H), 4.31 (q, J=7.3 Hz, 4H), 3.83 (s, 3H), 3.80 (s, 3H), 3.17 (dt, J=14.0, 7.2 Hz, 4H).

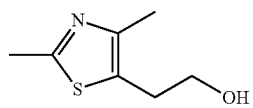

A solution of 2-(2,4-dimethylthiazol-5-yl)acetic acid (230 mg, 1.343 mmol) in dry THF (10 mL) was carefully added over 2 min to solution of 2M LAH (1.343 mL, 2.69 mmol) in dry THF (10 mL) at 0° C. The reaction mixture was allowed to warm to rt and was stirred for 6 h. The reaction was quenched with 0.2 mL of water (stir for 10 min), 0.2 mL of 15% NaOH/water (stir for 10 min), and then 0.4 mL of water. After stirring for 18 h, the mixture was filtered through celite. The filtrate was concentrated in vacuum. The residue was dried under high vacuum for 16 h to afford 2-(2,4-dimethylthiazol-5-yl)ethanol (180 mg, 1.145 mmol, 85% yield) as a clear viscous oil. $^1$H NMR (500 MHz, CDCl$_3$) δ 3.83 (t, J=6.3 Hz, 2H), 2.97 (t, J=6.3 Hz, 2H), 2.64 (s, 3H), 2.35 (s, 3H).

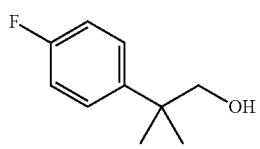

A solution of 2-(4-fluorophenyl)-2-methylpropanoic acid (1, 5.49 mmol) in dry THF (10 mL) was carefully added over 2 min to a solution of 2M LAH (10.98 mL, 10.98 mmol) in dry THF (20 mL) at 0° C. The reaction mixture was allowed to warm to rt and was stirred for 6 h. The reaction was quenched with 0.5 mL of water (stir for 10 min), 0.5 mL of 15% NaOH/water (stir for 10 min), and then 1.0 mL of water. After stirring for 18 h, the mixture was filtered through celite. The filtrate was concentrated in vacuum. The residue was dried under high vacuum for 16 h to afford 2-(4-fluorophenyl)-2-methylpropan-1-ol (875 mg, 5.20 mmol, 95% yield) as clear viscous oil. $^1$H NMR (500 MHz, CDCl$_3$) δ 7.42-7.32 (m, 2H), 7.08-6.98 (m, 2H), 3.61 (s, 2H), 1.34 (s, 6H).

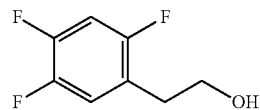

A solution of 2-(2,4,5-trifluorophenyl)acetic acid (1 g, 5.26 mmol) in dry THF (20 mL) was carefully added over 2 min to solution of 2M LAH (10.52 mL, 10.52 mmol) at 0° C. The reaction mixture was allowed to warm to rt and was stirred for 6 h. The reaction was quenched with 0.5 mL of water (stir for 10 min), 0.5 mL of 15% NaOH/water (stir for 10 min), and then 1.0 mL of water. After stirring for 18 h, the mixture was filtered through celite. The filtrate was concentrated in vacuum. The residue was dried under high vacuum for 16 h to afford 2-(2,4,5-trifluorophenyl)ethanol (850 mg, 4.83 mmol, 92% yield) as a clear viscous oil, which was used as is in the next step without further purification. $^1$H NMR (500 MHz, CDCl$_3$) δ 7.11 (ddd, J=10.3, 8.7, 7.2 Hz, 1H), 6.93 (td, J=9.7, 6.6 Hz, 1H), 3.87 (t, J=6.5 Hz, 2H), 2.88 (t, J=6.5 Hz, 2H).

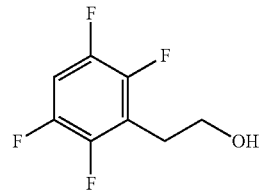 [SMILES: OCCc1c(F)c(F)cc(F)c1F]

A solution of 2-(perfluorophenyl)acetic acid (1 g, 4.42 mmol) in dry THF (20 mL) was carefully added over 2 min to solution of 2M LAH (8.85 mL, 8.85 mmol) at 0° C. The reaction mixture was allowed to warm to rt and was stirred for 6 h. The reaction was quenched with 0.5 mL of water (stir for 10 min), 0.5 mL of 15% NaOH/water (stir for 10 min), and then 1.0 mL of water. After stirring for 18 h, the mixture was filtered through celite. The filtrate was concentrated in vacuum. The residue was dried under high vacuum for 16 h. $^1$H NMR (500 MHz, CDCl$_3$) δ 7.04-6.89 (m, 1H), 3.89 (sxt, J=6.0 Hz, 2H), 3.08-2.98 (m, 1H), 2.91 (t, J=6.3 Hz, 1H), 1.59-1.51 (m, 1H).

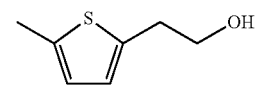

A solution of 2-(5-methylthiophen-2-yl)acetic acid (200 mg, 1.280 mmol) in dry THF (10 mL) was carefully added over 2 min to solution of 1M LAH (2.56 mL, 2.56 mmol) at 0° C. The reaction mixture was allowed to warm to rt and was stirred for 6 h. The reaction was quenched with 0.2 mL of water (stir for 10 min), 0.2 mL of 15% NaOH/water (stir for 10 min), and then 0.4 mL of water. After stirring for 18 h, the mixture was filtered through celite. The filtrate was concentrated in vacuum. The residue was dried under high vacuum for 16 h to afford 2-(5-methylthiophen-2-yl)ethanol (150 mg, 1.055 mmol, 82% yield) as clear viscous oil. $^1$H NMR (500 MHz, CDCl$_3$) δ 6.67 (d, J=3.3 Hz, 1H), 6.64-6.57 (m, 1H), 3.85 (t, J=6.2 Hz, 2H), 3.02 (t, J=6.2 Hz, 2H), 2.47 (s, 3H).

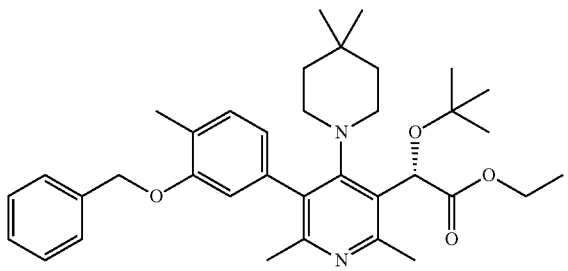 [SMILES: CCOC(=O)[C@@H](OC(C)(C)C)c1c(C)nc(C)c(-c2ccc(C)c(OCc3ccccc3)c2)c1N1CCC(C)(C)CC1]

A mixture of (S)-ethyl 2-(5-bromo-4-(4,4-dimethylpiperidin-1-yl)-2,6-dimethylpyridin-3-yl)-2-(tert-butoxy)acetate (0.02 g, 0.044 mmol), (3-fluoro-4-methylphenyl)boronic acid (0.014 g, 0.088 mmol) and 2M Na$_2$CO$_3$ (0.055 ml, 0.110 mmol) in DMF (1 mL) was degassed for 3 min. Then, Pd(Ph$_3$P)$_4$ (5.07 mg, 4.39 μmol) was degassed for 1 min and placed in a pre-heated oil bath at 90° C. After 9 h, cooled and purified by prep-HPLC to afford (S)-ethyl 2-(tert-butoxy)-2-(4-(4,4-dimethylpiperidin-1-yl)-5-(3-fluoro-4-methylphenyl)-2,6-dimethylpyridin-3-yl)acetate (0.0105 g, 0.022 mmol, 49.3% yield) as brown paste. LCMS (M+H)=485.3.

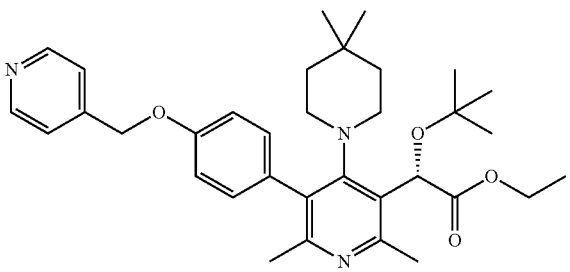 [SMILES: CCOC(=O)[C@@H](OC(C)(C)C)c1c(C)nc(C)c(-c2ccc(OCc3ccncc3)cc2)c1N1CCC(C)(C)CC1]

A mixture of (S)-ethyl 2-(5-bromo-4-(4,4-dimethylpiperidin-1-yl)-2,6-dimethylpyridin-3-yl)-2-(tert-butoxy)acetate (0.02 g, 0.044 mmol), (4-(pyridin-4-ylmethoxy)phenyl)boronic acid (0.020 g, 0.088 mmol) and 2M Na$_2$CO$_3$ (0.055 ml, 0.110 mmol) in DMF (1 mL) was degassed for 3 min. Then, Pd(Ph$_3$P)$_4$ (5.07 mg, 4.39 μmol) was degassed for 1 min and placed in a pre-heated oil bath at 90° C. After 9 h, cooled and purified by prep-HPLC to afford (S)-ethyl 2-(tert-butoxy)-2-(4-(4,4-dimethylpiperidin-1-yl)-2,6-dimethyl-5-(4-(pyridin-4-ylmethoxy)phenyl)pyridin-3-yl)acetate (0.013 g, 0.023 mmol, 52.9% yield) as brown paste. LCMS (M+H)=560.4.

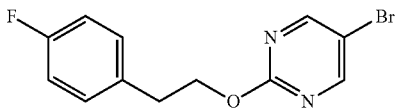 [SMILES: Fc1ccc(CCOc2ncc(Br)cn2)cc1]

To a solution of 2-(4-fluorophenyl)ethanol (0.566 g) in THF (10 mL) was added NaH (0.269 g). The mixture was stirred at room temperature for 2 hours, before 2,5-dibromopyrimidine (0.8 g) was added. The mixture was stirred at room temperature for 16 h. The reaction was quenched with water and extracted with EtOAc (2×20 mL). The organic layers were combined, dried over MgSO$_4$ and concentrated under vacuum. The residue was purified by silica gel column (Hex/EtOAc=100:5) to give 5-bromo-2-(4-fluorophenethoxy)pyrimidine (0.7 g). LCMS (M+H)=297.0.

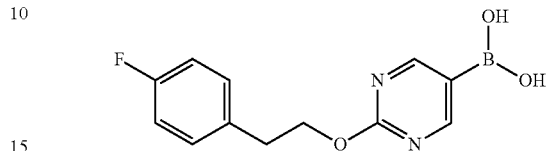

A mixture of 5-bromo-2-(4-fluorophenethoxy)pyrimidine (200 mg), 4,4,4',4',5,5,5',5'-octamethyl-2,2'-bi(1,3,2-dioxaborolane) (256 mg), [1,1'-bis(diphenylphosphino)ferrocene]dichloropalladium(II) (24.63 mg) and KOAc (198 mg) in 1,4-dioxane (8 mL) in a sealed tube was degassed with nitrogen for 2 minutes and then heated at 85° C. for 4 hours, followed by being stirred at room temperature for 24 h. The mixture was diluted with EtOAc, washed with water, brine, dried over MgSO$_4$ and concentrated under vacuum. The residue was purified by silica gel column (Hex/EtOAc=10:1) to give (2-(4-fluorophenethoxy)pyrimidin-5-yl)boronic acid (70 mg). LCMS (M+H)=263.1.

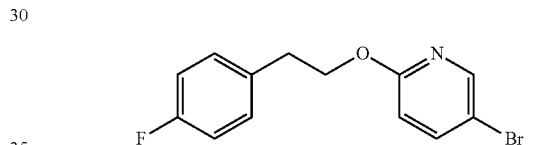

To a solution of 2-(4-fluorophenyl)ethanol (0.568 g) in THF (10 mL) was added NaH (0.270 g, 60% in oil). The mixture was stirred at room temperature for 2 hours, before 2,5-dibromopyridine (0.8 g) was added. The mixture was stirred at room temperature for 16 h. The reaction was quenched with water and extracted with EtOAc (2×20 mL). The organic layers were combined, dried over MgSO$_4$ and concentrated under vacuum. The residue was purified by silica gel column (Hex/EtOAc=100:5) to give 5-bromo-2-(4-fluorophenethoxy)pyridine (0.3 g). LCMS (M+H)=296.0.

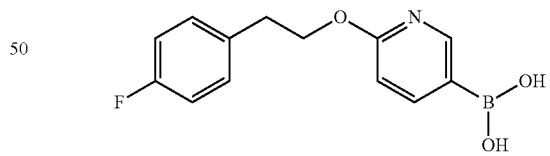

A mixture of 5-bromo-2-(4-fluorophenethoxy)pyridine (260 mg), 4,4,4',4',5,5,5',5'-octamethyl-2,2'-bi(1,3,2-dioxaborolane) (334 mg), [1,1'-bis(diphenylphosphino)ferrocene]dichloropalladium(II) (32.1 mg) and KOAc (259 mg) in 1,4-dioxane (8 mL) in a sealed tube was degassed with nitrogen for 2 minutes and then heated at 85° C. for 4 h, followed by being stirred at room temperature for 24 h. The mixture was diluted with EtOAc, washed with water, brine, dried over MgSO$_4$ and concentrated under vacuum. The crude residue containing desired (6-(4-fluorophenethoxy)pyridin-3-yl)boronic acid was used in the next step without purification.

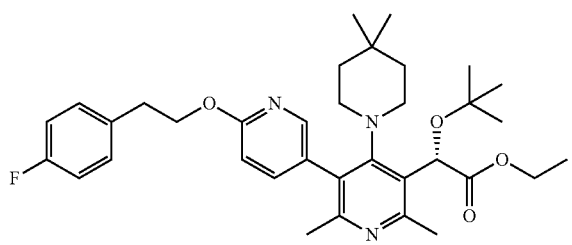 [SMILES: CCOC(=O)[C@@H](OC(C)(C)C)c1c(C)nc(C)c(-c2ccc(OCCc3ccc(F)cc3)nc2)c1N1CCC(C)(C)CC1]

To a mixture of (S)-ethyl 2-(5-bromo-4-(4,4-dimethylpiperidin-1-yl)-2,6-dimethylpyridin-3-yl)-2-(tert-butoxy)acetate (30 mg), (6-(4-fluorophenethoxy)pyridin-3-yl)boronic acid (18.9 mg) and $Cs_2CO_3$ (42.9 mg) in 1,4-dioxane (2 mL) and water (0.4 mL) was added $Pd(PPh_3)_4$ (7.6 mg). The mixture was flushed with nitrogen and then heated at 85° C. for 3 h. The mixture was diluted with water and then extracted with EtOAc (2×20 mL). The organic layers were combined, washed with brine and concentrated to give a residue, which was purified by the preparative HPLC to give (S)-ethyl 2-(tert-butoxy)-2-(4-(4,4-dimethylpiperidin-1-yl)-6'-(4-fluorophenethoxy)-2,6-dimethyl-[3,3'-bipyridin]-5-yl)acetate (3.6 mg). LCMS (M+H)=592.5.

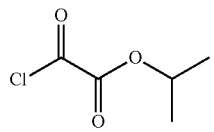

The propan-2-ol (38.2 mL, 499 mmol) was added drop wise over 15 min to a cold (0° C.), nitrogen purged solution of oxalyl dichloride (101 g, 799 mmol) and the reaction was stirred at room temperature for 2.5 h. Then a reflux condenser was fitted and a slight vacuum was applied for about 1 h until HCl gas was removed (the HCl was trapped in by a sat'd solution of $NaHCO_3$). The reflux condenser was removed and the flask was fitted with a short path distillation head. Excess reagent was removed by distillation under house vacuum (oil bath heated to 65° C.), and then the temperature was raised to between 85-95° C. and the product was distilled (NOTE: The 1$^{st}$ fraction of ~5 mL was discarded) to provide isopropyl 2-chloro-2-oxoacetate 52.62 g (70%).

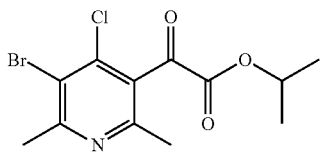 [SMILES: Cc1nc(C)c(C(=O)C(=O)OC(C)C)c(Cl)c1Br]

A solution of 2M isopropyl magnesium chloride (84 mL, 168 mmol) was added drop wise over 20 min to a cold (−70° C.), nitrogen purged solution of 3,5-dibromo-4-chloro-2,6-dimethylpyridine (48 g, 160 mmol) and copper(I)bromide-dimethyl sulfide complex (1.65 g, 8.02 mmol) in THF (240 mL), which was then allowed to warm to −10° C. over 60 min. The reaction mixture was transferred via cannula into a 1 L RB-flask containing isopropyl 2-chloro-2-oxoacetate (26.6 g, 176 mmol) in THF (160 mL) maintained at −60° C., and the reaction stirred an additional 2.5 h while being allowed to warm to −10° C. The reaction was quenched upon diluted with a mixture of 10% $NH_4Cl$ solution (80 mL) in ether (320 mL). The organic layer was washed with 160 mL of sat'd $NaHCO_3$/10% $NH_4Cl$ solution (1:1), brine, and dried ($Na_2SO_4$). The crude product was charged (DCM solution) to a 330 g ISCO silica gel cartridge and gradient eluted (5-20% EtOAc/hexanes) using an Isolera chromatography station gave isopropyl 2-(5-bromo-4-chloro-2,6-dimethylpyridin-3-yl)-2-oxoacetate 40.38 g (76%). $^1$H NMR (500 MHz, $CDCl_3$) δ 5.28-5.21 (m, 1H), 2.77 (s, 3H), 2.47 (s, 3H), 1.40 (d, J=6.3 Hz, 6H). LCMS (M+H)=336.04.

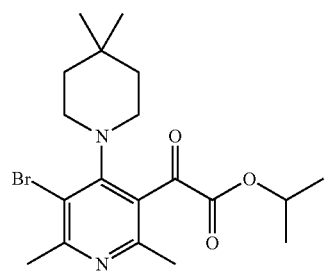 [SMILES: Cc1nc(C)c(C(=O)C(=O)OC(C)C)c(N2CCC(C)(C)CC2)c1Br]

To a stirred solution of isopropyl 2-(5-bromo-4-chloro-2,6-dimethylpyridin-3-yl)-2-oxoacetate (7.2 g, 21.52 mmol) and DIEA (4.13 mL, 23.67 mmol) in anhydrous acetonitrile (15 mL) was added 4,4-dimethylpiperidine (2.68 g, 23.67 mmol) in acetonitrile (15 mL). The resulting solution was placed in a pre-heated oil bath at 75° C. After heating (75-78° C.) for 24 h and the temperature was raised to 85° C. for 24 h. Another portion of DIEA (3.5 mL, 20.04 mmol) and 4,4-dimethylpiperidine (0.27 g, 2.4 mmol) in acetonitrile (3 mL) was added and hearted at 85° C. for a day.

The reaction mixture was diluted with ether (100 mL), washed with water (100 mL), brine (50 mL), dried ($MgSO_4$), filtered, concentrated and purified by ISCO 120 g cartridge (EtOAc/hex: 0 to 20%) to afford isopropyl 2-(5-bromo-4-(4,4-dimethylpiperidin-1-yl)-2,6-dimethylpyridin-3-yl)-2-oxoacetate (6.8 g, 16.53 mmol, 77% yield. $^1$H NMR (500 MHz, $CDCl_3$) δ 5.25-5.11 (m, 1H), 3.17 (br. s., 4H), 2.71 (s, 3H), 2.41 (s, 3H), 1.42-1.37 (m, 10H), 1.00 (s, 6H).). LCMS (M+H)=413.3.

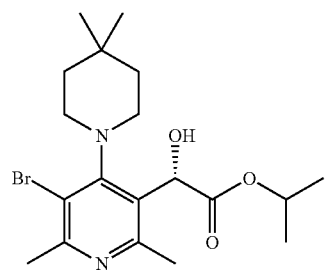 [SMILES: Cc1nc(C)c([C@H](O)C(=O)OC(C)C)c(N2CCC(C)(C)CC2)c1Br]

To a yellow solution of isopropyl 2-(5-bromo-4-(4,4-dimethylpiperidin-1-yl)-2,6-dimethylpyridin-3-yl)-2-oxoacetate (7.7 g, 18.72 mmol) and (R)-1-methyl-3,3-diphenylhexahydropyrrolo[1,2-c][1,3,2]oxazaborole (7.5 mL, 7.50 mmol) in anhydrous toluene (100 mL) was added drop wise 50% catecholborane/toluene (6 mL, 28.0 mmol) over 5 min at −50° C. Then, the reaction mixture was slowly warmed to −30° C. over 1 h and left in refrigerator (−20° C.) for 3 days. Then, the reaction mixture was diluted with EtOAc (100 mL) and 20 mL of 1M $Na_2CO_3$, and vigorously stirred for 30 min. Aqueous layer separated and organic layer washed with sat'd $Na_2CO_3$ (2×25 mL) by vigorously stirring for 15 each time, then dried ($MgSO_4$), filtered and concentrated to give crude product as light purple paste which was purified by flash chromatography using 0 to 40% EtOAc/hex to afford (S)-isopropyl 2-(5-bromo-4-(4,4-dimethylpiperidin-1-yl)-2,6-dimethylpyridin-3-yl)-2-hydroxyacetate (6.7 g, 15.72 mmol, 84% yield) as colorless thick paste. $^1$H NMR (500 MHz, CDCl$_3$) δ 5.85 (d, J=5.7 Hz, 1H), 5.59 (d, J=7.4 Hz, 1H), 5.08 (dt, J=12.5, 6.3 Hz, 1H), 3.98-3.88 (m, 1H), 3.88-3.78 (m, 1H), 2.76-2.68 (m, 1H), 2.67 (s, 3H), 2.64-2.58 (m, 1H), 2.57 (s, 3H), 1.73 (td, J=12.8, 4.8 Hz, 1H), 1.65-1.59 (m, 1H), 1.47-1.35 (m, 2H), 1.27 (d, J=6.3 Hz, 3H), 1.17 (d, J=6.1 Hz, 3H), 1.09 (s, 3H), 1.04 (s, 3H). LCMS (M+H)=414.6.

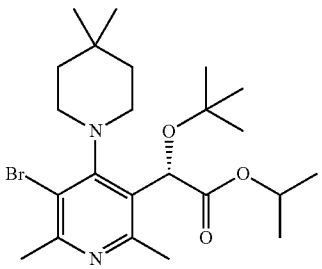 [SMILES: Cc1nc(C)c([C@H](OC(C)(C)C)C(=O)OC(C)C)c(N2CCC(C)(C)CC2)c1Br]

A stirred ice-cold yellow mixture of (S)-isopropyl 2-(5-bromo-4-(4,4-dimethylpiperidin-1-yl)-2,6-dimethylpyridin-3-yl)-2-hydroxyacetate (6.7 g, 16.21 mmol) and 70% HClO$_4$ (2.2 mL, 25.6 mmol) in dichloromethane (400 mL) was saturated with isobutylene gas by bubbling through the reaction mixture (10 min). The reaction mixture was cloudy sealed in a seal tube, stirred for 24 h at rt. The reaction mixture was recooled in a −10° C. bath, bubbled additional isobutylene (~15 min). The reaction mixture became a clear solution at this point. The tube was sealed and stirred at rt for 16 h. LCMs at this point showed incomplete reaction. So, the reaction mixture was cooled down to −30° C. and bubbled isobutene (~15 min). After 24 h, reaction mixture was neutralized with sat. Na$_2$CO$_3$ (20 mL), organic layer separated and aqueous layer was extracted with CH$_2$Cl$_2$ (25 mL). The combined organic layers were dried (MgSO$_4$), filtered, concentrated and purified on a ISCO 120 g column (EtOAc/hex: 0 to 40%) to afford (S)-isopropyl 2-(5-bromo-4-(4,4-dimethylpiperidin-1-yl)-2,6-dimethylpyridin-3-yl)-2-(tert-butoxy)acetate (5.43 g, 9.83 mmol, 60.7% yield) as a viscous oil. $^1$H NMR (500 MHz, CDCl$_3$) δ 6.26 (br. s., 1H), 5.09-4.97 (m, 1H), 4.06 (br. s., 1H), 3.51 (br. s., 1H), 2.90 (br. s., 1H), 2.65 (s, 3H), 2.56 (s, 3H), 1.72-1.54 (m, 3H), 1.47 (br. s., 1H), 1.37 (br. s., 1H), 1.23-1.20 (m, 12H), 1.15 (d, J=6.1 Hz, 3H), 1.09 (br. s., 3H), 1.04 (br. s., 3H). LCMS (M+H)=471.3.

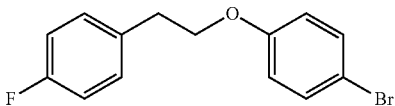 [SMILES: Fc1ccc(CCOc2ccc(Br)cc2)cc1]

To a stirred solution of 4-bromophenol (81.7 g, 472 mmol), 2-(4-fluorophenyl)ethanol (79 g, 567 mmol) and Ph$_3$P (149 g, 567 mmol) in THF (100 mL) cooled in an ice-water bath was added drop wise DEAD (93 ml, 590 mmol) over 20 min. Note: The reaction is exothermic and efficient cooling is highly recommended before initiating large scale reaction. After 1 h, cold bath was removed and stirred overnight (17 h) at rt. Then, the reaction mixture was concentrated, the resulting residue triturated with hexanes, filtered and the filter cake washed with 10% ether/hexanes (2-lit). The filtrate was concentrated and purified by flash chromatography (silica gel column 3"×11") using 4-lit hexanes and 2-lit 2% EtOAc/Hex to afford 1-bromo-4-(4-fluorophenethoxy)benzene (142 g, 469 mmol, 99% yield) as colorless liquid (contaminated with ~2.5% Ph$_3$P by $^1$HNMR). $^1$H NMR (500 MHz, CDCl$_3$) δ 7.41-7.36 (m, 2H), 7.28-7.22 (m, 2H), 7.05-6.99 (m, 2H), 6.82-6.76 (m, 2H), 4.14 (t, J=6.9 Hz, 2H), 3.08 (t, J=6.9 Hz, 2H).

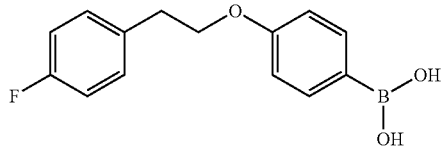 [SMILES: OB(O)c1ccc(OCCc2ccc(F)cc2)cc1]

To a stirred solution of 1-bromo-4-(4-fluorophenethoxy) benzene (142 g, 469 mmol) in THF (1000 mL) was added 2M n-BuLi/cyclohexane (293 ml, 586 mmol) over 15 min at −78° C. After 1.5 h, triisopropyl borate (131 ml, 563 mmol) was added to the light pink reaction mixture over 5 min and stirred for 2 h at −78° C. Then, the reaction was quenched by careful addition of 3M HCl (375 mL), cold bath was replaced with water bath, stirred for 1 h, diluted with ether (500 mL), aq. layer separated and organic layer washed with water (2×200 mL). The combined aq. layers extracted with ether (200 mL) and combined ether layers washed with brine (100 mL), dried (MgSO$_4$), filtered and concentrated to 200 mL. To this was added 250 mL hexanes and concentrated to about 300 mL and allowed to stand at rt. The precipitated solid was triturated with hexanes and filtered to give white solid which was used in next step without purification. $^1$H NMR (500 MHz, CDCl$_3$) δ 8.18-8.15 (m, 2H), 7.32-7.28 (m, 2H), 7.07-7.00 (m, 4H), 4.26 (t, J=6.9 Hz, 2H), 3.14 (t, J=6.9 Hz, 2H).

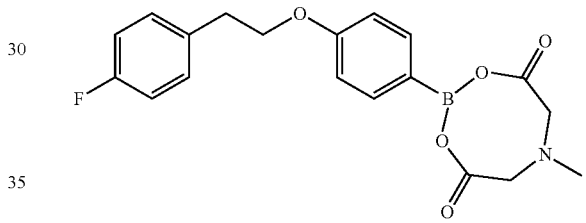

A slurry of (4-(4-fluorophenethoxy)phenyl)boronic acid (122 g, 469 mmol) and 2,2'-(methylazanediyl)diacetic acid (76 g, 516 mmol) in anhydrous toluene (500 mL) and DMSO (200 mL) was refluxed for 4 h. Then, cooled, diluted with EtOAc (500 mL), washed with water (5×200 mL), brine (2×100 mL), dried (MgSO$_4$), filtered and concentrated to give light orange foam which was purified by flash chromatography using 5-40% acetone/CH$_2$Cl$_2$ (5% increment per 2-lit) to afford 2-(4-(4-fluorophenethoxy)phenyl)-6-methyl-1,3,6,2-dioxazaborocane-4,8-dione (131.38 g, 354 mmol, 75% yield) as white solid. $^1$H NMR (500 MHz, CDCl$_3$) δ 7.43 (d, J=8.4 Hz, 2H), 7.28-7.24 (m, 2H), 7.04-6.99 (m, 2H), 6.92 (d, J=8.5 Hz, 2H), 4.17 (t, J=6.9 Hz, 2H), 4.00 (d, J=16.6 Hz, 2H), 3.76 (d, J=16.6 Hz, 2H), 3.08 (t, J=6.8 Hz, 2H), 2.54 (s, 3H). LCMS (M+H)=372.3.

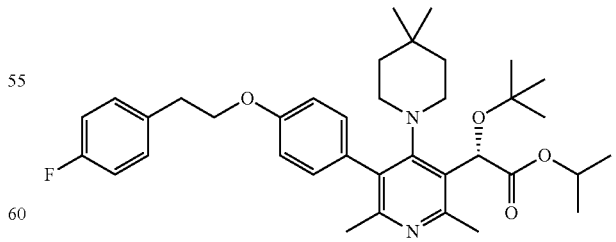

A mixture of (S)-isopropyl 2-(5-bromo-4-(4,4-dimethylpiperidin-1-yl)-2,6-dimethylpyridin-3-yl)-2-(tert-butoxy)acetate (1.0 g, 2.13 mmol), 2-(4-(4-fluorophenethoxy)phenyl)-6-methyl-1,3,6,2-dioxazaborocane-4,8-dione (0.87 g, 2.434 mmol), 2-dicyclohexylphosphino-2',6'-dimethoxybiphenyl (0.175 g, 0.426 mmol) and 2M K$_3$PO$_4$ (7.99 mL, 15.98 mmol)

in 1,4-Dioxane (200 mL) and Water (40.0 mL) was degassed for 10 min. Then, PdOAc2 (0.048 g, 0.213 mmol) was added, degassed for 5 min and mixture was heated at 80° C. for 3 h. After cooling to room temp, water was added and the mixture was extracted with ethyl acetate, washed with brine, dried (Na$_2$SO$_4$), filtered and concentrated the residue was then purified by Biotage (5-40% EtOAc/hexane) to afford (S)-isopropyl 2-(tert-butoxy)-2-(4-(4,4-dimethylpiperidin-1-yl)-5-(4-(4-fluorophenethoxy)phenyl)-2,6-dimethylpyridin-3-yl)acetate (1.056 g, 82% yield) as white foam. $^1$H NMR (500 MHz, CDCl$_3$) δ 7.32-7.26 (m, 2H), 7.18-7.14 (m, 1H), 7.09-7.01 (m, 3H), 6.99-6.93 (m, 2H), 6.07 (br. s., 1H), 5.10 (spt, J=6.2 Hz, 1H), 4.28-4.19 (m, 2H), 3.21 (d, J=12.0 Hz, 1H), 3.13 (t, J=6.9 Hz, 2H), 2.87 (t, J=12.1 Hz, 1H), 2.60 (s, 3H), 2.28 (d, J=12.8 Hz, 1H), 2.20 (s, 3H), 2.10-2.01 (m, 1H), 1.60-1.52 (m, 1H), 1.42-1.34 (m, 1H), 1.25 (d, J=6.3 Hz, 3H), 1.23 (d, J=6.3 Hz, 3H), 1.20 (s, 9H), 1.08 (d, J=12.3 Hz, 1H), 0.91 (s, 3H), 0.66 (s, 3H). 1H of piperidine was not resolved. LCMS (M+H)=606.5.

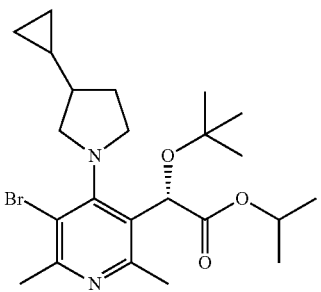 [SMILES: Cc1nc(C)c([C@H](OC(C)(C)C)C(=O)OC(C)C)c(N2CCC(C3CC3)C2)c1Br]

To a solution of 3-cyclopropylpyrrolidine (250 mg, 2.25 mmol) and DIEA (1.178 mL, 6.74 mmol) in anhydrous CH$_3$CN (15 mL) was added isopropyl 2-(5-bromo-4-chloro-2,6-dimethylpyridin-3-yl)-2-oxoacetate (752 mg, 2.25 mmol) at rt. The resulting mixture was placed in a pre-heated oil bath (80° C.) and stirred for 18 h before being cooled, concentrated, and charged (DCM) to a 40 g ISCO silica gel cartridge and gradient eluted (5-35% EtOAc/hexanes) using an Isolera chromatography station to give isopropyl 2-(5-bromo-4-(3-cyclopropylpyrrolidin-1-yl)-2,6-dimethylpyridin-3-yl)-2-oxoacetate 745 mg (81%). $^1$H NMR (500 MHz, DMSO-d$_6$) δ 5.05-5.00 (m, 1H), 3.25-3.19 (m, 2H), 3.15-3.11 (m, 1H), 2.94-2.90 (m, 1H), 2.62 (s, 3H), 2.36 (s, 3H), 2.06 (br. s., 1H), 1.73-1.69 (m, 2H), 1.29-1.27 (m, 6H), 0.72-0.69 (m, 1H), 0.45-0.40 (m, 2H), 0.16-0.10 (m, 2H). UPLC (M+H)=411.1.

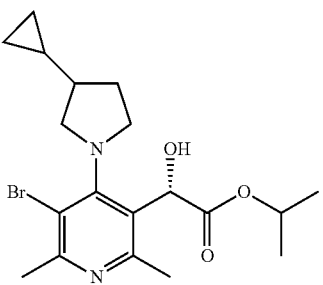 [SMILES: Cc1nc(C)c([C@H](O)C(=O)OC(C)C)c(N2CCC(C3CC3)C2)c1Br]

The benzo[d][1,3,2]dioxaborole (0.66 mL, 2.68 mmol; 50% soln in toluene) was added to a nitrogen purged solution of isopropyl 2-(5-bromo-4-(3-cyclopropylpyrrolidin-1-yl)-2,6-dimethylpyridin-3-yl)-2-oxoacetate (730 mg, 1.78 mmol) and 0.6 ml of 1M (R)-1-methyl-3,3-diphenylhexahydropyrrolo[1,2-c][1,3,2]oxazaborole (148 mg, 0.54 mmol) in toluene (18 mL) cooled to −50° C. The reaction was allowed to slowly warm to −15° C. and placed in the freezer for 18 h before being quenched with 1M Na$_2$CO$_3$ (5 mL) and stirred for 20 min. The organic layer was washed with brine and dried (MgSO$_4$). The crude product was charged (DCM) to a 40 g ISCO silica gel cartridge and gradient elution (5-50% EtOAc/hexanes) using an Isolera chromatography station gave (2S)-isopropyl 2-(5-bromo-4-(3-cyclopropylpyrrolidin-1-yl)-2,6-dimethylpyridin-3-yl)-2-hydroxyacetate 540 mg (74%) as a mixture of diastereomers; major isomer. $^1$H NMR (500 MHz, DMSO-d$_6$) δ 5.52 (s, 1H), 4.96-4.89 (m, 1H), 3.40-3.35 (m, 2H), 3.17-3.09 (m, 1H), 2.94-2.90 (m, 1H), 2.53 (s, 3H), 2.40 (s, 3H), 2.03 (br. s., 1H), 1.82-1.74 (m, 2H), 1.17-1.08 (m, 6H), 0.76-0.75 (m, 1H), 0.43-0.41 (m, 2H), 0.15-0.14 (m, 2H). UPLC (M+H)=413.2.

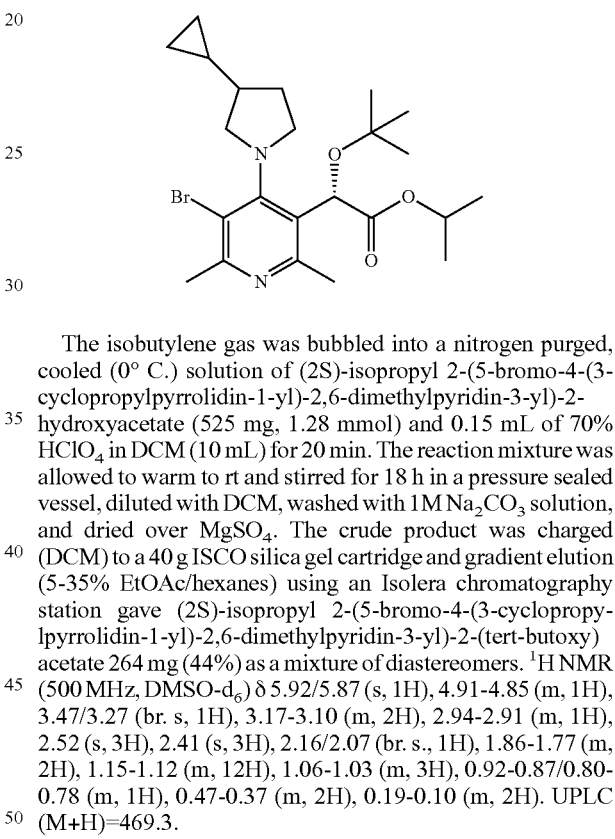

The isobutylene gas was bubbled into a nitrogen purged, cooled (0° C.) solution of (2S)-isopropyl 2-(5-bromo-4-(3-cyclopropylpyrrolidin-1-yl)-2,6-dimethylpyridin-3-yl)-2-hydroxyacetate (525 mg, 1.28 mmol) and 0.15 mL of 70% HClO$_4$ in DCM (10 mL) for 20 min. The reaction mixture was allowed to warm to rt and stirred for 18 h in a pressure sealed vessel, diluted with DCM, washed with 1M Na$_2$CO$_3$ solution, and dried over MgSO$_4$. The crude product was charged (DCM) to a 40 g ISCO silica gel cartridge and gradient elution (5-35% EtOAc/hexanes) using an Isolera chromatography station gave (2S)-isopropyl 2-(5-bromo-4-(3-cyclopropylpyrrolidin-1-yl)-2,6-dimethylpyridin-3-yl)-2-(tert-butoxy)acetate 264 mg (44%) as a mixture of diastereomers. $^1$H NMR (500 MHz, DMSO-d$_6$) δ 5.92/5.87 (s, 1H), 4.91-4.85 (m, 1H), 3.47/3.27 (br. s, 1H), 3.17-3.10 (m, 2H), 2.94-2.91 (m, 1H), 2.52 (s, 3H), 2.41 (s, 3H), 2.16/2.07 (br. s., 1H), 1.86-1.77 (m, 2H), 1.15-1.12 (m, 12H), 1.06-1.03 (m, 3H), 0.92-0.87/0.80-0.78 (m, 1H), 0.47-0.37 (m, 2H), 0.19-0.10 (m, 2H). UPLC (M+H)=469.3.

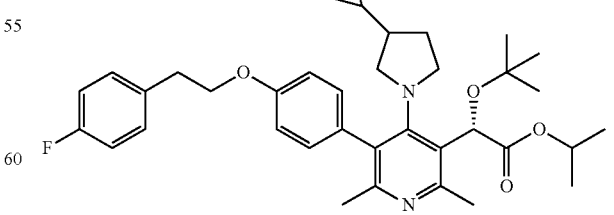

The Pd(Ph$_3$P)$_4$ (61.8 mg, 0.053 mmol) was added to a nitrogen purged and degassed solution of (2S)-isopropyl 2-(5-bromo-4-(3-cyclopropylpyrrolidin-1-yl)-2,6-dimethylpyridin-3-yl)-2-(tert-butoxy)acetate (125 mg, 0.27 mmol), (4-(4-fluorophenethoxy)phenyl)boronic acid (77 mg, 0.29 mmol), and potassium phosphate tribasic (397 mg, 1.9 mmol) in 1,4-dioxane (3.5 mL) and water (0.9 mL). The reaction mixture was stirred in a screw-capped pressure vessel for 4 h at 90° C., cooled, diluted with EtOAc, and the organic layer was washed with brine and dried (Na₂CO₃). The crude product was charged (DCM) to a 24 g ISCO silica gel cartridge and gradient elution (5-65% EtOAc/hexanes) using an Isolera chromatography station gave (2S)-isopropyl 2-(tert-butoxy)-2-(4-(3-cyclopropylpyrrolidin-1-yl)-5-(4-(4-fluorophenethoxy)phenyl)-2,6-dimethylpyridin-3-yl)acetate 80 mg (49.6%) as a mixture of diastereomers. ¹H NMR (500 MHz, DMSO-d₆) δ 7.39-7.36 (m, 2H), 7.21-7.20 (m, 1H), 7.15-7.12 (m, 2H), 7.03-6.94 (m, 3H), 5.77/5.75 (s, 1H), 4.96-4.91 (m, 1H), 4.21 (t, J=6.6 Hz, 2H) 3.17-3.13/3.01-2.97 (m, 1H), 3.05 (t, J=6.6 Hz, 2H), 2.84-2.74 (m, 2H), 2.70-2.67/2.63-2.60 (m, 1H), 2.42/2.41 (s, 3H), 2.07/2.05 (s, 3H), 1.71-1.64 (m, 1H), 1.42-1.22/1.03-0.097 (m, 2H), 1.19-1.17 (m, 3H), 1.14-1.10 (m, 12H), 0.52-0.47 (m, 1H), 0.32-0.23 (m, 2H), −0.30-0.15 (m, 2H). UPLC (M+H)=603.5.

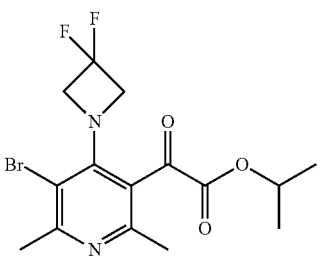 [SMILES: Cc1nc(C)c(C(=O)C(=O)OC(C)C)c(N2CC(F)(F)C2)c1Br]

To a solution of 3,3-difluoroazetidine, HCl (1.099 g, 8.48 mmol) and DIEA (4.0 mL, 23.1 mmol) in anhydrous CH₃CN (40 mL) was added isopropyl 2-(5-bromo-4-chloro-2,6-dimethylpyridin-3-yl)-2-oxoacetate (2.58 g, 7.1 mmol) at rt. The resulting mixture was placed in a pre-heated oil bath (80° C.) and stirred for 24 h; partially concentrated, and allowed to continue another 18 h before being cooled, concentrated, and charged (DCM) to a 120 g ISCO silica gel cartridge and gradient eluted (5-35% EtOAc/hexanes) using an Isolera chromatography station and gave isopropyl 2-(5-bromo-4-(3,3-difluoroazetidin-1-yl)-2,6-dimethylpyridin-3-yl)-2-oxoacetate 368 mg (12%). UPLC (M+H)=393.1.

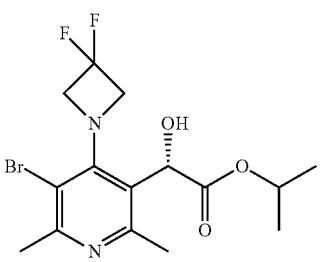 [SMILES: Cc1nc(C)c([C@H](O)C(=O)OC(C)C)c(N2CC(F)(F)C2)c1Br]

The 0.33 mL of benzo[d][1,3,2]dioxaborole (166 mg, 1.38 mmol) was added to a nitrogen purged solution of isopropyl 2-(5-bromo-4-(3,3-difluoroazetidin-1-yl)-2,6-dimethylpyridin-3-yl)-2-oxoacetate (360 mg, 0.920 mmol) and 0.28 mL of (R)-1-methyl-3,3-diphenylhexahydropyrrolo[1,2-c][1,3,2]oxazaborole (77 mg, 0.28 mmol) in toluene (10 mL) at −60° C. and allowed to warm to −15° C. before being placed in the freezer overnight. The reaction was quenched with 1M Na₂CO₃ (5 mL), diluted with EtOAc, and stirred for 20 min. The organic layer was washed with brine and dried (MgSO₄). The crude product was charged (DCM) to a 40 g ISCO silica gel cartridge and gradient elution (5-60% EtOAc/hexanes) using an Isolera chromatography station gave (S)-isopropyl 2-(5-bromo-4-(3,3-difluoroazetidin-1-yl)-2,6-dimethylpyridin-3-yl)-2-hydroxyacetate 186 mg (51%). ¹H NMR (500 MHz, DMSO-d₆) δ 5.24 (s, 1H), 4.97-4.94 (m, 1H), 4.74-4.71 (m, 2H), 4.54-4.51 (m, 2H), 2.50 (s, 3H), 2.33 (s, 3H), 1.19 (d, J=5.9 Hz, 3H), 1.13 (d, J=5.9 Hz, 3H). LCMS (M+H)=395.1.

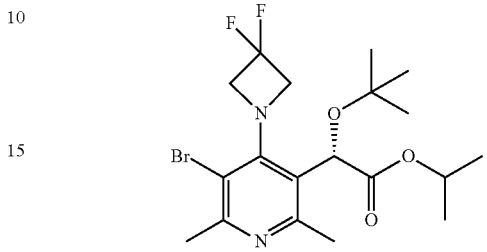

The isobutylene gas was bubbled into a nitrogen purged, cooled (0° C.) solution of (S)-isopropyl 2-(5-bromo-4-(3,3-difluoroazetidin-1-yl)-2,6-dimethylpyridin-3-yl)-2-hydroxyacetate (175 mg, 0.45 mmol) and 0.05 mL of 70% HClO₄ in DCM (5 mL) for 20 min. The reaction mixture was allowed to warm to rt and stirred for 18 h in a pressure sealed vessel, diluted with DCM, washed with 1M Na₂CO₃ solution, and dried over MgSO₄. The crude product was charged (DCM) to a 24 g ISCO silica gel cartridge and gradient elution (5-35% EtOAc/hexanes) using an Isolera chromatography gave (S)-isopropyl 2-(5-bromo-4-(3,3-difluoroazetidin-1-yl)-2,6-dimethylpyridin-3-yl)-2-(tert-butoxy)acetate 88 mg (44%). ¹H NMR (400 MHz, DMSO-d₆) δ 5.72 (s, 1H), 5.10-5.03 (m, 1H), 4.80-4.72 (m, 2H), 4.59-4.15 (m, 2H), 2.62 (s, 3H), 2.48 (s, 3H), 1.38 (d, J=6.1 Hz, 3H), 1.20 (s, 9H), 1.19 (d, J=6.1 Hz, 3H). UPLC (M+H)=451.3.

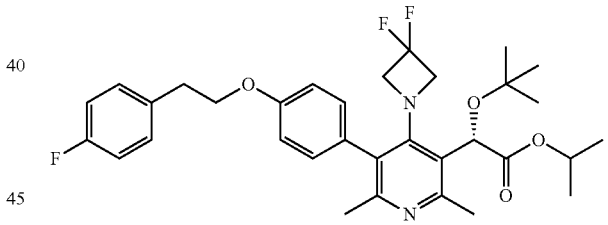

The Pd(Ph₃P)₄ (43.2 mg, 0.037 mmol) was added to a nitrogen purged and degassed solution of (S)-isopropyl 2-(5-bromo-4-(3,3-difluoroazetidin-1-yl)-2,6-dimethylpyridin-3-yl)-2-(tert-butoxy)acetate (84 mg, 0.187 mmol), (4-(4-fluorophenethoxy)phenyl)boronic acid (53.5 mg, 0.206 mmol), and sodium carbonate (139 mg, 1.31 mmol) in dioxane (2 mL) and water (0.15 mL) and stirred in a screw-capped pressure vessel for 4 h at 90° C. The reaction was allowed to cool, diluted with EtOAc, and the organic layer was washed with brine and dried (Na₂SO₄). The crude product was charged (DCM) to a 24 g ISCO silica gel cartridge and gradient elution (5-65% EtOAc/hexanes) using an Isolera chromatography station gave (S)-isopropyl 2-(tert-butoxy)-2-(4-(3,3-difluoroazetidin-1-yl)-5-(4-(4-fluorophenethoxy)phenyl)-2,6-dimethylpyridin-3-yl)acetate 60 mg (55%). ¹H NMR (500 MHz, DMSO-d₆) δ 7.40-7.37 (m, 2H), 7.29 (d, J=8.1 Hz, 1H), 7.14 (t, J=8.8 Hz, 2H), 7.04-6.95 (m, 3H), 5.22 (s, 1H), 5.01-4.95 (m, 1H), 4.23 (t, J=7.0 Hz, 2H), 4.07-4.00 (m, 2H), 3.87-3.80 (m, 2H), 3.06 (t, J=7.0 Hz, 2H), 2.35 (s, 3H), 2.05 (s, 3H), 1.21 (d, J=6.2 Hz, 3H), 1.18 (d, J=6.2 Hz, 3H), 1.12 (s, 9H). UPLC (M+H)=586.4.

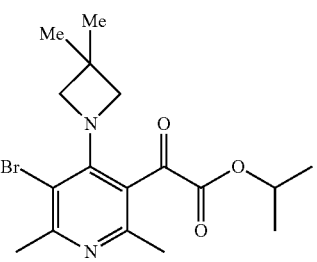

To a solution of 3,3-dimethylazetidine, HCl (1.0 g, 8.22 mmol) and DIEA (4.3 mL, 24.7 mmol) in anhydrous CH$_3$CN (40 mL) was added isopropyl 2-(5-bromo-4-chloro-2,6-dimethylpyridin-3-yl)-2-oxoacetate (2.75 g, 8.2 mmol) at rt. The resulting mixture was placed in a pre-heated oil bath (80° C.) and stirred for 24 h; concentrated, and charged (DCM) to a 80 g ISCO silica gel cartridge and gradient eluted (5-35% EtOAc/hexanes) using an Isolera chromatography station to give isopropyl 2-(5-bromo-4-(3,3-dimethylazetidin-1-yl)-2,6-dimethylpyridin-3-yl)-2-oxoacetate 1.6 g (50.8%). $^1$H NMR (500 MHz, DMSO-d$_6$) δ 5.15-5.11 (m, 1H), 3.79 (s, 4H), 2.48 (s, 3H), 2.19 (s, 3H), 1.31 (d, J=6.2 Hz, 6H), 1.18 (s, 6H). UPLC (M+H)=385.2.

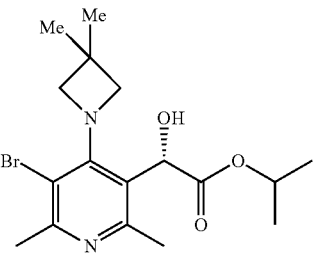 [SMILES: Cc1nc(C)c([C@H](O)C(=O)OC(C)C)c(N2CC(C)(C)C2)c1Br]

The 1.5 mL of benzo[d][1,3,2]dioxaborole (751 mg, 6.26 mmol) was added to a nitrogen purged solution of isopropyl 2-(5-bromo-4-(3,3-dimethylazetidin-1-yl)-2,6-dimethylpyridin-3-yl)-2-oxoacetate (1.6 g, 4.17 mmol) and 1.25 mL of (R)-1-methyl-3,3-diphenylhexahydropyrrolo[1,2-c][1,3,2] oxazaborole (347 mg, 1.25 mmol) in toluene (40 mL) at −60° C. and allowed to warm to −15° C. before being placed in the freezer overnight. The reaction was quenched with 1M Na$_2$CO$_3$ (15 mL), diluted with EtOAc, and stirred for 20 min. The organic layer was washed with brine and dried (Na$_2$SO$_4$). The crude product was charged (DCM) to an 80 g ISCO silica gel cartridge and gradient elution (5-35% EtOAc/hexanes) using an Isolera chromatography station gave (S)-isopropyl 2-(5-bromo-4-(3,3-dimethylazetidin-1-yl)-2,6-dimethylpyridin-3-yl)-2-hydroxyacetate 987 mg (61%). $^1$H NMR (500 MHz, DMSO-d$_6$) δ 5.16 (s, 1H), 4.97-4.92 (m, 1H), 4.13 (d, J=7.7 Hz, 2H), 4.04 (d, J=7.7 Hz, 2H), 2.42 (s, 3H), 2.21 (s, 3H), 1.22 (s, 6H), 1.17 (d, J=6.2 Hz, 3H), 1.12 (d, J=6.2 Hz, 3H). UPLC (M+H)=387.2.

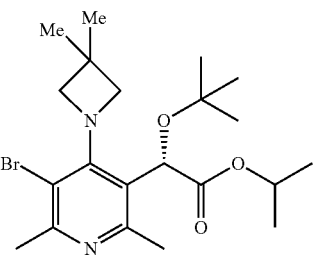 [SMILES: Cc1nc(C)c([C@H](OC(C)(C)C)C(=O)OC(C)C)c(N2CC(C)(C)C2)c1Br]

The isobutylene gas was bubbled into a nitrogen purged, cooled (0° C.) solution of (S)-isopropyl 2-(5-bromo-4-(3,3-dimethylazetidin-1-yl)-2,6-dimethylpyridin-3-yl)-2-hydroxyacetate (970 mg, 2.5 mmol) and 0.5 mL of 70% HClO$_4$ in DCM (20 mL) for 20 min. The reaction mixture was allowed to warm to rt and stirred for 18 h in a pressure sealed vessel, diluted with DCM, washed with 1M Na$_2$CO$_3$ solution, and dried over MgSO$_4$. The crude product was charged (DCM) to a 40 g ISCO silica gel cartridge and gradient elution (5-35% EtOAc/hexanes) using an Isolera chromatography station gave (S)-isopropyl 2-(5-bromo-4-(3,3-dimethylazetidin-1-yl)-2,6-dimethylpyridin-3-yl)-2-(tert-butoxy)acetate 578 mg (52%). $^1$H NMR (500 MHz, DMSO) δ 5.30 (s, 1H), 5.0-4.95 (m, 1H), 4.12 (d, J=7.2 Hz, 2H), 4.02 (br. s, 2H), 2.44 (s, 3H), 2.25 (br. s, 3H), 1.26 (s, 6H), 1.20 (d, J=6.3 Hz, 3H), 1.17 (d, J=6.3 Hz, 3H), 1.07 (s, 9H). UPLC (M+H)=443.3.

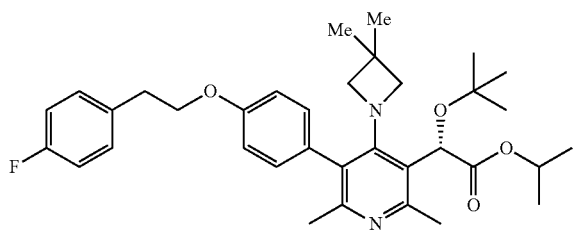 [SMILES: Cc1nc(C)c([C@H](OC(C)(C)C)C(=O)OC(C)C)c(N2CC(C)(C)C2)c1-c1ccc(OCCc2ccc(F)cc2)cc1]

The Pd(Ph$_3$P)$_4$ (57.6 mg, 0.05 mmol) was added to a nitrogen purged and degassed solution of (S)-isopropyl 2-(5-bromo-4-(3,3-dimethylazetidin-1-yl)-2,6-dimethylpyridin-3-yl)-2-(tert-butoxy)acetate (110 mg, 0.25 mmol), (4-(4-fluorophenethoxy)phenyl)boronic acid (71.3 mg, 0.27 mmol), and sodium carbonate (185 mg, 1.74 mmol) in dioxane (3 mL) and water (0.6 mL) and stirred in a screw-capped pressure vessel for 4 h at 90° C. The reaction was allowed to cool, diluted with EtOAc, and the organic layer was washed with brine and dried (Na$_2$SO$_4$). The crude product was charged (DCM) to a 24 g ISCO silica gel cartridge and gradient elution (5-65% EtOAc/hexanes) using an Isolera chromatography station gave (S)-isopropyl 2-(tert-butoxy)-2-(4-(3,3-dimethylazetidin-1-yl)-5-(4-(4-fluorophenethoxy) phenyl)-2,6-dimethylpyridin-3-yl)acetate 97 mg (67.5%). $^1$H NMR (500 MHz, DMSO-d$_6$) δ 7.40-7.37 (m, 2H), 7.32 (br. s, 1H), 7.14 (t, J=8.4 Hz, 2H), 6.99 (d, J=8.1 Hz, 1H), 6.93 (d, J=8.1 Hz, 1H), 6.78 (br. s, 1H), 5.20 (s, 1H), 5.02-4.97 (m, 1H), 4.20 (t, J=6.2 Hz, 2H), 3.44 (s, 4H), 3.05 (t, J=6.6 Hz, 2H), 1.99 (s, 3H), 1.89 (s, 3H), 1.21-1.18 (m, 6H), 1.11 (s, 9H), 1.02 (s, 6H). UPLC (M+H)=577.5.

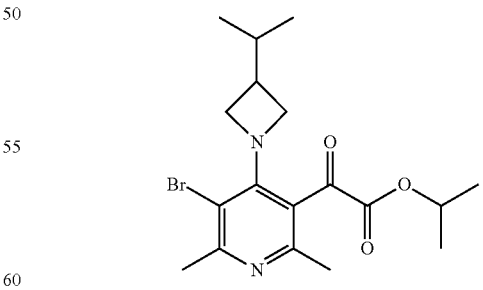

To a solution of 3-isopropylazetidine, HCl (1.0 g, 7.37 mmol) and DIEA (3.8 mL, 22.1 mmol) in anhydrous CH$_3$CN (35 mL) was added isopropyl 2-(5-bromo-4-chloro-2,6-dimethylpyridin-3-yl)-2-oxoacetate (2.47 g, 7.38 mmol) at rt. The resulting mixture was placed in a pre-heated oil bath (80° C.) and stirred for 24 h; concentrated, and charged (DCM) to a 80 g ISCO silica gel cartridge and gradient eluted (5-35% EtOAc/hexanes) using an Isolera chromatography station to give isopropyl 2-(5-bromo-4-(3-isopropylazetidin-1-yl)-2,6-dimethylpyridin-3-yl)-2-oxoacetate 895 mg (30.5%). $^1$H NMR (500 MHz, DMSO-d$_6$) δ 5.18-5.11 (m, 1H), 4.14 (t, J=8.8 Hz, 2H), 3.73 (t, J=8.1 Hz, 2H), 2.48 (s, 3H), 2.26-2.22 (m, 1H), 2.19 (s, 3H), 1.70-1.63 (m, 1H), 1.30 (d, J=6.2 Hz, 6H), 0.79 (d, J=6.6 Hz, 6H). UPLC (M+H)=399.2.

din-1-yl)-2,6-dimethylpyridin-3-yl)-2-(tert-butoxy)acetate 621 mg (90%) as a mixture of diastereomers. $^1$H NMR (500 MHz, DMSO-d$_6$) δ 5.28 (s, 1H), 5.02-4.97 (m, 1H), 4.57 (t, J=8.1 Hz, 1H), 4.40 (t, J=7.7 Hz, 1H), 4.02 (t, J=7.0 Hz, 1H), 3.91 (t, J=7.3 Hz, 1H), 2.44 (s, 3H), 2.33-2.29 (m, 1H), 2.25 (s, 3H), 1.74-1.70 (m, 1H), 1.21 (d, J=6.2 Hz, 3H), 1.17 (d, J=6.2 Hz, 3H), 1.06 (s, 9H), 0.84 (d, J=6.6 Hz, 6H). UPLC (M+H)=457.4.

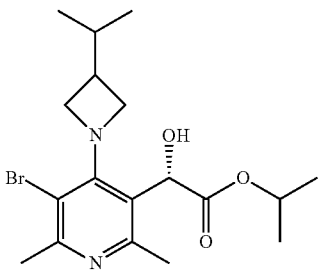 [SMILES: Cc1nc(C)c([C@H](O)C(=O)OC(C)C)c(N2CC(C(C)C)C2)c1Br]

The 0.7 mL of benzo[d][1,3,2]dioxaborole (396 mg, 3.3 mmol) was added to a nitrogen purged solution of isopropyl 2-(5-bromo-4-(3-isopropylazetidin-1-yl)-2,6-dimethylpyridin-3-yl)-2-oxoacetate (875 mg, 2.2 mmol) and 0.66 mL of (R)-1-methyl-3,3-diphenylhexahydropyrrolo[1,2-c][1,3,2]oxazaborole (183 mg, 0.66 mmol) in toluene (20 mL) at −60° C. and allowed to warm to −15° C. before being placed in the freezer overnight. The reaction was quenched with 1M Na$_2$CO$_3$ (5 mL), diluted with EtOAc, and stirred for 20 min. The organic layer was washed with brine and dried (MgSO$_4$). The crude product was charged (DCM) to a 80 g ISCO silica gel cartridge and gradient elution (5-35% EtOAc/hexanes) using an Isolera chromatography station gave (S)-isopropyl 2-(5-bromo-4-(3-isopropylazetidin-1-yl)-2,6-dimethylpyridin-3-yl)-2-hydroxyacetate 621 mg (71%) as a mixture of diastereomers. $^1$H NMR (500 MHz, DMSO-d$_6$) δ 5.19 (d, J=4.4 Hz, 1H), 4.96-4.92 (m, 1H), 4.50 (t, J=8.1 Hz, 1H), 4.39 (t, J=8.4 Hz, 1H), 4.07 (t, J=7.0 Hz, 1H), 3.97 (t, J=7.3 Hz, 1H), 2.42 (s, 3H), 2.21 (s, 3H), 2.21-2.17 (m, 1H), 1.73-1.67 (m, 1H), 1.17 (d, J=6.2 Hz, 3H), 1.12 (d, J=6.2 Hz, 3H), 0.83 (d, J=6.6 Hz, 6H). UPLC (M+H)=401.3.

The Pd(Ph$_3$P)$_4$ (38.1 mg, 0.033 mmol) was added to a nitrogen purged and degassed solution of (S)-isopropyl 2-(5-bromo-4-(3-isopropylazetidin-1-yl)-2,6-dimethylpyridin-3-yl)-2-(tert-butoxy)acetate (150 mg, 0.33 mmol), (4-(4-fluorophenethoxy)phenyl)boronic acid (94 mg, 0.36 mmol), and sodium carbonate (209 mg, 1.98 mmol) in dioxane (4.5 mL) and water (0.9 mL) and stirred in a screw-capped pressure vessel for 4 h at 90° C. The reaction was allowed to cool, diluted with EtOAc, and the organic layer was washed with brine and dried (Na$_2$SO$_4$). The crude product was charged (DCM) to a 24 g ISCO silica gel cartridge and gradient elution (5-75% EtOAc/hexanes) using an Isolera chromatography station gave (S)-isopropyl 2-(tert-butoxy)-2-(5-(4-(4-fluorophenethoxy)phenyl)-4-(3-isopropylazetidin-1-yl)-2,6-dimethylpyridin-3-yl)acetate 152 mg (78%) as a mixture of diastereomers. $^1$H NMR (500 MHz, DMSO-d$_6$) δ 7.39-7.36 (m, 2H), 7.31-7.30 (m, 1H), 7.14 (t, J=8.8 Hz, 2H), 7.00 (d, J=8.8 Hz, 1H), 6.94 (d, J=8.4 Hz, 1H), 6.82-6.80 (m, 1H), 5.18 (s, 1H), 5.03-4.98 (m, 1H), 4.21 (t, J=6.6 Hz, 2H), 3.43-3.25 (series m, 4H), 3.05 (t, J=6.6 Hz, 2H), 2.27 (s, 3H), 2.01 (s, 3H), 2.01-1.98 (m, 1H), 1.48-1.44 (m, 1H), 1.21-1.19 (m, 6H), 1.10 (s, 9H), 0.68 (d, J=6.6 Hz, 3H), 0.63 (d, J=6.6 Hz, 3H). UPLC (M+H)=591.6.

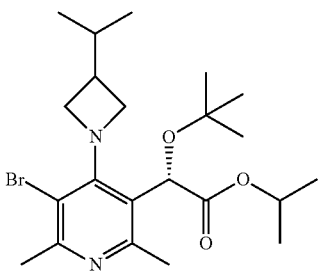 [SMILES: Cc1nc(C)c([C@H](OC(C)(C)C)C(=O)OC(C)C)c(N2CC(C(C)C)C2)c1Br]

The isobutylene gas was bubbled into a nitrogen purged, cooled (0° C.) solution of (S)-isopropyl 2-(5-bromo-4-(3-isopropylazetidin-1-yl)-2,6-dimethylpyridin-3-yl)-2-hydroxyacetate (601 mg, 1.5 mmol) and 0.5 mL of 70% HClO$_4$ in DCM (12 mL) for 20 min. The reaction mixture was allowed to warm to rt and stirred for 18 h in a pressure sealed vessel, diluted with DCM, washed with 1M Na$_2$CO$_3$ solution, and dried over MgSO$_4$. The crude product was charged (DCM) to a 40 g ISCO silica gel cartridge and gradient elution (5-50% EtOAc/hexanes) using an Isolera chromatography station gave (S)-isopropyl 2-(5-bromo-4-(3-isopropylazeti-

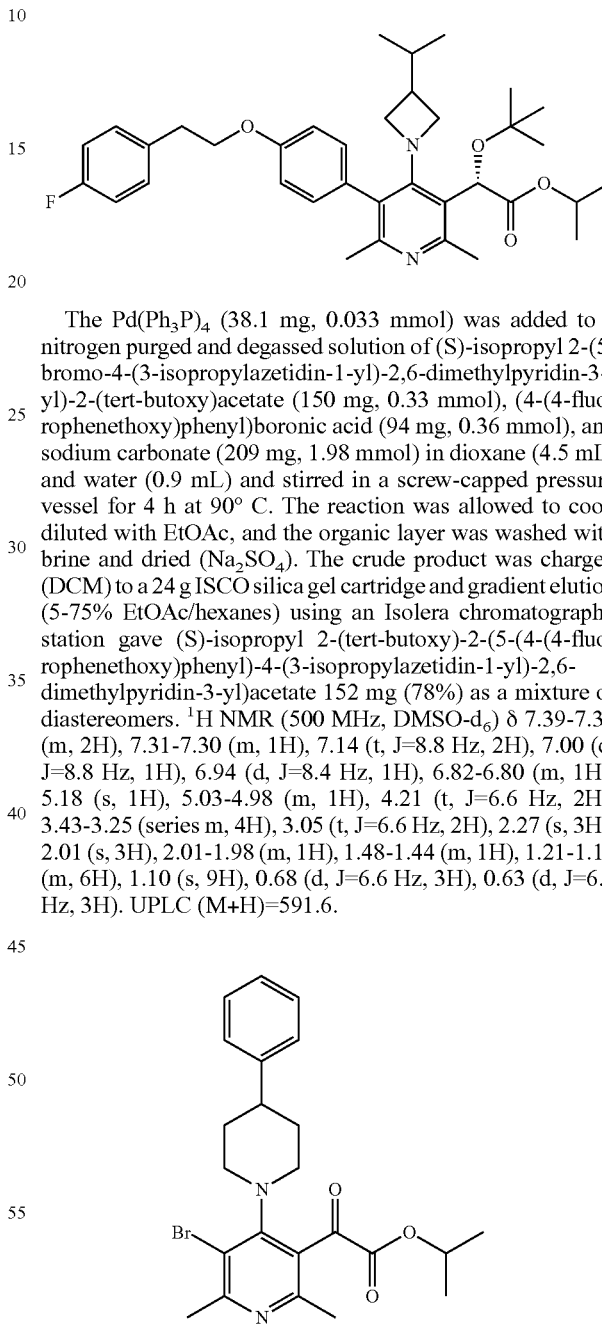

To a solution of 4-phenylpiperidine (1.25 g, 7.75 mmol) and DIEA (4.1 mL, 23.3 mmol) in anhydrous CH$_3$CN (40 mL) was added isopropyl 2-(5-bromo-4-chloro-2,6-dimethylpyridin-3-yl)-2-oxoacetate (2.59 g, 7.75 mmol) at rt. The resulting mixture was placed in a pre-heated oil bath (80° C.) and stirred for 24 h; concentrated, and charged (DCM) to a 80 g ISCO silica gel cartridge and gradient eluted (5-35%

EtOAc/hexanes) using an Isolera chromatography station to give isopropyl 2-(5-bromo-2,6-dimethyl-4-(4-phenylpiperidin-1-yl)pyridin-3-yl)-2-oxoacetate 2.63 g (74%). $^1$H NMR (500 MHz, DMSO-d$_6$) δ 7.34-7.31 (m, 2H), 7.25-7.20 (m, 3H), 5.11-5.06 (m, 1H), 3.50 (br. s, 2H), 2.94 (br. s, 2H), 2.68-2.63 (m, 1H), 2.63 (s, 3H), 2.13 (s, 3H), 1.81-1.78 (m, 2H), 1.60 (br. s, 2H), 1.26 (d, J=6.2 Hz, 6H). UPLC (M+H)=461.05.

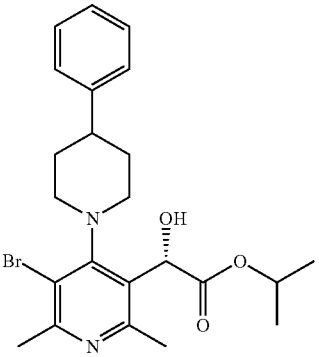 [SMILES: Cc1nc(C)c([C@H](O)C(=O)OC(C)C)c(N2CCC(c3ccccc3)CC2)c1Br]

The 2.2 mL of benzo[d][1,3,2]dioxaborole (1.22 g, 10.2 mmol) was added to a nitrogen purged solution of isopropyl 2-(5-bromo-2,6-dimethyl-4-(4-phenylpiperidin-1-yl)pyridin-3-yl)-2-oxoacetate (2.6 g, 5.66 mmol) and 1.7 mL of (R)-1-methyl-3,3-diphenylhexahydropyrrolo[1,2-c][1,3,2]oxazaborole (471 mg, 1.7 mmol) in toluene (50 mL) at −60° C. and allowed to warm to −15° C. before being placed in the freezer overnight. The reaction was quenched with 1M Na$_2$CO$_3$ (15 mL), diluted with EtOAc, and stirred for 20 min. The organic layer was washed with brine and dried (MgSO$_4$). The crude product was charged (DCM) to a 80 g ISCO silica gel cartridge and gradient elution (5-45% EtOAc/hexanes) using an Isolera chromatography station gave (S)-isopropyl 2-(5-bromo-2,6-dimethyl-4-(4-phenylpiperidin-1-yl)pyridin-3-yl)-2-hydroxyacetate 2.0 g (71%) as a mixture of diastereomers. $^1$H NMR (500 MHz, DMSO-d$_6$) δ 7.34-7.29 (m, 4H), 7.22-7.19 (m, 1H), 5.95 (s, 1H), 4.99-4.94 (m, 1H), 3.78-3.75 (m, 1H), 3.51-3.47 (m, 1H), 3.04-3.02 (m, 1H), 2.90-2.87 (m, 1H), 2.66-2.61 (m, 1H), 2.54 (s, 3H), 2.41 (s, 3H), 1.87-1.72 (m, 4H), 1.14 (d, J=6.2 Hz, 3H), 1.07 (d, J=5.9 Hz, 3H). UPLC (M+H)=463.2.

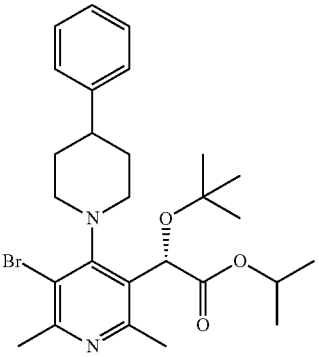 [SMILES: Cc1nc(C)c([C@H](OC(C)(C)C)C(=O)OC(C)C)c(N2CCC(c3ccccc3)CC2)c1Br]

The isobutylene gas was bubbled into a nitrogen purged, cooled (0° C.) solution of (S)-isopropyl 2-(5-bromo-2,6-dimethyl-4-(4-phenylpiperidin-1-yl)pyridin-3-yl)-2-hydroxyacetate (1.95 g, 1.5 mmol) and 0.6 mL of 70% HClO$_4$ in DCM (25 mL) for 20 min. The reaction mixture was allowed to warm to rt and stirred for 18 h in a pressure sealed vessel, diluted with DCM, washed with 1M Na$_2$CO$_3$ solution, and dried over MgSO$_4$. The crude product was charged (DCM) to a 80 g ISCO silica gel cartridge and gradient elution (5-50% EtOAc/hexanes) using an Isolera chromatography station gave (S)-isopropyl 2-(5-bromo-2,6-dimethyl-4-(4-phenylpiperidin-1-yl)pyridin-3-yl)-2-(tert-butoxy)acetate 970 mg (44.4%) as a mixture of diastereomers. $^1$H NMR (500 MHz, DMSO-d$_6$) δ 7.36-7.33 (m, 2H), 7.29-7.28 (m, 2H), 7.23-7.20 (m, 1H), 6.26 (s, 1H), 4.95-4.90 (m, 1H), 3.98 (br. s, 1H), 3.41 (br. s, 1H), 3.12 (br. s, 1H), 2.98 (br. s, 1H), 2.71 (br. s, 1H), 2.51 (s, 3H), 2.44 (s, 3H), 1.93 (br. s, 1H), 1.82-1.75 (m, 3H), 1.18 (s, 9H), 1.15 (d, J=6.2 Hz, 3H), 1.07 (d, J=5.9 Hz, 3H). UPLC (M+H)=519.2.

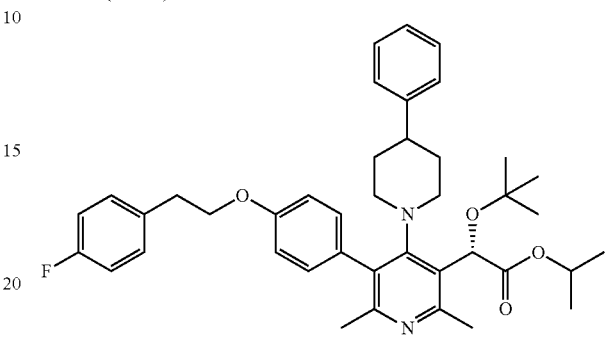

The Pd(Ph$_3$P)$_4$ (33.5 mg, 0.029 mmol) was added to a nitrogen purged and degassed solution of (S)-isopropyl 2-(5-bromo-2,6-dimethyl-4-(4-phenylpiperidin-1-yl)pyridin-3-yl)-2-(tert-butoxy)acetate (150 mg, 0.29 mmol), (4-(4-fluorophenethoxy)phenyl)boronic acid (83 mg, 0.32 mmol), and sodium carbonate (184 mg, 1.74 mmol) in dioxane (4.5 mL) and water (0.9 mL) and stirred in a screw-capped pressure vessel for 4 h at 90° C. The reaction was allowed to cool, diluted with EtOAc, and the organic layer was washed with brine and dried (Na$_2$SO$_4$). The crude product was charged (DCM) to a 24 g ISCO silica gel cartridge and gradient elution (5-65% EtOAc/hexanes) using an Isolera chromatography station gave (S)-isopropyl 2-(tert-butoxy)-2-(5-(4-(4-fluorophenethoxy)phenyl)-2,6-dimethyl-4-(4-phenylpiperidin-1-yl)pyridin-3-yl)acetate 98 mg (52%) as a mixture of diastereomers. $^1$H NMR (500 MHz, DMSO-d$_6$) δ 7.42-7.39 (m, 2H), 7.29-7.23 (m, 3H), 7.17-7.13 (m, 5H), 7.06-7.02 (m, 3H), 6.07 (s, 1H), 4.98-4.93 (m, 1H), 4.25 (t, J=7.0 Hz, 2H), 3.08 (t, J=6.2 Hz, 2H), 2.78-2.72 (m, 1H), 2.62-2.58 (m, 1H), 2.47 (br. s, 1H), 2.46 (s, 3H), 2.28 (br. s, 1H), 2.05 (s, 3H), 1.94-1.90 (m, 1H), 1.77-1.66 (m, 2H), 1.57 (br. s, 2H), 1.18 (br. s, 12H), 1.14 (d, J=5.5 Hz, 3H). UPLC (M+H)=653.5.

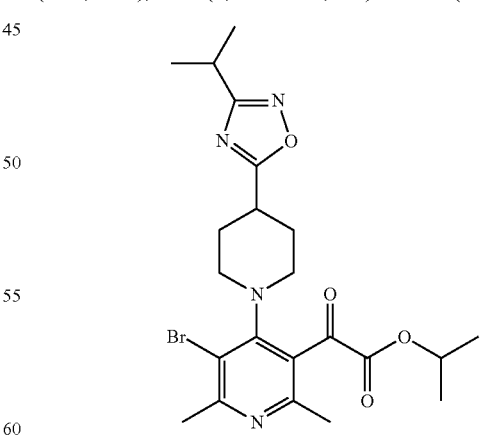

To a solution of 3-isopropyl-5-(piperidin-4-yl)-1,2,4-oxadiazole, HCl (1.70 g, 7.35 mmol) and DIEA (5.1 mL, 29.4 mmol) in anhydrous CH$_3$CN (40 mL) was added isopropyl 2-(5-bromo-4-chloro-2,6-dimethylpyridin-3-yl)-2-oxoacetate (2.46 g, 7.35 mmol) at rt. The resulting mixture was placed in a pre-heated oil bath (80° C.) and stirred for 24 h; concentrated, and charged (DCM) to a 80 g ISCO silica gel cartridge and gradient eluted (5-35% EtOAc/hexanes) using an Isolera chromatography station to give isopropyl 2-(5-bromo-4-(4-(3-isopropyl-1,2,4-oxadiazol-5-yl)piperidin-1-yl)-2,6-dimethylpyridin-3-yl)-2-oxoacetate 970 mg (27%). $^1$H NMR (500 MHz, DMSO-d$_6$) δ 5.04 (br. s, 1H), 3.18 (br. s, 2H), 3.07-3.02 (m, 2H), 2.89 (br. s, 1H), 2.62 (s, 3H), 2.31 (s, 3H), 2.05-2.02 (m, 2H), 1.64 (br. s, 2H), 1.26-1.24 (m, 12H). UPLC (M+H)=495.2.

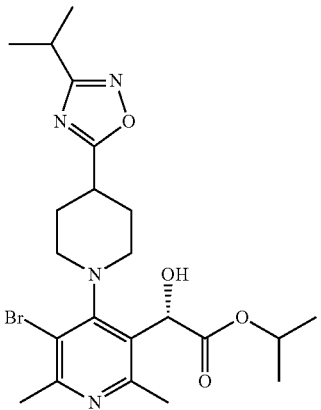 [SMILES: Cc1nc(C)c([C@H](O)C(=O)OC(C)C)c(N2CCC(c3nc(C(C)C)no3)CC2)c1Br]

The 1.6 mL of benzo[d][1,3,2]dioxaborole (416 mg, 3.47 mmol) was added to a nitrogen purged solution of isopropyl 2-(5-bromo-4-(4-(3-isopropyl-1,2,4-oxadiazol-5-yl)piperidin-1-yl)-2,6-dimethylpyridin-3-yl)-2-oxoacetate (950 mg, 1.93 mmol) and 0.6 mL of (R)-1-methyl-3,3-diphenylhexahydropyrrolo[1,2-c][1,3,2]oxazaborole (160 mg, 0.58 mmol) in toluene (20 mL) at −60° C. and allowed to warm to −15° C. before being placed in the freezer overnight. The reaction was quenched with 1M Na$_2$CO$_3$ (5 mL), diluted with EtOAc, and stirred for 20 min. The organic layer was washed with brine and dried (MgSO$_4$). The crude product was filtered, and charged (DCM) to a 40 g ISCO silica gel cartridge and gradient elution (5-60% EtOAc/hexanes) using an Isolera chromatography station gave (S)-isopropyl 2-(5-bromo-4-(4-(3-isopropyl-1,2,4-oxadiazol-5-yl)piperidin-1-yl)-2,6-dimethylpyridin-3-yl)-2-hydroxyacetate 550 mg (58%) as a mixture of diastereomers. $^1$H NMR (500 MHz, DMSO-d$_6$) δ 5.98/5.87 (s, 1H), 4.95-4.92 (m, 1H), 3.75-3.71 (m, 1H), 3.08-3.01 (m, 3H), 2.88-2.86 (m, 1H), 2.54 (s, 3H), 2.39 (s, 3H), 2.06-2.00 (m, 3H), 1.90-1.83 (m, 2H), 1.27 (d, J=6.6 Hz, 6H), 1.14 (d, J=5.9 Hz, 3H), 1.08 (d, J=5.9 Hz, 3H). UPLC (M+H)=497.2.

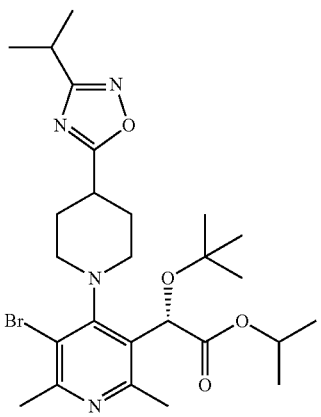 [SMILES: Cc1nc(C)c([C@H](OC(C)(C)C)C(=O)OC(C)C)c(N2CCC(c3nc(C(C)C)no3)CC2)c1Br]

The isobutylene gas was bubbled into a nitrogen purged, cooled (0° C.) solution of (S)-isopropyl 2-(5-bromo-4-(4-(3-isopropyl-1,2,4-oxadiazol-5-yl)piperidin-1-yl)-2,6-dimethylpyridin-3-yl)-2-hydroxyacetate (540 g, 1.1 mmol) and 0.15 mL of 70% HClO$_4$ in DCM (8 mL) for 20 min. The reaction mixture was allowed to warm to rt and stirred for 18 h in a pressure sealed vessel, diluted with DCM, washed with 1M Na$_2$CO$_3$ solution, and dried over Na$_2$SO$_4$. The crude product was charged (DCM) to a 40 g ISCO silica gel cartridge and gradient elution (5-65% EtOAc/hexanes) using an Isolera chromatography station gave (S)-isopropyl 2-(5-bromo-4-(4-(3-isopropyl-1,2,4-oxadiazol-5-yl)piperidin-1-yl)-2,6-dimethylpyridin-3-yl)-2-(tert-butoxy)acetate 469 mg (78%) as a mixture of diastereomers. $^1$H NMR (500 MHz, DMSO-d$_6$) δ 6.15 (br. s, 1H), 4.94-4.89 (m, 1H), 3.94-3.90 (m, 1H), 3.21-3.13 (m, 1H), 3.11-3.01 (m, 2H), 2.93-2.78 (m, 1H), 2.53 (s, 3H), 2.43 (s, 3H), 2.17-2.02 (m, 3H), 1.90-1.82 (m, 2H), 1.26 (d, J=7.0 Hz, 6H), 1.16-1.14 (m, 12H), 1.07 (d, J=5.9 Hz, 3H). UPLC (M+H)=553.2.

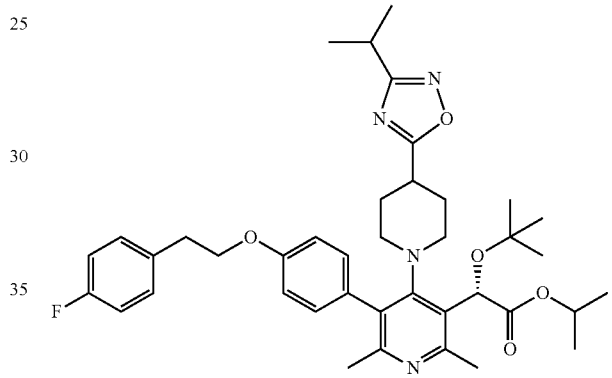

The diacetoxypalladium (6.11 mg, 0.027 mmol) was added to a nitrogen purged and degassed solution of (S)-isopropyl 2-(5-bromo-4-(4-(3-isopropyl-1,2,4-oxadiazol-5-yl)piperidin-1-yl)-2,6-dimethylpyridin-3-yl)-2-(tert-butoxy)acetate (150 mg, 0.272 mmol), 2-(4-(4-fluorophenethoxy)phenyl)-6-methyl-1,3,6,2-dioxazaborocane-4,8-dione (111 mg, 0.299 mmol), and 2-dicyclohexylphosphino-2',6'-dimethoxy-biphenyl (22.30 mg, 0.054 mmol), and potassium phosphate tribasic (432 mg, 2.040 mmol) in dioxane (4.5 mL) and water (0.9 mL) and stirred in a screw-capped pressure vessel for 4 h at 80° C. The reaction was allowed to cool, diluted with EtOAc, and the organic layer was washed with brine and dried (Na$_2$SO$_4$). The crude product was charged (DCM) to a 24 g ISCO silica gel cartridge and gradient elution (5-85% EtOAc/hexanes) using an Isolera chromatography station gave (S)-isopropyl 2-(tert-butoxy)-2-(5-(4-(4-fluorophenethoxy)phenyl)-4-(4-(3-isopropyl-1,2,4-oxadiazol-5-yl)piperidin-1-yl)-2,6-dimethylpyridin-3-yl)acetate 34.3 mg (18.4%) as a mixture of diastereomers. $^1$H NMR (500 MHz, DMSO-d$_6$) δ 7.41-7.39 (m, 2H), 7.24-7.22 (m, 1H), 7.17-7.13 (m, 2H), 7.03 (br. s, 2H), 6.96-6.94/6.87-6.86/6.80-6.78 (series m, 1H), 5.98 (br. s, 1H), 4.95 (br. s, 1H), 4.24 (t, J=6.2 Hz, 2H), 3.99-3.96 (m, 1H), 3.08 (t, J=6.2 Hz, 2H), 3.02-2.98 (m, 1H), 2.77-2.70 (m, 1H), 2.64-2.58 (m, 1H), 2.46 (s, 3H), 2.31-2.28 (m, 1H), 2.05 (s, 3H), 2.01-1.99 (m, 1H), 1.92-1.88 (m, 1H), 1.80 (br. s, 1H), 1.62-1.47 (m, 2H), 1.23-1.17 (m, 12H), 1.14 (s, 9H). UPLC (M+H)=687.5.

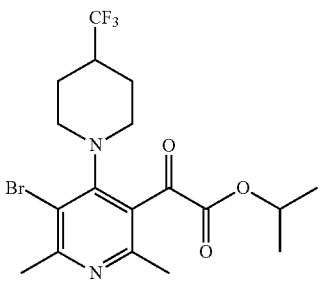

To a solution of 4-(trifluoromethyl)piperidine HCl (1.7 g, 8.97 mmol) and DIEA (3.13 mL, 17.9 mmol) in anhydrous CH$_3$CN (15 mL) was added isopropyl 2-(5-bromo-4-chloro-2,6-dimethylpyridin-3-yl)-2-oxoacetate (3.0 g, 8.97 mmol) at rt. The resulting mixture was placed in a pre-heated oil bath (80° C.) and stirred for 24 h; cooled, diluted with ether, washed with water, brine, and dried (MgSO$_4$). The crude product was charged (DCM) to a 80 g ISCO silica gel cartridge and gradient eluted (5-20% EtOAc/hexanes) using an Isolera chromatography station to give isopropyl 2-(5-bromo-2,6-dimethyl-4-(4-(trifluoromethyl)piperidin-1-yl) pyridin-3-yl)-2-oxoacetate 2.9 g (71%). $^1$H NMR (500 MHz, CDCl$_3$) δ 5.25-5.20 (m, 1H), 3.54-3.51 (m, 2H), 3.15 (dt, J=12.5, 2.0 Hz, 2H), 2.87 (s, 3H), 2.57 (s, 3H), 2.30-2.23 (m, 1H), 2.02-1.99 (m, 2H), 1.79 (dq, J=12.4, 4.1 Hz, 2H) 1.43 (d, J=6.2 Hz, 6H). UPLC (M+H)=453.2.

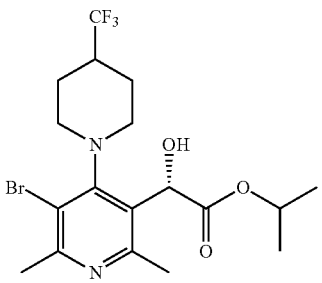

The 1.4 mL of benzo[d][1,3,2]dioxaborole (797 mg, 6.65 mmol) was added to a nitrogen purged solution of isopropyl 2-(5-bromo-2,6-dimethyl-4-(4-(trifluoromethyl)piperidin-1-yl)pyridin-3-yl)-2-oxoacetate (2 g, 4.43 mmol) and 0.89 mL of (R)-1-methyl-3,3-diphenylhexahydropyrrolo[1,2-c][1,3,2]oxazaborole (246 mg, 0.89 mmol) in toluene (40 mL) at −60° C. and allowed to warm to −15° C. before being placed in the freezer overnight. The reaction was quenched with 1M Na$_2$CO$_3$, diluted with EtOAc, and stirred for 30 min. The organic layer was washed with sat'd Na$_2$CO$_3$ solution, brine, and dried (MgSO$_4$). The crude product was charged (DCM) to a 40 g ISCO silica gel cartridge and gradient elution (0-30% EtOAc/hexanes) using an Isolera chromatography station gave isopropyl 2-(5-bromo-2,6-dimethyl-4-(4-(trifluoromethyl)piperidin-1-yl)pyridin-3-yl)-2-hydroxyacetate 2.04 g (100%) as a mixture of diastereomers. $^1$H NMR (500 MHz, DMSO-d$_6$) δ 5.97/5.82 (d, J=4.4 Hz, 1H), 4.97-4.92 (m, 1H), 3.65 (t, J=11.4 Hz, 1H), 3.20-3.17 (m, 1H), 2.99 (d, J=9.5 Hz, 1H), 2.85 (t, J=12.1 Hz, 1H), 2.53 (s, 3H), 2.40 (s, 3H), 2.31 (br. s, 1H), 1.83-1.77 (m, 2H), 1.69-1.55 (m, 2H), 1.15 (d, J=6.2 Hz, 3H), 1.07 (d, J=6.2 Hz, 3H). UPLC (M+H)=453.4.

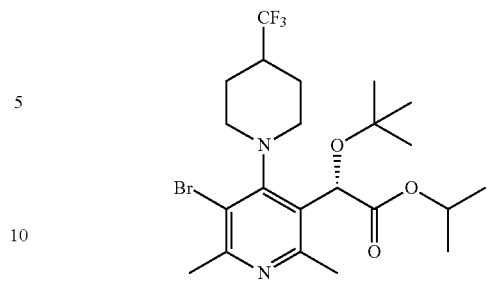

The isobutylene gas was bubbled into a nitrogen purged, cooled (0° C.) solution of 2-(5-bromo-2,6-dimethyl-4-(4-(trifluoromethyl)piperidin-1-yl)pyridin-3-yl)-2-hydroxyacetate (1.9 g, 4.19 mmol) and 0.4 mL of 70% HClO$_4$ in DCM (20 mL) for 20 min. The reaction mixture was allowed to warm to rt and stirred for 18 h in a pressure sealed vessel, after which it was recooled, and an additional 0.4 mL of 70% HClO4 was added, and the reaction stirred for 24 h at rt. The reaction was then diluted with DCM, washed with 1M Na$_2$CO$_3$ solution, and dried over MgSO$_4$. The crude product was charged (DCM) to a 80 g ISCO silica gel cartridge and gradient elution (5-12% EtOAc/hexanes) using an Isolera chromatography station gave (S)-isopropyl 2-(5-bromo-2,6-dimethyl-4-(4-(trifluoromethyl)piperidin-1-yl)pyridin-3-yl)-2-(tert-butoxy)acetate 1.9 g (90%) as a mixture of diastereomers. $^1$H NMR (500 MHz, DMSO) δ 6.11 (br. s, 1H), 4.93-4.91 (m, 1H), 3.84 (br. s, 1H), 3.209 (br. s, 1H), 3.08 (br. s, 1H), 2.89 (br. s, 1H), 2.53 (s, 3H), 2.44 (br. s, 3H), 1.96 (br. s, 1H), 1.86 (br. s, 2H), 1.64-1.53 (m, 2H), 1.16 (d, J=6.3 Hz, 3H), 1.14 (s, 9H), 1.07 (d, J=6.3 Hz, 3H). UPLC (M+H)=511.4.

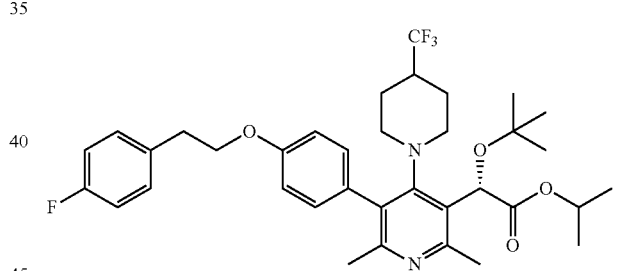

Palladium (II) acetate (6.61 mg, 0.029 mmol) was added to an argon-degassed solution of (S)-isopropyl 2-(5-bromo-2,6-dimethyl-4-(4-(trifluoromethyl)piperidin-1-yl)pyridin-3-yl)-2-(tert-butoxy)acetate (150 mg, 0.294 mmol), 2-(4-(4-fluorophenethoxy)phenyl)-6-methyl-1,3,6,2-dioxazaborocane-4,8-dione (120 mg, 0.324 mmol), dicyclohexyl(2',6'-dimethoxy-[1,1'-biphenyl]-2-yl)phosphine (24.18 mg, 0.059 mmol) and potassium phosphate tribasic (469 mg, 2.208 mmol) in dioxane (2 ml) and water (0.4 ml) stirred for 16 h at 80° C. and stirred in a screw-capped pressure vessel. The reaction was allowed to cool, diluted with EtOAc, and the organic layer was washed with brine and dried (MgSO$_4$). The crude product was charged (DCM) to a 40 g ISCO silica gel cartridge and gradient elution (0-100% EtOAc/hexanes) using an Isolera chromatography station gave (S)-isopropyl 2-(tert-butoxy)-2-(5-(4-(4-fluorophenethoxy)-phenyl)-2,6-dimethyl-4-(4-(trifluoromethyl)piperidin-1-yl)pyridin-3-yl)acetate 155 mg (82%) as a mixture of diastereomers. $^1$H NMR (500 MHz, DMSO-d$_6$) δ 7.41-7.38 (m, 2H), 7.22-7.21 (m, 1H), 7.15 (t, J=8.4 Hz, 2H), 7.02-6.98 (m, 3H), 5.92 (br. s, 1H), 4.96 (br. s, 1H), 4.23 (t, J=6.6 Hz, 2H), 3.42 (br. s, 2H), 3.07 (t, J=6.6 Hz, 2H), 2.60 (br. s, 2H), 2.46 (s, 3H), 2.06 (br. s, 1H), 2.04 (s, 3H), 1.88-1.70 (m, 2H), 1.62-1.52 (m, 2H), 1.19 (d, J=6.2 Hz, 3H), 1.13 (br. s, 12H). UPLC (M+H)=647.4.

J=10.6 Hz, 1H), 3.44 (br. s, 1H), 2.52 (s, 3H), 2.37 (s, 3H), 1.46-1.45 (m, 4H), 1.33-1.24 (m, 2H), 1.14 (d, J=6.2 Hz, 3H), 1.07 (d, J=6.2 Hz, 3H), 0.95/0.88 (s, 3H), 0.83 (t, J=7.0 Hz, 3H). UPLC (M+H)=429.3.

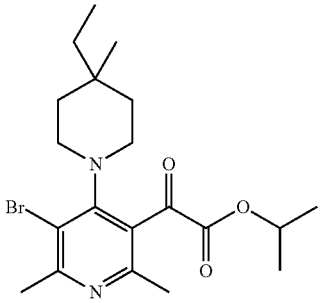 [SMILES: CCC1(C)CCN(c2c(Br)c(C)nc(C)c2C(=O)C(=O)OC(C)C)CC1]

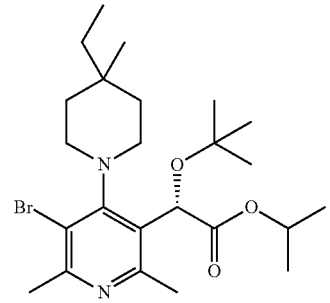 [SMILES: CCC1(C)CCN(c2c(Br)c(C)nc(C)c2[C@H](OC(C)(C)C)C(=O)OC(C)C)CC1]

To a solution of 4-ethyl-4-methylpiperidine (0.760 g, 5.98 mmol) and DIEA (2.1 mL, 11.9 mmol) in anhydrous CH$_3$CN (15 mL) was added isopropyl 2-(5-bromo-4-chloro-2,6-dimethylpyridin-3-yl)-2-oxoacetate (2.0 g, 5.98 mmol) at rt. The resulting mixture was placed in a pre-heated oil bath (80° C.) and stirred for 24 h; cooled, diluted with ether, washed with water, brine, and dried (MgSO$_4$). The crude product was charged (DCM) to a 80 g ISCO silica gel cartridge and gradient eluted (5-15% EtOAc/hexanes) using an Isolera chromatography station to give isopropyl 2-(5-bromo-4-(4-ethyl-4-methylpiperidin-1-yl)-2,6-dimethylpyridin-3-yl)-2-oxoacetate 2.51 g (99%). $^1$H NMR (500 MHz, CDCl$_3$) δ 5.07-5.02 (m, 1H), 3.32 (br. s, 2H), 3.18 (br.s, 2H), 2.61 (s, 3H), 2.29 (s, 3H), 1.29-1.28 (m 12H), 0.89 (s, 3H), 0.80 (t, J=7.3 Hz, 3H). UPLC (M+H)=427.3.

The isobutylene gas was bubbled into a nitrogen purged, cooled (0° C.) solution of (S)-isopropyl 2-(5-bromo-4-(4-ethyl-4-methylpiperidin-1-yl)-2,6-dimethylpyridin-3-yl)-2-hydroxyacetate (1.9 g, 4.19 mmol) and 0.6 mL of 70% HClO$_4$ in DCM (15 mL) for 20 min. The reaction mixture was allowed to warm to rt and stirred for 18 h in a pressure sealed vessel, after which it was recooled, and an additional 0.4 mL of 70% HClO4 was added at 0° C., and the reaction was stirred for 24 h at rt. The reaction was diluted with DCM, washed with 1M Na$_2$CO$_3$ solution, and dried over MgSO$_4$. The crude product was charged (DCM) to a 80 g ISCO silica gel cartridge and gradient elution (5-12% EtOAc/hexanes) using an Isolera chromatography station gave (S)-isopropyl 2-(5-bromo-4-(4-ethyl-4-methylpiperidin-1-yl)-2,6-dimethylpyridin-3-yl)-2-(tert-butoxy)acetate 1.67 g (64%) as a mixture of diastereomers. $^1$H NMR (500 MHz, DMSO-d$_6$) δ 6 (br. s, 1H), 4.94-4.89 (m, 1H), 3.98 (br. s, 1H), 3.45-3.39 (m, 2H), 2.82 (m, 1H), 2.53 (s, 3H), 2.42 (s, 3H), 1.53-1.43 (m, 4H), 1.32-1.26 (m, 2H), 1.14 (br. s, 12H), 1.07 (d, J=6.2 Hz, 3H), 0.99/0.91 (s, 3H), 0.8 (t, J=7.3 Hz, 3H). UPLC (M+H)=485.4.

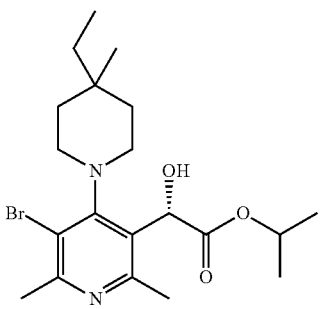

The 2.2 mL of benzo[d][1,3,2]dioxaborole (1.23 g, 10.4 mmol) was added to a nitrogen purged solution of isopropyl 2-(5-bromo-4-(4-ethyl-4-methylpiperidin-1-yl)-2,6-dimethylpyridin-3-yl)-2-oxoacetate (2.2 g, 5.17 mmol) and 2.1 mL of (R)-1-methyl-3,3-diphenylhexahydropyrrolo[1,2-c][1,3,2]oxazaborole (570 mg, 2.1 mmol) in toluene (50 mL) at −60° C. and allowed to warm to −15° C. before being placed in the freezer overnight. The reaction was quenched with 1M Na$_2$CO$_3$, diluted with EtOAc, and stirred for 30 min. The organic layer was washed with sat'd Na$_2$CO$_3$ solution, brine and dried (MgSO$_4$). The crude product was charged (DCM) to a 80 g ISCO silica gel cartridge and gradient elution (0-50% EtOAc/hexanes) using an Isolera chromatography station gave isopropyl (S)-isopropyl 2-(5-bromo-4-(4-ethyl-4-methylpiperidin-1-yl)-2,6-dimethylpyridin-3-yl)-2-hydroxyacetate 2.2 g (100%) as a mixture of diastereomers. $^1$H NMR (500 MHz, DMSO-d$_6$) δ 5.93 (m, 1H), 4.96-4.92 (m, 1H), 3.72 (t, J=11.7 Hz, 1H), 3.63-3.59 (m, 1H), 3.52 (t,

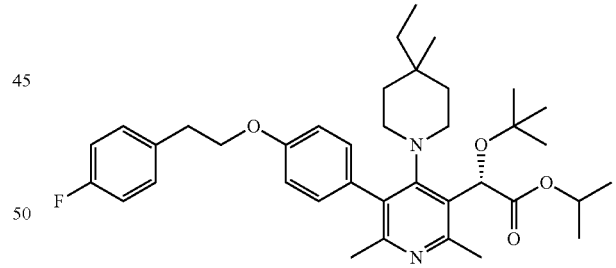

The Pd(Ph$_3$P)$_4$ (71 mg, 0.062 mmol) was added to a nitrogen purged and degassed solution of (S)-isopropyl 2-(5-bromo-2,6-dimethyl-4-(4-phenylpiperidin-1-yl)pyridin-3-yl)-2-(tert-butoxy)acetate (150 mg, 0.31 mmol), (4-(4-fluorophenethoxy)phenyl)boronic acid (89 mg, 0.34 mmol), and potassium phosphate tribasic (494 mg, 2.3 mmol) in dioxane (2 mL) and water (1.25 mL) and stirred in a screw-capped pressure vessel for 24 h at 80° C. The reaction was allowed to cool, diluted with EtOAc, and the organic layer was washed with brine and dried (MgSO$_4$). The crude product was charged (DCM) to a 40 g ISCO silica gel cartridge and gradient elution (0-25% EtOAc/hexanes) using an Isolera chromatography station (S)-isopropyl 2-(tert-butoxy)-2-(4-(4-ethyl-4-methylpiperidin-1-yl)-5-(4-(4-fluorophenethoxy)-phenyl)-2,6-dimethylpyridin-3-yl)acetate 148 mg (77%) as a mixture of diastereomers. $^1$H NMR (500 MHz, DMSO-$d_6$) δ 7.38-7.36 (m, 2H), 7.21 (d, J=8.4 Hz, 1H), 7.13 (t, J=7.7 Hz, 2H), 7.04-7.01 (m, 3H), 5.96 (br. s, 1H), 4.96-4.93 (m, 1H), 4.26-4.20 (m, 2H), 3.49-3.48 (m, 2H), 3.05 (t, J=6.2 Hz, 2H), 2.44 (s, 3H), 2.06 (s, 3H), 2.00-1.70 (m, 2H), 1.50-1.32 (m, 2H), 1.31-1.23 (m, 2H), 1.18 (d, J=6.2 Hz, 3H), 1.14-1.12 (m, 12H), 0.73-0.53 (m, 6H). UPLC (M+H)=619.6.

(100%) as a mixture of diastereomers. $^1$H NMR (500 MHz, DMSO-$d_6$) δ 5.94 (s, 1H), 4.94 (dt, J=12.3, 6.3 Hz, 1H), 3.57 (t, J=11.0 Hz, 1H), 3.34 (t, J=11.4 Hz 1H), 2.86 (d, J=11 Hz, 1H), 2.76 (d, J=11.0 Hz, 1H), 2.51 (s, 3H), 2.37 (s, 3H), 1.64-1.56 (m, 2H), 1.43 (br. s, 1H), 1.29-1.25 (m, 2H), 1.14 (d, J=6.2 Hz, 3H), 1.07 (d, J=6.2 Hz, 3H), 0.95 (d, J=6.2 Hz, 3H). UPLC (M+H)=401.2.

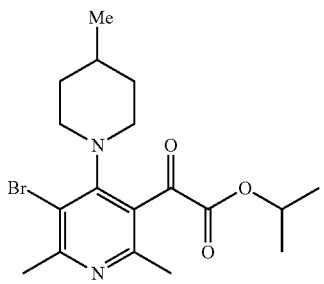

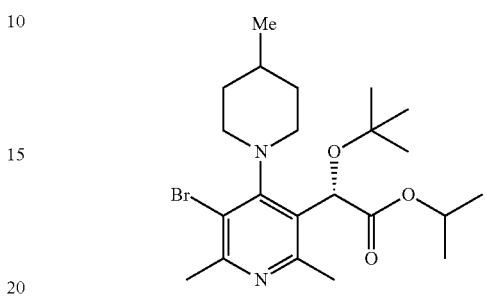

To a solution of 4-methylpiperidine (593 mg, 5.98 mmol) and DIEA (2.1 mL, 12 mmol) in anhydrous CH$_3$CN (15 mL) was added isopropyl 2-(5-bromo-4-chloro-2,6-dimethylpyridin-3-yl)-2-oxoacetate (2.0 g, 5.98 mmol) at rt. The resulting mixture was placed in a pre-heated oil bath (80° C.) and stirred for 24 h; cooled, diluted with ether, washed with water, brine, and dried (MgSO$_4$). The crude product was charged (DCM) to a 80 g ISCO silica gel cartridge and gradient eluted (5-35% EtOAc/hexanes) using an Isolera chromatography station gave isopropyl 2-(5-bromo-2,6-dimethyl-4-(4-methylpiperidin-1-yl)pyridin-3-yl)-2-oxoacetate 1.99 g (84%). $^1$H NMR (500 MHz, DMSO-$d_6$) δ 5.08-5.03 (m, 1H), 3.41-3.39 (m, 2H), 2.83 (br. s, 2H), 2.60 (s, 3H), 2.29 (s, 3H), 1.58 (d, J=12.5 Hz, 2H), 1.44 (br. s, 1H), 1.29 (d, J=6.2 Hz, 6H), 1.09-1.07 (m, 2H), 0.92 (d, J=6.2 Hz, 3H). UPLC (M+H)=399.2.

The isobutylene gas was bubbled into a nitrogen purged, cooled (0° C.) solution of (S)-isopropyl 2-(5-bromo-2,6-dimethyl-4-(4-methylpiperidin-1-yl)pyridin-3-yl)-2-hydroxyacetate (2.25 g, 5.63 mmol) and 0.53 mL of 70% HClO$_4$ in DCM (30 mL) for 20 min. The reaction mixture was allowed to warm to rt and stirred for 72 h in a pressure sealed vessel. The reaction was then diluted with DCM, washed with 1M Na$_2$CO$_3$ solution, and dried over MgSO$_4$. The crude product was charged (DCM) to a 80 g ISCO silica gel cartridge and gradient elution (0-12% EtOAc/hexanes) using an Isolera chromatography station gave (S)-isopropyl 2-(5-bromo-2,6-dimethyl-4-(4-methylpiperidin-1-yl)pyridin-3-yl)-2-(tert-butoxy)acetate 1.82 g (71%) as a mixture of diastereomers. $^1$H NMR (500 MHz, DMSO-$d_6$) δ 6.16 (s, 1H), 4.93-4.90 (m, 1H), 3.82-3.77 (m, 1H), 3.24 (t, J=10.6 Hz 1H), 2.98 (d, J=9.9 Hz, 1H), 2.74 (br. s, 1H), 2.51 (s, 3H), 2.41 (s, 3H), 1.73 (br. s, 1H), 1.62 (br. s, 1H), 1.49 (br. s, 1H), 1.28-1.23 (m, 2H), 1.16-1.14 (m, 12H), 1.07 (d, J=6.2 Hz, 3H), 0.97 (d, J=6.2 Hz, 3H). UPLC (M+H)=457.3.

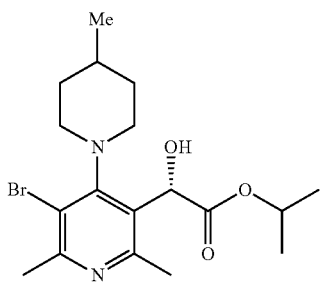 [SMILES: Cc1nc(C)c([C@H](O)C(=O)OC(C)C)c(N2CCC(C)CC2)c1Br]

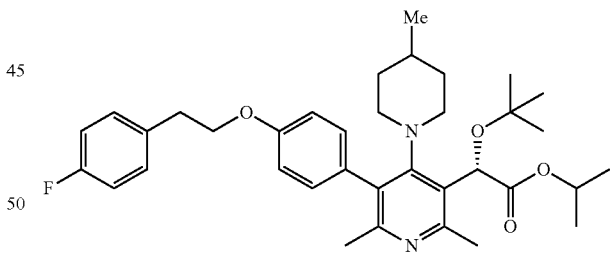

The 2.0 mL of benzo[d][1,3,2]dioxaborole (2.3 g, 9.56 mmol) was added to a nitrogen purged solution of isopropyl 2-(5-bromo-2,6-dimethyl-4-(4-methylpiperidin-1-yl)pyridin-3-yl)-2-oxoacetate (1.9 g, 4.78 mmol) and 1.9 mL of (R)-1-methyl-3,3-diphenylhexahydropyrrolo[1,2-c][1,3,2]oxazaborole (530 mg, 1.9 mmol) in toluene (45 mL) at −60° C. and allowed to warm to −15° C. before being placed in the freezer overnight. The reaction was quenched with 1M Na$_2$CO$_3$, diluted with EtOAc, and stirred for 30 min. The organic layer was washed with sat'd Na$_2$CO$_3$ solution, brine and dried (MgSO$_4$). The crude product was charged (DCM) to a 80 g ISCO silica gel cartridge and gradient elution (0-30% EtOAc/hexanes) using an Isolera chromatography station gave (S)-isopropyl 2-(5-bromo-2,6-dimethyl-4-(4-methylpiperidin-1-yl)pyridin-3-yl)-2-hydroxyacetate 1.9 g Pd(Ph$_3$P)$_4$ (76 mg, 0.066 mmol) was added to an argon-degassed solution of (S)-isopropyl 2-(5-bromo-2,6-dimethyl-4-(4-methylpiperidin-1-yl)pyridin-3-yl)-2-(tert-butoxy)acetate (150 mg, 0.329 mmol), 2-(4-(4-fluorophenethoxy)phenyl)-6-methyl-1,3,6,2-dioxazaborocane-4,8-dione (94 mg, 0.362 mmol), potassium phosphate tribasic (524 mg, 2.47 mmol) in dioxane (2 ml) and water (0.5 ml) stirred in a screw-capped pressure vessel for 16 h at 80° C. The reaction was allowed to cool, diluted with EtOAc, and the organic layer was washed with brine and dried (MgSO$_4$). The crude product was charged (DCM) to a 40 g ISCO silica gel cartridge and gradient elution (0-20% EtOAc/hexanes) using an Isolera chromatography station gave (S)-isopropyl 2-(tert-butoxy)-2-(5-(4-(4-fluorophenethoxy)phenyl)-2,6-dimethyl-4-(4-methylpiperidin-1-yl)pyridin-3-yl)acetate 139 mg (72%) as a mixture of diastereomers. ¹H NMR (500 MHz, DMSO-d₆) δ 7.44-7.38 (m, 2H), 7.20 (d, J=7.3 Hz, 1H), 7.15 (t, J=8.8 Hz, 2H), 7.03-6.94 (m, 3H), 5.97 (br. s, 1H), 4.96 (dt, J=12.3, 6.3 Hz, 1H), 4.23 (t, J=6.6 Hz, 2H), 3.36-3.29 (m, 4H), 3.07 (t, J=6.6 Hz, 2H), 2.43 (s, 3H), 2.04 (s, 3H), 1.75 (t, J=11.4 Hz, 1H), 1.52-1.47 (m, 1H), 1.37 (br. s, 1H), 1.19 (d, J=6.2 Hz, 3H), 1.15-1.13 (m, 12H), 1.08-1.02 (m, 2H), 0.84 (d, J=5.1 Hz, 3H). UPLC (M+H)=591.56.

(0-30% EtOAc/hexanes) using an Isolera chromatography station gave (S)-isopropyl 2-(5-bromo-4-(4-methoxy-4-methylpiperidin-1-yl)-2,6-dimethylpyridin-3-yl)-2-hydroxyacetate 1.48 g (95%) as a mixture of diastereomers. ¹H NMR (500 MHz, DMSO-d₆) δ 5.89 (br. s, 1H), 4.95-4.92 (m, 1H), 3.78 (t, J=11.0 Hz, 1H), 3.53 (t, J=10.6 Hz, 1H), 3.37-3.35 (m, 1H), 3.25 (br. s, 1H), 3.14 (s, 3H), 2.52 (s, 3H), 2.37 (s, 3H), 1.75-1.69 (m, 2H), 1.64-1.52 (m, 2H), 1.15-1.16 (m, 6H). 1.07 (d, J=6.2 Hz, 3H). UPLC (M+H)=431.3.

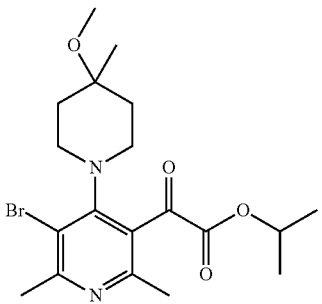

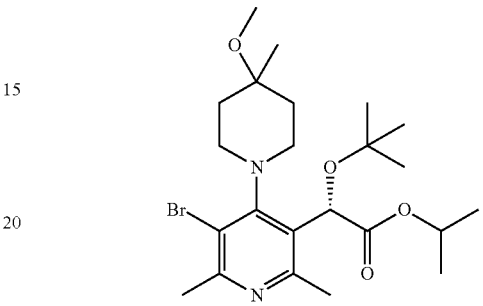

To a solution of 4-methoxy-4-methylpiperidine, HCl (1.0 g, 6.04 mmol) and DIEA (4.2 mL, 24.5 mmol) in anhydrous CH₃CN (30 mL) was added isopropyl 2-(5-bromo-4-chloro-2,6-dimethylpyridin-3-yl)-2-oxoacetate (3.4 g, 6.04 mmol) at rt. The resulting mixture was placed in a pre-heated oil bath (80° C.) and stirred for 24 h; cooled, diluted with ether, washed with water, brine, and dried (MgSO₄). The crude product was charged (DCM) to a 80 g ISCO silica gel cartridge and gradient eluted (5-35% EtOAc/hexanes) using an Isolera chromatography station gave isopropyl 2-(5-bromo-4-(4-methoxy-4-methylpiperidin-1-yl)-2,6-dimethylpyridin-3-yl)-2-oxoacetate 1.57 g (61%). ¹H NMR (500 MHz, DMSO-d₆) δ 5.08-5.03 (m, 1H), 3.44-3.40 (m, 4H), 3.11 (s, 3H), 2.60 (s, 3H), 2.29 (s, 3H), 1.67 (d, J=13.2 Hz, 2H), 1.43 (br. s., 2H), 1.29 (d, J=6.2 Hz, 6H), 1.11 (s, 3H). UPLC (M+H)=429.3.

The isobutylene gas was bubbled into a nitrogen purged, cooled (0° C.) solution of (S)-isopropyl 2-(5-bromo-4-(4-methoxy-4-methylpiperidin-1-yl)-2,6-dimethylpyridin-3-yl)-2-hydroxyacetate (1.45 g, 3.38 mmol) and 0.32 mL of 70% HClO₄ in DCM (30 mL) for 20 min. The reaction mixture was allowed to warm to rt and stirred for 48 h in a pressure sealed vessel. The reaction was then diluted with DCM, washed with 1M Na₂CO₃ solution, and dried over MgSO₄. The crude product was charged (DCM) to a 80 g ISCO silica gel cartridge and gradient elution (0-30% EtOAc/hexanes) using an Isolera chromatography station gave (S)-isopropyl 2-(5-bromo-4-(4-methoxy-4-methylpiperidin-1-yl)-2,6-dimethylpyridin-3-yl)-2-(tert-butoxy)acetate 1.35 g (82%) as a mixture of diastereomers. ¹H NMR (500 MHz, DMSO-d₆) δ 6.18 (br. s, 1H), 4.93-4.89 (m, 1H), 4.01 (br. s, 1H), 3.46 (t, J=11.0 Hz 1H), 3.37-3.28 (m, 2H), 3.15 (s, 3H), 2.52 (s, 3H), 2.42 (s, 3H), 1.79-1.51 (series m, 4H), 1.16-1.14 (m, 15H), 1.07 (d, J=6.2 Hz, 3H). UPLC (M+H)=487.4.

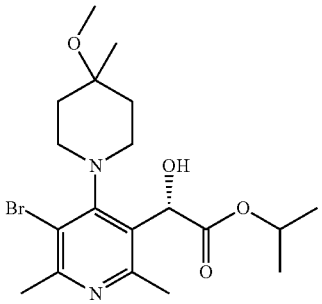 [SMILES: COC1(C)CCN(c2c(Br)c(C)nc(C)c2[C@H](O)C(=O)OC(C)C)CC1]

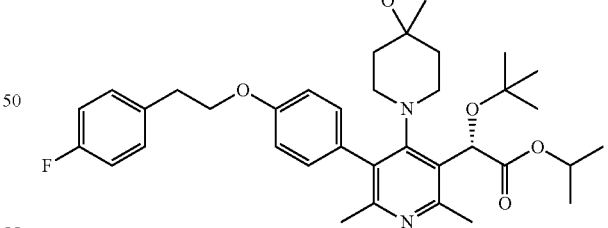

The 1.55 mL of benzo[d][1,3,2]dioxaborole (870 mg, 7.25 mmol) was added to a nitrogen purged solution of isopropyl 2-(5-bromo-4-(4-methoxy-4-methylpiperidin-1-yl)-2,6-dimethylpyridin-3-yl)-2-oxoacetate (1.55 g, 3.63 mmol) and 1.45 mL of (R)-1-methyl-3,3-diphenylhexahydropyrrolo[1,2-c][1,3,2]oxazaborole (402 mg, 1.45 mmol) in toluene (30 mL) at −60° C. and allowed to warm to −15° C. before being placed in the freezer overnight. The reaction was quenched with 1M Na₂CO₃, diluted with EtOAc, and stirred for 30 min. The organic layer was washed with sat'd Na₂CO₃ solution, brine, and dried (MgSO₄). The crude product was charged (DCM) to a 80 g ISCO silica gel cartridge and gradient elution PD(Ph₃P)₄ (143 mg, 0.124 mmol) was added to an argon-degassed solution of (S)-isopropyl 2-(5-bromo-4-(4-methoxy-4-methylpiperidin-1-yl)-2,6-dimethylpyridin-3-yl)-2-(tert-butoxy)acetate (300 mg, 0.618 mmol), 2-(4-(4-fluorophenethoxy)phenyl)-6-methyl-1,3,6,2-dioxazaborocane-4,8-dione (177 mg, 0.68 mmol), potassium phosphate tribasic (984 mg, 4.63 mmol) in dioxane (5 ml) and water (1 ml) stirred in a screw-capped pressure vessel for 16 h at 90° C. The reaction was allowed to cool, diluted with EtOAc, and the organic layer was washed with brine and dried (MgSO₄). The crude product was charged (DCM) to a 40 g ISCO silica gel cartridge and gradient elution (0-50% EtOAc/hexanes) using an Isolera chromatography station gave (S)-isopropyl 2-(tert-butoxy)-2-(5-(4-(4-fluorophenethoxy)phenyl)-4-(4-methoxy-4-methylpiperidin-1-yl)-2,6-dimethylpyridin-3-yl)acetate 300 mg (78%) as a mixture of diastereomers. $^1$H NMR (500 MHz, DMSO-$d_6$) δ 7.39-7.37 (m, 2H), 7.21-7.12 (m, 3H), 7.04-7.00 (m, 3H), 5.98 (br. s, 1H), 4.96-4.93 (m, 1H), 4.24-4.21 (m, 2H), 3.42-3.40 (m, 2H), 3.26-3.21 (m, 1H), 3.07-3.05 (m, 2H), 2.90-2.86 (m, 1H), 2.81 (s, 3H), 2.44 (s, 3H), 2.05 (s, 3H), 1.53-1.42 (m, 2H), 1.33-1.25 (m, 2H), 1.18 (d, J=6.2 Hz, 3H), 1.14-1.12 (m, 12H), 1.00/0.81 (s, 3H). UPLC (M+H)=621.6.

brine, and dried (MgSO$_4$). The crude product was charged (DCM) to a 80 g ISCO silica gel cartridge and gradient elution (0-30% EtOAc/hexanes) using an Isolera chromatography station gave (S)-isopropyl 2-(5-bromo-4-(4-cyano-4-methylpiperidin-1-yl)-2,6-dimethylpyridin-3-yl)-2-hydroxyacetate 674 mg (86%) as a mixture of diastereomers. $^1$H NMR (500 MHz, CD$_3$OD) δ 5.89 (s, 1H), 5.10-5.05 (m, 1H), 4.13-4.05 (m, 1H), 3.78 (dt, J=11.7, 3.7 Hz, 1H), 3.06 (d, J=12.2 Hz, 1H), 2.86 (d, J=12.2 Hz, 1H), 2.63 (s, 3H), 2.51 (s, 3H), 1.94-1.86 (m, 3H), 1.79-1.73 (m, 1H), 1.46 (s, 3H), 1.24 (d, J=6.1 Hz, 3H), 1.15 (d, J=6.2 Hz, 3H). UPLC (M+H)=426.3.

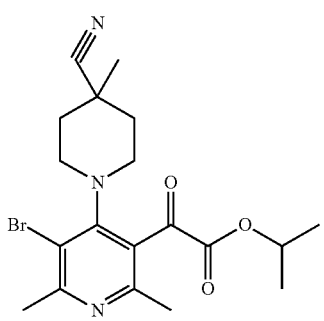 [SMILES: Cc1nc(C)c(C(=O)C(=O)OC(C)C)c(N2CCC(C)(C#N)CC2)c1Br]

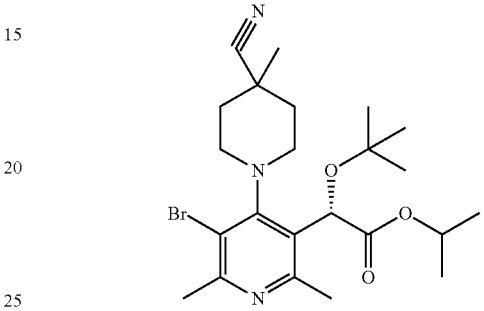

To a solution of 4-methylpiperidine-4-carbonitrile, HCl (1.0 g, 6.22 mmol) and DIEA (4.4 mL, 24.9 mmol) in anhydrous CH$_3$CN (30 mL) was added isopropyl 2-(5-bromo-4-chloro-2,6-dimethylpyridin-3-yl)-2-oxoacetate (2.1 g, 6.22 mmol) at rt. The resulting mixture was placed in a pre-heated oil bath (80° C.) and stirred for 72 h; cooled, diluted with ether, washed with water, brine, and dried (MgSO$_4$). The crude product was charged (DCM) to a 80 g ISCO silica gel cartridge and gradient eluted (5-35% EtOAc/hexanes) using an Isolera chromatography station to give isopropyl 2-(5-bromo-4-(4-cyano-4-methylpiperidin-1-yl)-2,6-dimethylpyridin-3-yl)-2-oxoacetate 1.0 g (38%). $^1$H NMR (500 MHz, DMSO-$d_6$) δ 5.08-5.03 (m, 1H), 3.54-3.40 (m, 4H), 2.61 (s, 3H), 2.30 (s, 3H), 1.92 (d, J=12.4 Hz, 2H), (2H missing), 1.35 (s, 3H), 1.28 (d, J=5.9 Hz, 6H). UPLC (M+H)=424.3.

The isobutylene gas was bubbled into a nitrogen purged, cooled (0° C.) solution of (S)-isopropyl 2-(5-bromo-4-(4-cyano-4-methylpiperidin-1-yl)-2,6-dimethylpyridin-3-yl)-2-hydroxyacetate (670 mg, 1.58 mmol) and 0.15 mL of 70% HClO$_4$ in DCM (15 mL) for 20 min. The reaction mixture was allowed to warm to rt and stirred for 48 h in a pressure sealed vessel. The reaction was then diluted with DCM, washed with 1M Na$_2$CO$_3$ solution, and dried over MgSO$_4$. The crude product was charged (DCM) to a 80 g ISCO silica gel cartridge and gradient elution (0-50% EtOAc/hexanes) using an Isolera chromatography station gave (S)-isopropyl 2-(5-bromo-4-(4-cyano-4-methylpiperidin-1-yl)-2,6-dimethylpyridin-3-yl)-2-(tert-butoxy)acetate 651 mg (86%) as a mixture of diastereomers. $^1$H NMR (500 MHz, DMSO-$d_6$) δ 6.06 (br. s, 1H), 4.93-4.89 (m, 1H), 4.03 (br. s, 1H), 3.43-3.41 (m, 2H), 3.00 (br. s, 1H), 2.53 (s, 3H), 2.43 (s, 3H), 2.05 (br. s, 1H), 1.93 (br. s, 1H), 1.80-1.71 (m, 1H), 1.58 (br. s, 1H), 1.42 (s, 3H), 1.15-1.13 (m, 12H), 1.05 (d, J=6.2 Hz, 3H). UPLC (M+H)=482.4.

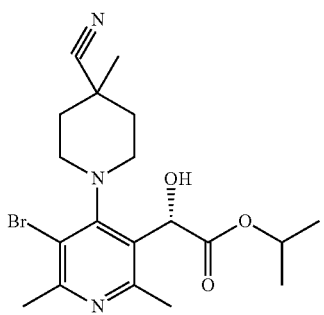 [SMILES: Cc1nc(C)c([C@H](O)C(=O)OC(C)C)c(N2CCC(C)(C#N)CC2)c1Br]

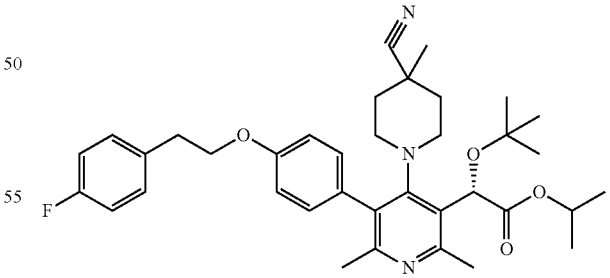

The 1.55 mL of benzo[d][1,3,2]dioxaborole (443 mg, 3.69 mmol) was added to a nitrogen purged solution of isopropyl 2-(5-bromo-4-(4-cyano-4-methylpiperidin-1-yl)-2,6-dimethylpyridin-3-yl)-2-oxoacetate (780 mg, 1.85 mmol) and 0.74 mL of (R)-1-methyl-3,3-diphenylhexahydropyrrolo[1,2-c][1,3,2]oxazaborole (205 mg, 0.74 mmol) in toluene (18 mL) at −60° C. and allowed to warm to −15° C. before being placed in the freezer overnight. The reaction was quenched with 1M Na$_2$CO$_3$, diluted with EtOAc, and stirred for 30 min. The organic layer was washed with sat'd Na$_2$CO$_3$ solution, Pd(Ph$_3$P)$_4$ (144 mg, 0.125 mmol) was added to an argon-degassed solution (S)-isopropyl 2-(5-bromo-4-(4-cyano-4-methylpiperidin-1-yl)-2,6-dimethylpyridin-3-yl)-2-(tert-butoxy)acetate (300 mg, 0.624 mmol), 2-(4-(4-fluorophenethoxy)phenyl)-6-methyl-1,3,6,2-dioxazaborocane-4,8-dione (179 mg, 0.687 mmol), potassium phosphate tribasic (994 mg, 4.68 mmol) in dioxane (4 ml) and water (0.8 ml) stirred in a screw-capped pressure vessel for 16 h at 90° C. The reaction was allowed to cool, diluted with EtOAc, and the organic layer was washed with brine and dried (MgSO₄). The crude product was charged (DCM) to a 40 g ISCO silica gel cartridge and gradient elution (0-70% EtOAc/hexanes) using an Isolera chromatography station gave (S)-isopropyl 2-(tert-butoxy)-2-(4-(4-cyano-4-methylpiperidin-1-yl)-5-(4-(4-fluorophenethoxy)phenyl)-2,6-dimethylpyridin-3-yl)acetate 291 mg (76%) as a mixture of diastereomers. ¹H NMR (500 MHz, DMSO-d₆) δ 7.38-7.3 (m, 2H), 7.19 (br. s, 1H), 7.13 (d, J=8.4 Hz, 2H), 7.08-7.06 (m, 1H), 7.02-7.00 (m, 2H), 5.91 (br. s, 1H), 4.94 (br. s, 1H), 4.28-4.23 (m, 1H), 4.19-4.15 (m, 1H), 3.44-3.40 (m, 4H), 3.05 (t, J=6.2 Hz, 2H), 2.45 (s, 3H), 2.06 (s, 3H), 1.80 (br. s, 1H), 1.69 (br. s, 1H), 1.55 (br. s, 1H), 1.34-1.32 (m, 1H), 1.29 (s, 3H), 1.18 (d, J=6.2 Hz, 3H), 1.15-1.1 (m, 12H). UPLC (M+H)=616.6.

placed in the freezer overnight. The reaction was quenched with 1M Na₂CO₃, diluted with EtOAc, and stirred for 30 min. The organic layer was washed with sat'd Na₂CO₃ solution, brine and dried (MgSO₄). The crude product was charged (DCM) to a 80 g ISCO silica gel cartridge and gradient elution (0-60% EtOAc/hexanes) using an Isolera chromatography station gave (S)-isopropyl 2-(5-bromo-2,6-dimethyl-4-(4-(propan-2-ylidene)piperidin-1-yl)pyridin-3-yl)-2-hydroxyacetate 1.0 g (100%). ¹H NMR (500 MHz, DMSO-d₆) δ 5.90 (d, J=3.3 Hz, 1H), 4.95 (dt, J=12.3, 6.2 Hz, 1H), 3.43-3.41 (m, 2H), 3.23 (t, J=10.6 Hz, 1H), 2.86 (d, J=10.3 Hz, 1H), 2.56-2.51 (m, 2H), 2.51 (s, 3H), 2.38 (s, 3H), 2.16-2.08 (m, 2H), 1.67 (s, 6H), 1.15 (d, J=6.2 Hz, 3H), 1.08 (d, J=6.2 Hz, 3H). UPLC (M+H)=427.2.

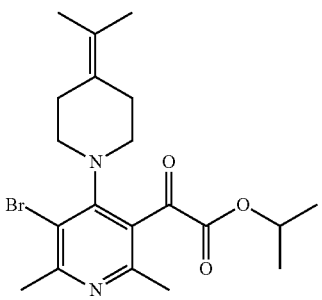 [SMILES: CC(C)=C1CCN(c2c(Br)c(C)nc(C)c2C(=O)C(=O)OC(C)C)CC1]

To a solution of 4-(propan-2-ylidene)piperidine (500 mg, 3.99 mmol) and DIEA (2.1 mL, 11.98 mmol) in anhydrous CH₃CN (30 mL) was added isopropyl 2-(5-bromo-4-chloro-2,6-dimethylpyridin-3-yl)-2-oxoacetate (1.48 g, 3.99 mmol) at rt. The resulting mixture was placed in a pre-heated oil bath (80° C.) and stirred for 24 h; cooled, diluted with ether, washed with water, brine, and dried (MgSO₄). The crude product was charged (DCM) to an 80 g ISCO silica gel cartridge and gradient eluted (0-35% EtOAc/hexanes) using an Isolera chromatography station gave isopropyl 2-(5-bromo-2,6-dimethyl-4-(4-(propan-2-ylidene)piperidin-1-yl)pyridin-3-yl)-2-oxoacetate 1.04 g (61.8%). ¹H NMR (500 MHz, DMSO-d₆) δ 5.09-5.04 (m, 1H), 3.50-3.48 (br. s, 2H), 3.03 (br. s, 2H), 2.60 (s, 3H), 2.30 (s, 3H), 2.23 (br. s, 4), 1.64 (s, 6H), 1.25 (d, J=6.2 Hz, 6H). UPLC (M+H)=425.3.

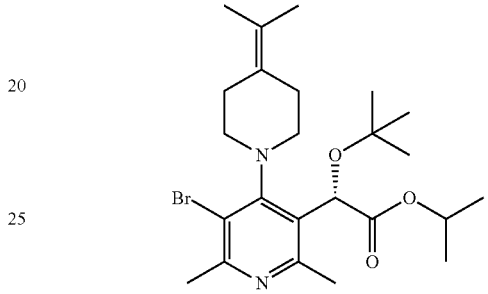

The isobutylene gas was bubbled into a nitrogen purged, cooled (0° C.) solution of (S)-isopropyl 2-(5-bromo-2,6-dimethyl-4-(4-(propan-2-ylidene)piperidin-1-yl)pyridin-3-yl)-2-hydroxyacetate (1.0 g, 2.3 mmol) and 0.30 mL of 70% HClO₄ in DCM (30 mL) for 20 min. The reaction mixture was allowed to warm to rt and stirred for 48 h in a pressure sealed vessel. The reaction was then diluted with DCM, washed with 1M Na₂CO₃ solution, and dried over MgSO₄. The crude product was charged (DCM) to a 80 g ISCO silica gel cartridge and gradient elution (0-50% EtOAc/hexanes) using an Isolera chromatography station gave (S)-isopropyl 2-(5-bromo-2,6-dimethyl-4-(4-(propan-2-ylidene)piperidin-1-yl)pyridin-3-yl)-2-(tert-butoxy)acetate 1.0 g (67%). ¹H NMR (500 MHz, DMSO-d₆) δ 6.24 (br. s, 1H), 4.95-4.90 (m, 1H), 3.68 (br. s, 1H), 3.18-3.12 (m, 1H), 3.06 (br. s, 1H), 2.83 (br. s, 1H), 2.72 (br. s, 1H), 2.59 (br. s, 1H), 2.51 (s, 3H), 2.43 (s, 3H), 2.13-2.01 (m, 2H), 1.68 (s, 6H), 1.17-1.15 (m, 12H), 1.08 (d, J=6.2 Hz, 3H). UPLC (M+H)=483.2.

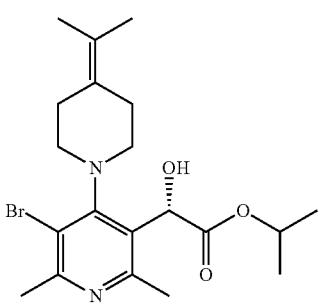 [SMILES: CC(C)=C1CCN(c2c(Br)c(C)nc(C)c2[C@H](O)C(=O)OC(C)C)CC1]

The 1.0 mL of benzo[d][1,3,2]dioxaborole (567 mg, 4.72 mmol) was added to a nitrogen purged solution of isopropyl 2-(5-bromo-2,6-dimethyl-4-(4-(propan-2-ylidene)piperidin-1-yl)pyridin-3-yl)-2-oxoacetate (1.0 g, 2.36 mmol) and 0.95 mL of (R)-1-methyl-3,3-diphenylhexahydropyrrolo[1,2-c][1,3,2]oxazaborole (262 mg, 0.95 mmol) in toluene (20 mL) at −60° C. and allowed to warm to −15° C. before being

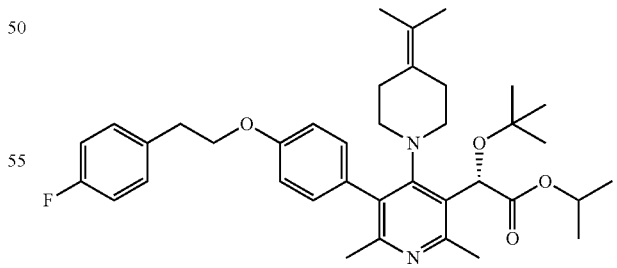

The diacetoxypalladium (11.5 mg, 0.051 mmol) was added to a argon purged and degassed solution of (S)-isopropyl 2-(5-bromo-2,6-dimethyl-4-(4-(propan-2-ylidene)piperidin-1-yl)pyridin-3-yl)-2-(tert-butoxy)acetate (247 mg, 0.513 mmol), 2-(4-(4-fluorophenethoxy)phenyl)-6-methyl-1,3,6,2-dioxazaborocane-4,8-dione (209 mg, 0.564 mmol), and 2-dicyclohexylphosphino-2',6'-dimethoxy-biphenyl (42.0 mg, 0.103 mmol), and potassium phosphate tribasic (817 mg, 3.85 mmol) in dioxane (4 mL) and water (1 mL) and stirred in a screw-capped pressure vessel for 16 h at 90° C. The reaction was allowed to cool, diluted with EtOAc, and the organic layer was washed with brine and dried (MgSO$_4$). The crude product was charged (DCM) to a 40 g ISCO silica gel cartridge and gradient elution (0-35% EtOAc/hexanes) using an Isolera chromatography station (S)-isopropyl 2-(tert-butoxy)-2-(5-(4-(4-fluorophenethoxy)phenyl)-2,6-dimethyl-4-(4-(propan-2-ylidene)piperidin-1-yl)pyridin-3-yl)acetate 155 mg (49%). $^1$H NMR (500 MHz, DMSO-d$_6$) δ 7.39-7.36 (m, 2H), 7.21-7.20 (m, 1H), 7.14 (t, J=8.4 Hz, 2H), 6.99 (t, J=8.1 Hz, 2H), 6.92 (d, J=8.1 Hz, 1H), 6.05 (br. s, 1H), 4.99-4.94 (m, 1H), 4.22 (t, J=6.6 Hz, 2H), 3.34 (br. s, 2H), 3.05 (t, J=6.6 Hz, 2H), 2.56 (br. s, 2H), 2.46 (s, 3H), 2.35 (br. s, 2H), 2.02 (s, 3H), 1.83 (br. s, 2H), 1.54 (s, 6H), 1.21 (d, J=5.9 Hz, 3H), 1.16-1.14 (m, 12H). UPLC (M+H)=617.4.

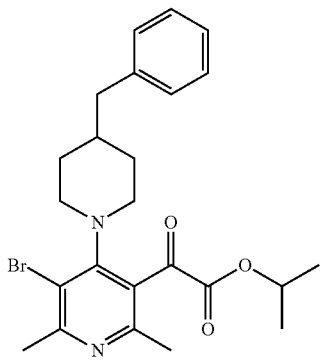

To a solution of 4-benzylpiperidine (0.80 g, 4.56 mmol) and DIEA (2.4 mL, 13.7 mmol) in anhydrous CH$_3$CN (30 mL) was added isopropyl 2-(5-bromo-4-chloro-2,6-dimethylpyridin-3-yl)-2-oxoacetate (1.7 g, 4.56 mmol) at rt. The resulting mixture was placed in a pre-heated oil bath (80° C.) and stirred for 18 h; cooled, diluted with ether, washed with water, brine, and dried (MgSO$_4$). The crude product was charged (DCM) to a 80 g ISCO silica gel cartridge and gradient eluted (0-25% EtOAc/hexanes) using an Isolera chromatography station gave isopropyl 2-(4-(4-benzylpiperidin-1-yl)-5-bromo-2,6-dimethylpyridin-3-yl)-2-oxoacetate 1.48 g (68%). $^1$H NMR (500 MHz, DMSO-d$_6$) δ 7.3-7.27 (m, 2H), 7.20-7.15 (m, 3H), 5.09-5.04 (m, 1H), 3.23 (br. s, 2H), 2.84 (br. s, 2H), 2.59 (s, 3H), 2.51-2.49 (m, 2H), 2.28 (s, 3H), 1.61 (br. s, 1), 1.55 (d, J=13.6 Hz, 2H), 1.30 (d, J=6.2 Hz, 6H), 1.14 (br. s, 2H). UPLC (M+H)=475.2.

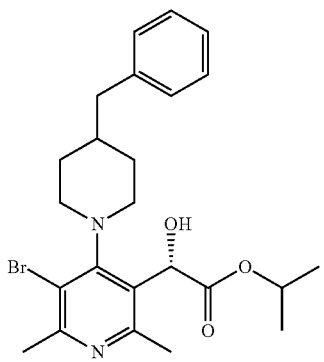 [SMILES: Cc1nc(C)c([C@H](O)C(=O)OC(C)C)c(N2CCC(Cc3ccccc3)CC2)c1Br]

The 1.3 mL of benzo[d][1,3,2]dioxaborole (709 mg, 5.91 mmol) was added to a nitrogen purged solution of isopropyl 2-(4-(4-benzylpiperidin-1-yl)-5-bromo-2,6-dimethylpyridin-3-yl)-2-oxoacetate (1.4 g, 2.96 mmol) and 1.2 mL of (R)-1-methyl-3,3-diphenylhexahydropyrrolo[1,2-c][1,3,2]oxazaborole (328 mg, 1.18 mmol) in toluene (30 mL) at −60° C. and allowed to warm to −15° C. before being placed in the freezer overnight. The reaction was quenched with 1M Na$_2$CO$_3$, diluted with EtOAc, and stirred for 30 min. The organic layer was washed with sat'd Na$_2$CO$_3$ solution, brine and dried (MgSO$_4$). The crude product was charged (DCM) to a 80 g ISCO silica gel cartridge and gradient elution (0-50% EtOAc/hexanes) using an Isolera chromatography station gave (S)-isopropyl 2-(4-(4-benzylpiperidin-1-yl)-5-bromo-2,6-dimethylpyridin-3-yl)-2-hydroxyacetate as a mixture of diastereomers 1.4 g (100%). $^1$H NMR (500 MHz, DMSO-d$_6$) δ 7.30-7.27 (m, 2H), 7.19-7.18 (m, 3H), 5.95/5.93 (s, 1H), 4.97-4.93 (m, 1H), 3.53 (t, J=11.4 Hz, 1H), 3.40-3.38 (m, 1H), 3.31 (t, J=11.7 Hz, 1H), 3.25 (br. s, 1H), 2.87 (d, J=10.3 Hz, 1H), 2.77 (d, J=10.6 Hz, 1H), 2.55/2.54 (s, 3H), 2.38 (s, 3H), 1.60-1.52 (m, 3H), 1.38-1.63 (m, 2H), 1.14 (d, J=5.9 Hz, 3H), 1.05 (d, J=5.9 Hz, 3H). UPLC (M+H)=477.1.

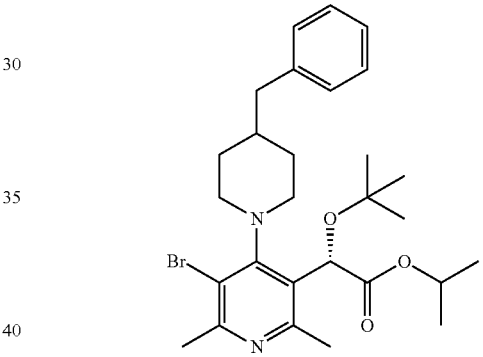

The isobutylene gas was bubbled into a nitrogen purged, cooled (0° C.) solution of (S)-isopropyl 2-(4-(4-benzylpiperidin-1-yl)-5-bromo-2,6-dimethylpyridin-3-yl)-2-hydroxyacetate (1.35 g, 2.84 mmol) and 0.27 mL of 70% HClO$_4$ in DCM (25 mL) for 20 min. The reaction mixture was allowed to warm to rt and stirred for 48 h in a pressure sealed vessel. The reaction was then diluted with DCM, washed with 1M Na$_2$CO$_3$ solution, and dried over MgSO$_4$. The crude product was charged (DCM) to a 80 g ISCO silica gel cartridge and gradient elution (0-25% EtOAc/hexanes) using an Isolera chromatography station gave (S)-isopropyl 2-(4-(4-benzylpiperidin-1-yl)-5-bromo-2,6-dimethylpyridin-3-yl)-2-(tert-butoxy)acetate 1.27 g (84%) as a mixture of diastereomers. $^1$H NMR (500 MHz, DMSO-d$_6$) δ 7.30-7.27 (m, 2H), 7.20-7.18 (m, 3H), 6.12 (br. s, 1H), 4.93-4.88 (m, 1H), 3.79-3.74 (m, 1H), 3.20 (t, J=12.5 Hz, 1H), 2.97-2.95 (m, 1H), 2.74 (br. s, 1H), 2.60 (d, J=5.1 Hz, 2H), 2.51 (s, 3H), 2.40 (s, 3H), 1.68 (br. s, 2H), 1.60-1.57 (m, 1H), 1.36-1.29 (m, 2H), 1.18 (d, J=6.2 Hz, 3H), 1.11 (s, 9H), 1.06 (d, J=6.2 Hz, 3H). UPLC (M+H)=533.3.

2.62 (s, 3H), 2.31 (s, 3H), 1.81-1.77 (m 2H), 1.66-1.57 (m, 2H), 1.37/1.33 (s, 3H), 1.28 (d, J=6.2 Hz, 6H). UPLC (M+H)=417.1.

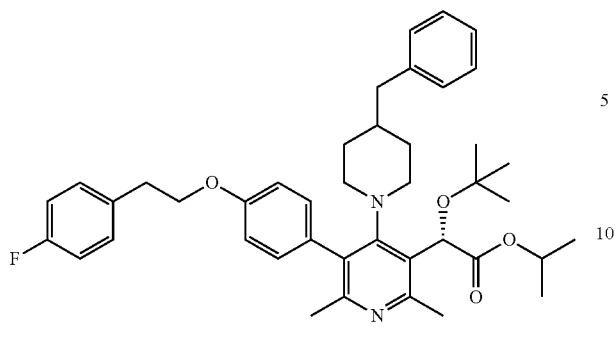

The diacetoxypalladium (11.3 mg, 0.05 mmol) was added to a argon purged and degassed solution of (S)-isopropyl 2-(4-(4-benzylpiperidin-1-yl)-5-bromo-2,6-dimethylpyridin-3-yl)-2-(tert-butoxy)acetate (267 mg, 0.502 mmol), 2-(4-(4-fluorophenethoxy)phenyl)-6-methyl-1,3,6,2-dioxazaborocane-4,8-dione (205 mg, 0.553 mmol), and 2-dicyclohexylphosphino-2',6'-dimethoxy-biphenyl (41 mg, 0.10 mmol), and potassium phosphate tribasic (800 mg, 3.77 mmol) in dioxane (4 mL) and water (0.8 mL) and stirred in a screw-capped pressure vessel for 16 h at 90° C. The reaction was allowed to cool, diluted with EtOAc, and the organic layer was washed with brine and dried (MgSO$_4$). The crude product was charged (DCM) to a 40 g ISCO silica gel cartridge and gradient elution (0-35% EtOAc/hexanes) using an Isolera chromatography station gave (S)-isopropyl 2-(4-(4-benzylpiperidin-1-yl)-5-(4-(4-fluorophenethoxy)phenyl)-2,6-dimethylpyridin-3-yl)-2-(tert-butoxy)acetate 131 mg (39%) as a mixture of diastereomers. $^1$H NMR (500 MHz, DMSO-d$_6$) δ 7.43-7.37 (m, 2H), 7.24-7.22 (m, 2H), 7.18-7.12 (m, 4H), 7.10 (t, J=7.3 Hz, 2H), 6.99-6.92 (m, 3H), 5.92 (s, 1H), 4.97-4.92 (m, 1H), 4.21 (t, J=6.2 Hz, 2H), 3.37-3.37 (m, 4H), 3.06 (t, J=6.2 Hz, 2H), 2.46 (br. s, 2H), 2.42 (s, 3H), 2.02 (s, 3H), 1.70 (t, J=8.8 Hz, 1H), 1.45-1.43 (m, 1H), 1.37-1.34 (m, 1H), 1.29-1.22 (m, 2H), 1.18 (d, J=6.2 Hz, 3H), 1.14 (d, J=3.2 Hz, 3H), 1.09 (m, 9H). UPLC (M+H)=667.5.

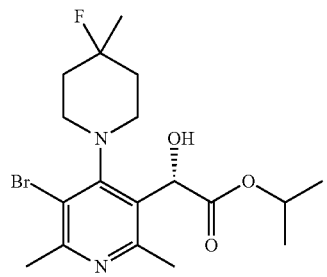

The 0.67 mL of benzo[d][1,3,2]dioxaborole (751 mg, 3.13 mmol) was added to a nitrogen purged solution of isopropyl 2-(5-bromo-4-(4-fluoro-4-methylpiperidin-1-yl)-2,6-dimethylpyridin-3-yl)-2-oxoacetate (650 mg, 1.57 mmol) and 0.63 mL of (R)-1-methyl-3,3-diphenylhexahydropyrrolo[1,2-c][1,3,2]oxazaborole (174 mg, 0.63 mmol) in toluene (15 mL) at −60° C. and allowed to warm to −15° C. before being placed in the freezer overnight. The reaction was quenched with 1M Na$_2$CO$_3$, diluted with EtOAc, and stirred for 30 min. The organic layer was washed with sat'd Na$_2$CO$_3$ solution, brine and dried (MgSO$_4$). The crude product was charged (DCM) to a 80 g ISCO silica gel cartridge and gradient elution (0-50% EtOAc/hexanes) using an Isolera chromatography station gave (S)-isopropyl 2-(5-bromo-4-(4-fluoro-4-methylpiperidin-1-yl)-2,6-dimethylpyridin-3-yl)-2-hydroxyacetate 620 mg (95%) as a mixture of diastereomers. $^1$H NMR (500 MHz, DMSO-d$_6$) δ 5.88/5.86 (s, 1H), 4.95-4.93 (m, 1H), 3.85-3.81 (m, 1H), 3.56 (t, J=11.4 Hz, 1H), 3.23/3.03 (br. s, 1H), 2.76-2.74/2.65-2.62 (m, 1H), 2.53 (s, 3H), 2.39 (s, 3H), 1.91-1.71 (m, 4H), 1.39/1.35 (s, 3H), 1.14 (d, J=5.9 Hz, 3H), 1.07 (d, J=6.2 Hz, 3H). UPLC (M+H)=419.1.

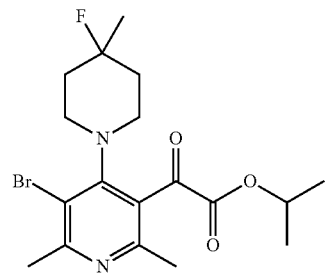 [SMILES: Cc1nc(C)c(C(=O)C(=O)OC(C)C)c(N2CCC(C)(F)CC2)c1Br]

To a solution 4-fluoro-4-methylpiperidine, HCl (0.50 g, 3.25 mmol) and DIEA (2.3 mL, 13.0 mmol) in anhydrous CH$_3$CN (30 mL) was added isopropyl 2-(5-bromo-4-chloro-2,6-dimethylpyridin-3-yl)-2-oxoacetate (1.2 g, 3.25 mmol) at rt. The resulting mixture was placed in a pre-heated oil bath (80° C.) and stirred for 24 h; cooled, diluted with ether, washed with water, brine, and dried (MgSO$_4$). The crude product was charged (DCM) to an 80 g ISCO silica gel cartridge and gradient eluted (0-25% EtOAc/hexanes) using an Isolera chromatography station to give isopropyl 2-(5-bromo-4-(4-fluoro-4-methylpiperidin-1-yl)-2,6-dimethylpyridin-3-yl)-2-oxoacetate 678 mg (50%). $^1$H NMR (500 MHz, CDCl$_3$) δ 5.09-5.05 (m, 1H), 3.34 (br. s, 2H), 2.85 (br. s., 2H),

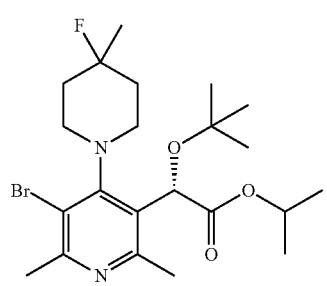 [SMILES: Cc1nc(C)c([C@H](OC(C)(C)C)C(=O)OC(C)C)c(N2CCC(C)(F)CC2)c1Br]

The isobutylene gas was bubbled into a nitrogen purged, cooled (0° C.) solution of (S)-isopropyl 2-(5-bromo-4-(4-fluoro-4-methylpiperidin-1-yl)-2,6-dimethylpyridin-3-yl)-2-hydroxyacetate (600 mg, 1.44 mmol) and 0.14 mL of 70% HClO$_4$ in DCM (15 mL) for 20 min. The reaction mixture was allowed to warm to rt and stirred for 5 days. The reaction was diluted with DCM, washed with 1M Na$_2$CO$_3$ solution, and dried over MgSO$_4$. The crude product was charged (DCM) to a 80 g ISCO silica gel cartridge and gradient elution (0-25% EtOAc/hexanes) using an Isolera chromatography station gave (S)-isopropyl 2-(5-bromo-4-(4-fluoro-4-methylpiperidin-1-yl)-2,6-dimethylpyridin-3-yl)-2-(tert-butoxy)acetate 529 mg (78%) as a mixture of diastereomers. $^1$H NMR (500 MHz, DMSO-d$_6$) 6 (br. s, 1H), 4.92-4.89 (m, 1H), 4.04 (br. s, 1H), 3.51-3.48 (m, 1H), 3.37-3.36 (m, 1H), 2.85 (br. s, 1H), 2.53 (s, 3H), 2.44 (br. s, 3H), 1.95-1.67 (m, 4H), 1.42/1.36 (s, 3H), 1.17-1.14 (m, 12H), 1.0 (d, J=6.2 Hz, 3H). UPLC (M+H)=475.2.

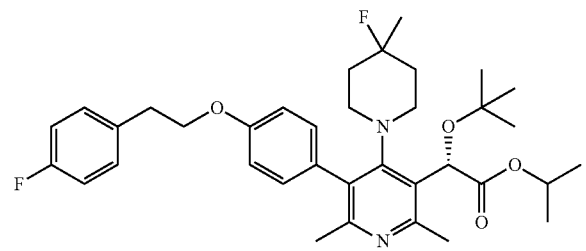 [SMILES: Cc1nc(C)c([C@H](OC(C)(C)C)C(=O)OC(C)C)c(N2CCC(C)(F)CC2)c1-c1ccc(OCCc2ccc(F)cc2)cc1]

The diacetoxypalladium (4.0 mg, 0.018 mmol) was added to a argon purged and degassed solution of (S)-isopropyl 2-(5-bromo-4-(4-fluoro-4-methylpiperidin-1-yl)-2,6-dimethylpyridin-3-yl)-2-(tert-butoxy)acetate (85 mg, 0.18 mmol), 2-(4-(4-fluorophenethoxy)phenyl)-6-methyl-1,3,6,2-dioxazaborocane-4,8-dione (73.3 mg, 0.197 mmol), and 2-dicyclohexylphosphino-2',6'-dimethoxy-biphenyl (14.7 mg, 0.036 mmol), and potassium phosphate tribasic (286 mg, 1.34 mmol) in dioxane (2 mL) and water (0.4 mL) and stirred in a screw-capped pressure vessel for 16 h at 90° C. The reaction was allowed to cool, diluted with EtOAc, and the organic layer was washed with brine, and dried (MgSO₄). The crude product was charged (DCM) to a 40 g ISCO silica gel cartridge and gradient elution (0-40% EtOAc/hexanes) using an Isolera chromatography station gave (S)-isopropyl 2-(tert-butoxy)-2-(4-(4-fluoro-4-methylpiperidin-1-yl)-5-(4-(4-fluorophenethoxy)phenyl)-2,6-dimethylpyridin-3-yl)acetate 85.1 mg (78%) as a mixture of diastereomers. ¹H NMR (500 MHz, DMSO-d₆) δ 7.40-7.37 (m, 2H), 7.22-7.20 (m, 1H), 7.14 (t, J=9.2 Hz, 2H), 7.02-7.00 (m, 3H), 5.94 (br. s, 1H), 4.96-4.93 (m, 1H), 4.22 (t, J=7.3 Hz, 2H), 3.41-3.39 (m, 4H), 3.06 (t, J=6.6 Hz, 2H), 2.47 (br. s, 3H), 2.05 (s, 3H), 1.69-1.43 (m, 4H), 1.24 (br. s, 3H), 1.18 (d, J=6.2 Hz, 3H), 1.13 (br. s, 12H). UPLC (M+H)=609.4.

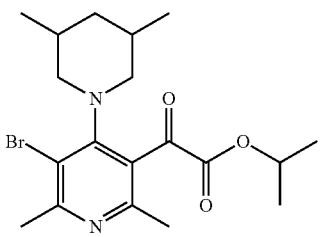 [SMILES: Cc1nc(C)c(C(=O)C(=O)OC(C)C)c(N2CC(C)CC(C)C2)c1Br]

To a solution of 3,5-dimethylpiperidine (1.1 g, 9.86 mmol) and DIEA (3.1 mL, 18 mmol) in anhydrous CH₃CN (40 mL) was added isopropyl 2-(5-bromo-4-chloro-2,6-dimethylpyridin-3-yl)-2-oxoacetate (3.0 g, 8.87 mmol) at rt. The resulting mixture was placed in a pre-heated oil bath (80° C.) and stirred for 24 h; cooled, concentrated, and charged (DCM) to a 120 g ISCO silica gel cartridge and gradient eluted (5-15% EtOAc/hexanes) using an Isolera chromatography station to give isopropyl 2-(5-bromo-4-(3,5-dimethylpiperidin-1-yl)-2,6-dimethylpyridin-3-yl)-2-oxoacetate 756 mg (20%) as a mixture of diastereomers. A sample of the product subjected to prep HPLC on Waters-Atlantis column (30×100 mm S5) running 15 min gradient from 10-100% B (MeOH/water/TFA), yielding two bands. The major isomer. ¹H NMR (500 MHz, CDCl3) δ 5.21-5.14 (m, 1H), 2.87 (br. s, 4H), 2.70 (s, 3H), 2.41 (s, 3H), 1.77-1.71 (m, 3H), 1.29 (d, J=6.2 Hz, 6H), 0.85 (d, J=6.6 Hz, 6H), 0.68 (q, J=11.9 Hz, 1H). UPLC (M+H)=413.15.

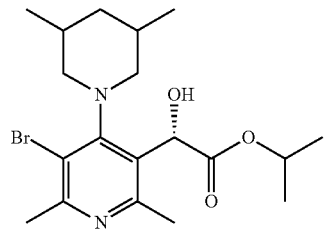 [SMILES: Cc1nc(C)c([C@H](O)C(=O)OC(C)C)c(N2CC(C)CC(C)C2)c1Br]

The 1.7 mL of benzo[d][1,3,2]dioxaborole (426 mg, 3.56 mmol) was added to a nitrogen purged solution of isopropyl 2-(5-bromo-4-(3,5-dimethylpiperidin-1-yl)-2,6-dimethylpyridin-3-yl)-2-oxoacetate (975 mg, 2.37 mmol) and 0.7 mL of (R)-1-methyl-3,3-diphenylhexahydropyrrolo[1,2-c][1,3,2]oxazaborole (197 mg, 0.7 mmol) in toluene (28 mL) at −60° C. and allowed to warm to −15° C. before being placed in the freezer overnight. The reaction was quenched with 1M Na₂CO₃, diluted with EtOAc, and stirred for 30 min. The organic layer was washed with sat'd Na₂CO₃ solution, brine and dried (MgSO₄). The crude product was charged (DCM) to a 80 g ISCO silica gel cartridge and gradient elution (0-30% EtOAc/hexanes) using an Isolera chromatography station gave (S)-isopropyl 2-(5-bromo-4-((3,5-dimethylpiperidin-1-yl)-2,6-dimethylpyridin-3-yl)-2-hydroxyacetate 720 mg (58%) as a mixture of diastereomers. ¹H NMR (500 MHz, CDCl3) δ 5.36 (s, 1H), 5.10-5.05 (m, 1H), 3.22-3.17 (m, 2H), 2.86-2.84 (m, 1H), 2.71-2.70 (m, 1H), 2.66 (s, 3H), 2.07 (s, 3H), 1.93 (br. s, 1H), 1.83-1.81 (m, 2H), 1.30-1.17 (m, 6H), 0.90-0.88 (m, 6H), 0.74 (q, J=12.5 Hz, 1H). UPLC (M+H)=415.3.

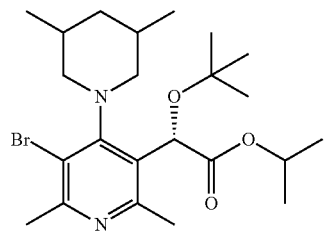 [SMILES: Cc1nc(C)c([C@H](OC(C)(C)C)C(=O)OC(C)C)c(N2CC(C)CC(C)C2)c1Br]

The isobutylene gas was bubbled into a nitrogen purged, cooled (0° C.) solution (S)-isopropyl 2-(5-bromo-4-((3,5-dimethylpiperidin-1-yl)-2,6-dimethylpyridin-3-yl)-2-hydroxyacetate (710 mg, 1.7 mmol) and 0.17 mL of 70% HClO₄ in DCM (25 mL) for 20 min. The reaction mixture was allowed to warm to rt and stirred for 24 h in a pressure sealed vessel. The reaction was then diluted with DCM, washed with 1M Na₂CO₃ solution, and dried over MgSO₄. The crude product was charged (DCM) to a 40 g ISCO silica gel cartridge and gradient elution (0-12% EtOAc/hexanes) using an Isolera chromatography station gave (S)-isopropyl 2-(5-bromo-4-((3,5-dimethylpiperidin-1-yl)-2,6-dimethylpyridin-3-yl)-2-(tert-butoxy)acetate 373 mg (46%) as a mixture of diastereomers. ¹H NMR (500 MHz, CDCl3) δ 6.22 (s, 1H), 5.07-5.02 (m, 1H), 3.38 (t, J=10.7 Hz, 1H), 3.01-2.99 (m, 1H), 2.86 (t, J=10.9 Hz, 1H), 2.76 (br. s, 1H), 2.64 (s, 3H), 2.55 (s, 3H), 1.86-1.84 (m, 3H), 1.22 (d, J=6.3 Hz, 3H), 1.20 (s, 9H), 1.14 (d, J=6.3 Hz, 3H), 0.91 (d, J=6.3 Hz, 3H), 0.88 (d, J=6.6 Hz, 3H), 0.81-0.74 (m, 1H). UPLC (M+H)=471.4.

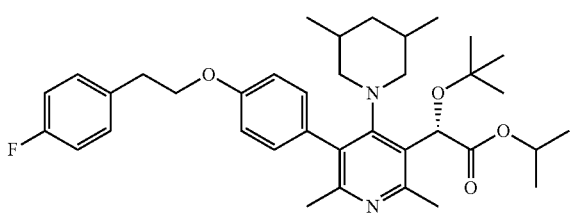 [SMILES: Cc1nc(C)c([C@H](OC(C)(C)C)C(=O)OC(C)C)c(N2CC(C)CC(C)C2)c1-c1ccc(OCCc2ccc(F)cc2)cc1]

The diacetoxypalladium (5 mg, 0.021 mmol) was added to an argon purged and degassed solution (S)-isopropyl 2-(5-bromo-4-((3,5-dimethylpiperidin-1-yl)-2,6-dimethylpyridin-3-yl)-2-(tert-butoxy)acetate (100 mg, 0.213 mmol), 2-(4-(4-fluorophenethoxy)phenyl)-6-methyl-1,3,6,2-dioxazaborocane-4,8-dione (87 mg, 0.234 mmol), and 2-dicyclohexylphosphino-2',6'-dimethoxy-biphenyl (17.5 mg, 0.043 mmol), and potassium phosphate tribasic (339 mg, 1.6 mmol) in dioxane (3 mL) and water (0.6 mL) and stirred in a screw-capped pressure vessel for 16 h at 90° C. The reaction was allowed to cool, diluted with EtOAc, and the organic layer was washed with brine and dried (MgSO$_4$). The crude product was charged (DCM) to a 24 g ISCO silica gel cartridge and gradient elution (5-65% EtOAc/hexanes) using an Isolera chromatography station gave (S)-isopropyl 2-(tert-butoxy)-2-(4-((3,5-dimethylpiperidin-1-yl)-5-(4-(4-fluorophenethoxy)phenyl)-2,6-dimethylpyridin-3-yl)acetate 45 mg (35%). $^1$H NMR (500 MHz, DMSO) δ 7.40-7.37 (m, 2H), 7.21-7.19 (m, 1H), 7.14 (t, J=8.8 Hz, 2H), 7.01 (d, J=8.8 Hz, 2H), 6.94-6.93 (m, 1H), 5.91 (br. s, 1H), 4.97-4.93 (m, 1H), 4.26-4.22 (m, 2H), 3.39-3.39 (m, 3H), 3.32-3.21 (m, 1H), 3.06 (t, J=6.6 Hz, 2H), 2.43 (s, 3H), 2.04 (s, 3H), 1.72-1.65 (m, 2H), 1.28-1.24 (m, 1H), 1.20 (d, J=6.2 Hz, 3H), 1.14 (d, J=6.2 Hz, 3H), 1.11 (s, 9H), 0.74 (d, J=5.5 Hz, 3H), 0.54 (d, J=6.2 Hz, 3H), 0.29-0.22 (m, 1H). UPLC (M+H)=605.7.

Example 1

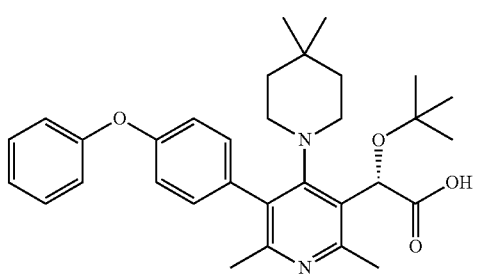 [SMILES: Cc1nc(C)c([C@H](OC(C)(C)C)C(=O)O)c(N2CCC(C)(C)CC2)c1-c1ccc(Oc2ccccc2)cc1]

A mixture of (S)-ethyl 2-(tert-butoxy)-2-(4-(4,4-dimethylpiperidin-1-yl)-2,6-dimethyl-5-(4-phenoxyphenyl)pyridin-3-yl)acetate (0.016 g, 0.029 mmol) and LiOH (7.03 mg, 0.294 mmol) in 9:1 EtOH/H$_2$O (2 mL) was refluxed for 4 h. The, cooled and purified by prep-HPLC to afford (S)-2-(tert-butoxy)-2-(4-(4,4-dimethylpiperidin-1-yl)-2,6-dimethyl-5-(4-phenoxyphenyl)pyridin-3-yl)acetic acid (0.0132 g, 0.026 mmol, 87% yield) as solid. $^1$H NMR (500 MHz, CDCl$_3$) δ 7.35-7.40 (m, 2H), 7.22-7.27 (m, 1H), 7.08-7.18 (m, 4H), 7.03-7.08 (m, 2H), 6.01 (br. s., 1H), 3.35-3.70 (m, 1H), 2.80-3.08 (m, 1H), 2.65 (s, 3H), 2.28-2.38 (m, 1H), 2.26 (s, 3H), 2.06-2.21 (m, 1H), 1.18-1.42 (m, 4H), 1.26 (s, 9H), 0.82 (br.s., 3H), 0.75 (br.s., 3H). LCMS (M+H)=517.4.

Example 2

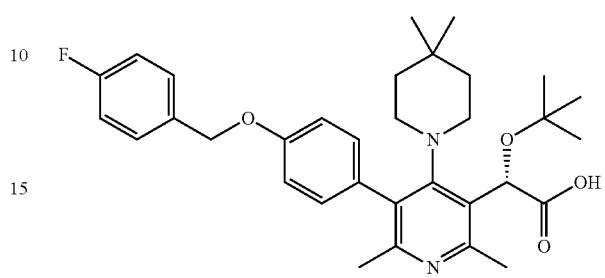

A mixture of (S)-ethyl 2-(tert-butoxy)-2-(4-(4,4-dimethylpiperidin-1-yl)-5-(4-((4-fluorobenzyl)oxy)phenyl)-2,6-dimethylpyridin-3-yl)acetate (0.0372 g, 0.065 mmol) and LiOH (0.015 g, 0.645 mmol) in 9:1 EtOH/H$_2$O (2 mL) was refluxed for 2 h. Then, cooled and purified by prep-HPLC to afford (S)-2-(tert-butoxy)-2-(4-(4,4-dimethylpiperidin-1-yl)-5-(4-((4-fluorobenzyl)oxy)phenyl)-2,6-dimethylpyridin-3-yl)acetic acid (0.0318 g, 0.058 mmol, 90% yield) as white solid. $^1$H NMR (500 MHz, CDCl$_3$) δ 7.43-7.49 (m, 2H), 7.15-7.19 (m, 1H), 7.09-7.14 (m, 2H), 7.02-7.08 (m, 3H), 5.78 (br. s., 1H), 5.07-5.15 (m, 2H), 2.74 (s, 3H), 2.28 (s, 3H), 1.25-1.37 (m, 4H), 1.23 (s, 9H), 0.78 (br. s., 6H). 4H of piperidine are missing. LCMS (M+H)=549.5.

Example 3

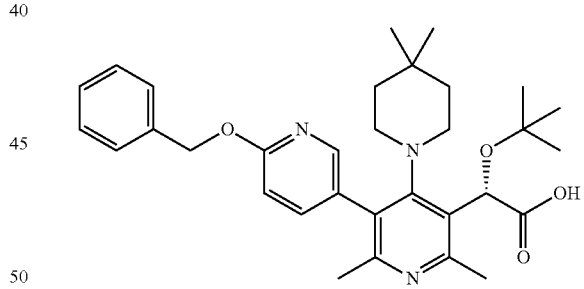

A solution of (S)-ethyl 2-(6'-(benzyloxy)-4-(4,4-dimethylpiperidin-1-yl)-2,6-dimethyl-[3,3'-bipyridin]-5-yl)-2-(tert-butoxy)acetate (0.014 g, 0.025 mmol) and LiOH (5.99 mg, 0.250 mmol) in 9:1 EtOH/H$_2$O (2 mL) was refluxed for 3 h. Then, cooled and purified by prep-HPLC to afford (S)-2-(6'-(benzyloxy)-4-(4,4-dimethylpiperidin-1-yl)-2,6-dimethyl-[3,3'-bipyridin]-5-yl)-2-(tert-butoxy)acetic acid (0.0089 g, 0.017 mmol, 66.9% yield) as white solid. $^1$H NMR (500 MHz, CDCl$_3$) δ 8.08 (d, J=2.2 Hz, 0.5H), 7.99 (d, J=1.7 Hz, 0.5H), 7.46-7.54 (m, 3H), 7.33-7.45 (m, 3H), 6.94 (dd, J=5.8, 8.4 Hz, 1H), 5.93 (br. s., 1H), 5.40-5.55 (m, 2H), 3.40-3.70 (m, 0.5H), 2.74-3.11 (m, 0.5H), 2.67 (s, 3H), 2.28 (s, 1.5H), 2.25 (s, 1.5H), 1.94-2.20 (m, 1H), 1.27-1.40 (m, 4H), 1.25 (s, 4.5H), 1.24 (s, 4.5H), 0.80 (br.s., 6H). LCMS (M+H)=532.4.

Example 4

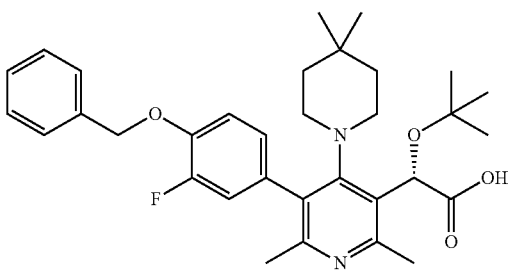 [SMILES: Cc1nc(C)c([C@H](OC(C)(C)C)C(=O)O)c(N2CCC(C)(C)CC2)c1-c1ccc(OCc2ccccc2)c(F)c1]

A mixture of (S)-ethyl 2-(5-(4-(benzyloxy)-3-fluorophenyl)-4-(4,4-dimethylpiperidin-1-yl)-2,6-dimethylpyridin-3-yl)-2-(tert-butoxy)acetate (0.019 g, 0.033 mmol) and LiOH (7.89 mg, 0.329 mmol) in 9:1 EtOH/H$_2$O (2 mL) was refluxed for 3 h. Then, cooled and purified by prep-HPLC to afford (S)-2-(5-(4-(benzyloxy)-3-fluorophenyl)-4-(4,4-dimethylpiperidin-1-yl)-2,6-dimethylpyridin-3-yl)-2-(tert-butoxy)acetic acid (0.0162 g, 0.030 mmol, 90% yield) as white solid. $^1$H NMR (500 MHz, CDCl$_3$) δ 7.47-7.51 (m, 2H), 7.42 (dt, J=3.0, 7.3 Hz, 2H), 7.34-7.39 (m, 1H), 7.08 (t, J=8.4 Hz, 1H), 7.03 (dd, J=1.9, 11.5 Hz, 0.5H), 6.89-6.94 (m, 1H), 6.80 (d, J=8.2 Hz, 0.5H), 5.83 (br. s., 0.6H), 5.78 (br. s., 0.4H), 5.18-5.26 (m, 2H), 2.74 (s, 1.3H), 2.72 (s, 1.7H), 2.27 (s, 1.7H), 2.26 (s, 1.3H), 1.26-1.39 (m, 4H), 1.23 (s, 9H), 0.82 (br. s., 6H). 4H of piperidine were not resolved. LCMS (M+H)=549.47.

Example 5

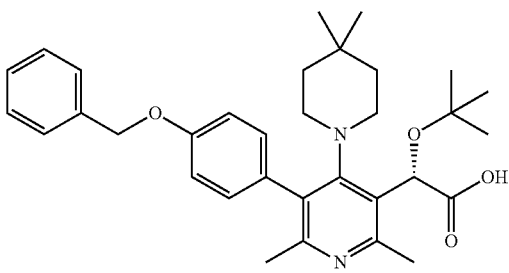 [SMILES: Cc1nc(C)c([C@H](OC(C)(C)C)C(=O)O)c(N2CCC(C)(C)CC2)c1-c1ccc(OCc2ccccc2)cc1]

A mixture of (S)-ethyl 2-(5-(4-(benzyloxy)phenyl)-4-(4,4-dimethylpiperidin-1-yl)-2,6-dimethylpyridin-3-yl)-2-(tert-butoxy)acetate (0.0224 g, 0.040 mmol) and LiOH (9.60 mg, 0.401 mmol) in 9:1 EtOH/H$_2$O (2 mL) was refluxed for 3 h. Then, cooled and purified by prep-HPLC to afford (S)-2-(5-(4-(benzyloxy)phenyl)-4-(4,4-dimethylpiperidin-1-yl)-2,6-dimethylpyridin-3-yl)-2-(tert-butoxy)acetic acid (0.018 g, 0.034 mmol, 85% yield) as white solid. $^1$H NMR (400 MHz, CDCl$_3$) δ 7.32-7.49 (m, 5H), 7.12-7.16 (m, 1H), 6.97-7.08 (m, 3H), 5.65 (br. s., 1H), 5.09-5.18 (m, 2H), 2.81 (s, 3H), 2.29 (s, 3H), 1.23-1.38 (m, 4H), 1.20 (s, 9H), 0.77 (br. s., 6H). 4H of piperidine were not resolved. LCMS (M+H)=531.4.

Example 6

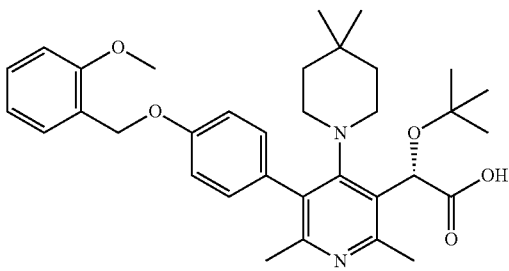 [SMILES: COc1ccccc1COc1ccc(-c2c(C)nc(C)c([C@H](OC(C)(C)C)C(=O)O)c2N2CCC(C)(C)CC2)cc1]

A mixture of (S)-ethyl 2-(tert-butoxy)-2-(4-(4,4-dimethylpiperidin-1-yl)-5-(4-((2-methoxybenzyl)oxy)phenyl)-2,6-dimethylpyridin-3-yl)acetate (0.036 g, 0.061 mmol) and LiOH (0.015 g, 0.611 mmol) in 9:1 EtOH/H$_2$O (2 mL0 was refluxed for 3 h. Then, cooled and purified by prep-HPLC to afford (S)-2-(tert-butoxy)-2-(4-(4,4-dimethylpiperidin-1-yl)-5-(4-((2-methoxybenzyl)oxy)phenyl)-2,6-dimethylpyridin-3-yl)acetic acid (0.0247 g, 0.044 mmol, 72.0% yield) as white solid. $^1$H NMR (500 MHz, CDCl$_3$) δ 7.50 (dd, J=1.5, 7.5 Hz, 1H), 7.34 (dt, J=1.7, 7.8 Hz, 1H), 7.14-7.17 (m, 1H), 7.06-7.10 (m, 3H), 7.01 (dt, J=1.0, 7.5 Hz, 1H), 6.95 (d, J=8.2 Hz, 1H), 5.94 (br. s., 1H), 5.17-5.24 (m, 2H), 3.91 (s, 3H), 3.61 (br. s., 1H), 2.90 (br. s., 1H), 2.66 (s, 3H), 2.24 (s, 3H), 1.24 (s, 9H), 0.88 (br.s., 3H), 0.68 (br.s., 3H). 6H of piperidine were not resolved. LCMS (M+H)=561.4.

Example 7

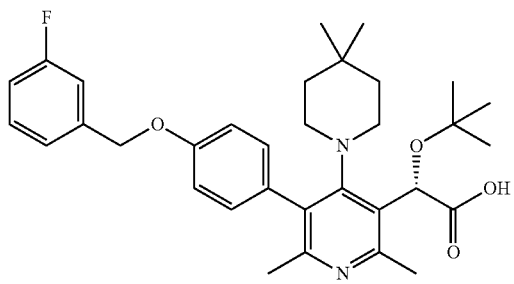 [SMILES: Cc1nc(C)c([C@H](OC(C)(C)C)C(=O)O)c(N2CCC(C)(C)CC2)c1-c1ccc(OCc2cccc(F)c2)cc1]

A mixture of (S)-ethyl 2-(tert-butoxy)-2-(4-(4,4-dimethylpiperidin-1-yl)-5-(4-((3-fluorobenzyl)oxy)phenyl)-2,6-dimethylpyridin-3-yl)acetate (0.0325 g, 0.056 mmol) and LiOH (0.013 g, 0.564 mmol) in 9:1 EtOH/H$_2$O (2 mL0 was refluxed for 3 h. Then, cooled and purified by prep-HPLC to afford (S)-2-(tert-butoxy)-2-(4-(4,4-dimethylpiperidin-1-yl)-5-(4-((3-fluorobenzyl)oxy)phenyl)-2,6-dimethylpyridin-3-yl)acetic acid (0.0269 g, 0.049 mmol, 87% yield) as white solid. $^1$H NMR (500 MHz, CDCl$_3$) δ 7.39 (dt, J=5.8, 7.9 Hz, 1H), 7.25 (d, J=7.7 Hz, 1H), 7.16-7.23 (m, 2H), 7.01-7.10 (m, 4H), 5.95 (br. s., 1H), 5.12-5.19 (m, 2H), 3.62 (br. s., 1H), 2.88 (br. s., 1H), 2.65 (s, 3H), 2.23 (s, 3H), 1.24 (s, 9H), 0.87 (br.s., 3H), 0.67 (br. s., 3H). 6H of piperidine were not resolved. LCMS (M+H)=549.4.

Example 8

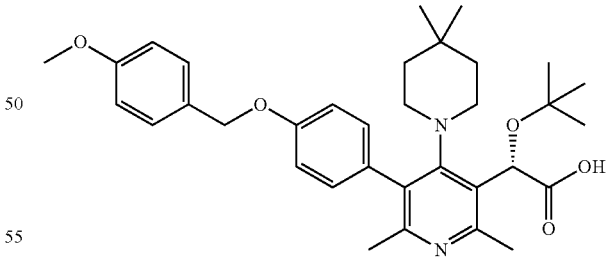

A mixture of (S)-ethyl 2-(tert-butoxy)-2-(4-(4,4-dimethylpiperidin-1-yl)-5-(4-((4-methoxybenzyl)oxy)phenyl)-2,6-dimethylpyridin-3-yl)acetate (0.0348 g, 0.059 mmol) and LiOH (0.014 g, 0.591 mmol) in 9:1 EtOH/H$_2$O (2 mL0 was refluxed for 3 h. Then, cooled and purified by prep-HPLC to afford (S)-2-(tert-butoxy)-2-(4-(4,4-dimethylpiperidin-1-yl)-5-(4-((4-methoxybenzyl)oxy)phenyl)-2,6-dimethylpyridin-3-yl)acetic acid (0.0279 g, 0.050 mmol, 84% yield) as white solid. $^1$H NMR (500 MHz, CDCl$_3$) δ 7.41 (d, J=8.0 Hz, 2H), 7.16 (d, J=7.7 Hz, 1H), 7.03-7.08 (m, 3H), 6.96 (d, J=7.9

Hz, 2H), 5.97 (br. s., 1H), 5.04-5.11 (m, 2H), 3.85 (s, 3H), 3.59 (br. s., 1H), 2.91 (br. s., 1H), 2.63 (br. s., 3H), 2.24-2.30 (m, 1H), 2.22 (s, 3H), 2.02-2.14 (m, 1H), 1.24 (s, 9H), 0.87 (br.s., 3H), 0.67 (br. s., 3H). 4H of piperidine were not resolved. LCMS (M+H)=561.4.

Example 9

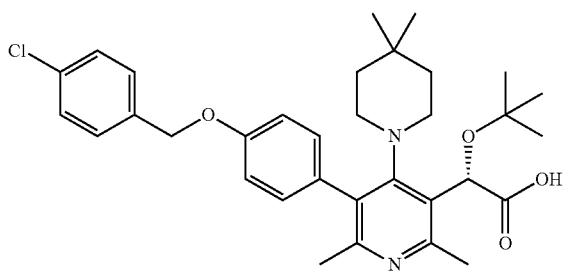 [SMILES: Cc1nc(C)c([C@H](OC(C)(C)C)C(=O)O)c(N2CCC(C)(C)CC2)c1-c1ccc(OCc2ccc(Cl)cc2)cc1]

A mixture of (S)-ethyl 2-(tert-butoxy)-2-(5-(4-((4-chlorobenzyl)oxy)phenyl)-4-(4,4-dimethylpiperidin-1-yl)-2,6-dimethylpyridin-3-yl)acetate (0.0344 g, 0.058 mmol) and LiOH (0.014 g, 0.580 mmol) in 9:1 EtOH/H$_2$O (2 mL0 was refluxed for 3 h. Then, cooled and purified by prep-HPLC to afford (S)-2-(tert-butoxy)-2-(5-(4-((4-chlorobenzyl)oxy)phenyl)-4-(4,4-dimethylpiperidin-1-yl)-2,6-dimethylpyridin-3-yl)acetic acid (0.0258 g, 0.046 mmol, 79% yield) as white solid. $^1$H NMR (500 MHz, CDCl$_3$) δ 7.38-7.44 (m, 4H), 7.15-7.20 (m, 1H), 7.01-7.10 (m, 3H), 5.99 (br. s., 1H), 5.08-5.16 (m, 2H), 3.57 (br. s., 1H), 2.90 (br. s., 1H), 2.64 (s, 3H), 2.24-2.32 (m, 1H), 2.22 (s, 3H), 1.97-2.13 (m, 1H), 1.25 (s, 9H), 0.88 (br.s., 3H), 0.64 (br. s., 3H). 4H of piperidine were not resolved. LCMS (M+H)=565.3.

Example 10

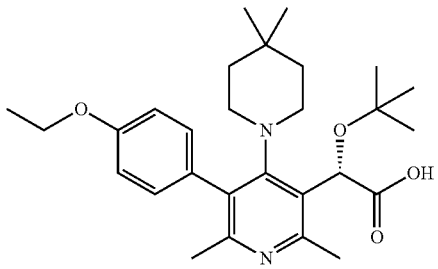 [SMILES: CCOc1ccc(-c2c(C)nc(C)c([C@H](OC(C)(C)C)C(=O)O)c2N2CCC(C)(C)CC2)cc1]

A mixture of (S)-ethyl 2-(tert-butoxy)-2-(4-(4,4-dimethylpiperidin-1-yl)-5-(4-ethoxyphenyl)-2,6-dimethylpyridin-3-yl)acetate (0.013 g, 0.026 mmol) and LiOH (6.27 mg, 0.262 mmol) in 9:1 EtOH/H$_2$O (1 ml) was refluxed for 3 h. Then, cooled and purified by prep-HPLC to afford (S)-2-(tert-butoxy)-2-(4-(4,4-dimethylpiperidin-1-yl)-5-(4-ethoxyphenyl)-2,6-dimethylpyridin-3-yl)acetic acid (0.0105 g, 0.022 mmol, 86% yield) as solid. $^1$H NMR (500 MHz, CDCl$_3$) δ 7.12-7.17 (m, 1H), 7.03-7.07 (m, 1H), 6.95-7.01 (m, 2H), 5.90 (br. s., 1H), 4.06-4.17 (m, 2H), 3.46-3.88 (m, 1H), 2.75-3.08 (m, 1H), 2.70 (s, 3H), 2.25 (s, 3H), 1.91-2.43 (m, 2H), 1.48 (t, J=7.0 Hz, 3H), 1.13-1.37 (m, 4H), 1.25 (s, 9H), 0.78 (br.s., 6H). LCMS (M+H)=469.3.

Example 11

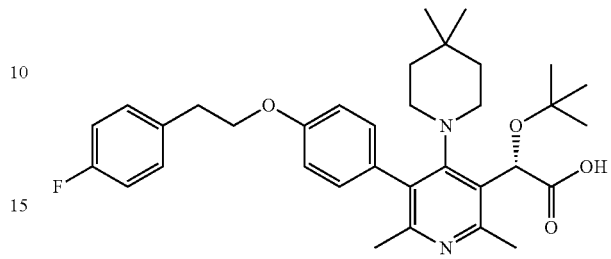

A mixture of (S)-ethyl 2-(tert-butoxy)-2-(4-(4,4-dimethylpiperidin-1-yl)-5-(4-(4-fluorophenethoxy)phenyl)-2,6-dimethylpyridin-3-yl)acetate (0.009 g, 0.015 mmol) and LiOH (3.65 mg, 0.152 mmol) in 9:1 EtOH/H$_2$O (1 mL) was refluxed for 3 h. Then, cooled and purified by prep-HPLC to afford (S)-2-(tert-butoxy)-2-(4-(4,4-dimethylpiperidin-1-yl)-5-(4-(4-fluorophenethoxy)phenyl)-2,6-dimethylpyridin-3-yl)acetic acid (0.0081 g, 0.014 mmol, 94% yield) as white solid. Alternatively, to a solution of (S)-isopropyl 2-(tert-butoxy)-2-(4-(4,4-dimethylpiperidin-1-yl)-5-(4-(4-fluorophenethoxy)phenyl)-2,6-dimethylpyridin-3-yl)acetate (0.302 g, 0.5 mmol) in ethanol (5 mL) and water (0.500 mL) was added KOH (0.281 g, 5.00 mmol). The solution was heated at 75° C. for 8 h. The solvent in the mixture was evaporated. The remaining residue was treated with water (5 mL), and acidified with 1 N HCl (5.1 mL) to pH~2. The resulting mixture was stirred for 1 h. The solid was collected on a filter, washed with water, dried under vacuum to give (0.281 g, 100%) as beige solid. $^1$H NMR (500 MHz, CDCl$_3$) δ 7.27-7.32 (m, 2H), 7.12-7.18 (m, 1H), 7.01-7.09 (m, 3H), 6.95-7.00 (m, 2H), 5.95 (br. s., 1H), 4.16-4.29 (m, 2H), 3.61 (br. s., 1H), 3.13 (t, J=6.9 Hz, 2H), 2.77-3.02 (m, 1H), 2.66 (s, 3H), 2.22 (s, 3H), 1.99-2.37 (m, 2H), 1.25 (s, 9H), 1.07-1.40 (m, 4H), 0.88 (br.s., 3H), 0.68 (br. s., 3H). LCMS (M+H)=563.3.

Example 12

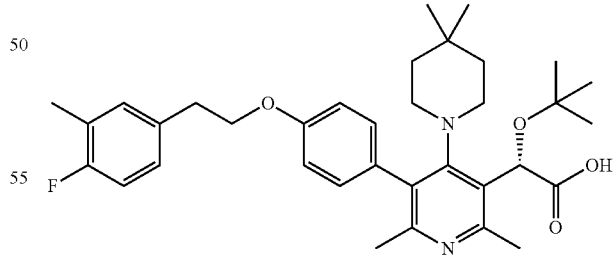

A mixture of (S)-ethyl 2-(tert-butoxy)-2-(4-(4,4-dimethylpiperidin-1-yl)-5-(4-(4-fluoro-3-methylphenethoxy)phenyl)-2,6-dimethylpyridin-3-yl)acetate (0.035 g, 0.058 mmol) and LiOH (0.014 g, 0.579 mmol) in 9:1 EtOH/H$_2$O (2 mL) was refluxed for 3 h. Then, cooled and purified by prep-HPLC to afford (S)-2-(tert-butoxy)-2-(4-(4,4-dimethylpiperidin-1-yl)-5-(4-(4-fluoro-3-methylphenethoxy)phenyl)-2,6-dimethylpyridin-3-yl)acetic acid (0.0298 g, 0.052 mmol, 89% yield) as white solid. ¹H NMR (500 MHz, CDCl₃) δ 7.12-7.17 (m, 2H), 7.04-7.12 (m, 2H), 6.95-7.01 (m, 3H), 5.96 (br. s., 1H), 4.16-4.28 (m, 2H), 3.60 (br. s., 1H), 3.09 (t, J=7.0 Hz, 2H), 2.80-3.01 (m, 1H), 2.66 (s, 3H), 2.30 (d, J=1.7 Hz, 3H), 2.19-2.32 (m, 1H), 2.22 (s, 3H), 1.97-2.15 (m, 1H), 1.25 (s, 9H), 0.87 (br. s., 3H), 0.68 (br. s., 3H). 4H of piperidine were not resolved. LCMS (M+H)=577.3.

Example 13

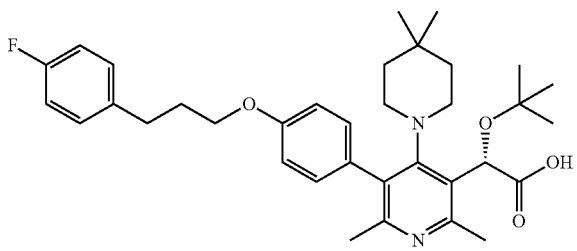 [SMILES: Cc1nc(C)c([C@H](OC(C)(C)C)C(=O)O)c(N2CCC(C)(C)CC2)c1-c1ccc(OCCCc2ccc(F)cc2)cc1]

A mixture of (S)-ethyl 2-(tert-butoxy)-2-(4-(4,4-dimethylpiperidin-1-yl)-5-(4-(3-(4-fluorophenyl)propoxy)phenyl)-2,6-dimethylpyridin-3-yl)acetate (0.031 g, 0.051 mmol) and LiOH (0.012 g, 0.513 mmol) in 9:1 EtOH/H₂O (2 mL) was refluxed for 4 h. Then, cooled and purified by prep-HPLC to afford (S)-2-(tert-butoxy)-2-(4-(4,4-dimethylpiperidin-1-yl)-5-(4-(3-(4-fluorophenyl)propoxy)phenyl)-2,6-dimethylpyridin-3-yl)acetic acid (0.0254 g, 0.044 mmol, 86% yield) as solid. ¹H NMR (500 MHz, CDCl₃) δ 7.18-7.22 (m, 2H), 7.13-7.17 (m, 1H), 7.04-7.08 (m, 1H), 6.95-7.03 (m, 4H), 5.95 (br. s., 1H), 3.98-4.07 (m, 2H), 3.43-3.78 (m, 1H), 2.87-3.06 (m, 1H), 2.84 (t, J=7.7 Hz, 2H), 2.67 (s, 3H), 2.36 (br. s., 1H), 2.24 (s, 3H), 2.10-2.18 (m, 2H), 1.93-2.09 (m, 1H), 1.48-1.68 (m, 1H), 1.28-1.40 (m, 2H), 1.25 (s, 9H), 1.10-1.22 (m, 1H), 0.88 (br.s., 3H), 0.69 (br.s., 3H). LCMS (M+H)=577.3.

Example 14

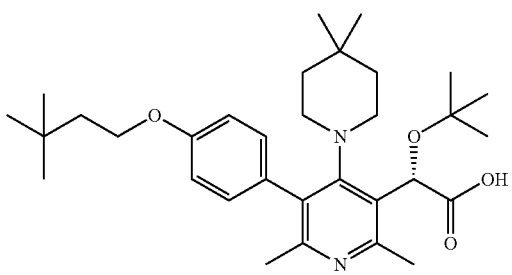 [SMILES: Cc1nc(C)c([C@H](OC(C)(C)C)C(=O)O)c(N2CCC(C)(C)CC2)c1-c1ccc(OCCC(C)(C)C)cc1]

A mixture of (S)-ethyl 2-(tert-butoxy)-2-(5-(4-(3,3-dimethylbutoxy)phenyl)-4-(4,4-dimethylpiperidin-1-yl)-2,6-dimethylpyridin-3-yl)acetate (0.02 g, 0.036 mmol) and LiOH (8.66 mg, 0.362 mmol) in 9:1 EtOH/H₂O (2 mL) was refluxed for 4 h. Then, cooled and purified by prep-HPLC to afford (S)-2-(tert-butoxy)-2-(5-(4-(3,3-dimethylbutoxy)phenyl)-4-(4,4-dimethylpiperidin-1-yl)-2,6-dimethylpyridin-3-yl)acetic acid (0.0158 g, 0.030 mmol, 83% yield) as white solid. ¹H NMR (500 MHz, CDCl₃) δ 7.12-7.16 (m, 1H), 7.06 (d, J=7.7 Hz, 1H), 6.96-7.00 (m, 2H), 5.92 (br. s., 1H), 4.06-4.15 (m, 2H), 3.46-3.81 (m, 1H), 2.90 (br. s., 1H), 2.69 (br. s., 3H), 2.27-2.42 (m, 1H), 2.25 (s, 3H), 1.95-2.17 (m, 1H), 1.79 (t, J=7.3 Hz, 2H), 1.50-1.64 (m, 1H), 1.27-1.40 (m, 3H), 1.25 (s, 9H), 1.04 (s, 9H), 0.81 (br.s., 6H). LCMS (M+H)=525.3.

Example 15

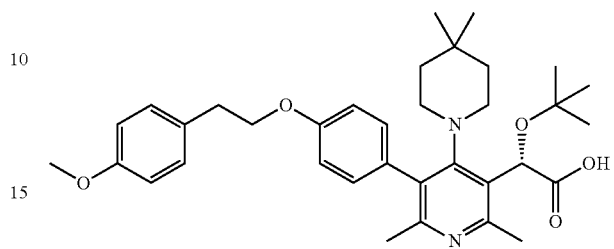

A mixture of (S)-ethyl 2-(tert-butoxy)-2-(4-(4,4-dimethylpiperidin-1-yl)-5-(4-(4-methoxyphenethoxy)phenyl)-2,6-dimethylpyridin-3-yl)acetate (0.032 g, 0.053 mmol) and 1M NaOH (0.159 ml, 0.159 mmol) in EtOH (2 mL) was refluxed for 4 h. Then, cooled and purified by prep-HPLC to afford (S)-2-(tert-butoxy)-2-(4-(4,4-dimethylpiperidin-1-yl)-5-(4-(4-methoxyphenethoxy)phenyl)-2,6-dimethylpyridin-3-yl) acetic acid (0.0257 g, 0.045 mmol, 84% yield) as white solid. ¹H NMR (500 MHz, CDCl₃) δ 7.27-7.23 (m, 2H), 7.14 (dd, J=8.5, 2.0 Hz, 1H), 7.09-7.04 (m, 1H), 7.01-6.96 (m, 2H), 6.93-6.88 (m, 2H), 6.00 (br. s., 1H), 4.26-4.17 (m, 2H), 3.83 (s, 3H), 3.57 (br. s., 1H), 3.10 (t, J=7.1 Hz, 2H), 2.93 (br. s., 1H), 2.64 (s, 3H), 2.34 (br. s., 1H), 2.21 (s, 3H), 2.16-2.01 (m, 1H), 1.68-1.47 (m, 2H), 1.40-1.28 (m, 2H), 1.25 (s, 9H), 0.88 (br.s., 3H), 0.68 (br. s., 3H). LCMS (M+H)=575.4.

Examples 16-18

A mixture of (S)-ethyl 2-(tert-butoxy)-2-(5-(4-(4-cyanophenethoxy)phenyl)-4-(4,4-dimethylpiperidin-1-yl)-2,6-dimethylpyridin-3-yl)acetate (0.0305 g, 0.051 mmol) and 1M NaOH (0.061 ml, 0.061 mmol) in EtOH (1 mL) was refluxed for 4 h. Then, cooled and purified by prep-HPLC to afford example 16-18.

Example 16

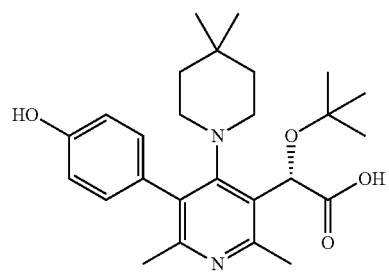 [SMILES: Cc1nc(C)c([C@H](OC(C)(C)C)C(=O)O)c(N2CCC(C)(C)CC2)c1-c1ccc(O)cc1]

(S)-2-(tert-Butoxy)-2-(4-(4,4-dimethylpiperidin-1-yl)-5-(4-hydroxyphenyl)-2,6-dimethylpyridin-3-yl)acetic acid (0.006 g, 0.014 mmol, 26.7% yield), white solid. ¹H NMR (500 MHz, METHANOL-d₄) δ 7.23-7.18 (m, 1H), 7.03-6.99 (m, 1H), 6.98-6.94 (m, 2H), 5.52 (s, 1H), 2.76 (br. s., 2H), 2.70 (s, 3H), 2.32 (s, 3H), 1.39 (br. s., 4H), 1.21 (s, 9H), 0.87 (s, 6H). 2H of piperidine were not resolved. LCMS (M+H)=441.3.

Example 17

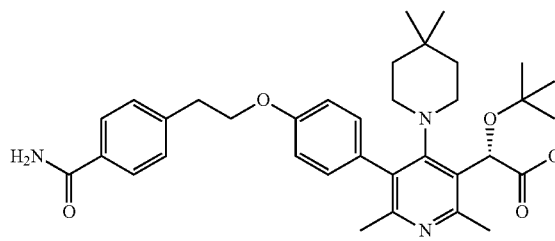

(S)-2-(tert-Butoxy)-2-(5-(4-(4-carbamoylphenethoxy) phenyl)-4-(4,4-dimethylpiperidin-1-yl)-2,6-dimethylpyridin-3-yl)acetic acid (0.0022 g, 3.74 µmol, 7.34% yield), white solid. $^1$H NMR (500 MHz, CDCl$_3$) δ 7.82 (d, J=8.2 Hz, 2H), 7.43 (d, J=8.4 Hz, 2H), 7.18-7.13 (m, 1H), 7.09-7.04 (m, 1H), 6.97 (d, J=8.8 Hz, 2H), 6.00 (br. s., 2H), 5.59 (br. s., 1H), 4.33-4.23 (m, 2H), 3.56 (br. s., 1H), 3.21 (t, J=6.7 Hz, 2H), 2.92 (br. s., 1H), 2.63 (s, 3H), 2.26 (br. s., 1H), 2.14-1.98 (m, 1H), 1.39-1.27 (m, 4H), 1.26 (s, 9H), 0.88 (br. s., 3H), 0.66 (br. s., 3H). LCMS (M+H)=588.4.

Example 18

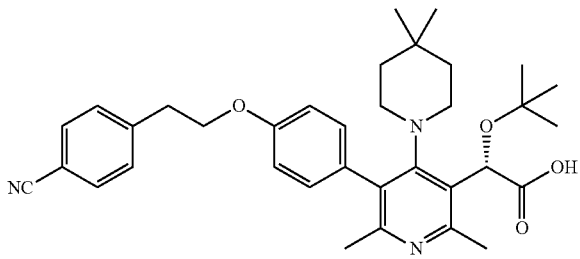 [SMILES: Cc1nc(C)c([C@H](OC(C)(C)C)C(=O)O)c(N2CCC(C)(C)CC2)c1-c1ccc(OCCc2ccc(C#N)cc2)cc1]

(S)-2-(tert-Butoxy)-2-(5-(4-(4-cyanophenethoxy)phenyl)-4-(4,4-dimethylpiperidin-1-yl)-2,6-dimethylpyridin-3-yl)acetic acid (0.0034 g, 5.97 µmol, 11.70% yield), white solid. $^1$H NMR (500 MHz, CDCl$_3$) δ 7.68-7.63 (m, 2H), 7.45 (d, J=8.4 Hz, 2H), 7.18-7.13 (m, 1H), 7.08-7.03 (m, 1H), 6.96 (d, J=8.8 Hz, 2H), 5.91 (br. s., 1H), 4.32-4.22 (m, 2H), 3.65 (br. s., 1H), 3.22 (t, J=6.5 Hz, 2H), 2.97-2.74 (m, 1H), 2.68 (s, 3H), 2.39-2.25 (m, 1H), 2.22 (s, 3H), 2.15-1.98 (m, 1H), 1.38-1.27 (m, 4H), 1.24 (s, 9H), 0.78 (br. s., 6H). LCMS (M+H)=570.4.

Example 19-20

A mixture of (S)-ethyl 2-(tert-butoxy)-2-(5-(4-((4-cyanobenzyl)oxy)phenyl)-4-(4,4-dimethylpiperidin-1-yl)-2,6-dimethylpyridin-3-yl)acetate (0.0304 g, 0.052 mmol) and 1M NaOH (0.062 ml, 0.062 mmol) in EtOH (1 mL) was heated at 70-75° C. for 7 h. Then, cooled and purified by prep-HPLC to afford example 19 and 20

Example 19

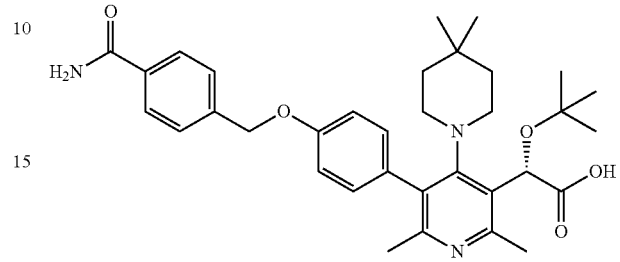

(S)-2-(tert-Butoxy)-2-(5-(4-((4-carbamoylbenzyl)oxy) phenyl)-4-(4,4-dimethylpiperidin-1-yl)-2,6-dimethylpyridin-3-yl)acetic acid (0.0094 g, 0.016 mmol, 31.5% yield), white solid. $^1$H NMR (500 MHz, CDCl$_3$) δ 7.90-7.85 (m, 2H), 7.58 (d, J=8.2 Hz, 2H), 7.21-7.17 (m, 1H), 7.12-7.03 (m, 3H), 6.03 (br. s., 2H), 5.64 (br. s., 1H), 5.28-5.17 (m, 2H), 3.52 (br. s., 1H), 2.92 (br. s., 1H), 2.62 (s, 3H), 2.35-2.23 (m, 1H), 2.22 (s, 3H), 2.11-2.02 (m, 1H), 1.39-1.27 (m, 4H), 1.26 (s, 9H), 0.90 (br. s., 3H), 0.64 (br. s., 3H). LCMS (M+H)=574.4.

Example 20

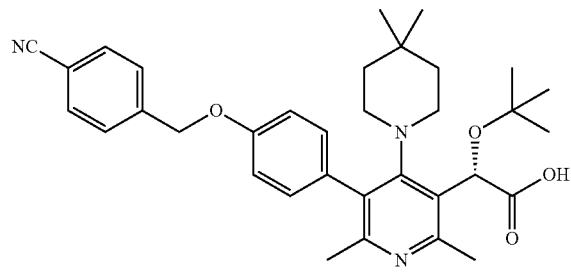 [SMILES: Cc1nc(C)c([C@H](OC(C)(C)C)C(=O)O)c(N2CCC(C)(C)CC2)c1-c1ccc(OCc2ccc(C#N)cc2)cc1]

(S)-2-(tert-Butoxy)-2-(5-(4-((4-cyanobenzyl)oxy)phenyl)-4-(4,4-dimethylpiperidin-1-yl)-2,6-dimethylpyridin-3-yl)acetic acid (0.0083 g, 0.015 mmol, 28.7% yield), white solid. $^1$H NMR (500 MHz, CDCl$_3$) δ 7.74-7.70 (m, 2H), 7.61 (d, J=8.5 Hz, 2H), 7.20 (dd, J=8.3, 2.0 Hz, 1H), 7.11-7.02 (m, 3H), 6.00 (br. s., 1H), 5.27-5.18 (m, 2H), 3.56 (br. s., 1H), 2.89 (br. s., 1H), 2.64 (s, 3H), 2.40-2.26 (m, 1H), 2.23 (s, 3H), 2.15-1.94 (m, 1H), 1.43-1.28 (m, 4H), 1.26 (s, 9H), 0.95 (m, 3H), 0.65 (br. s., 3H). LCMS (M+H)=556.4.

Example 21-22

A solution of (2S)-ethyl 2-(tert-butoxy)-2-(4-(4,4-dimethylpiperidin-1-yl)-5-(4-((1-(4-fluorophenyl)propan-2-yl) oxy)phenyl)-2,6-dimethylpyridin-3-yl)acetate (0.0735 g, 0.122 mmol) and 1M NaOH (0.365 ml, 0.365 mmol) in EtOH (4 mL) was refluxed for 5 h. Then, cooled and purified by prep-HPLC to afford example 21 and 22.

Example 21

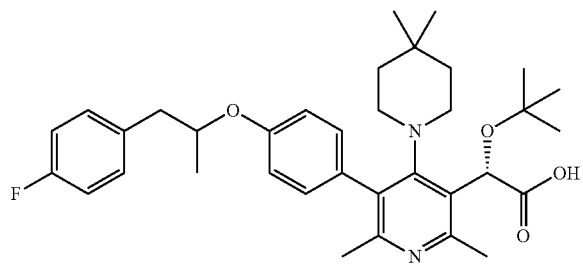

(2S)-2-(tert-Butoxy)-2-(4-(4,4-dimethylpiperidin-1-yl)-5-(4-((1-(4-fluorophenyl)propan-2-yl)oxy)phenyl)-2,6-dimethylpyridin-3-yl)acetic acid (0.0316 g, 0.055 mmol, 45.1% yield), white solid, 85:15 mixture of diastereomers. Repurified to get single diastereomer (0.025 g, 95:5). ¹H NMR (500 MHz, CDCl₃) δ 7.25-7.20 (m, 2H), 7.14 (dd, J=8.4, 2.2 Hz, 1H), 7.07 (dd, J=8.3, 2.0 Hz, 1H), 7.04-6.93 (m, 4H), 6.01 (br. s., 1H), 4.63 (sxt, J=6.1 Hz, 1H), 3.52 (br. s., 1H), 3.08 (dd, J=13.9, 6.0 Hz, 1H), 2.93 (br. s., 1H), 2.89 (dd, J=13.9, 6.1 Hz, 1H), 2.63 (s, 3H), 2.31 (br. s., 1H), 2.23 (s, 3H), 2.16-2.02 (m, 1H), 1.35 (d, J=6.0 Hz, 3H), 1.26 (s, 9H), 0.88 (br. s., 4H), 0.62 (br. s., 3H). 4H of piperidine were not resolved. LCMS (M+H)=577.5.

Example 22

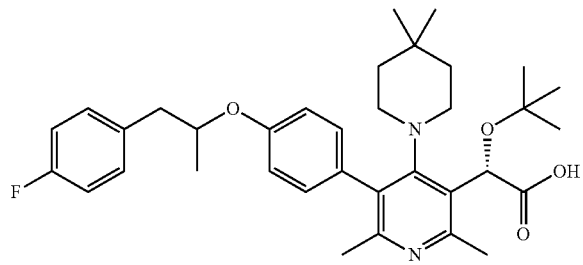

(2S)-2-(tert-Butoxy)-2-(4-(4,4-dimethylpiperidin-1-yl)-5-(4-((1-(4-fluorophenyl)propan-2-yl)oxy)phenyl)-2,6-dimethylpyridin-3-yl)acetic acid (0.0264 g, 0.046 mmol, 37.7% yield), white solid, 2:98 mixture of diastereomers. ¹H NMR (500 MHz, CDCl₃) δ 7.27-7.22 (m, 2H), 7.14 (dd, J=8.6, 2.1 Hz, 1H), 7.08-7.04 (m, 1H), 7.03-6.98 (m, 2H), 6.98-6.94 (m, 2H), 5.99 (br. s., 1H), 4.60-4.67 (m, 1H), 3.55 (br. s., 1H), 3.08 (dd, J=13.9, 6.1 Hz, 1H), 2.91 (dd, J=13.9, 5.8 Hz, 1H), 2.83-2.99 (br. s., 1H), 2.64 (s, 3H), 2.23 (s, 3H), 2.17-1.95 (m, 1H), 1.34 (d, J=6.1 Hz, 3H), 1.26 (s, 9H), 0.88 (br. s., 3H), 0.64 (br. s., 3H). 4H of piperidine were not resolved. LCMS (M+H)=577.5.

Example 23

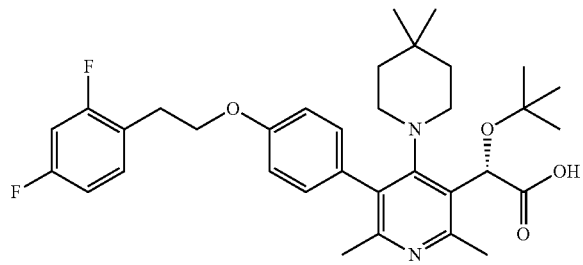

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(2,4-difluorophenyl)ethanol (33.7 mg, 0.213 mmol) and Ph₃P-resin (33.6 mg, 0.128 mmol) in THF (2 mL) was added DEAD (0.020 mL, 0.128 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(5-(4-(2,4-difluorophenethoxy)phenyl)-4-(4,4-dimethylpiperidin-1-yl)-2,6-dimethylpyridin-3-yl)acetic acid (8.6 mg, 0.015 mmol, 34.7% yield). ¹H NMR (500 MHz, DMSO-d₆) δ 7.53-7.45 (m, 1H), 7.28-7.15 (m, 2H), 7.11-6.90 (m, 4H), 5.82 (s, 1H), 4.31-4.18 (m, 2H), 3.08 (t, J=6.6 Hz, 2H), 2.84-2.76 (m, 1H), 2.43 (s, 3H), 2.17 (d, J=10.6 Hz, 1H), 2.05 (s, 3H), 1.49 (br. s., 1H), 1.34-1.27 (m, 1H), 1.17 (d, J=12.5 Hz, 1H), 1.12 (s, 9H), 1.02 (d, J=12.8 Hz, 1H), 0.85 (s, 3H), 0.60 (s, 3H). LCMS (M+H)=581.5.

Example 24

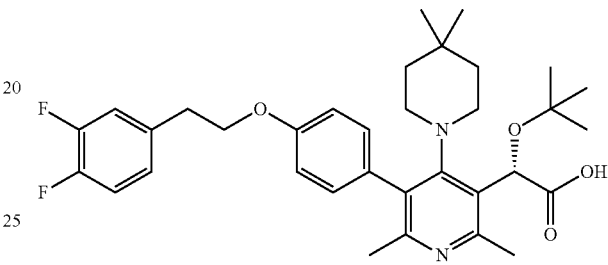

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(3,4-difluorophenyl)ethanol (33.7 mg, 0.213 mmol) and Ph₃P-resin (33.5 mg, 0.128 mmol) in THF (2 mL) was added DEAD (0.020 mL, 0.128 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(5-(4-(3,4-difluorophenethoxy)phenyl)-4-(4,4-dimethylpiperidin-1-yl)-2,6-dimethylpyridin-3-yl)acetic acid (1.7 mg, 2.93 μmol, 6.86% yield). ¹H NMR (500 MHz, DMSO-d₆) δ 7.48-7.39 (m, 1H), 7.39-7.32 (m, 1H), 7.24-7.14 (m, 2H), 7.07-6.99 (m, 3H), 5.86 (s, 1H), 4.34-4.18 (m, 2H), 3.24 (br. s., 1H), 3.07 (t, J=6.4 Hz, 2H), 2.85-2.76 (m, 1H), 2.44 (s, 3H), 2.18 (d, J=10.3 Hz, 1H), 2.05 (s, 3H), 1.98-1.90 (m, 1H), 1.49 (br. s., 1H), 1.36-1.23 (m, 1H), 1.18 (d, J=13.2 Hz, 1H), 1.13 (s, 9H), 1.02 (d, J=13.2 Hz, 1H), 0.85 (s, 3H), 0.60 (s, 3H). LCMS (M+H)=581.5.

Example 25

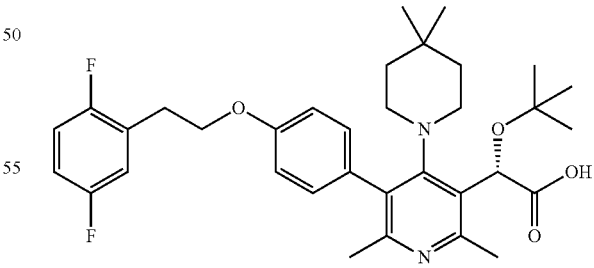

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(2,5-difluorophenyl)ethanol (33.7 mg, 0.213 mmol) and Ph₃P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h.

Mixture was then cooled and purified by prep-HPLC to afford (S)-2-(tert-butoxy)-2-(5-(4-(2,5-difluorophenethoxy)phenyl)-4-(4,4-dimethylpiperidin-1-yl)-2,6-dimethylpyridin-3-yl)acetic acid (3.2 mg, 5.51 μmol, 12.91% yield). ¹H NMR (500 MHz, DMSO-d₆) δ 7.33-7.27 (m, 1H), 7.27-7.17 (m, 3H), 7.17-7.11 (m, 1H), 7.07-6.98 (m, 4H), 5.87 (s, 1H), 4.32-4.23 (m, 2H), 3.09 (t, J=6.2 Hz, 2H), 2.80 (t, J=11.9 Hz, 1H), 2.43 (s, 3H), 2.05 (s, 3H), 1.98-1.91 (m, 1H), 1.49 (br. s., 1H), 1.29 (br. s., 1H), 1.18 (d, J=11.7 Hz, 1H), 1.13 (s, 9H), 1.05-0.95 (m, 1H), 0.85 (br. s., 3H), 0.60 (br. s., 3H). LCMS (M+H)=581.2.

Example 26

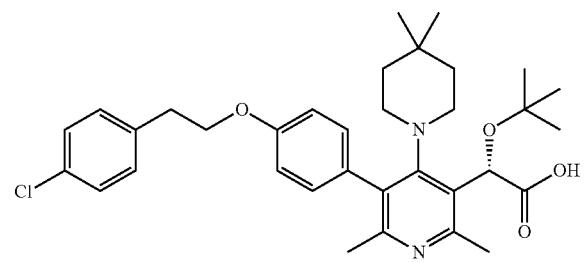 [SMILES: Cc1nc(C)c([C@H](OC(C)(C)C)C(=O)O)c(N2CCC(C)(C)CC2)c1-c1ccc(OCCc2ccc(Cl)cc2)cc1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(4-chlorophenyl)ethanol (33.4 mg, 0.213 mmol) and Ph₃P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(5-(4-(4-chlorophenethoxy)phenyl)-4-(4,4-dimethylpiperidin-1-yl)-2,6-dimethylpyridin-3-yl)acetic acid (6.9 mg, 0.012 mmol, 27.9% yield). ¹H NMR (500 MHz, DMSO-d₆) δ7.21 (d, J=8.4 Hz, 1H), 7.07-6.93 (m, 3H), 5.83 (s, 1H), 4.34-4.19 (m, 2H), 3.34 (br. s., 1H), 3.28 (br. s., 1H), 3.06 (t, J=6.6 Hz, 2H), 2.79 (t, J=12.1 Hz, 1H), 2.43 (s, 3H), 2.18 (d, J=9.2 Hz, 1H), 2.05 (s, 3H), 1.98-1.93 (m, 1H), 1.91 (s, 3H), 1.49 (br. s., 1H), 1.29 (br. s., 1H), 1.18 (d, J=11.7 Hz, 1H), 1.12 (s, 9H), 1.02 (d, J=13.9 Hz, 1H), 0.85 (s, 3H), 0.60 (s, 3H). LCMS (M+H)=579.5.

Example 27

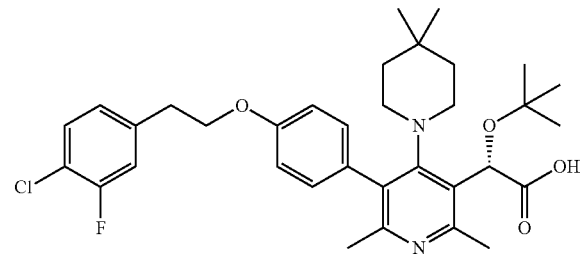 [SMILES: Cc1nc(C)c([C@H](OC(C)(C)C)C(=O)O)c(N2CCC(C)(C)CC2)c1-c1ccc(OCCc2ccc(Cl)c(F)c2)cc1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(4-chloro-3-fluorophenyl)ethanol (37.3 mg, 0.213 mmol) and Ph₃P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(5-(4-(4-chloro-3-fluorophenethoxy) phenyl)-4-(4,4-dimethylpiperidin-1-yl)-2,6-dimethylpyridin-3-yl)acetic acid (6.6 mg, 0.011 mmol, 25.9% yield). ¹H NMR (500 MHz, DMSO-d₆) δ 7.53 (t, J=8.1 Hz, 1H), 7.42 (d, J=10.6 Hz, 1H), 7.22 (t, J=7.9 Hz, 2H), 7.07-6.95 (m, 3H), 5.83 (s, 1H), 4.34-4.19 (m, 2H), 3.28 (d, J=11.7 Hz, 2H), 3.09 (t, J=6.6 Hz, 2H), 2.79 (t, J=12.3 Hz, 1H), 2.43 (s, 3H), 2.18 (d, J=11.0 Hz, 1H), 2.05 (s, 3H), 1.97-1.91 (m, 1H), 1.49 (br. s., 1H), 1.35-1.22 (m, 1H), 1.17 (d, J=11.0 Hz, 1H), 1.12 (s, 9H), 1.06-0.95 (m, 1H), 0.85 (s, 3H), 0.59 (s, 3H). LCMS (M+H)=597.5.

Example 28

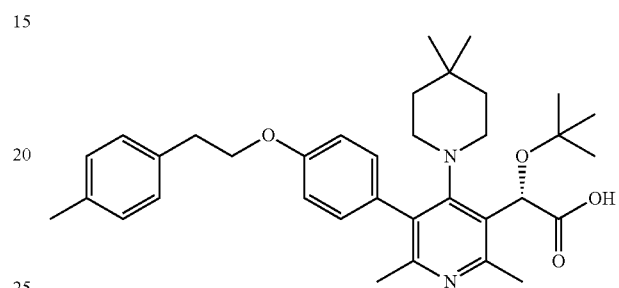

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(p-tolyl)ethanol (29.1 mg, 0.213 mmol) and Ph₃P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-(4-methylphenethoxy)phenyl)pyridin-3-yl)acetic acid (7.3 mg, 0.013 mmol, 30.6% yield). ¹H NMR (500 MHz, DMSO-d₆) δ 7.17 (d, J=7.7 Hz, 3H), 7.09 (d, J=8.1 Hz, 2H), 7.02-6.93 (m, 3H), 5.80 (br. s., 1H), 4.25-4.13 (m, 2H), 2.96 (t, J=6.2 Hz, 2H), 2.41 (s, 3H), 2.24 (s, 3H), 2.03 (s, 3H), 1.21 (br. s., 2H), 1.09 (s, 9H), 0.77 (s., 3H), 0.62 (s., 3H). 6H of piperidine were not resolved. LCMS (M+H)=559.15.

Example 29

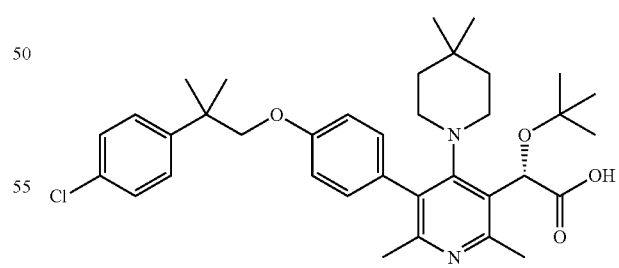

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(4-chlorophenyl)-2-methylpropan-1-ol (39.4 mg, 0.213 mmol) and Ph₃P (56.0 mg, 0.213 mmol) in THF (2 mL) was added DEAD (0.014 mL, 0.085 mmol) at rt and the mixture was heated at 70° C. for 16 h. The reaction mixture was then cooled, concentrated and purified by prep-HPLC to afford desired ester, LCMS (M+H)=635.4. Ester was the treated with 1N NaOH (0.213 mL, 0.213 mmol) in MeOH (1 mL) at 75° C. for 16 h. Mixture was then cooled and purified by prep-HPLC to afford (S)-2-(tert-butoxy)-2-(5-(4-(2-(4-chlorophenyl)-2-methylpropoxy)phenyl)-4-(4,4-dimethylpiperidin-1-yl)-2,6-dimethylpyridin-3-yl)acetic acid (2.5 mg, 3.91 μmol, 9.16% yield). $^1$H NMR (500 MHz, DMSO-$d_6$) δ 7.54-7.48 (m, J=8.8 Hz, 2H), 7.40-7.32 (m, J=8.4 Hz, 2H), 7.18 (d, J=8.1 Hz, 1H), 7.03-6.92 (m, 3H), 5.81 (s, 1H), 4.10 (d, J=9.2 Hz, 1H), 4.03 (d, J=9.2 Hz, 1H), 3.39 (br. s., 1H), 3.28 (br. s., 1H), 2.83-2.75 (m, 1H), 2.43 (s, 3H), 2.16 (d, J=7.7 Hz, 1H), 2.04 (s, 3H), 1.97-1.88 (m, 1H), 1.47 (d, J=8.8 Hz, 1H), 1.40 (s, 6H), 1.28 (br. s., 1H), 1.17 (d, J=11.4 Hz, 1H), 1.12 (s, 9H), 1.05-0.93 (m, 1H), 0.85 (s, 3H), 0.59 (s, 3H). LCMS (M+H)=607.5.

Example 30

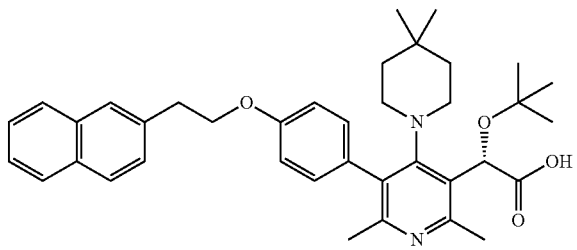 [SMILES: Cc1nc(C)c([C@H](OC(C)(C)C)C(=O)O)c(N2CCC(C)(C)CC2)c1-c1ccc(OCCc2ccc3ccccc3c2)cc1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(naphthalen-2-yl)ethanol (36.8 mg, 0.213 mmol) and Ph$_3$P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-(2-(naphthalen-2-yl)ethoxy)phenyl)pyridin-3-yl)acetic acid (2.7 mg, 4.54 μmol, 10.64% yield). $^1$H NMR (500 MHz, DMSO-$d_6$) δ 7.92-7.80 (m, 4H), 7.57-7.46 (m, 3H), 7.21 (d, J=8.4 Hz, 1H), 7.10-6.93 (m, 3H), 5.83 (s, 1H), 4.45-4.26 (m, 2H), 3.45-3.24 (m, 3H), 2.80 (t, J=11.2 Hz, 1H), 2.43 (s, 3H), 2.17 (br. s., 1H), 2.05 (s, 3H), 1.99-1.91 (m, 1H), 1.48 (br. s., 1H), 1.37-1.27 (m, 1H), 1.17 (d, J=13.9 Hz, 1H), 1.12 (s, 9H), 1.02 (d, J=11.7 Hz, 1H), 0.84 (s, 3H), 0.60 (s, 3H). LCMS (M+H)=595.5.

Example 31

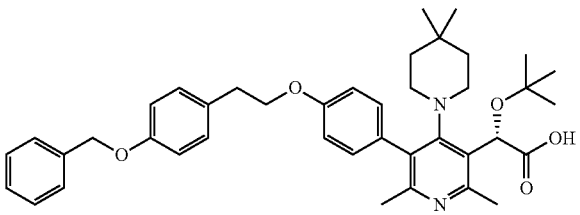 [SMILES: Cc1nc(C)c([C@H](OC(C)(C)C)C(=O)O)c(N2CCC(C)(C)CC2)c1-c1ccc(OCCc2ccc(OCc3ccccc3)cc2)cc1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(4-(benzyloxy)phenyl)ethanol (48.7 mg, 0.213 mmol) and Ph$_3$P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(5-(4-(4-(benzyloxy)phenethoxy)phenyl)-4-(4,4-dimethylpiperidin-1-yl)-2,6-dimethylpyridin-3-yl)-2-(tert-butoxy)acetic acid (3.9 mg, 5.99 μmol, 14.04% yield). $^1$H NMR (500 MHz, DMSO-$d_6$) δ 7.50-7.29 (m, 6H), 7.28-7.12 (m, 3H), 7.07-6.89 (m, 4H), 5.85 (br. s., 1H), 5.09 (br. s., 2H), 4.20 (d, J=11.0 Hz, 2H), 3.34 (br. s., 1H), 3.25 (br. s., 2H), 2.99 (br. s., 1H), 2.80 (br. s., 1H), 2.43 (br. s., 3H), 2.17 (br. s., 1H), 2.06 (br. s., 3H), 1.92 (br. s., 1H), 1.48 (br. s., 1H), 1.28 (br. s., 1H), 1.13 (br. s., 9H), 1.04 (br. s., 1H), 0.85 (br. s., 3H), 0.60 (br. s., 3H). LCMS (M+H)=651.6.

Example 32

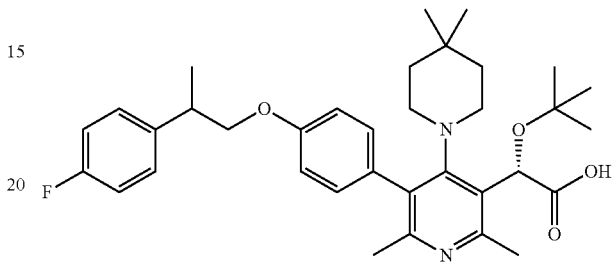

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(4-fluorophenyl)propan-1-ol (32.9 mg, 0.213 mmol) and Ph$_3$P (55.8 mg, 0.213 mmol) in THF (2 mL) was added DEAD (0.014 mL, 0.085 mmol) and the resulting mixture was heated at 70° C. for 16 h. Mixture was then cooled and purified by prep HPLC to afford desired ester. Ester was then treated with 1N NaOH (0.427 mL, 0.427 mmol) in MeOH (1 mL) at 75° C. for 16 h. Mixture was then cooled and purified by prep HPLC to afford (2S)-2-(tert-butoxy)-2-(4-(4,4-dimethylpiperidin-1-yl)-5-(4-(2-(4-fluorophenyl)propoxy)phenyl)-2,6-dimethylpyridin-3-yl)acetic acid (7.5 mg, 0.013 mmol, 30.5% yield) as inseparable mixture of diastereomers. $^1$H NMR (500 MHz, DMSO-$d_6$) δ 7.43-7.35 (m, 2H), 7.20-7.12 (m, 3H), 7.05-6.90 (m, 3H), 5.37 (s, 1H), 4.19-4.02 (m, 2H), 3.29-3.20 (m, 1H), 2.66 (t, J=11.9 Hz, 1H), 2.42 (s, 3H), 2.11 (d, J=11.4 Hz, 1H), 2.02 (s, 3H), 1.83 (t, J=12.5 Hz, 1H), 1.51 (br. s., 1H), 1.33 (d, J=7.0 Hz, 3H), 1.28 (br. s., 1H), 1.24 (br. s., 1H), 1.11 (br. s., 1H), 1.06 (s, 9H), 0.97 (d, J=12.8 Hz, 1H), 0.83 (s, 3H), 0.62 (s, 3H). LCMS (M+H)=577.5.

Example 33

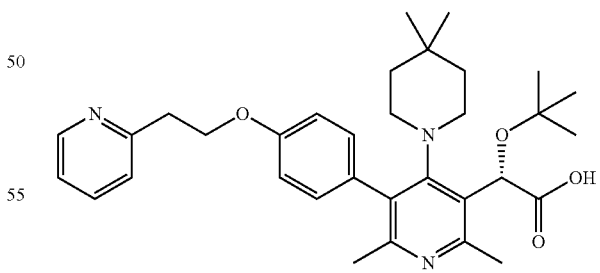

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(pyridin-2-yl)ethanol (26.3 mg, 0.213 mmol) and Ph$_3$P (56.0 mg, 0.213 mmol) in THF (2 mL) was added DEAD (0.034 mL, 0.213 mmol) at rt. After 18 h, the reaction mixture was concentrated and the residue was purified by prep-HPLC to afford desired ester, which was treated with 1N NaOH (0.213 mL, 0.213 mmol) in MeOH (1 mL) at 70° C. for 16 h. Mixture was then cooled and purified by prep HPLC to afford (S)-2-(tert-butoxy)-2-(4-(4,4-dimethylpiperidin-1-yl)-2,6-dimethyl-5-(4-(2-(pyridin-2-yl)ethoxy)phenyl)pyridin-3-yl)acetic acid (9.7 mg, 0.018 mmol, 41.6% yield). ¹H NMR (500 MHz, DMSO-d₆) δ 8.53 (d, J=4.4 Hz, 1H), 7.74 (td, J=7.7, 1.8 Hz, 1H), 7.38 (d, J=7.7 Hz, 1H), 7.26 (dd, J=7.2, 5.3 Hz, 1H), 7.20 (d, J=8.4 Hz, 1H), 7.08-6.95 (m, 3H), 5.85 (s, 1H), 4.50-4.38 (m, 2H), 3.35-3.20 (m, 3H), 2.80 (t, J=12.3 Hz, 1H), 2.43 (s, 3H), 2.18 (d, J=12.1 Hz, 1H), 2.06 (s, 3H), 1.98-1.91 (m, 1H), 1.55-1.46 (m, 1H), 1.34-1.26 (m, 1H), 1.18 (d, J=12.5 Hz, 1H), 1.13 (s, 9H), 1.03 (d, J=12.5 Hz, 1H), 0.85 (s, 3H), 0.61 (s, 3H). LCMS (M+H)=546.5.

Example 34

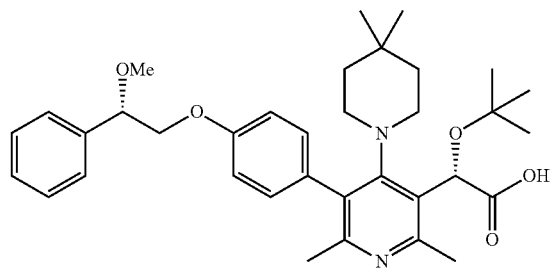 [SMILES: CO[C@H](COc1ccc(-c2c(C)nc(C)c([C@H](OC(C)(C)C)C(=O)O)c2N2CCC(C)(C)CC2)cc1)c1ccccc1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), (S)-2-methoxy-2-phenylethanol (32.5 mg, 0.213 mmol) and Ph₃P (56.0 mg, 0.213 mmol) in THF (2 mL) was added DEAD (0.034 mL, 0.213 mmol) at rt. After 18 h, the reaction mixture was concentrated and the residue was purified by prep-HPLC to afford desired ester, which was treated with 1N NaOH (0.213 mL, 0.213 mmol) in MeOH (1 mL) at 70° C. for 16 h. Mixture was then cooled and purified by prep HPLC to afford (S)-2-(tert-butoxy)-2-(4-(4,4-dimethylpiperidin-1-yl)-5-(4-((S)-2-methoxy-2-phenylethoxy)phenyl)-2,6-dimethylpyridin-3-yl)acetic acid (4.2 mg, 7.31 μmol, 17.12% yield). ¹H NMR (500 MHz, DMSO-d₆) δ 7.47-7.39 (m, 4H), 7.38-7.31 (m, 1H), 7.20 (d, J=8.1 Hz, 1H), 7.07-6.96 (m, 3H), 5.79 (s, 1H), 4.63 (dd, J=7.3, 3.7 Hz, 1H), 4.22 (dd, J=10.5, 7.9 Hz, 1H), 4.07 (dd, J=10.6, 3.7 Hz, 1H), 3.55-3.34 (m, 4H), 2.84-2.77 (m, 1H), 2.43 (s, 3H), 2.17 (d, J=8.4 Hz, 1H), 2.05 (s, 3H), 1.97-1.92 (m, 1H), 1.49 (br. s., 1H), 1.39-1.27 (m, 1H), 1.19 (br. s., 1H), 1.12 (s, 9H), 1.02 (d, J=12.1 Hz, 1H), 0.85 (s, 3H), 0.62 (s, 3H). LCMS (M+H)=575.5.

Example 35

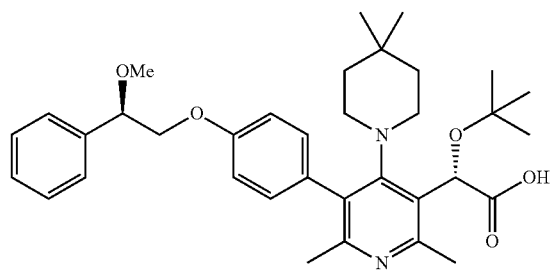 [SMILES: CO[C@@H](COc1ccc(-c2c(C)nc(C)c([C@H](OC(C)(C)C)C(=O)O)c2N2CCC(C)(C)CC2)cc1)c1ccccc1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), (R)-2-methoxy-2-phenylethanol (32.5 mg, 0.213 mmol) and Ph₃P (56.0 mg, 0.213 mmol) in THF (2 mL) was added DEAD (0.034 mL, 0.213 mmol) at rt. After 18 h, the reaction mixture was concentrated and the residue was purified by prep-HPLC to afford desired ester, which was treated with 1N NaOH (0.213 mL, 0.213 mmol) in MeOH (1 mL) at 70° C. for 16 h. Mixture was then cooled and purified by prep HPLC to afford (S)-2-(tert-butoxy)-2-(4-(4,4-dimethylpiperidin-1-yl)-5-(4-((R)-2-methoxy-2-phenylethoxy)phenyl)-2,6-dimethylpyridin-3-yl)acetic acid (9.9 mg, 0.017 mmol, 40.4% yield). ¹H NMR (500 MHz, DMSO-d₆) δ 7.47-7.39 (m, 4H), 7.38-7.31 (m, 1H), 7.20 (d, J=8.1 Hz, 1H), 7.07-6.96 (m, 3H), 5.79 (s, 1H), 4.63 (dd, J=7.3, 3.7 Hz, 1H), 4.22 (dd, J=10.5, 7.9 Hz, 1H), 4.12 (dd, J=10.6, 3.7 Hz, 1H), 3.55-3.34 (m, 4H), 2.84-2.77 (m, 1H), 2.43 (s, 3H), 2.17 (d, J=8.4 Hz, 1H), 2.05 (s, 3H), 1.97-1.92 (m, 1H), 1.49 (br. s., 1H), 1.39-1.27 (m, 1H), 1.19 (br. s., 1H), 1.12 (s, 9H), 1.02 (d, J=12.1 Hz, 1H), 0.85 (s, 3H), 0.62 (s, 3H). LCMS (M+H)=575.5.

Example 36

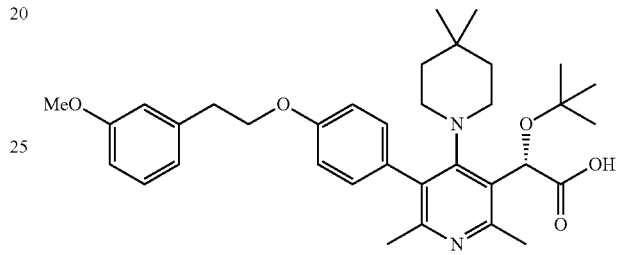

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(3-methoxyphenyl)ethanol (32.5 mg, 0.213 mmol) and Ph₃P-resin (55.8 mg, 0.213 mmol) in THF (2 mL) was added DEAD (0.014 mL, 0.085 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-5-(4-(3-methoxyphenethoxy)phenyl)-2,6-dimethylpyridin-3-yl)acetic acid (11.9 mg, 0.021 mmol, 48.5% yield). ¹H NMR (500 MHz, DMSO-d₆) δ 7.26-7.18 (m, 2H), 7.07-6.98 (m, 3H), 6.94-6.87 (m, 2H), 6.82-6.78 (m, 1H), 5.81 (s, 1H), 4.31-4.17 (m, 2H), 3.31 (br. s., 2H), 3.04 (t, J=6.8 Hz, 2H), 2.86-2.76 (m, 1H), 2.43 (s, 3H), 2.16 (br. s., 1H), 2.05 (s, 3H), 1.98-1.92 (m, 1H), 1.50 (br. s., 1H), 1.36-1.23 (m, 1H), 1.17 (d, J=11.7 Hz, 1H), 1.12 (s, 9H), 1.02 (d, J=14.7 Hz, 1H), 0.85 (s, 3H), 0.61 (s, 3H). 2H of piperidine were not resolved. LCMS (M+H)=575.5.

Example 37

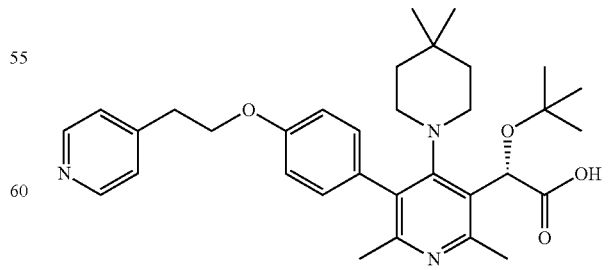

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(pyridin-4-yl)

ethanol (26.3 mg, 0.213 mmol) and Ph₃P (56 mg, 0.213 mmol) in THF (2 mL) was added DEAD (0.034 mL, 0.213 mmol) at rt. After 18 h, the reaction mixture was concentrated and the residue was purified by prep-HPLC to afford desired ester, which was treated with 1N NaOH (0.213 mL, 0.213 mmol) in MeOH (1 mL) at 70° C. for 3 h. Please note that (M+H)=441 is the major product. Mixture was then cooled and purified by prep HPLC to afford (S)-2-(tert-butoxy)-2-(4-(4,4-dimethylpiperidin-1-yl)-2,6-dimethyl-5-(4-(2-(pyridin-4-yl)ethoxy)phenyl)pyridin-3-yl)acetic acid (1 mg, 1.832 μmol, 4.29% yield). ¹H NMR (400 MHz, METHANOL-d₄) δ 8.48 (d, J=5.6 Hz, 2H), 7.45 (d, J=6.1 Hz, 2H), 7.33-7.21 (m, 1H), 7.13-7.01 (m, 3H), 5.57 (s, 1H), 4.38 (t, J=6.5 Hz, 2H), 3.20 (t, J=6.2 Hz, 2H), 2.72 (br. s., 2H), 2.67 (s, 3H), 2.26 (s, 3H), 1.98-1.93 (m, 2H), 1.36 (br. s., 4H), 1.20 (s, 9H), 0.83 (s, 6H). LCMS (M+H)=546.4.

Example 38

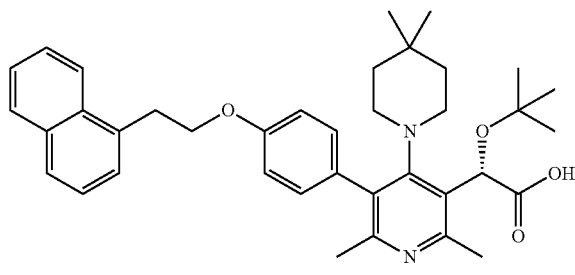 [SMILES: Cc1nc(C)c([C@H](OC(C)(C)C)C(=O)O)c(N2CCC(C)(C)CC2)c1-c1ccc(OCCc2cccc3ccccc23)cc1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(naphthalen-1-yl)ethanol (36.8 mg, 0.213 mmol) and Ph₃P (55.8 mg, 0.213 mmol) in THF (2 mL) was added DEAD (0.014 mL, 0.085 mmol) at rt. After 18 h, the reaction mixture was concentrated and the residue was purified by prep-HPLC to afford desired ester, which was treated with 1N NaOH (0.213 mL, 0.213 mmol) in MeOH (1 mL) at 70° C. for 16 h. Mixture was then cooled and purified by prep HPLC to afford (S)-2-(tert-butoxy)-2-(4-(4,4-dimethylpiperidin-1-yl)-2,6-dimethyl-5-(4-(2-(naphthalen-1-yl)ethoxy)phenyl)pyridin-3-yl)acetic acid (14.6 mg, 0.025 mmol, 57.5% yield). ¹H NMR (500 MHz, DMSO-d₆) δ 8.18 (d, J=8.4 Hz, 1H), 7.95 (d, J=8.1 Hz, 1H), 7.84 (d, J=8.1 Hz, 1H), 7.60-7.44 (m, 4H), 7.21 (d, J=8.1 Hz, 1H), 7.05 (s, 2H), 7.02 (d, J=8.8 Hz, 1H), 5.86 (br. s., 1H), 4.46-4.25 (m, 2H), 3.56 (t, J=6.6 Hz, 2H), 3.36 (br. s., 1H), 2.19 (br. s., 1H), 2.45 (s, 3H), 2.19 (br. s., 1H), 2.06 (s, 3H), 1.47 (br. s., 1H), 1.25 (d, J=7.7 Hz, 2H), 1.13 (s, 9H), 0.81 (br. s., 3H), 0.65 (br. s., 3H). 2H of piperidine were not resolved. LCMS (M+H)=595.4.

Example 39

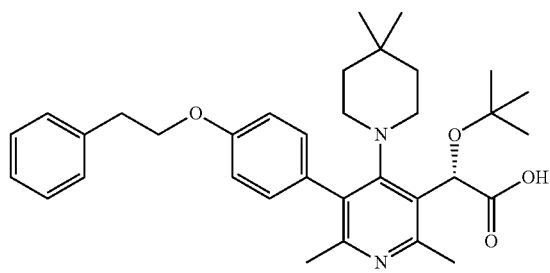 [SMILES: Cc1nc(C)c([C@H](OC(C)(C)C)C(=O)O)c(N2CCC(C)(C)CC2)c1-c1ccc(OCCc2ccccc2)cc1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-phenylethanol (26.1 mg, 0.213 mmol) and Ph₃P-resin (55.8 mg, 0.213 mmol) in THF (2 mL) was added DEAD (0.020 mL, 0.128 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-phenethoxyphenyl)pyridin-3-yl)acetic acid (4.6 mg, 8.44 μmol, 19.79% yield). ¹H NMR (500 MHz, DMSO-d₆) δ 7.38-7.29 (m, 4H), 7.27-7.17 (m, 2H), 7.08-6.93 (m, 3H), 5.70 (br. s., 1H), 4.32-4.18 (m, 2H), 3.51-3.42 (m, 2H), 3.06 (d, J=7.0 Hz, 1H), 2.81-2.68 (m, 1H), 2.43 (s, 3H), 2.17 (d, J=13.2 Hz, 1H), 2.05 (s, 3H), 1.96-1.90 (m, 1H), 1.50 (br. s., 1H), 1.29 (br. s., 1H), 1.15 (d, J=11.7 Hz, 1H), 1.11 (s, 9H), 1.01 (d, J=11.0 Hz, 1H), 0.85 (br. s., 3H), 0.62 (br. s., 3H). LCMS (M+H)=545.5.

Example 40

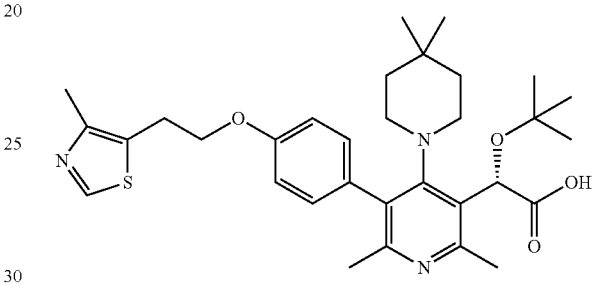

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(4-methylthiazol-5-yl)ethanol (30.6 mg, 0.213 mmol) and Ph₃P-resin (55.8 mg, 0.213 mmol) in THF (2 mL) was added DEAD (0.020 mL, 0.128 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-(2-(4-methylthiazol-5-yl)ethoxy)phenyl)pyridin-3-yl)acetic acid (4.2 mg, 7.42 μmol, 17.39% yield). ¹H NMR (500 MHz, DMSO-d₆) δ 8.87 (s, 1H), 7.39 (d, J=8.4 Hz, 1H), 7.17 (s, 1H), 7.13-7.08 (m, 2H), 5.54 (s, 1H), 4.54-4.41 (m, 6H), 4.26-4.15 (m, 2H), 2.68 (s, 3H), 2.37 (s, 3H), 2.29 (s, 3H), 1.28 (br. s., 4H), 1.15 (s, 9H), 0.80 (br. s., 6H). LCMS (M+H)=566.5.

Example 41

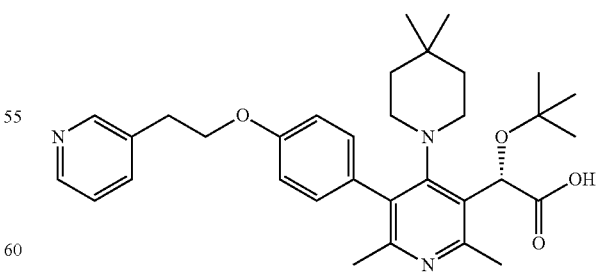

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (20 mg, 0.043 mmol), 2-(pyridin-3-yl)ethanol (26.3 mg, 0.213 mmol) and Ph₃P (56 mg, 0.213 mmol) in THF (2 mL) was added DEAD (0.034 mL, 0.213 mmol) at rt. After 18 h, the reaction mixture was concentrated and the residue was purified by prep-HPLC to afford desired ester which was treated with 1N NaOH (0.213 mL, 0.213 mmol) in MeOH (1 mL) at 75° C. for 5 h. Mixture was then cooled and purified by prep HPLC to afford (S)-2-(tert-butoxy)-2-(4-(4,4-dimethylpiperidin-1-yl)-2,6-dimethyl-5-(4-(2-(pyridin-3-yl)ethoxy)phenyl)pyridin-3-yl)acetic acid (6.5 mg, 0.012 mmol, 27.9% yield). $^1$H NMR (500 MHz, DMSO-$d_6$) δ 8.62 (s, 1H), 8.51 (d, J=4.0 Hz, 1H), 7.90 (d, J=7.7 Hz, 1H), 7.49-7.44 (m, 1H), 7.36 (d, J=8.4 Hz, 1H), 7.26 (s, 1H), 7.16 (s, 1H), 7.06 (s, 1H), 5.56 (s, 1H), 4.40-4.20 (m, 2H), 3.43 (br. s., 2H), 3.13 (t, J=6.2 Hz, 2H), 2.74-2.66 (m, 4H), 2.26 (s, 3H), 1.28 (br. s., 3H), 1.15 (s, 9H), 0.79 (br. s., 6H). 2H of piperidine were not resolved. LCMS (M+H)=546.5.

Example 42

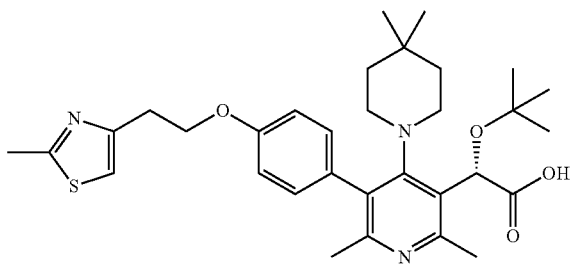 [SMILES: Cc1nc(CCOc2ccc(-c3c(C)nc(C)c([C@H](OC(C)(C)C)C(=O)O)c3N3CCC(C)(C)CC3)cc2)cs1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (25 mg, 0.053 mmol), 2-(2-methylthiazol-4-yl)ethanol (22.92 mg, 0.160 mmol) and Ph$_3$P-resin (69.7 mg, 0.267 mmol) in THF (2 mL) was added DEAD (0.025 mL, 0.160 mmol) at rt. After 18 h, mixture was filtered to remove polymer, concentrated and treated with 1N NaOH (1.067 mL, 1.067 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-(2-(2-methylthiazol-4-yl)ethoxy)phenyl)pyridin-3-yl)acetic acid (19.4 mg, 0.034 mmol, 64.3% yield). $^1$H NMR (500 MHz, DMSO-$d_6$) δ 7.26-7.18 (m, 2H), 7.08-6.97 (m, 3H), 5.83 (s, 1H), 4.41-4.28 (m, 2H), 3.40-3.30 (m, 2H), 3.14 (t, J=6.4 Hz, 2H), 2.80 (t, J=12.1 Hz, 1H), 2.64 (s, 3H), 2.43 (s, 3H), 2.17 (d, J=11.0 Hz, 1H), 2.06 (s, 3H), 1.99-1.93 (m, 1H), 1.49 (br. s., 1H), 1.30 (br. s., 1H), 1.18 (d, J=11.4 Hz, 1H), 1.13 (s, 9H), 1.03 (d, J=10.6 Hz, 1H), 0.85 (br. s., 3H), 0.61 (br. s., 3H). LCMS (M+H)=566.6.

Example 43

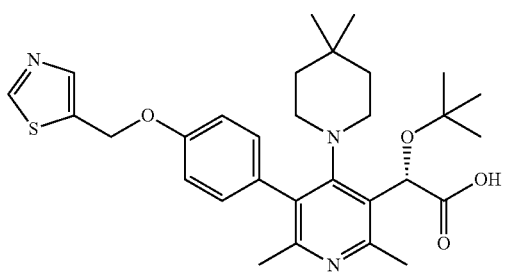 [SMILES: Cc1nc(C)c([C@H](OC(C)(C)C)C(=O)O)c(N2CCC(C)(C)CC2)c1-c1ccc(OCc2cncs2)cc1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (25 mg, 0.053 mmol), thiazol-5-yl-methanol (18.43 mg, 0.160 mmol) and Ph$_3$P-resin (69.7 mg, 0.267 mmol) in THF (2 mL) was added DEAD (0.025 mL, 0.160 mmol) at rt. After 18 h, mixture was filtered to remove polymer, concentrated and treated with 1N NaOH (1.067 mL, 1.067 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-(thiazol-5-ylmethoxy)phenyl)pyridin-3-yl)acetic acid (14.1 mg, 0.026 mmol, 49.2% yield). $^1$H NMR (500 MHz, DMSO-$d_6$) δ 9.13 (s, 1H), 8.03 (s, 1H), 7.25 (d, J=8.8 Hz, 1H), 7.17-7.09 (m, 2H), 7.09-7.03 (m, 1H), 5.83 (s, 1H), 5.54-5.40 (m, 2H), 3.28 (d, J=10.3 Hz, 1H), 2.78 (t, J=11.0 Hz, 1H), 2.43 (s, 3H), 2.17 (d, J=10.3 Hz, 1H), 2.06 (s, 3H), 1.97-1.82 (m, 1H), 1.49 (br. s., 1H), 1.28 (d, J=12.1 Hz, 1H), 1.17 (d, J=11.7 Hz, 1H), 1.13 (s, 9H), 1.01 (d, J=9.9 Hz, 1H), 0.85 (br. s., 3H), 0.58 (s, 3H). LCMS (M+H)=538.5.

Example 44

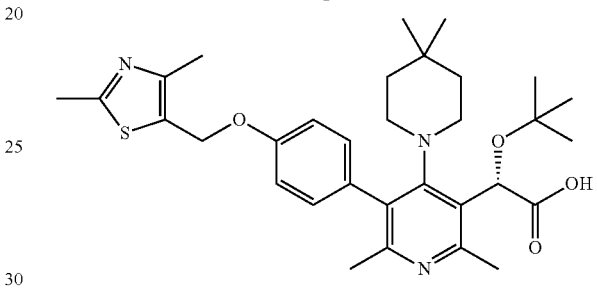

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (25 mg, 0.053 mmol), (2,4-dimethylthiazol-5-yl)methanol (22.92 mg, 0.160 mmol) and Ph$_3$P-resin (69.7 mg, 0.267 mmol) in THF (2 mL) was added DEAD (0.025 mL, 0.160 mmol) at rt. After 18 h, mixture was filtered to remove polymer, concentrated and treated with 1N NaOH (1.067 mL, 1.067 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-5-(4-((2,4-dimethylthiazol-5-yl)methoxy)phenyl)-2,6-dimethylpyridin-3-yl)acetic acid (17.7 mg, 0.031 mmol, 58.6% yield). $^1$H NMR (500 MHz, DMSO-$d_6$) δ 7.29-7.21 (m, 1H), 7.14-7.01 (m, 3H), 5.84 (s, 1H), 5.36-5.15 (m, 2H), 3.27 (d, J=7.7 Hz, 1H), 2.79 (t, J=11.9 Hz, 1H), 2.58 (s, 3H), 2.44 (s, 3H), 2.34 (s, 3H), 2.18 (d, J=12.5 Hz, 1H), 2.06 (s, 3H), 1.96-1.87 (m, 1H), 1.49 (br. s., 1H), 1.36-1.25 (m, 1H), 1.18 (d, J=12.8 Hz, 1H), 1.13 (s, 9H), 1.01 (d, J=11.7 Hz, 1H), 0.85 (br. s., 3H), 0.59 (br. s., 3H). LCMS (M+H)=566.6.

Example 45

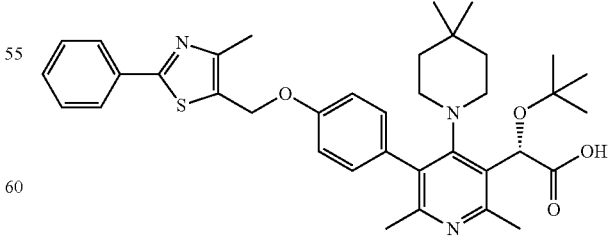

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (25 mg, 0.053 mmol), (4-methyl-2-phenylthiazol-5-yl)methanol (32.9 mg, 0.160 mmol) and Ph$_3$-resin (69.7 mg, 0.267 mmol) in THF (2 mL) was added DEAD (0.025 mL, 0.160 mmol) at rt. After 18 h, mixture was filtered to remove polymer, concentrated and treated with 1N NaOH (1.067 mL, 1.067 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-((4-methyl-2-phenylthiazol-5-yl)methoxy)phenyl)pyridin-3-yl)acetic acid (11.6 mg, 0.018 mmol, 34.6% yield). $^1$H NMR (500 MHz, DMSO-$d_6$) δ 7.89 (d, J=7.3 Hz, 2H), 7.52-7.41 (m, 4H), 7.25 (d, J=8.1 Hz, 1H), 7.14 (t, J=7.9 Hz, 2H), 7.10-7.04 (m, 1H), 5.82 (br. s., 1H), 5.41 (q, J=12.8 Hz, 2H), 3.26 (d, J=11.7 Hz, 1H), 2.77 (br. s., 1H), 2.47 (s, 3H), 2.43 (s, 3H), 2.15 (d, J=10.3 Hz, 1H), 2.07 (s, 3H), 1.88 (br. s., 1H), 1.46 (br. s., 1H), 1.24 (br. s., 1H), 1.15 (br. s., 1H), 1.12 (s, 9H), 0.92 (d, J=10.3 Hz, 1H), 0.77 (br. s., 3H), 0.51 (br. s., 3H). LCMS (M+H)=628.6.

Example 46

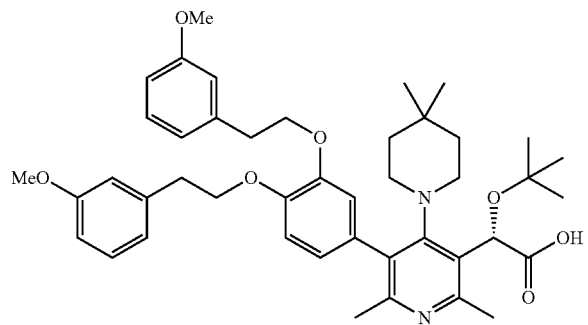 [SMILES: COc1cccc(CCOc2ccc(-c3c(C)nc(C)c([C@H](OC(C)(C)C)C(=O)O)c3N3CCC(C)(C)CC3)cc2OCCc2cccc(OC)c2)c1]

A mixture of (S)-ethyl 2-(5-bromo-4-(4,4-dimethylpiperidin-1-yl)-2,6-dimethylpyridin-3-yl)-2-(tert-butoxy)acetate (20 mg, 0.044 mmol), (3,4-bis(3-methoxyphenethoxy)phenyl)boronic acid (24.11 mg, 0.057 mmol) and 2M $Na_2CO_3$ (0.055 mL, 0.110 mmol) in 1,4-Dioxane (1 mL) was degassed for 10 min. Then, $Pd(Ph_3P)_4$ (2.54 mg, 2.196 μmol) was added, degassed for 5 min and placed in a pre-heated oil bath at 90° C. After 9 h, cooled, concentrated and purified by prep HPLC to afford desired ester (M+H)=753.9. Ester was then treated with 1N NaOH (0.220 mL, 0.220 mmol) in MeOH (1 mL) at 75° C. for 3 h. Mixture was cooled and purified by prep HPLC to afford (S)-2-(5-(3,4-bis(3-methoxyphenethoxy)phenyl)-4-(4,4-dimethylpiperidin-1-yl)-2,6-dimethylpyridin-3-yl)-2-(tert-butoxy)acetic acid (4.7 mg, 6.48 μmol, 14.76% yield). $^1$H NMR (500 MHz, DMSO-$d_6$) δ 7.26-7.14 (m, 2H), 7.06 (dd, J=12.7, 8.3 Hz, 1H), 6.92-6.84 (m, 5H), 6.83-6.74 (m, 2H), 6.72 (s, 0.6H), 6.64 (d, J=8.1 Hz, 0.4H), 5.82 (br. s., 0.6H), 5.80 (br. s., 0.4H), 4.26-4.10 (m, 5H), 3.71 (s, 2H), 3.70 (s, 2H), 3.05-2.93 (m, 5H), 2.81 (br. s., 1H), 2.42 (s, 3H), 2.22 (br. s., 1H), 2.07 (d, J=9.5 Hz, 3H), 1.97 (d, J=12.5 Hz, 1H), 1.49 (br. s., 1H), 1.29 (br. s., 1H), 1.17 (br. s., 1H), 1.12 (d, J=2.6 Hz, 9H), 1.02 (br. s., 1H), 0.84 (br. s., 3H), 0.62 (br. s., 2H), 0.56 (br. s., 1H). LCMS (M+H)=725.8.

Example 47

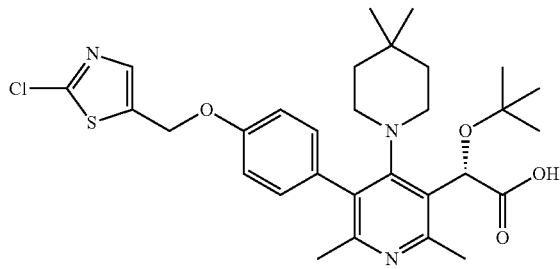 [SMILES: Cc1nc(C)c([C@H](OC(C)(C)C)C(=O)O)c(N2CCC(C)(C)CC2)c1-c1ccc(OCc2cnc(Cl)s2)cc1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (25 mg, 0.053 mmol), (2-chlorothiazol-5-yl)methanol (23.94 mg, 0.160 mmol) and $Ph_3$P-resin (69.7 mg, 0.267 mmol) in THF (2 mL) was added DEAD (0.025 mL, 0.160 mmol) at rt. After 18 h, mixture was filtered to remove polymer, concentrated and treated with 1N NaOH (1.067 mL, 1.067 mmol) in MeOH (1 mL) at 75° C. for 16 h. Mixture was then cooled and purified by prep-HPLC to afford (S)-2-(tert-butoxy)-2-(5-(4-((2-chlorothiazol-5-yl)methoxy)phenyl)-4-(4,4-dimethylpiperidin-1-yl)-2,6-dimethylpyridin-3-yl)acetic acid (0.9 mg, 1.573 μmol, 2.95% yield). $^1$H NMR (400 MHz, METHANOL-$d_4$) δ 7.69 (s, 1H), 7.37-7.32 (m, 1H), 7.24-7.17 (m, 2H), 7.16-7.10 (m, 1H), 5.55 (s, 1H), 5.42 (s, 2H), 2.68 (s, 3H), 2.28 (s, 3H), 1.36 (br. s., 3H), 1.31 (br. s., 1H), 1.20 (s, 9H), 0.84 (s, 6H). 4H of piperidine were not resolved. LCMS (M+H)=572.5.

Example 48

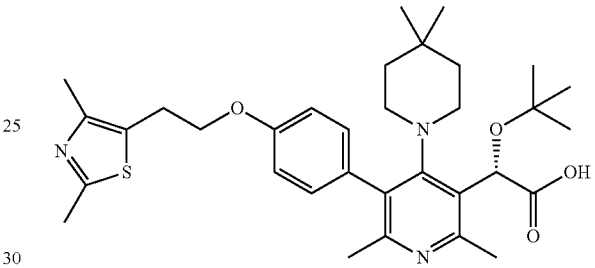

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (100 mg, 0.213 mmol), 2-(2,4-dimethylthiazol-5-yl)ethanol (101 mg, 0.640 mmol) and $Ph_3$P (168 mg, 0.640 mmol) in THF (2 mL) was added DEAD (0.101 mL, 0.640 mmol) at rt. After 18 h, the reaction mixture was concentrated and the residue was purified by prep-HPLC to afford desired ester. (M+H)=608.6. Ester was then treated with 1N NaOH (1.067 mL, 1.067 mmol) in MeOH (2 mL) at 75° C. for 3 h. Mixture was then cooled and purified by prep HPLC to afford (S)-2-(tert-butoxy)-2-(4-(4,4-dimethylpiperidin-1-yl)-5-(4-(2-(2,4-dimethylthiazol-5-yl)ethoxy)phenyl)-2,6-dimethylpyridin-3-yl)acetic acid (50 mg, 0.082 mmol, 38.4% yield) as white solid. $^1$H NMR (500 MHz, METHANOL-$d_4$) δ 7.30 (d, J=8.5 Hz, 1H), 7.18-7.01 (m, 3H), 5.56 (s, 1H), 4.25 (t, J=5.9 Hz, 2H), 3.25 (t, J=5.9 Hz, 2H), 2.74 (d, J=12.5 Hz, 1H), 2.68 (s, 3H), 2.62 (s, 3H), 2.36 (s, 3H), 2.27 (s, 3H), 1.37 (br. s., 4H), 1.20 (s, 9H), 0.84 (s, 6H). 4H of piperidine were not resolved. LCMS (M+H)=580.6.

Example 49

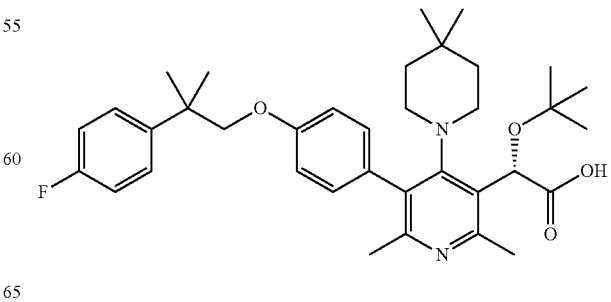

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (100 mg, 0.213 mmol), 2-(4-fluorophenyl)-2-methylpropan-1-ol (179 mg, 1.067 mmol) and Ph₃P (280 mg, 1.067 mmol) in THF (3 mL) was added DIAD (0.207 mL, 1.067 mmol) at rt and the mixture was heated at 70° C. for 16 h. The reaction mixture was then cooled, concentrated and purified by prep-HPLC to afford desired ester, LCMS (M+H)=619.8. Ester was the treated with 1N NaOH (1.067 mL, 1.067 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-5-(4-(2-(4-fluorophenyl)-2-methylpropoxy)phenyl)-2,6-dimethylpyridin-3-yl)acetic acid (32 mg, 0.054 mmol, 25.4% yield). ¹H NMR (500 MHz, DMSO-d₆) δ 7.57-7.48 (m, 2H), 7.22-7.09 (m, 3H), 7.03-6.91 (m, 3H), 5.82 (s, 1H), 4.09 (d, J=9.2 Hz, 1H), 4.02 (d, J=9.2 Hz, 1H), 3.29-3.27 (m, 1H), 2.78 (t, J=12.1 Hz, 1H), 2.43 (s, 3H), 2.16 (br. s., 1H), 2.04 (s, 3H), 1.97-1.92 (m, 1H), 1.49 (br. s., 1H), 1.41 (s, 6H), 1.28 (br. s., 1H), 1.18 (br. s., 1H), 1.12 (s, 9H), 1.02 (d, J=11.7 Hz, 1H), 0.85 (br. s., 3H), 0.60 (br. s., 3H). LCMS (M+H)=591.6.

Example 50

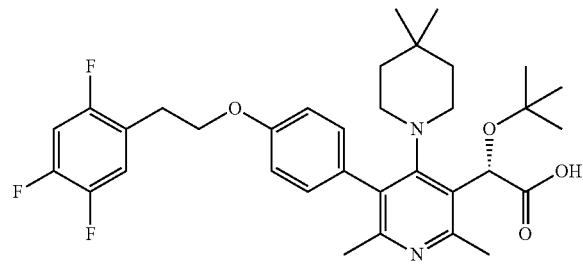 [SMILES: Cc1nc(C)c([C@H](OC(C)(C)C)C(=O)O)c(N2CCC(C)(C)CC2)c1-c1ccc(OCCc2cc(F)c(F)cc2F)cc1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (25 mg, 0.053 mmol), 2-(2,4,5-trifluorophenyl)ethanol (47.0 mg, 0.267 mmol) and Ph₃P-resin (69.7 mg, 0.267 mmol) in THF (2 mL) was added DIAD (0.052 mL, 0.267 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-(2-(2,4,5-trifluorophenethoxy)phenyl)pyridin-3-yl)acetic acid (25.2 mg, 0.042 mmol, 79% yield). ¹H NMR (500 MHz, DMSO-d₆) δ 7.60-7.46 (m, 2H), 7.21 (d, J=8.4 Hz, 1H), 7.08-6.87 (m, 3H), 5.85 (br. s., 1H), 4.26 (q, J=6.2 Hz, 2H), 3.23 (br. s., 1H), 3.07 (t, J=6.2 Hz, 2H), 2.85-2.73 (m, 1H), 2.43 (s, 3H), 2.16 (br. s., 1H), 2.05 (s, 3H), 1.96-1.86 (m, 1H), 1.48 (br. s., 1H), 1.29 (br. s., 1H), 1.17 (d, J=13.6 Hz, 1H), 1.13 (s, 9H), 1.01 (d, J=12.5 Hz, 1H), 0.84 (br. s., 3H), 0.59 (br. s., 3H). LCMS (M+H)=599.2.

Example 51

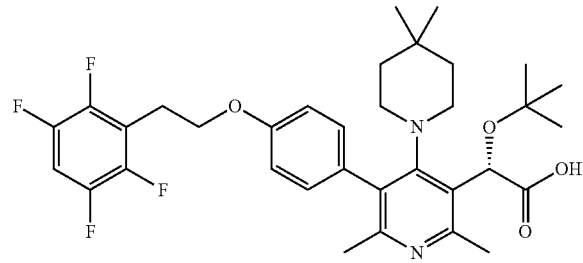 [SMILES: Cc1nc(C)c([C@H](OC(C)(C)C)C(=O)O)c(N2CCC(C)(C)CC2)c1-c1ccc(OCCc2c(F)c(F)cc(F)c2F)cc1]

To a stirred solution of (S)-ethyl 2-(tert-butoxy)-2-(4-(4,4-dimethylpiperidin-1-yl)-5-(4-hydroxyphenyl)-2,6-dimeth-ylpyridin-3-yl)acetate (25 mg, 0.053 mmol), 2-(2,3,5,6-tetrafluorophenyl)ethanol (51.8 mg, 0.267 mmol) and Ph₃P-resin (69.7 mg, 0.267 mmol) in THF (2 mL) was added DIAD (0.052 mL, 0.267 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-(2,3,5,6-tetrafluorophenethoxy)phenyl)pyridin-3-yl)acetic acid (7.4 mg, 0.012 mmol, 22.49% yield). ¹H NMR (500 MHz, DMSO-d₆) δ 7.48 (br. s., 1H), 7.21 (d, J=8.4 Hz, 1H), 7.08-6.88 (m, 3H), 5.81 (s, 1H), 4.34-4.20 (m, 2H), 3.29 (br. s., 1H), 3.13 (t, J=6.4 Hz, 2H), 2.82-2.76 (m, 1H), 2.43 (s, 3H), 2.16 (br. s., 1H), 2.04 (s, 3H), 1.94 (br. s., 1H), 1.48 (br. s., 1H), 1.29 (br. s., 1H), 1.17 (d, J=13.2 Hz, 1H), 1.12 (s, 9H), 1.00 (d, J=11.0 Hz, 1H), 0.84 (br. s., 3H), 0.59 (br. s., 3H). LCMS+H)=617.2.

Example 52

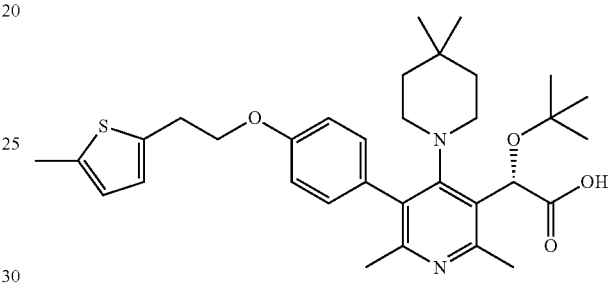

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (50 mg, 0.107 mmol), 2-(5-methylthiophen-2-yl)ethanol (76 mg, 0.533 mmol) and Ph₃P (139 mg, 0.533 mmol) in THF (2 mL) was added DIAD (0.104 mL, 0.533 mmol) at rt. After 18 h, mixture was filtered to remove polymer, concentrated and treated with 1N NaOH (0.854 mL, 0.854 mmol) in MeOH (1 mL) at 75° C. for 16 h. Mixture was then cooled and purified by prep-HPLC to afford (S)-2-(tert-butoxy)-2-(4-(4,4-dimethylpiperidin-1-yl)-2,6-dimethyl-5-(4-(2-(5-methylthiophen-2-yl)ethoxy)phenyl)pyridin-3-yl)acetic acid (13 mg, 0.023 mmol, 21.57% yield). ¹H NMR (500 MHz, DMSO-d₆) δ 7.20 (d, J=8.8 Hz, 1H), 7.10-6.91 (m, 4H), 6.73 (d, J=3.3 Hz, 1H), 6.63 (br. s., 1H), 5.82 (s, 1H), 4.29-4.07 (m, 3H), 3.26 (br. s., 1H), 3.17 (t, J=6.1 Hz, 1H), 2.43 (s, 3H), 2.38 (s, 3H), 2.15 (br. s., 1H), 2.05 (s, 3H), 1.28 (br. s., 2H), 1.17 (d, J=16.5 Hz, 1H), 1.11 (s, 9H), 1.07-0.94 (m, 2H), 0.83 (br. s., 3H), 0.60 (br. s., 3H). LCMS (M+H)=565.3.

Example 53

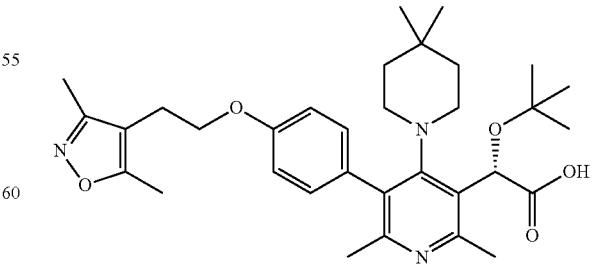

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (50 mg, 0.107 mmol), 2-(3,5-dimethylisoxazol-4-yl)ethanol (75 mg, 0.533 mmol) and Ph₃P-resin (139 mg, 0.533 mmol) in THF (2 mL) was added DIAD (0.104 mL, 0.533 mmol) at rt. After 18 h, mixture was filtered to remove polymer, concentrated and treated with 1N NaOH (1.067 mL, 1.067 mmol) in MeOH (2 mL) at 75° C. for 16 h. Mixture was then cooled and purified by prep-HPLC to afford (S)-2-(tert-butoxy)-2-(5-(4-(2-(3,5-dimethylisoxazol-4-yl)ethoxy)phenyl)-4-(4,4-dimethylpiperidin-1-yl)-2,6-dimethylpyridin-3-yl)acetic acid (25 mg, 0.044 mmol, 41.6% yield). $^1$H NMR (500 MHz, DMSO-$d_6$) δ 7.20 (d, J=8.8 Hz, 1H), 7.07-6.92 (m, 3H), 5.75 (s, 1H), 4.17-4.01 (m, 2H), 3.41 (br. s., 1H), 3.17 (s, 2H), 2.79 (t, J=6.2 Hz, 2H), 2.42 (s, 3H), 2.34 (s, 3H), 2.21 (s, 3H), 2.17 (d, J=12.5 Hz, 1H), 2.06-2.02 (m, 2H), 1.93 (br. s., 1H), 1.49 (br. s., 1H), 1.29 (br. s., 1H), 1.16 (d, J=13.6 Hz, 1H), 1.11 (s, 9H), 1.01 (d, J=9.9 Hz, 1H), 0.84 (br. s., 3H), 0.61 (br. s., 3H). LCMS (M+H)=564.4.

Example 54

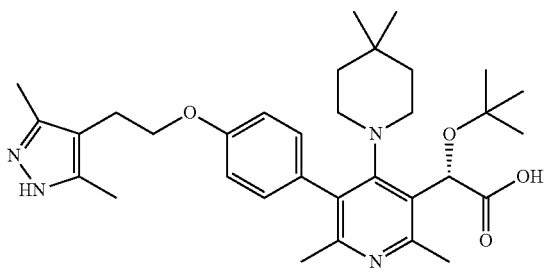 [SMILES: Cc1n[nH]c(C)c1CCOc1ccc(-c2c(C)nc(C)c([C@H](OC(C)(C)C)C(=O)O)c2N2CCC(C)(C)CC2)cc1]

To a stirred solution of (S)-ethyl 2-(tert-butoxy)-2-(4-(4,4-dimethylpiperidin-1-yl)-5-(4-hydroxyphenyl)-2,6-dimethylpyridin-3-yl)acetate (50 mg, 0.107 mmol), 2-(3,5-dimethyl-1H-pyrazol-4-yl)ethanol (74.8 mg, 0.533 mmol) and Ph$_3$P-resin (139 mg, 0.533 mmol) in THF (2 mL) was added DIAD (0.104 mL, 0.533 mmol) at rt. After 18 h, mixture was filtered to remove polymer, concentrated and treated with 1N NaOH (1.067 mL, 1.067 mmol) in MeOH (2 mL) at 75° C. for 16 h. Mixture was then cooled and purified by prep-HPLC to afford (S)-2-(tert-butoxy)-2-(5-(4-(2-(3,5-dimethyl-1H-pyrazol-4-yl)ethoxy)phenyl)-4-(4,4-dimethylpiperidin-1-yl)-2,6-dimethylpyridin-3-yl)acetic acid (7 mg, 0.012 mmol, 11.66% yield). $^1$H NMR (500 MHz, DMSO-$d_6$) δ 7.19 (d, J=8.4 Hz, 1H), 7.09-6.86 (m, 3H), 5.81 (br. s., 1H), 4.11-3.94 (m, 2H), 3.29 (br. s., 1H), 3.17 (s, 3H), 2.78-2.74 (m, 2H), 2.42 (s, 3H), 2.13 (s, 5H), 2.04 (s, 3H), 1.48 (br. s., 1H), 1.28 (br. s., 1H), 1.23 (br. s., 1H), 1.19 (br. s., 1H), 1.11 (s, 9H), 1.03 (br. s., 1H), 0.84 (br. s., 3H), 0.61 (br. s., 3H). LCMS (M+H)=563.4.

Example 55

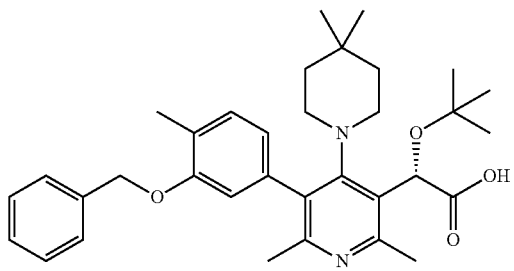 [SMILES: Cc1ccc(-c2c(C)nc(C)c([C@H](OC(C)(C)C)C(=O)O)c2N2CCC(C)(C)CC2)cc1OCc1ccccc1]

A solution of (S)-ethyl 2-(5-(3-(benzyloxy)-4-methylphenyl)-4-(4,4-dimethylpiperidin-1-yl)-2,6-dimethylpyridin-3-yl)-2-(tert-butoxy)acetate (0.0121 g, 0.021 mmol) and 1M NaOH (0.211 ml, 0.211 mmol) in EtOH (1 mL) was refluxed for 6 h. Then, cooled and purified by prep-HPLC to afford (S)-2-(5-(3-(benzyloxy)-4-methylphenyl)-4-(4,4-dimethylpiperidin-1-yl)-2,6-dimethylpyridin-3-yl)-2-(tert-butoxy)acetic acid (0.0103 g, 0.019 mmol, 90% yield) as solid and ~3:2 mixture of isomers by H-NMR. LCMS (M+H)=545.25.

Example 56

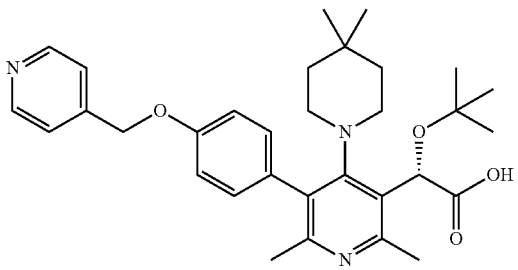 [SMILES: Cc1nc(C)c([C@H](OC(C)(C)C)C(=O)O)c(N2CCC(C)(C)CC2)c1-c1ccc(OCc2ccncc2)cc1]

A solution of (S)-ethyl 2-(tert-butoxy)-2-(4-(4,4-dimethylpiperidin-1-yl)-2,6-dimethyl-5-(4-(pyridin-4-ylmethoxy)phenyl)pyridin-3-yl)acetate (0.013 g, 0.023 mmol) and 1M NaOH (0.232 ml, 0.232 mmol) in EtOH (1 mL) was refluxed for 6 h. Then, cooled and purified by prep-HPLC to afford (S)-2-(tert-butoxy)-2-(4-(4,4-dimethylpiperidin-1-yl)-2,6-dimethyl-5-(4-(pyridin-4-ylmethoxy)phenyl)pyridin-3-yl)acetic acid (0.0101 g, 0.019 mmol, 82% yield) as solid. $^1$H NMR (500 MHz, DMSO-$d_6$) δ 8.58 (d, J=5.5 Hz, 2H), 7.45 (d, J=5.1 Hz, 2H), 7.25 (d, J=7.7 Hz, 1H), 7.14-7.05 (m, 3H), 5.86 (s, 1H), 5.32-5.23 (m, 2H), 3.22 (d, J=12.1 Hz, 1H), 2.78 (t, J=12.3 Hz, 1H), 2.44 (s, 3H), 2.17 (d, J=11.4 Hz, 1H), 2.06 (s, 3H), 1.95-1.86 (m, 1H), 1.53-1.44 (m, 1H), 1.33-1.23 (m, 1H), 1.19-1.14 (m, 1H), 1.13 (s, 9H), 1.00 (d, J=12.5 Hz, 1H), 0.85 (s, 3H), 0.56 (s, 3H). LCMS (M+H)=532.25.

Examples 57-66 were prepared according to the general procedure described below.

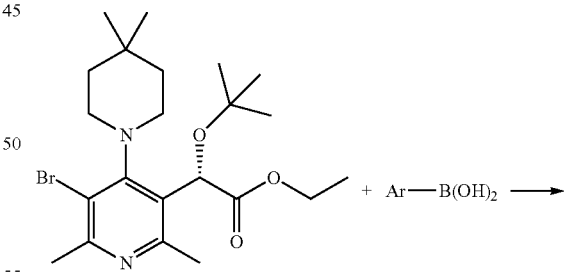

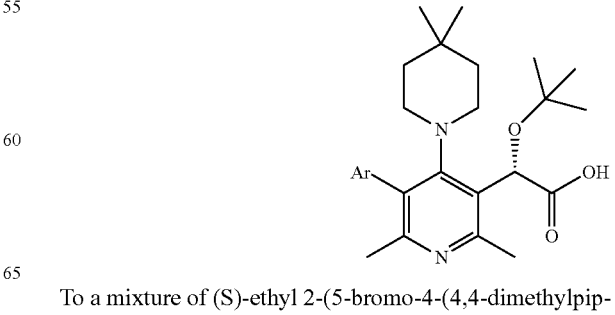

To a mixture of (S)-ethyl 2-(5-bromo-4-(4,4-dimethylpiperidin-1-yl)-2,6-dimethylpyridin-3-yl)-2-(tert-butoxy)acetate (1 eq.), aryl boronic acid (1-5 eq.) and Cs₂CO₃ (2-10 eq.) in 1,4-dioxane and water (volume ratio 20:1 to 1:1) was added Pd(PPh₃)₄ (0.01-1 eq.). The mixture was flushed with nitrogen and then heated at 50-150° C. for 1 to 48 hours. The mixture was diluted with water and then extracted with EtOAc. The organic layers were combined, washed with brine and concentrated to give a crude product, which was diluted with MeOH and H₂O (20:1 to 1:1), before NaOH (0.1-5 N) was added. The mixture was heated at 50-150° C. for 1 to 48 hours. All the solvents were removed under vacuum and the residue was purified by preparative HPLC to give the desired product.

| Name | Ar—B(OH)₂ | Structure | LCMS (M + H) |
|---|---|---|---|
| (S)-2-(tert-butoxy)-2-(4-(4,4-dimethylpiperidin-1-yl)-5-(2-methoxypyrimidin-5-yl)-2,6-dimethylpyridin-3-yl)acetic acid | | 57 | 457.3 |
| (S)-2-(tert-butoxy)-2-(4-(4,4-dimethylpiperidin-1-yl)-5-(2-(4-fluoro-phenethoxy)pyrimidin-5-yl)-2,6-dimethylpyridin-3-yl)acetic acid | | 58 | 565.4 |
| (S)-2-(tert-butoxy)-2-(4-(4,4-dimethylpiperidin-1-yl)-5-(3-fluoro-4-propoxyphenyl)-2,6-dimethylpyridin-3-yl)acetic acid | | 59 | 501.3 |
| (S)-2-(tert-butoxy)-2-(4-(4,4-dimethylpiperidin-1-yl)-2,6-dimethyl-5-(3,4,5-trimethoxyphenyl)pyridin-3-yl)acetic acid | | 60 | 515.3 |

| Name | Ar—B(OH)₂ | Structure | LCMS (M + H) |
|---|---|---|---|
| (S)-2-(tert-butoxy)-2-(4-(4,4-dimethylpiperidin-1-yl)-5-(3-methoxy-4-methylphenyl)-2,6-dimethylpyridin-3-yl)acetic acid | | 61 | 469.3 |
| (S)-2-(tert-butoxy)-2-(4-(4,4-dimethylpiperidin-1-yl)-5-(3-methoxyphenyl)-2,6-dimethylpyridin-3-yl)acetic acid | | 62 | 455.3 |
| (S)-2-(tert-butoxy)-2-(5-(3-chloro-4-isopropoxyphenyl)-4-(4,4-dimethylpiperidin-1-yl)-2,6-dimethylpyridin-3-yl)acetic acid | | 63 | 517.3 |
| (S)-2-(tert-butoxy)-2-(5-(3,5-dimethyl-4-propoxyphenyl)-4-(4,4-dimethylpiperidin-1-yl)-2,6-dimethylpyridin-3-yl)acetic acid | | 64 | 511.3 |
| (S)-2-(tert-butoxy)-2-(4-(4,4-dimethylpiperidin-1-yl)-5-(4-ethoxy-3-fluorophenyl)-2,6-dimethylpyridin-3-yl)acetic acid | | 65 | 487.3 |

| Name | Ar—B(OH)₂ | Structure | LCMS (M + H) |
|---|---|---|---|
| (S)-2-(tert-butoxy)-2-(4-(4,4-dimethylpiperidin-1-yl)-5-(4-fluoro-3-methoxyphenyl)-2,6-dimethylpyridin-3-yl)acetic acid | HO-B(OH)-C₆H₃(OMe)(F) | 66 | 473.3 |

Example 67

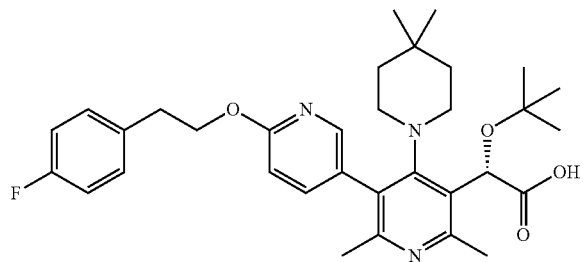

To a solution of (S)-ethyl 2-(tert-butoxy)-2-(4-(4,4-dimethylpiperidin-1-yl)-6'-(4-fluorophenethoxy)-2,6-dimethyl-[3,3'-bipyridin]-5-yl)acetate (3.6 mg) in MeOH (0.5 mL)/THF (0.5 mL) was added sodium hydroxide (0.030 mL, 0.030 mmol). The mixture was stirred at r.t for 4 hrs. The mixture was acidified by 1N HCl to pH~4.

Solvent was removed under vacuum and the residue was purified by prep-HPLC to afford of (S)-2-(tert-butoxy)-2-(4-(4,4-dimethylpiperidin-1-yl)-6'-(4-fluorophenethoxy)-2,6-dimethyl-[3,3'-bipyridin]-5-yl)acetic acid. LCMS (M+H)=564.3.

Example 68

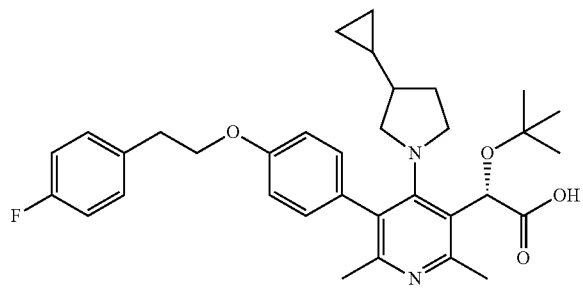 [SMILES: Cc1nc(C)c([C@H](OC(C)(C)C)C(=O)O)c(N2CCC(C3CC3)C2)c1-c1ccc(OCCc2ccc(F)cc2)cc1]

The 0.40 mL of 1M sodium hydroxide (15.93 mg, 0.40 mmol) was added to a solution of (2S)-isopropyl 2-(tert-butoxy)-2-(4-(3-cyclopropylpyrrolidin-1-yl)-5-(4-(4-fluorophenethoxy)phenyl)-2,6-dimethylpyridin-3-yl)acetate (60 mg, 0.10 mmol) in ethanol (2.5 mL) and stirred for 18 h at 90° C. The reaction mixture was neutralized with 1N HCl solution, extracted with EtOAc, and the organic layer was washed with brine, and dried (MgSO₄). The crude material was purified by prep HPLC to afford (2S)-2-(tert-butoxy)-2-(4-(3-cyclopropylpyrrolidin-1-yl)-5-(4-(4-fluorophenethoxy)phenyl)-2,6-dimethylpyridin-3-yl)acetic acid 38.3 mg (69%) as a mixture of diastereomers. ¹H NMR (500 MHz, DMSO-d₆) δ 7.39-7.36 (m, 2H), 7.20-7.19 (m, 1H), 7.15-7.11 (m, 2H), 7.03-6.97 (m, 3H), 5.62/5.61 (s, 1H), 4.21 (t, J=6.6 Hz, 2H) 3.21-2.58 (series m, 6H), 2.44/2.43 (s, 3H), 2.06/2.04 (s, 3H), 1.69-1.64 (m, 1H), 1.41-1.22 (m, 2H), 1.10/1.09 (s, 9H), 0.51-0.45 (m, 1H), 0.32-0.23 (m, 2H), −0.50-0.15 (m, 2H). UPLC (M+H)=603.5.

Example 69

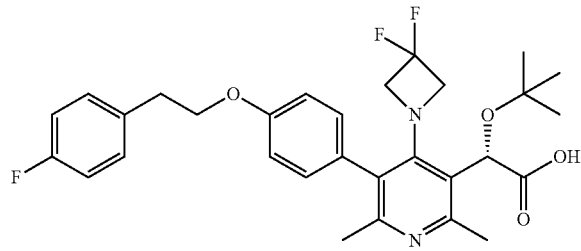 [SMILES: Cc1nc(C)c([C@H](OC(C)(C)C)C(=O)O)c(N2CC(F)(F)C2)c1-c1ccc(OCCc2ccc(F)cc2)cc1]

The 0.40 mL of 1M sodium hydroxide (14.78 mg, 0.37 mmol) was added to a solution (S)-isopropyl 2-(tert-butoxy)-2-(4-(3,3-difluoroazetidin-1-yl)-5-(4-(4-fluorophenethoxy)phenyl)-2,6-dimethylpyridin-3-yl)acetate (54 mg, 0.09 mmol) in ethanol (2 mL) and stirred for 18 h at 90° C. The reaction mixture was neutralized with 1N HCl solution, extracted with EtOAc, and the organic layer was washed with brine, and dried (MgSO₄). The crude material was purified by prep to afford (S)-2-(tert-butoxy)-2-(4-(3,3-difluoroazetidin-1-yl)-5-(4-(4-fluorophenethoxy)phenyl)-2,6-dimethylpyridin-3-yl)acetic acid 46 mg (92%). ¹H NMR (500 MHz, DMSO-d₆) δ 7.40-7.37 (m, 2H), 7.28 (d, J=8.4 Hz, 1H), 7.14 (t, J=8.8 Hz, 2H), 7.04-6.95 (m, 3H), 5.03 (s, 1H), 4.23 (t, J=6.6 Hz, 2H) 4.04 (t, J=12.8 Hz, 4H), 3.06 (t, J=6.6 Hz, 2H), 2.40 (s, 3H), 2.05 (s, 3H), 1.09 (s, 9H). UPLC (M+H)=544.05.

Example 70

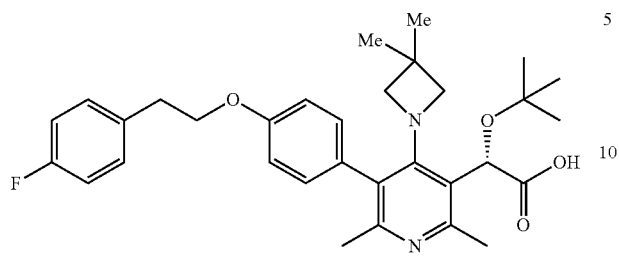

The 0.60 mL of 1M sodium hydroxide (16.64 mg, 0.42 mmol) was added to a solution (S)-isopropyl 2-(tert-butoxy)-2-(4-(3,3-dimethylazetidin-1-yl)-5-(4-(4-fluorophenethoxy)phenyl)-2,6-dimethylpyridin-3-yl)acetate (60 mg, 0.10 mmol) in ethanol (2 mL) and stirred for 18 h at 90° C. The reaction mixture was neutralized with 1N HCl solution, extracted with EtOAc, and the organic layer was washed with brine, and dried (MgSO$_4$). The crude material was purified by prep HPLC to give (S)-2-(tert-butoxy)-2-(4-(3,3-dimethylazetidin-1-yl)-5-(4-(4-fluorophenethoxy)phenyl)-2,6-dimethylpyridin-3-yl)acetic acid 40 mg (72%). $^1$H NMR (500 MHz, DMSO-d$_6$) δ 7.40-7.37 (m, 2H), 7.26 (br. s, 1H), 7.14 (t, J=8.8 Hz, 2H), 7.0 (d, J=9.2 Hz, 1H), 6.96 (d, J=6.6 Hz, 1H), 6.86 (br. s, 1H), 5.04 (s, 1H), 4.21 (t, J=6.2 Hz, 2H) 3.47 (br. s, 4H), 3.05 (t, J=6.2 Hz, 2H), 2.01 (s, 3H), 1.91 (s, 3H), 1.10 (s, 9H), 1.02 (s, 6H). UPLC (M+H)=535.45.

Example 71

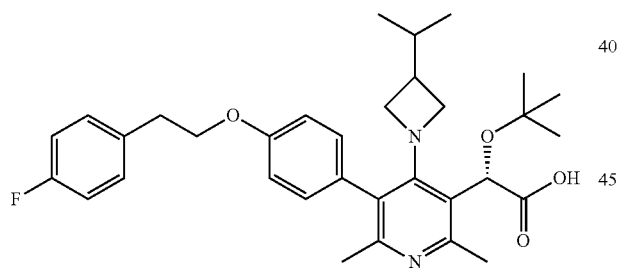

The 0.98 mL of 1M sodium hydroxide (39.3 mg, 0.98 mmol) was added to a solution (S)-isopropyl 2-(tert-butoxy)-2-(5-(4-(4-fluorophenethoxy)phenyl)-4-(3-isopropylazetidin-1-yl)-2,6-dimethylpyridin-3-yl)acetate (145 mg, 0.245 mmol) in ethanol (3 mL) and stirred for 18 h at 90° C. The reaction mixture was neutralized with 1N HCl solution, extracted with EtOAc, and the organic layer was washed with brine, and dried (MgSO$_4$). The crude material was purified by prep HPLC to afford (S)-2-(tert-butoxy)-2-(5-(4-(4-fluorophenethoxy)phenyl)-4-(3-isopropylazetidin-1-yl)-2,6-dimethylpyridin-3-yl)acetic acid 99.4 mg (74%) as a mixture of diastereomers. $^1$H NMR (500 MHz, DMSO-d$_6$) δ 7.36 (t, J=8.1 Hz, 2H), 7.30 (br. s, 1H), 7.12 (t, J=8.8 Hz, 2H), 7.1 (d, J=8.1 Hz, 1H), 6.97 (d, J=8.1 Hz, 1H), 6.86 (br. s, 1H), 4.93 (s, 1H), 4.21 (t, J=6.6 Hz, 2H) 3.96 (br. s, 1H), 3.86 (br. s, 1H), 3.70 (br. s, 1H), 3.47 (br. s, 1H), 3.03 (t, J=6.2 Hz, 2H), 2.39 (s, 3H), 2.07 (s, 3H), 2.05-2.01 (m, 1H), 1.52-1.47 (m, 1H), 1.08 (s, 9H), 0.65 (d, J=6.2 Hz, 6H). UPLC (M+H)=549.5.

Example 72

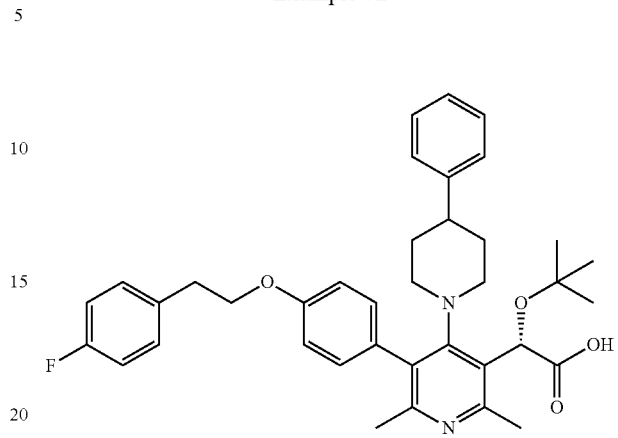

The potassium hydroxide (72.2 mg, 1.28 mmol) was added to a solution (S)-isopropyl 2-(tert-butoxy)-2-(5-(4-(4-fluorophenethoxy)phenyl)-2,6-dimethyl-4-(4-phenylpiperidin-1-yl)pyridin-3-yl)acetate (84 mg, 0.13 mmol) in ethanol (3 mL) and stirred for 3 h at 90° C. The reaction mixture was neutralized with 1N HCl solution, extracted with EtOAc, and the organic layer was washed with brine, and dried (MgSO$_4$). The crude material was purified by prep HPLC to afford (S)-2-(tert-butoxy)-2-(5-(4-(4-fluorophenethoxy)phenyl)-2,6-dimethyl-4-(4-phenylpiperidin-1-yl)pyridin-3-yl)acetic acid 51.2 mg (65%) as a mixture of diastereomers. $^1$H NMR (500 MHz, DMSO-d$_6$) δ 7.41-7.39 (m, 2H), 7.28-7.22 (m, 3H), 7.17-7.13 (m, 5H), 7.05-7.01 (m, 3H), 5.88 (br. s, 1H), 4.24 (t, J=6.2 Hz, 2H), 3.59-3.58 (m, 1H), 3.09-3.06 (m, 2H), 2.75-2.71 (m, 1H), 2.58-2.56 (m, 1H), 2.47 (s, 3H), 2.26-2.22 (br. s, 1H), 2.05 (s, 3H), 1.94-1.81 (m, 2H), 1.65-1.50 (m, 3H), 1.18 (s, 9H). UPLC (M+H)=611.4.

Example 73

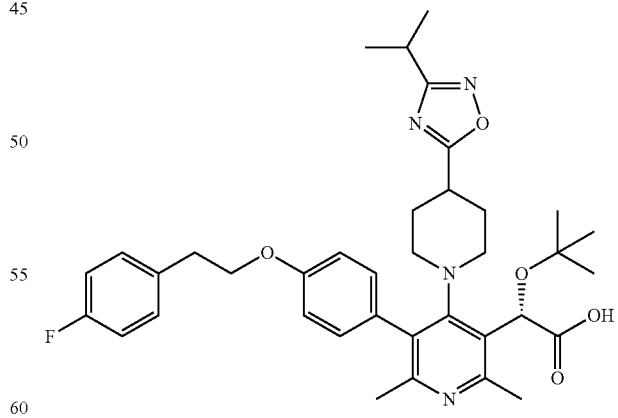

The potassium hydroxide (20.4 mg, 0.36 mmol) was added to a solution (S)-isopropyl 2-(tert-butoxy)-2-(5-(4-(4-fluorophenethoxy)phenyl)-4-(4-(3-isopropyl-1,2,4-oxadiazol-5-yl)piperidin-1-yl)-2,6-dimethylpyridin-3-yl)acetate (25 mg, 0.036 mmol) in ethanol (1 mL) and stirred for 3 h at 90° C. The reaction mixture was neutralized with 1N HCl solution, extracted with EtOAc, and the organic layer was washed with brine, and dried (MgSO$_4$). The crude material was purified by prep HPLC to afford (S)-2-(tert-butoxy)-2-(5-(4-(4-fluorophenethoxy)phenyl)-4-(3-isopropyl-1,2,4-oxadiazol-5-yl)piperidin-1-yl)-2,6-dimethylpyridin-3-yl)acetic acid 11 mg (47%) as a mixture of diastereomers. $^1$H NMR (500 MHz, DMSO-d$_6$) δ 7.41-7.39 (m, 2H), 7.23-7.22 (m, 1H), 7.17-7.13 (m, 2H), 7.02-7.01 (m, 2H), 6.96-6.94/6.86-6.84/6.80-6.77 (series m, 1H), 5.73 (br. s, 1H), 4.24 (t, J=6.6 Hz, 2H), 3.67-3.65 (m, 1H), 3.07 (t, J=6.6 Hz, 2H), 3.03-2.97 (m, 1H), 2.72-2.67 (m, 2H), 2.58-2.56 (m, 1H), 2.46 (s, 3H), 2.04 (s, 3H), 1.87-1.75 (m, 4H), 1.67-1.62 (m, 1H), 1.23 (d, J=6.6 Hz, 6H), 1.12 (s, 9H). UPLC (M+H)=645.4.

Example 74

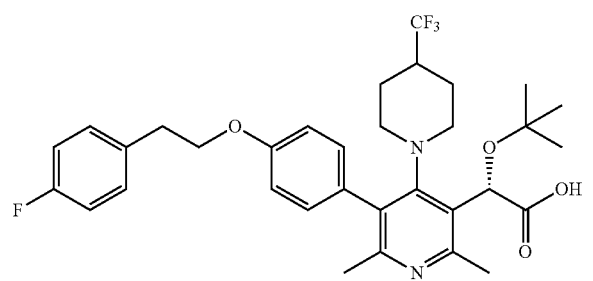 [SMILES: Cc1nc(C)c([C@H](OC(C)(C)C)C(=O)O)c(N2CCC(C(F)(F)F)CC2)c1-c1ccc(OCCc2ccc(F)cc2)cc1]

The 0.23 mL of 1M sodium hydroxide (9.3 mg, 0.23 mmol) was added to a solution (S)-isopropyl 2-(tert-butoxy)-2-(5-(4-(4-fluorophenethoxy)phenyl)-2,6-dimethyl-4-(4-(trifluoromethyl)piperidin-1-yl)pyridin-3-yl)acetate (50 mg, 0.078 mmol) in ethanol (1 mL) and stirred for 24 h at 90° C. An additional 0.23 mL sodium hydroxide was added and the reaction was continued for 24 h. The reaction mixture was neutralized with 1N HCl solution, extracted with EtOAc, and the organic layer was washed with brine, and dried (MgSO$_4$). The crude material was purified by prep to afford (S)-2-(tert-butoxy)-2-(5-(4-(4-fluorophenethoxy)phenyl)-2,6-dimethyl-4-(4-(trifluoromethyl)piperidin-1-yl)pyridin-3-yl)acetic acid 42 mg (89%) as a mixture of diastereomers. $^1$H NMR (500 MHz, DMSO-d$_6$) δ 7.41-7.38 (m, 2H), 7.21-7.20 (m, 1H), 7.14 (t, J=8.8 Hz, 2H), 7.0 (d, J=8.4 Hz, 2H), 6.95 (d, J=7.7 Hz, 1H), 5.54 (br. s, 1H), 4.23 (t, J=6.7 Hz, 2H), 3.96-3.94 (m, 2H), 3.07 (t, J=6.6 Hz, 2H), 2.90/2.74 (s, 2H), 2.46 (s, 3H), 2.55 (br. s, 1H), 2.03 (s, 3H), 1.72-1.61 (m, 3H), 1.56-1.54 (m, 1H), 1.10 (s, 9H). UPLC (M+H)=603.5.

Example 75

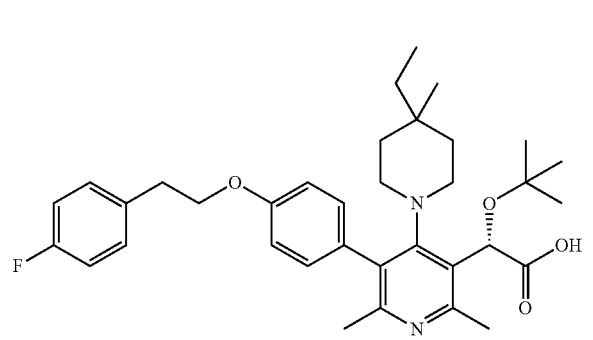 [SMILES: CCC1(C)CCN(c2c(-c3ccc(OCCc4ccc(F)cc4)cc3)c(C)nc(C)c2[C@H](OC(C)(C)C)C(=O)O)CC1]

The 1.86 mL of 1M sodium hydroxide (74 mg, 1.86 mmol) was added to a solution (S)-isopropyl 2-(tert-butoxy)-2-(4-(4-ethyl-4-methylpiperidin-1-yl)-5-(4-(4-fluorophenethoxy)phenyl)-2,6-dimethylpyridin-3-yl)acetate (128 mg, 0.207 mmol) in ethanol (2 mL) and stirred for 24 h at 90° C. An additional 0.8 mL sodium hydroxide was added and the reaction was continued for 24 h. The reaction mixture was neutralized with 1N HCl solution, extracted with EtOAc, and the organic layer was washed with brine, and dried (MgSO$_4$). The crude material was purified by prep HPLC to give (S)-2-(tert-butoxy)-2-(4-(4-ethyl-4-methylpiperidin-1-yl)-5-(4-(4-fluorophenethoxy)phenyl)-2,6-dimethylpyridin-3-yl)acetic acid 116 mg (97%) as a mixture of diastereomers. $^1$H NMR (500 MHz, DMSO-d$_6$) δ 7.38-7.35 (m, 2H), 7.20-7.18 (m, 1H), 7.13 (t, J=9.1 Hz, 2H), 7.03-7.00 (m, 3H), 5.85 (s, 1H), 4.27-4.18 (m, 2H), 3.52 (br. s, 2H), 3.27-3.21 (m, 1H), 3.04 (t, J=6.6 Hz, 2H), 2.84-2.97 (m, 1H), 2.43 (s, 3H), 2.19-2.14 (br. s, 1H), 2.05 (s, 3H), 1.96-1.91 (m, 1H), 1.49-1.38 (m, 1H), 1.29-1.23 (m, 1H), 1.17-1.12 (m, 1H), 1.12 (br. s, 9H), 1.01-0.99 (m, 1H), 0.75-0.72 (m, 3H), 0.54 (br. s, 3H). UPLC (M+H)=577.5.

Example 76

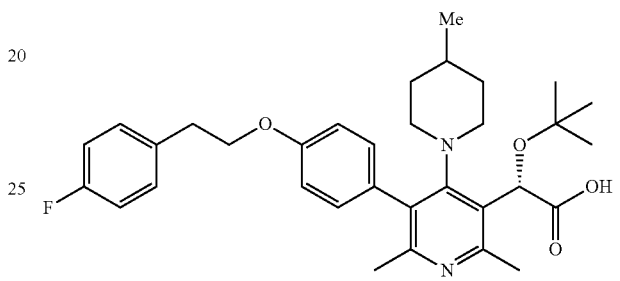

The 1.32 mL of 1M sodium hydroxide (52.8 mg, 1.32 mmol) was added to a (S)-isopropyl 2-(tert-butoxy)-2-(5-(4-(4-fluorophenethoxy)phenyl)-2,6-dimethyl-4-(4-methylpiperidin-1-yl)pyridin-3-yl)acetate (130 mg, 0.22 mmol) in ethanol (1 mL) and stirred for 24 h at 85° C. An additional 0.31 mL sodium hydroxide was added and the reaction was continued for 24 h. The reaction mixture was neutralized with 1N HCl solution, extracted with EtOAc, and the organic layer was washed with brine, and dried (MgSO$_4$). The crude material was purified by prep HPLC to afford (S)-2-(tert-butoxy)-2-(5-(4-(4-fluorophenethoxy)phenyl)-2,6-dimethyl-4-(4-methylpiperidin-1-yl)pyridin-3-yl)acetic acid 58 mg (48%) as a mixture of diastereomers. $^1$H NMR (500 MHz, DMSO-d$_6$) δ 7.40-7.37 (m, 2H), 7.19 (d, J=9.2 Hz, 1H), 7.14 (t, J=8.8 Hz, 2H), 7.00-6.95 (m, 3H), 5.84 (s, 1H), 4.22 (t, J=6.6 Hz, 2H), 3.44-3.39 (m, 4H), 3.06 (t, J=6.6 Hz, 2H), 2.43 (s, 3H), 2.03 (s, 3H), 1.72-1.68 (m, 1H), 1.49 (d, J=12.1 Hz, 1H), 1.34 (d, J=7.0 Hz, 1H), 1.24-1.20 (m, 1H), 1.12 (s, 9H), 1.06-1.01 (m, 1H), 0.83 (d, J=3.7 Hz, 3H). UPLC (M+H)=549.6.

Example 77

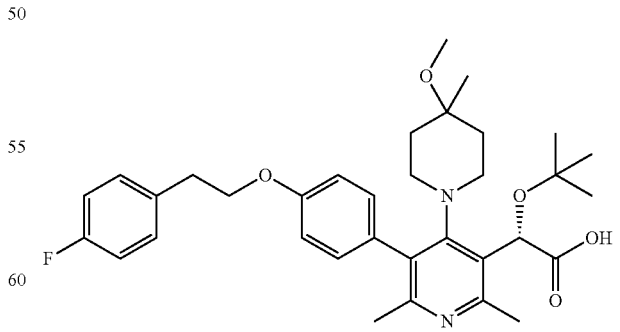

The potassium hydroxide (230 mg, 4.1 mmol) was added to a gave (S)-isopropyl 2-(tert-butoxy)-2-(5-(4-(4-fluorophenethoxy)phenyl)-4-(4-methoxy-4-methylpiperidin-1-yl)-2,6-dimethylpyridin-3-yl)acetate (255 mg, 0.41 mmol) in ethanol (4 mL) and stirred for 6 h at 90° C. The reaction mixture was neutralized with 1N HCl solution, extracted with EtOAc, and the organic layer was washed with brine, and dried (MgSO₄). The crude material was purified by prep to give (S)-2-(tert-butoxy)-2-(5-(4-(4-fluorophenethoxy)phenyl)-4-(4-methoxy-4-methylpiperidin-1-yl)-2,6-dimethylpyridin-3-yl)acetic acid 51 mg (21%) as a mixture of diastereomers. $^1$H NMR (500 MHz, DMSO-$d_6$) δ 7.39-7.36 (m, 2H), 7.19-7.12 (m, 3H), 7.02-6.99 (m, 3H), 5.81 (s, 1H), 4.24-4.21 (m, 2H), 3.49 (br. s, 4H), 3.07-3.04 (m, 2H), 2.89/2.81 (s, 3H), 2.44 (s, 3H), 2.04 (s, 3H), 1.59-1.45 (m, 3H), 1.32-1.25 (m, 1H), 1.12 (br. s, 9H), 0.99/0.81 (s, 3H). UPLC (M+H)=579.5.

Example 78

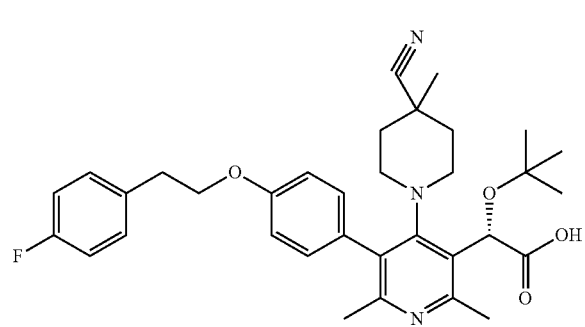 [SMILES: Cc1nc(C)c([C@H](OC(C)(C)C)C(=O)O)c(N2CCC(C)(C#N)CC2)c1-c1ccc(OCCc2ccc(F)cc2)cc1]

The potassium hydroxide (213 mg, 3.8 mmol) was added to a (S)-isopropyl 2-(tert-butoxy)-2-(4-(4-cyano-4-methylpiperidin-1-yl)-5-(4-(4-fluorophenethoxy)phenyl)-2,6-dimethylpyridin-3-yl)acetate (233 mg, 0.38 mmol) in ethanol (4 mL) and stirred for 6 h at 90° C. The reaction mixture was neutralized with 1N HCl solution, extracted with EtOAc, and the organic layer was washed with brine, and dried (MgSO₄). The crude material was purified by prep HPLC to afford (S)-2-(tert-butoxy)-2-(4-(4-cyano-4-methylpiperidin-1-yl)-5-(4-(4-fluorophenethoxy)phenyl)-2,6-dimethylpyridin-3-yl)acetic acid 41.8 mg (19%) as a mixture of diastereomers. $^1$H NMR (500 MHz, DMSO-$d_6$) δ 7.38-7.35 (m, 2H), 7.19 (d, J=7.3 Hz, 1H), 7.13 (d, J=8.8 Hz, 2H), 7.07-7.05 (m, 1H), 7.01-6.99 (m, 2H), 5.61 (s, 1H), 4.27-4.23 (m, 1H), 4.19-4.15 (m, 1H), 3.51 (br. s, 4H), 3.04 (t, J=6.6 Hz, 2H), 2.48 (s, 3H), 2.05 (s, 3H), 1.73-1.59 (m, 3H), 1.39-1.35 (m, 1H), 1.26 (s, 3H), 1.12 (s, 9H). UPLC (M+H)=574.5.

Example 79

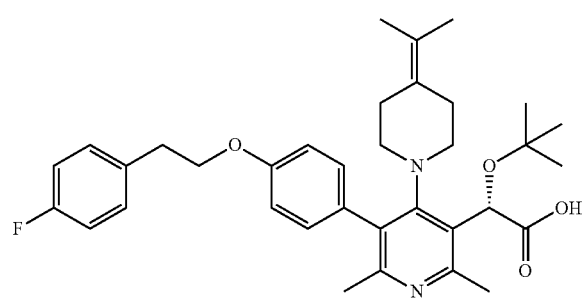 [SMILES: CC(C)=C1CCN(c2c(-c3ccc(OCCc4ccc(F)cc4)cc3)c(C)nc(C)c2[C@H](OC(C)(C)C)C(=O)O)CC1]

The potassium hydroxide (54.6 mg, 0.97 mmol) was added to a station (S)-isopropyl 2-(tert-butoxy)-2-(5-(4-(4-fluorophenethoxy)phenyl)-2,6-dimethyl-4-(4-(propan-2-ylidene)piperidin-1-yl)pyridin-3-yl)acetate (60 mg, 0.097 mmol) in ethanol (2 mL) and stirred for 6 h at 90° C. The reaction mixture was neutralized with 1N HCl solution, extracted with EtOAc, and the organic layer was washed with brine, and dried (MgSO₄). The crude material was purified by prep HPLC to afford (S)-2-(tert-butoxy)-2-(5-(4-(4-fluorophenethoxy)phenyl)-2,6-dimethyl-4-(4-(propan-2-ylidene)piperidin-1-yl)pyridin-3-yl)acetic acid 39.3 mg (70%). $^1$H NMR (500 MHz, DMSO-$d_6$) δ 7.38-7.35 (m, 2H), 7.19 (d, J=8.4 Hz, 1H), 7.13 (t, J=8.4 Hz, 2H), 6.97 (t, J=8.1 Hz, 2H), 6.90 (d, J=8.1 Hz, 1H), 5.84 (s, 1H), 4.21 (t, J=6.2 Hz, 2H), 3.53 (br. s, 4H), 3.04 (t, J=6.2 Hz, 2H), 2.44 (s, 3H), 2.31-2.28 (m, 1H), 2.05 (br. s, 1H), 2.00 (s, 3H), 1.83 (br. s, 1H), 1.65 (br. s, 1H), 1.56 (s, 3H), 1.49 (s, 3H), 1.12 (s, 9H). UPLC (M+H)=575.3.

Example 80

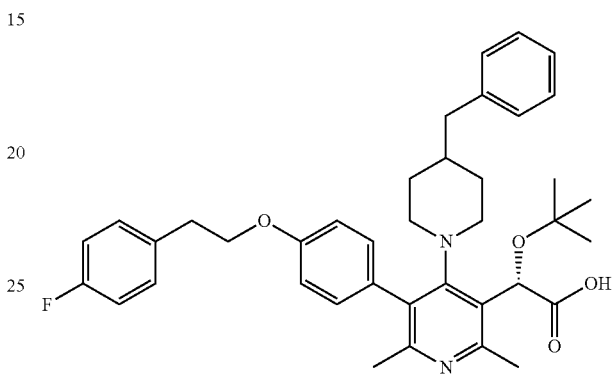

The potassium hydroxide (86 mg, 1.54 mmol) was added to a station (S)-isopropyl 2-(4-(4-benzylpiperidin-1-yl)-5-(4-(4-fluorophenethoxy)phenyl)-2,6-dimethylpyridin-3-yl)-2-(tert-butoxy)acetate (102 mg, 0.154 mmol) in ethanol (3 mL) and stirred for 12 h at 90° C. The reaction mixture was neutralized with 1N HCl solution, extracted with EtOAc, and the organic layer was washed with brine, and dried (MgSO₄). The crude material was purified by prep HPLC to give (S)-2-(4-(4-benzylpiperidin-1-yl)-5-(4-(4-fluorophenethoxy)phenyl)-2,6-dimethylpyridin-3-yl)-2-(tert-butoxy)acetic acid 24.3 mg (25%) as a mixture of diastereomers. $^1$H NMR (500 MHz, DMSO-$d_6$) δ 7.40-7.37 (m, 2H), 7.24-7.22 (m, 2H), 7.18-7.12 (m, 4H), 7.10 (t, J=7.7 Hz, 2H), 6.99-6.92 (m, 3H), 5.77 (s, 1H), 4.21 (t, J=6.6 Hz, 2H), 3.47-3.37 (m, 4H), 3.06 (t, J=6.2 Hz, 2H), 2.46-2.44 (m, 2H), 2.42 (s, 3H), 2.01 (s, 3H), 1.66 (t, J=10.6 Hz, 1H), 1.44-1.41 (m, 1H), 1.34-1.22 (m, 3H), 1.09 (m, 9H). UPLC (M+H)=625.4.

Example 81

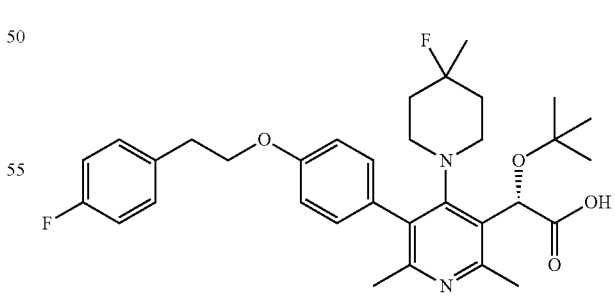

The potassium hydroxide (55.3 mg, 0.986 mmol) was added to a solution gave (S)-isopropyl 2-(tert-butoxy)-2-(4-(4-fluoro-4-methylpiperidin-1-yl)-5-(4-(4-fluorophenethoxy)phenyl)-2,6-dimethylpyridin-3-yl)acetate (60 mg, 0.099 mmol) in ethanol (2 mL) and stirred for 6 h at 90° C. The reaction mixture was neutralized with 1N HCl solution, extracted with EtOAc, and the organic layer was washed with brine, and dried (MgSO$_4$). The crude material was purified by prep HPLC to give (S)-2-(tert-butoxy)-2-(4-(4-fluoro-4-methylpiperidin-1-yl)-5-(4-(4-fluorophenethoxy)phenyl)-2,6-dimethylpyridin-3-yl)acetic acid 49.2 mg (88%) as a mixture of diastereomers. $^1$H NMR (500 MHz, DMSO-d$_6$) δ 7.40-7.37 (m, 2H), 7.20-7.18 (m, 1H), 7.14 (t, J=8.8 Hz, 2H), 7.03-6.99 (m, 3H), 5.71 (s, 1H), 4.22 (t, J=6.6 Hz, 2H), 3.47 (br. s, 2H), 3.34-3.32 (m, 1H), 3.06 (t, J=6.6 Hz, 2H), 2.83 (t, J=12.5 Hz, 1H), 2.47 (s, 3H), 2.03 (s, 3H), 1.85 (br. s, 1H), 1.65-1.49 (m, 3H), 1.26/1.22 (s, 3H), 1.13 (s, 9H). UPLC (M+H)=567.4.

Example 82

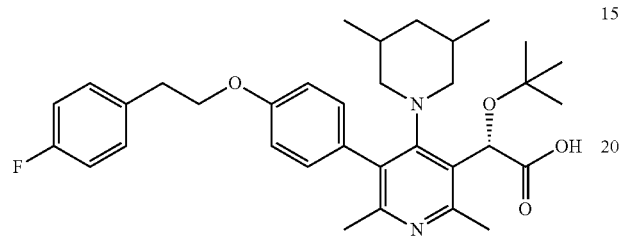

The 0.3 mL of 1M sodium hydroxide (12 mg, 0.0 mmol) was added to a (S)-isopropyl 2-(tert-butoxy)-2-(4-((3,5-dimethylpiperidin-1-yl)-5-(4-(4-fluorophenethoxy)phenyl)-2,6-dimethylpyridin-3-yl)acetate (30 mg, 0.05 mmol) in ethanol (1.5 mL) and stirred for 24 h at 85° C. The reaction mixture was neutralized with 1N HCl solution, extracted with EtOAc, and the organic layer was washed with brine, and dried (MgSO$_4$). The crude material was purified by prep HPLC (to afford (S)-2-(tert-butoxy)-2-(4-((3,5-dimethylpiperidin-1-yl)-5-(4-(4-fluorophenethoxy)phenyl)-2,6-dimethylpyridin-3-yl)acetic acid 10.3 mg (37%) as a mixture of diastereomers. $^1$H NMR (500 MHz, DMSO) δ 7.40-7.37 (m, 2H), 7.29-7.10 (m, 1H), 7.14 (t, J=8.8 Hz, 2H), 7.10 (d, J=8.8 Hz, 2H), 6.94-6.92 (m, 1H), 5.77 (s, 1H), 4.28-4.22 (m, 2H), 3.40 (br. s, 4H), 3.06 (t, J=6.6 Hz, 2H), 2.44 (s, 3H), 2.03 (s, 3H), 1.76 (br. s, 1H), 1.67-1.64 (m, 1H), 1.22 (t, J=8.1 Hz, 1H), 1.11 (s, 9H), 0.72 (d, J=6.1 Hz, 1H), 0.53 (d, J=6.2 Hz, 3H), 0.26 (q, J=11 Hz, 1H). UPLC (M+H)=563.6.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I

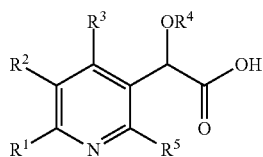

where:
$R^1$ is alkyl;
$R^2$ is phenyl, pyridinyl, pyrimidinyl, or pyridazinyl, and is substituted with 1 substituent selected from hydroxy, alkoxy, (Ar$^1$)O, and (Ar$^1$)alkoxy, (Ar$^1$)(alkoxy)alkoxy, and is also substituted with 0-3 substituents selected from halo, alkyl, haloalkyl, alkoxy, and haloalkoxy;
$R^3$ is azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, alkyl, haloalkyl, cycloalkyl, halocycloalkyl, alkenyl, alkoxy, haloalkoxy, CON(R$^6$)(R$^7$), phenyl, benzyl, or (alkyl)oxadiazolyl;
$R^4$ is alkyl or haloalkyl;
$R^5$ is alkyl;
$R^6$ is hydrogen or alkyl;
$R^7$ is hydrogen or alkyl; and
Ar$^1$ is phenyl, naphthyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, pyridinyl, pyridazinyl, pyrimidinyl, or pyridazinyl, and is substituted with 0-3 substituents selected from halo, alkyl, haloalkyl, alkoxy, haloalkoxy, phenyl, and benzyloxy;
or a pharmaceutically acceptable salt thereof.

2. A compound of claim 1 where
$R^1$ is alkyl;
$R^2$ is phenyl or pyridinyl and is substituted with 1 substituent selected from alkoxy, (Ar$^1$)O, and (Ar$^1$)alkoxy, and is also substituted with 0-3 substituents selected from halo, alkyl, haloalkyl, alkoxy, and haloalkoxy;
$R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, alkoxy, and haloalkoxy;
$R^4$ is alkyl or haloalkyl;
$R^5$ is alkyl; and
Ar$^1$ is phenyl substituted with 0-3 substituents selected from halo, alkyl, haloalkyl, alkoxy, and haloalkoxy;
or a pharmaceutically acceptable salt thereof.

3. A compound of claim 2 where $R^1$ is alkyl; $R^2$ is phenyl or pyridinyl and is substituted with 1 substituent selected from alkoxy, (Ar$^1$)O, or (Ar$^1$)alkoxy, and is also substituted with 0-3 substituents selected from halo, alkyl, haloalkyl, alkoxy, and haloalkoxy; $R^3$ is piperidinyl substituted with 0-3 alkyl substituents; $R^4$ is alkyl; $R^5$ is alkyl; and Ar$^1$ is phenyl substituted with 0-3 substituents selected from halo, alkyl, haloalkyl, alkoxy, and haloalkoxy; or a pharmaceutically acceptable salt thereof.

4. A compound of claim 1 where $R^2$ is phenyl substituted with 1 substituent selected from alkoxy, (Ar$^1$)O, or (Ar$^1$)alkoxy, and is also substituted with 0-3 substituents selected from halo, alkyl, haloalkyl, alkoxy, and haloalkoxy.

5. A compound of claim 1 where $R^3$ is piperidinyl substituted with 0-3 substituents selected from cyano, halo, alkyl, haloalkyl, cycloalkyl, halocycloalkyl, alkenyl, alkoxy, haloalkoxy, CON(R$^6$)(R$^7$), phenyl, benzyl, and (alkyl)oxadiazolyl.

6. A compound of claim 5 where $R^3$ is piperidinyl, gem-disubstituted in the 4-position with 2 substituents selected from cyano, halo, alkyl, haloalkyl, cycloalkyl, halocycloalkyl, alkenyl, alkoxy, haloalkoxy, CON(R$^6$)(R$^7$), phenyl, benzyl, or (alkyl)oxadiazolyl.

7. A compound of claim 1 selected from the group consisting of
(S)-2-(tert-Butoxy)-2-(4-(4,4-dimethylpiperidin-1-yl)-2,6-dimethyl-5-(4-phenoxyphenyl)pyridin-3-yl)acetic acid;
(S)-2-(tert-Butoxy)-2-(4-(4,4-dimethylpiperidin-1-yl)-5-(4-((4-fluorobenzyl)oxy)phenyl)-2,6-dimethylpyridin-3-yl)acetic acid;

(S)-2-(6'-(Benzyloxy)-4-(4,4-dimethylpiperidin-1-yl)-2, 6-dimethyl-[3,3'-bipyridin]-5-yl)-2-(tert-butoxy)acetic acid;

(S)-2-(5-(4-(Benzyloxy)-3-fluorophenyl)-4-(4,4-dimethylpiperidin-1-yl)-2,6-dimethylpyridin-3-yl)-2-(tert-butoxy)acetic acid;

(S)-2-(5-(4-(Benzyloxy)phenyl)-4-(4,4-dimethylpiperidin-1-yl)-2,6-dimethylpyridin-3-yl)-2-(tert-butoxy)acetic acid;

(S)-2-(tert-Butoxy)-2-(4-(4,4-dimethylpiperidin-1-yl)-5-(4-((2-methoxybenzyl)oxy)phenyl)-2,6-dimethylpyridin-3-yl)acetic acid;

(S)-2-(tert-Butoxy)-2-(4-(4,4-dimethylpiperidin-1-yl)-5-(4-((3-fluorobenzyl)oxy)phenyl)-2,6-dimethylpyridin-3-yl)acetic acid;

(S)-2-(tert-Butoxy)-2-(4-(4,4-dimethylpiperidin-1-yl)-5-(4-((4-methoxybenzyl)oxy)phenyl)-2,6-dimethylpyridin-3-yl)acetic acid;

(S)-2-(tert-Butoxy)-2-(5-(4-((4-chlorobenzyl)oxy)phenyl)-4-(4,4-dimethylpiperidin-1-yl)-2,6-dimethylpyridin-3-yl)acetic acid;

(S)-2-(tert-Butoxy)-2-(4-(4,4-dimethylpiperidin-1-yl)-5-(4-ethoxyphenyl)-2,6-dimethylpyridin-3-yl)acetic acid;

(S)-2-(tert-Butoxy)-2-(4-(4,4-dimethylpiperidin-1-yl)-5-(4-(4-fluorophenethoxy)phenyl)-2,6-dimethylpyridin-3-yl)acetic acid;

(S)-2-(tert-Butoxy)-2-(4-(4,4-dimethylpiperidin-1-yl)-5-(4-(4-fluoro-3-methylphenethoxy)phenyl)-2,6-dimethylpyridin-3-yl)acetic acid;

(S)-2-(tert-Butoxy)-2-(4-(4,4-dimethylpiperidin-1-yl)-5-(4-(3-(4-fluorophenyl)propoxy)phenyl)-2,6-dimethylpyridin-3-yl)acetic acid;

(S)-2-(tert-Butoxy)-2-(5-(4-(3,3-dimethylbutoxy)phenyl)-4-(4,4-dimethylpiperidin-1-yl)-2,6-dimethylpyridin-3-yl)acetic acid;

(S)-2-(tert-Butoxy)-2-(4-(4,4-dimethylpiperidin-1-yl)-5-(4-(4-methoxyphenethoxy)phenyl)-2,6-dimethylpyridin-3-yl)acetic acid;

(S)-2-(tert-Butoxy)-2-(4-(4,4-dimethylpiperidin-1-yl)-5-(4-hydroxyphenyl)-2,6-dimethylpyridin-3-yl)acetic acid;

(S)-2-(tert-Butoxy)-2-(5-(4-(4-carbamoylphenethoxy)phenyl)-4-(4,4-dimethylpiperidin-1-yl)-2,6-dimethylpyridin-3-yl)acetic acid;

(S)-2-(tert-Butoxy)-2-(5-(4-(4-cyanophenethoxy)phenyl)-4-(4,4-dimethylpiperidin-1-yl)-2,6-dimethylpyridin-3-yl)acetic acid;

(S)-2-(tert-Butoxy)-2-(5-(4-((4-carbamoylbenzyl)oxy)phenyl)-4-(4,4-dimethylpiperidin-1-yl)-2,6-dimethylpyridin-3-yl)acetic acid;

(S)-2-(tert-Butoxy)-2-(5-(4-((4-cyanobenzyl)oxy)phenyl)-4-(4,4-dimethylpiperidin-1-yl)-2,6-dimethylpyridin-3-yl)acetic acid;

(2S)-2-(tert-Butoxy)-2-(4-(4,4-dimethylpiperidin-1-yl)-5-(4-((1-(4-fluorophenyl)propan-2-yl)oxy)phenyl)-2,6-dimethylpyridin-3-yl)acetic acid;

(2S)-2-(tert-Butoxy)-2-(4-(4,4-dimethylpiperidin-1-yl)-5-(4-((1-(4-fluorophenyl)propan-2-yl)oxy)phenyl)-2,6-dimethylpyridin-3-yl)acetic acid;

(S)-2-(tert-Butoxy)-2-(5-(4-(2,4-difluorophenethoxy)phenyl)-4-(4,4-dimethylpiperidin-1-yl)-2,6-dimethylpyridin-3-yl)acetic acid;

(S)-2-(tert-Butoxy)-2-(5-(4-(3,4-difluorophenethoxy)phenyl)-4-(4,4-dimethylpiperidin-1-yl)-2,6-dimethylpyridin-3-yl)acetic acid;

(S)-2-(tert-Butoxy)-2-(5-(4-(2,5-difluorophenethoxy)phenyl)-4-(4,4-dimethylpiperidin-1-yl)-2,6-dimethylpyridin-3-yl)acetic acid;

(S)-2-(tert-Butoxy)-2-(5-(4-(4-chlorophenethoxy)phenyl)-4-(4,4-dimethylpiperidin-1-yl)-2,6-dimethylpyridin-3-yl)acetic acid;

(S)-2-(tert-Butoxy)-2-(5-(4-(4-chloro-3-fluorophenethoxy)phenyl)-4-(4,4-dimethylpiperidin-1-yl)-2,6-dimethylpyridin-3-yl)acetic acid;

(S)-2-(tert-Butoxy)-2-(4-(4,4-dimethylpiperidin-1-yl)-2,6-dimethyl-5-(4-(4-methylphenethoxy)phenyl)pyridin-3-yl)acetic acid;

(S)-2-(tert-Butoxy)-2-(5-(4-(2-(4-chlorophenyl)-2-methylpropoxy)phenyl)-4-(4,4-dimethylpiperidin-1-yl)-2,6-dimethylpyridin-3-yl)acetic acid;

(S)-2-(tert-Butoxy)-2-(4-(4,4-dimethylpiperidin-1-yl)-2,6-dimethyl-5-(4-(2-(naphthalen-2-yl)ethoxy)phenyl)pyridin-3-yl)acetic acid;

(S)-2-(5-(4-(4-(Benzyloxy)phenethoxy)phenyl)-4-(4,4-dimethylpiperidin-1-yl)-2,6-dimethylpyridin-3-yl)-2-(tert-butoxy)acetic acid;

(2S)-2-(tert-Butoxy)-2-(4-(4,4-dimethylpiperidin-1-yl)-5-(4-(2-(4-fluorophenyl)propoxy)phenyl)-2,6-dimethylpyridin-3-yl)acetic acid;

(S)-2-(tert-Butoxy)-2-(4-(4,4-dimethylpiperidin-1-yl)-2,6-dimethyl-5-(4-(2-(pyridin-2-yl)ethoxy)phenyl)pyridin-3-yl)acetic acid;

(S)-2-(tert-Butoxy)-2-(4-(4,4-dimethylpiperidin-1-yl)-5-(4-((S)-2-methoxy-2-phenylethoxy)phenyl)-2,6-dimethylpyridin-3-yl)acetic acid;

(S)-2-(tert-Butoxy)-2-(4-(4,4-dimethylpiperidin-1-yl)-5-(4-((R)-2-methoxy-2-phenylethoxy)phenyl)-2,6-dimethylpyridin-3-yl)acetic acid;

(S)-2-(tert-Butoxy)-2-(4-(4,4-dimethylpiperidin-1-yl)-5-(4-(3-methoxyphenethoxy)phenyl)-2,6-dimethylpyridin-3-yl)acetic acid;

(S)-2-(tert-Butoxy)-2-(4-(4,4-dimethylpiperidin-1-yl)-2,6-dimethyl-5-(4-(2-(pyridin-4-yl)ethoxy)phenyl)pyridin-3-yl)acetic acid;

(S)-2-(tert-Butoxy)-2-(4-(4,4-dimethylpiperidin-1-yl)-2,6-dimethyl-5-(4-(2-(naphthalen-1-yl)ethoxy)phenyl)pyridin-3-yl)acetic acid;

(S)-2-(tert-Butoxy)-2-(4-(4,4-dimethylpiperidin-1-yl)-2,6-dimethyl-5-(4-phenethoxyphenyl)pyridin-3-yl)acetic acid;

(S)-2-(tert-Butoxy)-2-(4-(4,4-dimethylpiperidin-1-yl)-2,6-dimethyl-5-(4-(2-(4-methylthiazol-5-yl)ethoxy)phenyl)pyridin-3-yl)acetic acid;

(S)-2-(tert-Butoxy)-2-(4-(4,4-dimethylpiperidin-1-yl)-2,6-dimethyl-5-(4-(2-(pyridin-3-yl)ethoxy)phenyl)pyridin-3-yl)acetic acid;

(S)-2-(tert-Butoxy)-2-(4-(4,4-dimethylpiperidin-1-yl)-2,6-dimethyl-5-(4-(2-(2-methylthiazol-4-yl)ethoxy)phenyl)pyridin-3-yl)acetic acid;

(S)-2-(tert-Butoxy)-2-(4-(4,4-dimethylpiperidin-1-yl)-2,6-dimethyl-5-(4-(thiazol-5-ylmethoxy)phenyl)pyridin-3-yl)acetic acid;

(S)-2-(tert-Butoxy)-2-(4-(4,4-dimethylpiperidin-1-yl)-5-(4-((2,4-dimethylthiazol-5-yl)methoxy)phenyl)-2,6-dimethylpyridin-3-yl)acetic acid;

(S)-2-(tert-Butoxy)-2-(4-(4,4-dimethylpiperidin-1-yl)-2,6-dimethyl-5-(4-((4-methyl-2-phenylthiazol-5-yl)methoxy)phenyl)pyridin-3-yl)acetic acid;

(S)-2-(5-(3,4-Bis(3-methoxyphenethoxy)phenyl)-4-(4,4-dimethylpiperidin-1-yl)-2,6-dimethylpyridin-3-yl)-2-(tert-butoxy)acetic acid;

(S)-2-(tert-Butoxy)-2-(5-(4-((2-chlorothiazol-5-yl)methoxy)phenyl)-4-(4,4-dimethylpiperidin-1-yl)-2,6-dimethylpyridin-3-yl)acetic acid;

(S)-2-(tert-Butoxy)-2-(4-(4,4-dimethylpiperidin-1-yl)-5-(4-(2-(2,4-dimethylthiazol-5-yl)ethoxy)phenyl)-2,6-dimethylpyridin-3-yl)acetic acid;

(S)-2-(tert-Butoxy)-2-(4-(4,4-dimethylpiperidin-1-yl)-5-(4-(2-(4-fluorophenyl)-2-methylpropoxy)phenyl)-2,6-dimethylpyridin-3-yl)acetic acid;

(S)-2-(tert-Butoxy)-2-(4-(4,4-dimethylpiperidin-1-yl)-2,6-dimethyl-5-(4-(2,4,5-trifluorophenethoxy)phenyl)pyridin-3-yl)acetic acid;

(S)-2-(tert-Butoxy)-2-(4-(4,4-dimethylpiperidin-1-yl)-2,6-dimethyl-5-(4-(2,3,5,6-tetrafluorophenethoxy)phenyl)pyridin-3-yl)acetic acid;

(S)-2-(tert-Butoxy)-2-(4-(4,4-dimethylpiperidin-1-yl)-2,6-dimethyl-5-(4-(2-(5-methylthiophen-2-yl)ethoxy)phenyl)pyridin-3-yl)acetic acid;

(S)-2-(tert-Butoxy)-2-(5-(4-(2-(3,5-dimethylisoxazol-4-yl)ethoxy)phenyl)-4-(4,4-dimethylpiperidin-1-yl)-2,6-dimethylpyridin-3-yl)acetic acid;

(S)-2-(tert-Butoxy)-2-(5-(4-(2-(3,5-dimethyl-1H-pyrazol-4-yl)ethoxy)phenyl)-4-(4,4-dimethylpiperidin-1-yl)-2,6-dimethylpyridin-3-yl)acetic acid;

(S)-2-(5-(3-(Benzyloxy)-4-methylphenyl)-4-(4,4-dimethylpiperidin-1-yl)-2,6-dimethylpyridin-3-yl)-2-(tert-butoxy)acetic acid;

(S)-2-(tert-Butoxy)-2-(4-(4,4-dimethylpiperidin-1-yl)-2,6-dimethyl-5-(4-(pyridin-4-ylmethoxy)phenyl)pyridin-3-yl)acetic acid;

(S)-2-(tert-Butoxy)-2-(4-(4,4-dimethylpiperidin-1-yl)-5-(2-methoxypyrimidin-5-yl)-2,6-dimethylpyridin-3-yl)acetic acid;

(S)-2-(tert-Butoxy)-2-(4-(4,4-dimethylpiperidin-1-yl)-5-(2-(4-fluorophenethoxy)pyrimidin-5-yl)-2,6-dimethylpyridin-3-yl)acetic acid;

(S)-2-(tert-Butoxy)-2-(4-(4,4-dimethylpiperidin-1-yl)-5-(3-fluoro-4-propoxyphenyl)-2,6-dimethylpyridin-3-yl)acetic acid;

(S)-2-(tert-Butoxy)-2-(4-(4,4-dimethylpiperidin-1-yl)-2,6-dimethyl-5-(3,4,5-trimethoxyphenyl)pyridin-3-yl)acetic acid;

(S)-2-(tert-Butoxy)-2-(4-(4,4-dimethylpiperidin-1-yl)-5-(3-methoxy-4-methylphenyl)-2,6-dimethylpyridin-3-yl)acetic acid;

(S)-2-(tert-Butoxy)-2-(4-(4,4-dimethylpiperidin-1-yl)-5-(3-methoxyphenyl)-2,6-dimethylpyridin-3-yl)acetic acid;

(S)-2-(tert-Butoxy)-2-(5-(3-chloro-4-isopropoxyphenyl)-4-(4,4-dimethylpiperidin-1-yl)-2,6-dimethylpyridin-3-yl)acetic acid;

(S)-2-(tert-Butoxy)-2-(5-(3,5-dimethyl-4-propoxyphenyl)-4-(4,4-dimethylpiperidin-1-yl)-2,6-dimethylpyridin-3-yl)acetic acid;

(S)-2-(tert-Butoxy)-2-(4-(4,4-dimethylpiperidin-1-yl)-5-(4-ethoxy-3-fluorophenyl)-2,6-dimethylpyridin-3-yl)acetic acid;

(S)-2-(tert-Butoxy)-2-(4-(4,4-dimethylpiperidin-1-yl)-5-(4-fluoro-3-methoxyphenyl)-2,6-dimethylpyridin-3-yl)acetic acid;

(S)-2-(tert-Butoxy)-2-(4-(4,4-dimethylpiperidin-1-yl)-6'-(4-fluorophenethoxy)-2,6-dimethyl-[3,3'-bipyridin]-5-yl)acetic acid;

(2S)-2-(tert-Butoxy)-2-(4-(3-cyclopropylpyrrolidin-1-yl)-5-(4-(4-fluorophenethoxy)phenyl)-2,6-dimethylpyridin-3-yl)acetic acid;

(S)-2-(tert-Butoxy)-2-(4-(3,3-difluoroazetidin-1-yl)-5-(4-(4-fluorophenethoxy)phenyl)-2,6-dimethylpyridin-3-yl)acetic acid;

(S)-2-(tert-Butoxy)-2-(4-(3,3-dimethylazetidin-1-yl)-5-(4-(4-fluorophenethoxy)phenyl)-2,6-dimethylpyridin-3-yl)acetic acid;

(S)-2-(tert-Butoxy)-2-(5-(4-(4-fluoro-phenethoxy)phenyl)-4-(3-isopropylazetidin-1-yl)-2,6-dimethylpyridin-3-yl)acetic acid;

(S)-2-(tert-Butoxy)-2-(5-(4-(4-fluorophenethoxy)phenyl)-2,6-dimethyl-4-(4-phenylpiperidin-1-yl)pyridin-3-yl)acetic acid;

(S)-2-(tert-Butoxy)-2-(5-(4-(4-fluorophenethoxy)phenyl)-4-(4-(3-isopropyl-1,2,4-oxadiazol-5-yl)piperidin-1-yl)-2,6-dimethylpyridin-3-yl)acetic acid;

(S)-2-(tert-Butoxy)-2-(5-(4-(4-fluorophenethoxy)phenyl)-2,6-dimethyl-4-(4-(trifluoromethyl)piperidin-1-yl)pyridin-3-yl)acetic acid;

(S)-2-(tert-Butoxy)-2-(4-(4-ethyl-4-methylpiperidin-1-yl)-5-(4-(4-fluorophenethoxy)phenyl)-2,6-dimethylpyridin-3-yl)acetic acid;

(S)-2-(tert-Butoxy)-2-(5-(4-(4-fluorophenethoxy)phenyl)-2,6-dimethyl-4-(4-methylpiperidin-1-yl)pyridin-3-yl)acetic acid;

(S)-2-(tert-Butoxy)-2-(5-(4-(4-fluorophenethoxy)phenyl)-4-(4-methoxy-4-methylpiperidin-1-yl)-2,6-dimethylpyridin-3-yl)acetic acid;

(S)-2-(tert-Butoxy)-2-(4-(4-cyano-4-methylpiperidin-1-yl)-5-(4-(4-fluorophenethoxy)phenyl)-2,6-dimethylpyridin-3-yl)acetic acid;

(S)-2-(tert-Butoxy)-2-(5-(4-(4-fluorophenethoxy)phenyl)-2,6-dimethyl-4-(4-(propan-2-ylidene)piperidin-1-yl)pyridin-3-yl)acetic acid;

(S)-2-(4-(4-Benzylpiperidin-1-yl)-5-(4-(4-fluorophenethoxy)phenyl)-2,6-dimethylpyridin-3-yl)-2-(tert-butoxy)acetic acid;

(S)-2-(tert-Butoxy)-2-(4-(4-fluoro-4-methylpiperidin-1-yl)-5-(4-(4-fluorophenethoxy)phenyl)-2,6-dimethylpyridin-3-yl)acetic acid; and (S)-2-(tert-Butoxy)-2-(4-((3,5-dimethylpiperidin-1-yl)-5-(4-(4-fluorophenethoxy)phenyl)-2,6-dimethylpyridin-3-yl)acetic acid;

or a pharmaceutically acceptable salt thereof.

8. A compound of claim 1 selected from the group consisting of (S)-2-(tert-butoxy)-2-(4-(4,4-dimethylpiperidin-1-yl)-5-(4-((4-fluorobenzyl)oxy)phenyl)-2,6-dimethylpyridin-3-yl)acetic acid;

(S)-2-(tert-butoxy)-2-(4-(4,4-dimethylpiperidin-1-yl)-5-(4-((4-methoxybenzyl)oxy)phenyl)-2,6-dimethylpyridin-3-yl)acetic acid;

(S)-2-(tert-butoxy)-2-(4-(4,4-dimethylpiperidin-1-yl)-5-(4-(4-fluorophenethoxy)phenyl)-2,6-dimethylpyridin-3-yl)acetic acid;

(S)-2-(tert-butoxy)-2-(4-(4,4-dimethylpiperidin-1-yl)-5-(4-(4-fluoro-3-methylphenethoxy)phenyl)-2,6-dimethylpyridin-3-yl)acetic acid;

(S)-2-(tert-butoxy)-2-(5-(4-(2,4-difluorophenethoxy)phenyl)-4-(4,4-dimethylpiperidin-1-yl)-2,6-dimethylpyridin-3-yl)acetic acid;

(2S)-2-(tert-Butoxy)-2-(4-(4,4-dimethylpiperidin-1-yl)-5-(4-((1-(4-fluorophenyl)propan-2-yl)oxy)phenyl)-2,6-dimethylpyridin-3-yl)acetic acid;

(S)-2-(tert-butoxy)-2-(4-(4,4-dimethylpiperidin-1-yl)-2,6-dimethyl-5-(4-(2-(pyridin-4-yl)ethoxy)phenyl)pyridin-3-yl)acetic acid;

(S)-2-(tert-butoxy)-2-(4-(4,4-dimethylpiperidin-1-yl)-2,6-dimethyl-5-(4-(2-(4-methylthiazol-5-yl)ethoxy)phenyl)pyridin-3-yl)acetic acid;

(S)-2-(tert-butoxy)-2-(4-(4,4-dimethylpiperidin-1-yl)-5-(4-(2-(2,4-dimethylthiazol-5-yl)ethoxy)phenyl)-2,6-dimethylpyridin-3-yl)acetic acid;

(S)-2-(tert-butoxy)-2-(4-(4,4-dimethylpiperidin-1-yl)-5-(4-(2-(4-fluorophenyl)-2-methylpropoxy)phenyl)-2,6-dimethylpyridin-3-yl)acetic acid;

(S)-2-(tert-butoxy)-2-(4-(4-ethyl-4-methylpiperidin-1-yl)-5-(4-(4-fluorophenethoxy)phenyl)-2,6-dimethylpyridin-3-yl)acetic acid;

(S)-2-(tert-butoxy)-2-(5-(4-(2-(3,5-dimethylisoxazol-4-yl)ethoxy)phenyl)-4-(4,4-dimethylpiperidin-1-yl)-2,6-dimethylpyridin-3-yl)acetic acid; and (S)-2-(tert-butoxy)-2-(4-(4-fluoro-4-methylpiperidin-1-yl)-5-(4-(4-fluorophenethoxy)phenyl)-2,6-dimethylpyridin-3-yl)acetic acid;

or a pharmaceutically acceptable salt thereof.

9. A compound of Formula II

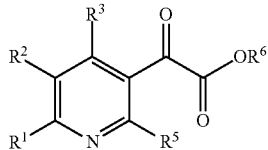

II where $R^1$ is hydrogen or alkyl; $R^2$ is halo; $R^3$ is halo; $R^5$ is hydrogen or alkyl; and $R^6$ is alkyl.

10. A compound of Formula III

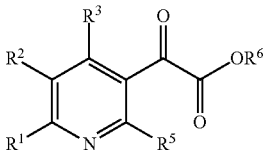

III where $R^1$ is hydrogen or alkyl; $R^2$ is halo; $R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, alkoxy, cyano, and haloalkoxy; $R^5$ is hydrogen or alkyl; and $R^6$ is alkyl.

11. A compound of Formula IV

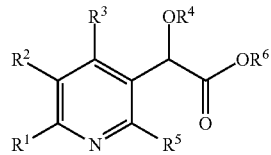

IV where $R^1$ is hydrogen or alkyl; $R^2$ is halo; $R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, alkoxy, cyano, and haloalkoxy; $R^4$ is hydrogen or alkyl; $R^5$ is hydrogen or alkyl; and $R^6$ is alkyl.

12. A composition useful for treating HIV infection comprising a therapeutic amount of a compound of claim 1 and a pharmaceutically acceptable carrier.

13. A method for treating HIV infection comprising administering a therapeutically effective amount of a compound of claim 1, or a pharmaceutically acceptable salt thereof, to a patient in need thereof.

* * * * *